(12) United States Patent
Vorechovsky et al.

(10) Patent No.: US 9,745,577 B2
(45) Date of Patent: Aug. 29, 2017

(54) REDUCING INTRON RETENTION

(71) Applicant: University of Southampton, Southampton, Hampshire (GB)

(72) Inventors: Igor Vorechovsky, Southampton (GB); Jana Kralovicova, Southampton (GB)

(73) Assignee: UNIVERSITY OF SOUTHAMPTON, Southampton, Hampshire (GB)

( * ) Notice: Subject to any disclaimer, the term of this patent is extended or adjusted under 35 U.S.C. 154(b) by 0 days.

(21) Appl. No.: 14/741,071

(22) Filed: Jun. 16, 2015

(65) Prior Publication Data

US 2016/0017322 A1   Jan. 21, 2016

(30) Foreign Application Priority Data

Jun. 16, 2014  (GB) .................................. 1410693.4

(51) Int. Cl.

| | | |
|---|---|---|
| C07H 21/02 | (2006.01) | |
| C07H 21/04 | (2006.01) | |
| C12N 15/113 | (2010.01) | |
| C12Q 1/68 | (2006.01) | |
| C12N 15/11 | (2006.01) | |

(52) U.S. Cl.

CPC .......... *C12N 15/113* (2013.01); *C12N 15/111* (2013.01); *C12Q 1/6883* (2013.01); *C12N 2310/11* (2013.01); *C12N 2310/113* (2013.01); *C12N 2310/315* (2013.01); *C12N 2310/321* (2013.01); *C12N 2310/346* (2013.01); *C12N 2320/33* (2013.01)

(58) Field of Classification Search

CPC ........................ C12N 15/113; C12N 2310/11
See application file for complete search history.

(56) References Cited

U.S. PATENT DOCUMENTS

| | | | |
|---|---|---|---|
| 4,866,042 A | 9/1989 | Neuwelt | |
| 5,151,510 A | 9/1992 | Stec et al. | |
| 5,656,612 A | 8/1997 | Monia | |
| 5,665,593 A | 9/1997 | Kole et al. | |
| 5,914,396 A | 6/1999 | Cook et al. | |
| 5,916,808 A | 6/1999 | Kole et al. | |
| 5,976,879 A | 11/1999 | Kole et al. | |
| 6,166,197 A | 12/2000 | Cook et al. | |
| 6,210,892 B1 | 4/2001 | Bennett et al. | |
| 6,294,520 B1 | 9/2001 | Naito | |
| 6,451,991 B1 | 9/2002 | Martin et al. | |
| 6,632,427 B1 | 10/2003 | Finiels et al. | |
| 6,677,445 B1 | 1/2004 | Innis et al. | |
| 6,756,523 B1 | 6/2004 | Kahn et al. | |
| 6,846,921 B2 | 1/2005 | Innis et al. | |
| 6,936,589 B2 | 8/2005 | Naito | |
| 6,963,589 B1 | 11/2005 | Sugata et al. | |
| 7,015,315 B1 | 3/2006 | Cook et al. | |
| 7,101,993 B1 | 9/2006 | Cook et al. | |
| 7,432,249 B2 | 10/2008 | Crooke | |
| 7,432,250 B2 | 10/2008 | Crooke | |
| 7,557,198 B2 * | 7/2009 | Davis ................... | C12Q 1/6886 536/23.1 |
| 8,067,569 B2 | 11/2011 | Iversen et al. | |
| 8,124,745 B2 | 2/2012 | Allerson et al. | |
| 8,258,109 B2 | 9/2012 | Bennett et al. | |
| 8,436,163 B2 | 5/2013 | Iversen et al. | |
| 8,450,467 B2 | 5/2013 | Manoharan et al. | |
| 8,637,478 B2 | 1/2014 | Bennett | |
| 8,846,885 B2 | 9/2014 | Hirai et al. | |
| 8,895,722 B2 | 11/2014 | Iversen et al. | |
| 9,193,969 B2 | 11/2015 | Montefeltro et al. | |
| 2004/0063129 A1 | 4/2004 | Gaarde et al. | |
| 2004/0219515 A1 | 11/2004 | Bentwich | |
| 2005/0221354 A1 | 10/2005 | Mounts | |
| 2005/0233327 A1 | 10/2005 | Welch et al. | |
| 2006/0134670 A1 | 6/2006 | Piu | |
| 2007/0009899 A1 | 1/2007 | Mounts | |
| 2007/0087376 A1 | 4/2007 | Potashkin | |
| 2007/0249538 A1 | 10/2007 | Sazani et al. | |
| 2008/0269123 A1 | 10/2008 | Li et al. | |
| 2009/0186846 A1 | 7/2009 | Chabot et al. | |
| 2009/0264353 A1 | 10/2009 | Orum et al. | |

(Continued)

FOREIGN PATENT DOCUMENTS

| | | |
|---|---|---|
| CN | 103667438 A | 3/2014 |
| EP | 0549615 A1 | 7/1993 |

(Continued)

OTHER PUBLICATIONS

Aartsma-Rus, et al. Antisense-mediated exon skipping: a versatile tool with therapeutic and research applications.RNA. Oct. 2007;13(10):1609-24. Epub Aug. 7, 2007.

Aly, et al. Extreme genetic risk for type 1A diabetes. Proc Natl Acad Sci U S A. Sep. 19, 2006;103(38):14074-9. Epub Sep. 11, 2006.

Balagurumoorthy, et al. Hairpin and parallel quartet structures for telomeric sequences. Nucleic Acids Res. Aug. 11, 1992;20(15):4061-7.

Balkwill, et al. Repression of translation of human estrogen receptor alpha by G-quadruplex formation. Biochemistry. Dec. 8, 2009;48(48):11487-95. doi: 10.1021/bi901420k.

Barratt, et al. Remapping the insulin gene/IDDM2 locus in type 1 diabetes. Diabetes. Jul. 2004;53(7):1884-9.

Baughan, et al. Delivery of bifunctional RNAs that target an intronic repressor and increase SMN levels in an animal model of spinal muscular atrophy. Hum Mol Genet. May 1, 2009;18(9):1600-11. doi: 10.1093/hmg/ddp076. Epub Feb. 19, 2009.

(Continued)

*Primary Examiner* — Amy Bowman

(74) *Attorney, Agent, or Firm* — Wilson Sonsini Goodrich & Rosati

(57) ABSTRACT

Disclosed herein are methods, compositions, polynucleic acid polymers, assays, and kits for inducing processing of a partially processed mRNA transcript to remove a retained intron to produce a fully processed mRNA transcript that encodes a full-length functional form of a protein. Also described herein are methods and compositions for treating a disease or condition characterized by impaired production of a full-length functional form of a protein or for treating a disease or condition characterized by a defective splicing in a subject.

17 Claims, 8 Drawing Sheets

(56) References Cited

U.S. PATENT DOCUMENTS

| | | | |
|---|---|---|---|
| 2010/0166784 | A1 | 7/2010 | Murphy et al. |
| 2011/0124591 | A1 | 5/2011 | Bennett |
| 2012/0190728 | A1 | 7/2012 | Bennett et al. |
| 2013/0109850 | A1 | 5/2013 | Prakash et al. |
| 2013/0253036 | A1 | 9/2013 | Collard et al. |
| 2013/0289092 | A1 | 10/2013 | Rigo et al. |
| 2014/0128449 | A1 | 5/2014 | Liu et al. |
| 2014/0186839 | A1 | 7/2014 | Margulies et al. |
| 2014/0194610 | A1 | 7/2014 | Verdine et al. |
| 2014/0235605 | A1 | 8/2014 | Shiffman et al. |
| 2014/0343127 | A1 | 11/2014 | Kammler |
| 2014/0349290 | A1 | 11/2014 | Watnick et al. |
| 2014/0378526 | A1 | 12/2014 | Rossi et al. |
| 2014/0378527 | A1 | 12/2014 | Van Deutekom |
| 2014/0378533 | A1 | 12/2014 | Freier |
| 2015/0004217 | A1 | 1/2015 | Guild et al. |
| 2015/0018540 | A1 | 1/2015 | Prakash et al. |
| 2015/0184153 | A1 | 7/2015 | Freier et al. |
| 2015/0337310 | A1 | 11/2015 | Walker et al. |
| 2016/0017322 | A1 | 1/2016 | Vorechovsky et al. |
| 2016/0244762 | A1 | 8/2016 | Vorechovsky et al. |
| 2017/0101641 | A1 | 4/2017 | Vorechovsky et al. |

FOREIGN PATENT DOCUMENTS

| | | |
|---|---|---|
| EP | 2114981 B1 | 5/2013 |
| WO | WO-9402501 A1 | 2/1994 |
| WO | WO-9426887 A1 | 11/1994 |
| WO | WO-2006107846 A2 | 10/2006 |
| WO | WO-2011057350 A1 | 5/2011 |
| WO | WO-2014012081 A2 | 1/2014 |
| WO | WO-2014031575 A1 | 2/2014 |
| WO | WO-2014172698 A1 | 10/2014 |
| WO | WO-2015035091 A1 | 3/2015 |
| WO | WO-2015193651 A1 | 12/2015 |
| WO | WO-2016054615 A2 | 4/2016 |
| WO | WO-2016077837 A1 | 5/2016 |

OTHER PUBLICATIONS

Beaudoin, et al. 5'-UTR G-quadruplex structures acting as translational repressors. Nucleic Acids Res. Nov. 2010;38(20):7022-36. doi: 10.1093/nar/gkq557. Epub Jun. 22, 2010.

Bicknell, et al. Introns in UTRs: why we should stop ignoring them. Bioessays. Dec. 2012;34(12):1025-34. doi: 10.1002/bies.201200073. Epub Oct. 26, 2012.

Booy, et al. The RNA helicase RHAU (DHX36) unwinds a G4-quadruplex in human telomerase RNA and promotes the formation of the P1 helix template boundary. Nucleic Acids Res. May 2012;40(9):4110-24. doi: 10.1093/nar/gkr1306. Epub Jan. 11, 2012.

Boutz, et al. Detained introns are a novel, widespread class of post-transcriptionally spliced introns. Genes Dev. Jan. 1, 2015;29(1):63-80. doi: 10.1101/gad.247361.114.

Braunschweig, et al. Widespread intron retention in mammals functionally tunes transcriptomes. Widespread intron retention in mammals functionally tunes transcriptomes. Genome Res. Nov. 2014;24(11):1774-86. doi: 10.1101/gr.177790.114. Epub Sep. 25, 2014.

Buchman, et al. Comparison of intron-dependent and intron-independent gene expression. Mol Cell Biol. Oct. 1988;8(10):4395-405.

Bugaut, et al. 5'-UTR RNA G-quadruplexes: translation regulation and targeting. Nucleic Acids Res. Jun. 2012;40(11):4727-41. doi: 10.1093/nar/gks068. Epub Feb. 20, 2012.

Bugaut, et al. An RNA hairpin to G-quadruplex conformational transition. J Am Chem Soc. Dec. 12, 2012;134(49):19953-6. doi: 10.1021/ja308665g. Epub Nov. 29, 2012.

Buratti, et al. DBASS3 and DBASS5: databases of aberrant 3'- and 5'-splice sites. Nucleic Acids Res. Jan. 2011;39(Database issue):D86-91. doi: 10.1093/nar/gkq887. Epub Oct. 6, 2010.

Buratti, et al. RNA folding affects the recruitment of SR proteins by mouse and human polypurinic enhancer elements in the fibronectin EDA exon. Mol Cell Biol. Feb. 2004;24(3):1387-400.

Callis, et al. Introns increase gene expression in cultured maize cells. Genes Dev. Dec. 1987;1(10):1183-200.

Cavaloc, et al. The splicing factors 9G8 and SRp20 transactivate splicing through different and specific enhancers. RNA. Mar. 1999;5(3):468-83.

Cazzola, et al. Translational pathophysiology: a novel molecular mechanism of human disease. Blood. Jun. 1, 2000;95(11):3280-8.

Collie, et al. The application of DNA and RNA G-quadruplexes to therapeutic medicines. Chem Soc Rev. Dec. 2011;40(12):5867-92. doi: 10.1039/c1cs15067g. Epub Jul. 25, 2011.

Creacy, et al. G4 resolvase 1 binds both DNA and RNA tetramolecular quadruplex with high affinity and is the major source of tetramolecular quadruplex G4-DNA and G4-RNA resolving activity in HeLa cell lysates. J Biol Chem. Dec. 12, 2008;283(50):34626-34. doi: 10.1074/jbc.M806277200. Epub Oct. 7, 2008.

Culler, et al. Functional selection and systematic analysis of intronic splicing elements identify active sequence motifs and associated splicing factors. Nucleic Acids Res. Aug. 2010;38(15):5152-65. doi: 10.1093/nar/gkq248. Epub Apr. 12, 2010.

Davies, et al. A genome-wide search for human type 1 diabetes susceptibility genes. Nature. Sep. 8, 1994;371(6493):130-6.

Decorsiere, et al. Essential role for the interaction between hnRNP H/F and a G quadruplex in maintaining p53 pre-mRNA 3'-end processing and function during DNA damage. Genes Dev. Feb. 1, 2011;25(3):220-5. doi: 10.1101/gad.607011.

Derecka, et al. Occurrence of a quadruplex motif in a unique insert within exon C of the bovine estrogen receptor alpha gene (ESR1). Biochemistry. Sep. 7, 2010;49(35):7625-33. doi: 10.1021/bi100804f.

Didiot, et al. The G-quartet containing FMRP binding site in FMR1 mRNA is a potent exonic splicing enhancer. Nucleic Acids Res. Sep. 2008;36(15):4902-12. doi: 10.1093/nar/gkn472. Epub Jul. 24, 2008.

Dominski, et al. Restoration of correct splicing in thalassemic pre-mRNA by antisense oligonucleotides. Proc Natl Acad Sci U S A. Sep. 15, 1993;90(18):8673-7.

Du, et al. Correction of prototypic ATM splicing mutations and aberrant ATM function with antisense morpholino oligonucleotides. Proc Natl Acad Sci U S A. Apr. 3, 2007;104(14):6007-12. Epub Mar. 26, 2007.

Eddy, et al. G4 motifs correlate with promoter-proximal transcriptional pausing in human genes. Nucleic Acids Res. Jul. 2011;39(12):4975-83. doi: 10.1093/nar/gkr079. Epub Mar. 3, 2011.

Emerick, et al. Multivariate analysis and visualization of splicing correlations in single-gene transcriptomes. BMC Bioinformatics. Jan. 18, 2007;8:16.

Fededa, et al. A polar mechanism coordinates different regions of alternative splicing within a single gene. Mol Cell. Aug. 5, 2005;19(3):393-404.

Fred, et al. The human insulin mRNA is partly translated via a cap- and eIF4A-independent mechanism. Biochem Biophys Res Commun. Sep. 9, 2011;412(4):693-8. doi: 10.1016/j.bbrc.2011.08.030. Epub Aug. 16, 2011.

Galante, et al. Detection and evaluation of intron retention events in the human transcriptome. RNA. May 2004;10(5):757-65.

Garner, et al. Selectivity of small molecule ligands for parallel and anti-parallel DNA G-quadruplex structures. Org Biomol Chem. Oct. 21, 2009;7(20):4194-200. doi: 10.1039/b910505k. Epub Aug. 14, 2009.

Gomez, et al. Telomerase downregulation induced by the G-quadruplex ligand 12459 in A549 cells is mediated by hTERT RNA alternative splicing. Nucleic Acids Res. Jan. 16, 2004;32(1):371-9. Print 2004.

Goyenvalie, et al. Therapeutic approaches to muscular dystrophy. Hum Mol Genet. Apr. 15, 2011;20(R1):R69-78. doi: 10.1093/hmg/ddr105. Epub Mar. 24, 2011.

Hai, et al. A G-tract element in apoptotic agents-induced alternative splicing. Nucleic Acids Res. Jun. 2008;36(10):3320-31. doi: 10.1093/nar/gkn207. Epub Apr. 24, 2008.

Hargous, et al. Molecular basis of RNA recognition and TAP binding by the SR proteins SRp20 and 9G8. EMBO J. Nov. 1, 2006;25(21):5126-37. Epub Oct. 12, 2006.

(56) References Cited

OTHER PUBLICATIONS

Hegele, et al. Dynamic protein-protein interaction wiring of the human spliceosome. Mol Cell. Feb. 24, 2012;45(4):567-80. doi: 10.1016/j.molcel.2011.12.034.
Hua, et al. Antisense correction of SMN2 splicing in the CNS rescues necrosis in a type III SMA mouse model. Genes Dev. Aug. 1, 2010;24(15):1634-44. doi: 10.1101/gad.1941310. Epub Jul. 12, 2010.
Hunt, et al. Negligible impact of rare autoimmune-locus coding-region variants on missing heritability. Nature. Jun. 13, 2013;498(7453):232-5. doi: 10.1038/nature12170. Epub May 22, 2013.
Iwamoto, et al. Transcription-dependent nucleolar cap localization and possible nuclear function of DExH RNA helicase RHAU. Exp Cell Res. Apr. 1, 2008;314(6):1378-91. doi: 10.1016/j.yexcr.2008. 01.006. Epub Jan. 16, 2008.
Ke, et al. Quantitative evaluation of all hexamers as exonic splicing elements. Genome Res. Aug. 2011;21(8):1360-74. doi: 10.1101/gr. 119628.110. Epub Jun. 9, 2011.
Kikin, et al. QGRS Mapper: a web-based server for predicting G-quadruplexes in nucleotide sequences. Nucleic Acids Res. Jul. 1, 2006;34(Web Server issue):W676-82.
Kole, et al. RNA therapeutics: beyond RNA interference and antisense oligonucleotides. Nat Rev Drug Discov. Jan. 20, 2012;11(2):125-40. doi: 10.1038/nrd3625.
Kralovicova, et al. Allele-specific recognition of the 3' splice site of INS intron 1. Hum Genet. Oct. 2010;128(4):383-400. doi: 10.1007/s00439-010-0860-1. Epub Jul. 14, 2010.
Kralovicova, et al. Compensatory signals associated with the activation of human GC 5' splice sites. Nucleic Acids Res. Sep. 1, 2011;39(16):7077-91. doi: 10.1093/nar/gkr306. Epub May 23, 2011.
Kralovicova, et al. Identification of U2AF(35)-dependent exons by RNA-Seq reveals a link between 3' splice-site organization and activity of U2AF-related proteins. Nucleic Acids Res. Apr. 20, 2015;43(7):3747-63. doi: 10.1093/nar/gkv194. Epub Mar. 16, 2015.
Kralovicova, et al. Optimal antisense target reducing INS intron 1 retention is adjacent to a parallel G quadruplex. Nucleic Acids Res. Jul. 2014;42(12):8161-73. doi: 10.1093/nar/gku507. Epub Jun. 17, 2014.
Kralovicova, et al. Phenotypic consequences of branch point substitutions. Hum Mutat. Aug. 2006;27(8):803-13.
Kralovicova, et al. Position-dependent repression and promotion of DQB1 intron 3 splicing by GGGG motifs. J Immunol. Feb. 15, 2006;176(4):2381-8.
Kralovicova, et al. Variants in the human insulin gene that affect pre-mRNA splicing: is -23HphI a functional single nucleotide polymorphism at IDDM2? Diabetes. Jan. 2006;55(1):260-4.
Le Hir, et al. How introns influence and enhance eukaryotic gene expression. Trends Biochem Sci. Apr. 2003;28(4):215-20.
Lei, et al. Identification of splicing silencers and enhancers in sense Alus: a role for pseudoacceptors in splice site repression. Mol Cell Biol. Aug. 2005;25(16):6912-20.
Lorenz, et al. 2D meets 4G: G-Quadruplexes in RNA Secondary Structure Prediction. IEEE/ACM Trans Comput Biol Bioinform. Jul.-Aug. 2013;10(4):832-44. doi: 10.1109/TCBB.2013.7.
Makishima, et al. Mutations in the spliceosome machinery, a novel and ubiquitous pathway in leukemogenesis. Blood. Apr. 5, 2012;119(14):3203-10. doi: 10.1182/blood-2011-12-399774. Epub Feb. 9, 2012.
Marcel, et al. G-quadruplex structures in TP53 intron 3: role in alternative splicing and in production of p53 mRNA isoforms. Carcinogenesis. Mar. 2011;32(3):271-8. doi: 10.1093/carcin/bgq253. Epub Nov. 26, 2010
Mayeda, et al. Surveying cis-acting sequences of pre-mRNA by adding antisense 2'-O-methyl oligoribonucleotides to a splicing reaction. J Biochem. Sep. 1990;108(3):399-405.
Melko, et al. Functional characterization of the AFF (AF4/FMR2) family of RNA-binding proteins: insights into the molecular pathology of FRAXE intellectual disability. Hum Mol Genet. May 15, 2011;20(10):1873-85. doi: 10.1093/hmg/ddr069. Epub Feb. 17, 2011.
Millevoi, et al. G-quadruplexes in RNA biology. Wiley Interdiscip Rev RNA. Jul.-Aug. 2012;3(4):495-507. doi: 10.1002/wrna.1113. Epub Apr. 4, 2012.
Morris, et al. An RNA G-quadruplex is essential for cap-independent translation initiation in human VEGF IRES. J Am Chem Soc. Dec. 22, 2010;132(50):17831-9. doi: 10.1021/ja106287x. Epub Nov. 24, 2010.
Neidle, S. and Balasubramanian, S. (2006) Quadruplex Nucleic Acids. RSC Biomolecular Sciences, Cambridge, UK.
Nussinov. Conserved quartets near 5' intron junctions in primate nuclear pre-mRNA. J Theor Biol. Jul. 8, 1988;133(1):73-84.
Pacheco, et al. Diversity of vertebrate splicing factor U2AF35: identification of alternatively spliced U2AF1 mRNAS. J Biol Chem. Jun. 25, 2004;279(26):27039-49. Epub Apr. 19, 2004.
Pacheco, et al. RNA interference knockdown of hU2AF35 impairs cell cycle progression and modulates alternative splicing of Cdc25 transcripts. Mol Biol Cell. Oct. 2006;17(10):4187-99. Epub Jul. 19, 2006.
Papaemmanuil, et al. Clinical and biological implications of driver mutations in myelodysplastic syndromes. Blood. Nov. 21, 2013;122(22):3616-27; quiz 3699. doi: 10.1182/blood-2013-08-518886. Epub Sep. 12, 2013.
Pastor, et al. Interaction of hnRNPA1/A2 and DAZAP1 with an Alu-derived intronic splicing enhancer regulates ATM aberrant splicing. PLoS One. 2011;6(8):e23349. doi: 10.1371/journal.pone.0023349. Epub Aug. 8, 2011.
Peng, et al. Functional importance of different patterns of correlation between adjacent cassette exons in human and mouse. BMC Genomics. Apr. 26, 2008;9:191. doi: 10.1186/1471-2164-9-191.
Pugliese, et al. The insulin gene is transcribed in the human thymus and transcription levels correlated with allelic variation at the INS VNTR-IDDM2 susceptibility locus for type 1 diabetes. Nat Genet. Mar. 1997;15(3):293-7.
Ruskin, et al. A factor, U2AF, is required for U2 snRNP binding and splicing complex assembly. Cell. Jan. 29, 1988;52(2):207-19.
Sakabe, et al. Sequence features responsible for intron retention in human. BMC Genomics. Feb. 26, 2007;8:59.
Samatanga, et al. The high kinetic stability of a G-quadruplex limits hnRNP F gRRM3 binding to G-tract RNA. Nucleic Acids Res. Feb. 1, 2013;41(4):2505-16. doi: 10.1093/nar/gks1289. Epub Dec. 28, 2012.
Schwarze, et al. Redefinition of exon 7 in the COL1A1 gene of type I collagen by an intron 8 splice-donor-site mutation in a form of osteogenesis imperfecta: influence of intron splice order on outcome of splice-site mutation. Am J Hum Genet. Aug. 1999;65(2):336-44.
Singh, et al. An antisense microwalk reveals critical role of an intronic position linked to a unique long-distance interaction in pre-mRNA splicing. RNA. Jun. 2010;16(6):1167-81. doi: 10.1261/rna.2154310. Epub Apr. 22, 2010.
Sirand-Pugnet, et al. An intronic (A/U)GGG repeat enhances the splicing of an alternative intron of the chicken beta-tropomyosin pre-mRNA. Nucleic Acids Res. Sep. 11, 1995;23(17):3501-7.
Smith, et al. Alternative pre-mRNA splicing: the logic of combinatorial control. Trends Biochem Sci. Aug. 2000;25(8):381-8.
Stead, et al. Global haplotype diversity in the human insulin gene region. Genome Res. Sep. 2003;13(9):2101-11.
Thisted, et al. Optimized RNA targets of two closely related triple KH domain proteins, heterogeneous nuclear ribonucleoprotein K and alphaCP-2KL, suggest Distinct modes of RNA recognition. J Biol Chem. May 18, 2001;276(20):17484-96. Epub Feb. 2, 2001.
Vafiadis, et al. Insulin expression in human thymus is modulated by INS VNTR alleles at the IDDM2 locus. Nat Genet. Mar. 1997;15(3):289-92.
Voelker, et al. A comprehensive computational characterization of conserved mammalian intronic sequences reveals conserved motifs associated with constitutive and alternative splicing. Genome Res. Jul. 2007;17(7):1023-33. Epub May 24, 2007.
Wahl, et al. The spliceosome: design principles of a dynamic RNP machine. Cell. Feb. 20, 2009;136(4):701-18. doi: 10.1016/j.cell. 2009.02.009.

(56) References Cited

OTHER PUBLICATIONS

Wang, et al. A complex network of factors with overlapping affinities represses splicing through intronic elements. Nat Struct Mol Biol. Jan. 2013;20(1):36-45. doi: 10.1038/nsmb.2459. Epub Dec. 16, 2012.

Wang, et al. Intronic splicing enhancers, cognate splicing factors and context-dependent regulation rules. Nat Struct Mol Biol. Oct. 2012;19(10):1044-52. doi: 10.1038/nsmb.2377. Epub Sep. 16, 2012.

Wang, et al. Regulation of insulin preRNA splicing by glucose. Proc Natl Acad Sci U S A. Apr. 29, 1997;94(9):4360-5.

Wieland, et al. RNA quadruplex-based modulation of gene expression. Chem Biol. Jul. 2007;14(7):757-63.

Xing, et al. The multiassembly problem: reconstructing multiple transcript isoforms from EST fragment mixtures. Genome Res. Mar. 2004;14(3):426-41. Epub Feb. 12, 2004.

Yeo, et al. Discovery and analysis of evolutionarily conserved intronic splicing regulatory elements. PLoS Genet. May 25, 2007;3(5):e85. Epub Apr. 13, 2007.

Yoshida, et al. Frequent pathway mutations of splicing machinery in myelodysplasia. Nature. Sep. 11, 2011;478(7367):64-9. doi: 10.1038/nature10496.

Zhang, et al. Insulin as an autoantigen in NOD/human diabetes. Curr Opin Immunol. Feb. 2008;20(1):111-8. doi: 10.1016/j.coi.2007.11.005.

Zhang, et al. The kinetics and folding pathways of intramolecular G-quadruplex nucleic acids. J Am Chem Soc. Nov. 21, 2012;134(46):19297-308. doi: 10.1021/ja309851t. Epub Nov. 12, 2012.

Altschul SF et al. Basic local alignment search tool. J. Mol. Biol., vol. 215, No. 3, pp. 403-410, (Oct. 5, 1990).

Amarnath, S. et al. The PDL1-PD1 Axis Converts Human TH1 Cells into Regulatory T Cells. Science Translational Medicine, vol. 3, No. 111, pp. 1-13. (Nov. 30, 2011).

Au, K.S. et al. Molecular Genetic Basis of Tuberous Sclerosis Complex: From Bench to Bedside. Journal of Child Neurology. vol. 19, No. 9 (Sep. 2004).

Battistini et al. A new CACNA1A gene mutation in acetazolamide-responsive familial hemiplegic migraine and ataxia. Neurology, vol. 53, No. 1, pp. 38-43 (Jul. 13, 1999).

Berge, SM et al. Pharmaceutical Salts Journal of Pharmaceutical Sciences, vol. 66, No. 1, pp. 1-19 (1977).

Berger, W. et al. The molecular basis of human retinal and vitreoretinal diseases. Progress in Retinal and Eye Research. vol. 29, pp. 335-375 (2010).

Blencowe, Benjamin. Reflections for the 20th anniversary issue of RNA journal. RNA Journal, vol. 21, No. 4, pp. 573-575 (2015).

Boothby, T. et al. Removal of Retained Introns Regulates Translation in the Rapidly Developing Gametophyte of Marsilea vestita. Developmental Cell vol. 24, pp. 517-529, (Mar. 11, 2013).

Buckley, P.T. et al. Cytoplasmic intron retention, function, splicing, and the sentinel RNA hypothesis. WIREs RNA, vol. 5, pp. 223-2330 (Mar./Apr. 2014).

Co-pending U.S. Appl. No. 14/874,420, filed Oct. 3, 2015.

Deere, J. et al. Antisense Phosphorodiamidate Morpholino Oligomer Length and Target Position Effects on Gene-Specific Inhibition in *Escherichia coli*. Antimicrobial Agents Andchemotherapy, vol. 49, No. 1, p. 249-255(Jan. 2005.

Dias, N. et al. Antisense oligonucleotides: basic concepts and mechanisms Mol. Cancer Ther. vol. 1, pp. 347-355, (Mar. 2002).

Ding, H. et al. DeliveringPD-1 inhibitory signal concomitant with blocking ICOS co-stimulation suppresses lupus-like syndrome in autoimmune BXSB mice. Clinical Immunology, vol. 118, pp. 258-267, (2006).

Ducros et al. Recurrence of the T666M calcium channel CACNA1A gene mutation in familial hemiplegic migraine with progressive cerebellar ataxia. Am J Hum Genet. vol. 64, No. 1, pp. 89-98 (Jan. 1999).

Duryagina R, et al. Overexpression of Jagged-1 and its intracellular domain in human mesenchymal stromal cells differentially affect the interaction with hematopoietic stem and progenitor cells. Stem Cells Dev. vol. 22, No. 20, pp. 2736-2750 (2013).

Fletcher, Sue et al. Antisense suppression of donor splice site mutations in the dystrophin gene transcript. Molecular Genetics & Genomic Medicine, vol. 1, No. 3, pp. 162-173, Jun. 13, 2013.

Friedman, KJ et al. Correction of aberrant splicing of the cystic fibrosis transmembrane conductance regulator (CFTR) gene by antisense oligonucleotides. J Biol Chem. Dec. 17, 1999;274(51):36193-36199.

Friend, KL et al. Detection of a novel missense mutation and second recurrent mutation in the CACNA1A gene in individuals with EA-2 and FHM. Hum Genet. vol. 105(3):261-5 (Sep. 1999).

Furukawa & Kish 2008, Gene Reviews Pagon Ra et al. eds. Univ. Of WA Seattle, NCBI Bookshelf ID NBK1437.

Geary et al. Absolute Bioavailability of 29-O-(2-Methoxyethyl)-Modified Antisense Oligonucleotides following Intraduodenal Instillation in Rats. J Pharmacol Exp Ther. vol. 296, No. 3, pp. 898-904 (Mar. 2001).

Geary, RS, et al., Pharmacokinetic properties of 2'-O-(2-methoxyethyl)-modified oligonucleotide analogs in rats. J Pharmacol Exp Ther. vol. 296, No. 3, pp. 890-897 (Mar. 2001).

Gianchecchi, E. et al. Recent insights into the role of the PD-1/PD-L1 pathway in immunological tolerance and autoimmunity Autoimmunity Reviews vol. 12, pp. 1091-1100, (2013).

Gohring, J. et al. Imaging of Endogenous MessengerRNA Splice Variants in Living Cells Reveals Nuclear Retention of Transcripts Inaccessible to Nonsense-Mediated Decay in Arabidopsis. The Plant Cell. vol. 26, pp. 754-764.(Feb. 2014).

Hamdan, F. et al. Mutations in SYNGAP1 in Autosomal Nonsyndromic Mental Retardation. The New England Journal of Medicine. N. Engl. Med. vol. 360, No. 6, pp. 599, (Feb. 5, 2009).

Heyn, P. et al. Introns and gene expression: Cellular constraints, transcriptional regulation, and evolutionary consequences. Bioessays vol. 37, pp. 148-154 (2014).

Hirata et al. Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand. J. Immunology vol. 174 pp. 1888-1897 (2005).

International Application No. PCT/GB2015/051756 International Search Report and Written Opinion Mailed Nov. 30, 2015.

International Application No. PCT/US2015/53896 International Search Report and Written Opinion dated Mar. 3, 2016.

Jarver, P. et al., A Chemical View of Oligonucleotides for Exon Skipping and Related Drug Applications, Nucleic Acid Therapeutics vol. 24, No. (1), pp. 37-47, (2014).

Jurkiewicz, D. et al. Spectrum of JAG1 gene mutations in Polish patients with Alagille syndrome. J. Appl. Genetics vol. 55, pp. 329-336, (2014).

Katsani, K.R. et al. Functional Genomics Evidence Unearths New Moonlighting Roles of Outer Ring Coat Nucleoporins. Scientific Reports. vol. 4, No. 4655 (Apr. 11, 2014).

Keir, M.E. et al. PD-1 and Its Ligands in Tolerance and Immunity. Annu. Rev. Immunol. vol. 26, pp. 677-704 (2008).

LaPlanche et al. Phosphorothioate-modified oligodeoxyribonucleotides. III. NMR and UV spectroscoptc studies of thRp-Rp,Sp-Sp, anRp-Sduplexes, [d(GGsAATTCC)]2, derived from diastereomeriO-ethyl phosphorothioates Nucleic Acids Res. vol. 14, No. 22, pp. 9081-9093 (Nov. 25, 1986).

Lee, E.S. et al. The Consensus 5' Splice Site Motif Inhibits mRNA Nuclear Export. PLoS One vol. 10, No. 3, p. e0122743 (Mar. 31, 2015).

Li et al. PD-L1—Driven Tolerance Protects Neurogenin3-Induced Islet Neogenesis to Reverse Established Type 1 Diabetes in NOD Mice. Diabetes vol. 64, pp. 529-540 (Feb. 2015; epub Oct. 20, 2014).

Lu, F. Conditional JAG1 Mutation Shows the Developing Heart Is More Sensitive Than Developing Liver to JAG1 Dosage. Am. J. Hum. Genet. vol. 72, pp. 1065-1070 (2003).

Ludecke et al. Recessively inherited L-DOPA-responsive parkinsonism in infancy caused by a point mutation (L205P) in the tyrosine hydroxylase gene Hum. Mol. Genet. vol. 5, pp. 1023-1028, (1996).

(56) References Cited

OTHER PUBLICATIONS

Mansouri, S. et al. Epstein-Barr Virus EBNA1 Protein Regulates Viral Latency through Effects on let-7 MicroRNA and Dicer. Journal of Virology, vol. 88, No. 19, pp. 11166-11177, (Oct. 2014).
Marquez, Y. et al. Unmasking alternative splicing inside protein-coding exons defines exitrons and their role in proteome plasticity. Genome vol. 25, pp. 995-1007 (2015).
Miller at al. 1993-2015 Gene Reviews Eds. Pagon RA et al. Seattle (WA); University of WA, Seattle Bookshelf ID NBK1318.
Mochizuki, T. et al. PKD2, a gene for polycystic kidney disease that encodes an integral membrane protein. Science vol. 272, pp. 1339-1342 (1996).
Mulley et al. A new molecular mechanism for severe myoclonic epilepsy of infancy: Exonic deletions in SCN1A.Neurol. vol. 67, pp. 1094-1095 (2006).
Mulley et al. SCN1A mutations and epilepsy. Hum. Muta. vol. 25, pp. 535-542 (2005).
Nishi, M. et al. Insulin gene mutations and diabetes. Journal of Diabetes Investigation vol. 2 Issue 2 (Apr. 2011).
Oda, T. et al. Identification and cloning of the human homolog (JAG) of the rat Jagged1 gene from the Alagille syndrome critical region at 20p12.Genomics vol. 43, No. 3, pp. 376-379 (1997).
Okazaki, T. et al. PD-1 and PD-1 ligands: from discovery to clinical application. International Immunology (The Japanese Society for Immunology), vol. 19, No. 7, pp. 813-824, (2007).
Penton, A.L. Notch signaling in human development and disease. Seminars in Cell & Developmental Biology. vol. 23, pp. 450-457 (2012).
Ray, D. et al. A compendium of RNA-binding motifs for decoding gene regulation. Nature. vol. 499, No. 7457, pp. 172-177 (Jul. 11, 2013).
Rendu, J. et al. Hum Gene Ther. Exon skipping as a therapeutic strategy applied to an RYR1 mutation with pseudo-exon inclusion causing a severe core myopathy. Jul. 2013;24(7):702-13. doi: 10.1089/hum.2013.052.
Reynolds, DM et al. Aberrant Splicing in the PKD2 Gene as a Cause of Polycystic Kidney Disease. Am. Soc. Nephrol. vol. 10, pp. 2342-2351 (1999).
Ritprajak et al. Keratinocyte-Associated B7-H1 Directly Regulates Cutaneous Effector CD8+ T Cell Responses. J Immunology vol. 184, pp. 4918-4925 (2010).
RNA 2-14 The Nineteenth Annual Meeting of the RNA Society. Quebec City, Canada. (Jun. 3- 8, 2014).
Roberts, Jennifer et al. Efficient and Persistent Splice Switching by Systemically Delivered LNA Oligonucleotides in Mice. Molecular Therapy, Nature Publishing, vol. 14, No. 4, pp. 471-475, Oct. 1, 2006.
Rosenbloom et al. The UCSC Genome Browser database: 2015 Update. Nucleic Acids Research 43, Database Issue doi:101093/nar/gku1177.
Sierakowska, H et al. Repair of thalassemic human beta-globin mRNA in mammalian cells by antisense oligonucleotides. Proc Natl Acad Sci U S A. Nov. 12, 1996;93(23):12840-4.
Skjevik et al. The N-Terminal Sequence of Tyrosine Hydroxylase is a Conformationally Versatile Motif That Binds 14-3-3 Proteins and Membranes. J. Mol. Bio. vol. 426, pp. 150-168 (2014).
Stec et al. Automated solid-phase synthesis, separation, and stereochemistry of phosphorothioate analogs of oligodeoxyribonucleotides J. Am. Chem. Soc., 1984, 106 (20), pp. 6077-6079 (1984).
Stein et al. Physicochemical properties of phosphorothioate oligodeoxynucleotides. Nucleic Acids Res. Apr. 25, 1988;16(8):3209-21.
Summerton, James. Morpholino Antisense Oligos: Applications in Biopharmaceutical Research Morpholinos constitute a radical redesign of DNA, providing decisive advantages over the more conventional oligo types used for modulating gene expression. Innovations in Pharmaceutical Technology Issue No. 17 (2005).
Swaans, RJM et al. Four novel mutations in the Tyrosine Hydroxylase gene in patients with infantile parkinsonism Annals of Human Genetic, vol. 64, No. 1, pp. 25-31, (Jan. 2000).
Tabrez, S. et al. A Synopsis of the Role of Tyrosine Hydroxylase in Parkinson's Disease. CNS & Neurological Disorders—Drug Targets vol. 11, No. 4 (2012).
Tilgner et al. Deep Sequencing of subcellular RNA factions shows splicing to be predominantly co-transcriptional in the human genome but inefficient for lncRNAs. Genome Research vol. 22, No. 9, pp. 1616-1625 (2012).
Torres, V.E. et al. Autosomal dominant polycystic kidney disease: the last 3 years. Kidney International vol. 76, pp. 149-168 (May 20, 2009).
Trabattoni, M. et al. Costimulatory Pathways in Multiple Disease Sclerosis: Distinctive Expression of PD-1 and PD-L1 in Patients with Different Patterns of Disease. J. Immunol. vol. 183, pp. 4984-4993 (2009).
Turnpenny, P.D. et al. Alagille syndrome: pathogenesis, diagnosis and management. European Journal of Human Genetics vol. 20, pp. 251-257 (2012.
Uhlmann, E. et al. Antisense oligonucleotides: a new therapeutic principle. Chemical Reviews vol. 90, No. 4, pp. 543-584 (Jun. 1990).
Verhaart, I.E.C. AON-Mediated Exon Skipping for Duchenne Muscular Dystrophy. Chapter 3. pp. 1-26 (Aug. 1, 2012).
Vieira, N. et al. Jagged 1Rescues the Duchenne Muscular Dystrophy Phenotype. Cell vol. 163, pp. 1204-1213 (Nov. 19, 2015).
Wan et al. Synthesis, biophysical properties and biological activity of second generation antisense oligonucleotides containing chiral phosphorothioate linkages. Nucleic Acids Research, vol. 42, No. 22, pp. 13456-13468 (2014).
Wang et al. Human Adenovirus Type 36 Enhances Glucose Uptake in Diabetic and Nondiabetic Human Skeletal Muscle Cells Independent of Insulin Signaling. Diabetes vol. 57, pp. 1861-1869 (2008).
Yang, Y. et al. Oligomerization of the polycystin-2 C-terminal tail and effects on its Ca2+binding properties. J. Bio. Chem. vol. 290, No. 16, pp. 10544-10554 (2015).
Zhang, J. et al. PowerBLAST: A New Network BLAST Application for Interactive or Automated Sequence Analysis and Annotation Genome Res., vol. 7, pp. 649-656, (1997).
Zon et al. Phosphorothioate oligonucleotides: chemistry, purification, analysis, scale-up and future directions. Anti Cancer Drug Design vol. 6, No. 6, pp. 539-568 (1991).
Zon G. and Stec, W.J. (1991) in Eckstein, F. (ed.), Oligonucleotides and Analogues: A Practical Approach. Oxford University Press, Oxford, UK, pp. 87-108.
Aizer AA, et al. Lack of reduction in racial disparities in cancer-specific mortality over a 20-year period. Cancer. 2014;120:1532-9.
Anders S. et al. Detecting differential usage of exons from RNA-seq data. Genome Res. 2012;22(10):2008-17. Epub Jun. 23, 2012.doi: gr.133744.111 [pii] 10.1101/gr.133744.111. PubMed PMID: 22722343.
Bakkenist CJ, Kastan MB. DNA damage activates ATM through intermolecular autophosphorylation and dimer dissociation. Nature. 2003;421(6922):499-506. doi: 10.1038/nature01368. PubMed PMID: 12556884.
Beli P, et al., Proteomic investigations reveal a role for RNA processing factor THRAP3 in the DNA damage response. Mol Cell. 2012;46(2):212-25. doi: 10.1016/j.molcel.2012.01.026. PubMed PMID: 22424773; PubMed Central PMCID: PMC3565437.
Bethke L, et al. Comprehensive analysis of the role of DNA repair gene polymorphisms on risk of glioma. Hum Mol Genet. 2008;17(6):800-5. Epub Dec. 1, 2007.doi: ddm351 [pii] 10.1093/hmg/ddm351. PubMed PMID: 18048407.
Blencowe BJ. Splicing regulation: the cell cycle connection. Curr Biol. 2003;13(4):R149-51. PubMed PMID: 12593819.
Bonnen, P.E., et al. Haplotypes at ATM identify coding-sequence variation and indicate a region of extensive linkage disequilibrium. Am J Hum Genet. 2000;67(6):1437-51. Epub Nov. 15, 2000.doi: S0002-9297(07)63213-3 [pii] 10.1086/316908. PubMed PMID: 11078475.

(56) References Cited

OTHER PUBLICATIONS

Brooks, A.N., et al. A pan-cancer analysis of transcriptome changes associated with somatic mutations in U2AF1 reveals commonly altered splicing events. PLoS One. 2014; 9(1):e87361. Epub Feb. 6, 2014.doi: 10.1371/journal.pone.0087361 PONE-D-13-26905 [pii]. PubMed PMID: 24498085.

Burns, CG, et al. Connections between pre-mRNA processing and regulation of the eukaryotic cell cycle. Front Horm Res. 1999; 25:59-82.

Chambers, A.L., et al. The INO80 chromatin remodeling complex prevents polyploidy and maintains normal chromatin structure at centromeres. Genes Dev. 2012; 26(23):2590-603. Epub Dec. 5, 2012.doi: 26/23/2590 [pii] 10.1101/gad.199976.112. PubMed PMID: 23207916.

Chen, M.S., et al. Chk1 kinase negatively regulates mitotic function of Cdc25A phosphatase through 14-3-3 binding. Mol Cell Biol. 2003; 23(21):7488-97. PubMed PMID: 14559997; PubMed Central PMCID: PMC207598.

Chen, T., et al. A functional single nucleotide polymorphism in promoter of ATM is associated with longevity. Mech Ageing Dev. 2010; 131:636-40.

Choi, HH, et al. CHK2 kinase promotes pre-mRNA splicing via phosphorylating CDK11p110. Oncogene. 2014; 33:108-15.

Colla, S., et al. Telomere dysfunction drives aberrant hematopoietic differentiation and myelodysplastic syndrome. Cancer Cell. 2015; 27(5):644-57. doi: 10.1016/j.ccell.2015.04.007. PubMed PMID: 25965571.

Consortium. TGP. An integrated map of genetic variation from 1,092 human genomes. Nature (London). 2012; 491:56-65.

Corey, S.J., et al. A non-classical translocation involving 17q12 (retinoic acid receptor alpha) in acute promyelocytic leukemia (APML) with atypical features. Leukemia. 1994; 8(8):1350-3. PubMed PMID: 8057672.

Corvelo, A., et al. Genome-wide association between branch point properties and alternative splicing. PLoS Comput Biol. 2010; 6(11):e1001016. Epub Dec. 3, 2010.doi: 10.1371/journal.pcbi. 1001016. PubMed PMID: 21124863.

Scott, S.P., et al. Missense mutations but not allelic variants alter the function of ATM by dominant interference in patients with breast cancer. Proc Natl Acad Sci USA. 2002;99:925-30.

Coulombe-Huntington J., et al. Fine-Scale Variation and Genetic Determinants of Alternative Splicing across Individuals. PLoS Genet. 2009; 5(12):e1000766. Epub Dec. 17, 2009.doi: 10.1371/journal.pgen.1000766. PubMed PMID: 20011102.

Dedic, T. et al. Alagille Syndrome Mimicking Biliary Atresia in Early Infancy, PLOS OONE, 10(11):e0143939: pp. 1-7 (Nov. 20, 2015).

Divina, P. et al. Ab initio prediction of cryptic splice-site activation and exon skipping. Eur J Hum Genet. 2009; 17:759-65.

Dutertre, M., et al. et al. DNA damage: RNA-binding proteins protect from near and far. Trends Biochem Sci. 2014; 39(3):141-9. Epub Feb. 19, 2014.doi: S0968-0004(14)00015-2 [pii] 10.1016/j.tibs.2014.01.003. PubMed PMID: 24534650.

El Bougrini, J., et al. PML positively regulates interferon gamma signaling. Biochimie. 2011; 93(3):389-98. doi: 10.1016/j.biochi. 2010.11.005. PubMed PMID: 21115099.

Fairbrother, W.G., et al. Predictive identification of exonic splicing enhancers in human genes. Science. 2002; 297(5583):1007-13. PubMed PMID: 12114529.

Ferreira, P.G., et al. Transcriptome characterization by RNA sequencing identifies a major molecular and clinical subdivision in chronic lymphocytic leukemia. Genome Res. 2014; 24:212-26.

Gibson, G. Hints of hidden heritability in GWAS. Nat Genet. 2010; 42(7):558-60. Epub Jun. 29, 2010.doi: ng0710-558 [pii] 10.1038/ng0710-558. PubMed PMID: 20581876.

Gozani, O., et al. A potential role for U2AF-SAP 155 interactions in recruiting U2 snRNP to the branch site. Mol Cell Biol. 1998; 18(8):4752-60. PubMed PMID: 9671485.

Graveley, B.R. The haplo-spliceo-transcriptome: common variations in alternative splicing in the human population. Trends Genet. 2008; 24(1):5-7. Epub Dec. 7, 2007.doi: S0168-9525(07)00349-6 [pii] 10.1016/j.tig.2007.10.004. PubMed PMID: 18054116.

Gutell, R.R., et al. A story: unpaired adenosine bases in ribosomal RNAs. J Mol Biol. 2000; 304(3):335-54. Epub Nov. 25, 2000.doi: 10.1006/jmbi.2000.4172 S0022-2836(00)94172-X [pii]. PubMed PMID: 11090278.

Guth, S., et al. Dual function for U2AF(35) in AG-dependent pre-mRNA splicing. Mol Cell Biol. 2001;21(22):7673-81. PubMed PMID: 11604503.

Hamdan, F. F. et al. De Novo SYNGAP1 Mutations in Nonsyndromic Intellectual Disability and Autism, Biol. Psychiatry, 69:898-901 (2011).

Hastings, M.L., et al. Control of pre-mRNA splicing by the general splicing factors PUF60 and U2AF. PLoS ONE. 2007;2:e538. PubMed PMID: 17579712.

He, Y.H., et al. Association of the insulin-like growth factor binding protein 3 (IGFBP-3) polymorphism with longevity in Chinese nonagenarians and centenarians. Aging (Milano). 2014;6:944-56.

Hernan, I. et al. Cellular Expression and siRNA-Mediated Interference of Rhodopsin cis-Acting Splicing Mutants Associated with Autosomal Dominant Retinitis Pigmentosa, Invest Ophthalmol. Vis. Sci. (2011) 52:3723-3729.

Hishida, A. et al. Polymorphisms in PPAR Genes (PPARD, PPARG, and PPARGC1A) and the Risk of Chronic Kidney Disease in Japanese: Cross-Sectional Data from the J-MICC Study. PPAR 2013; 980471 pp. 1-8.

*Homo sapiens* pre-mRNA processing factor 3 (PRPF3), mRNA, NCBI Reference Sequence: NM_004698.2 Accessed Apr. 6, 2017.

Hua, Y., et al. Enhancement of SMN2 exon 7 inclusion by antisense oligonucleotides targeting the exon. PLoS Biol. 2007;5(4):e73. Epub Mar. 16, 2007.doi: 06-PLBI-RA-1492R3 [pii] 10.1371/journal.pbio.0050073. PubMed PMID: 17355180.

Huynh, K.D., et al. BCoR, a novel corepressor involved in BCL-6 repression. Genes Dev. 2000;14(14):1810-23. PubMed PMID: 10898795; PubMed Central PMCID: PMC316791.

International Application No. PCT/GB2015/051756 International Preliminary Report on Patentability, Dec. 26, 2016.

International Application No. PCT/GB2016/053136 International Search Report and Written Opinion Mailed Mar. 6, 2017.

International Application No. PCT/GB2016/053136 Partial International Search Report Mailed Jan. 19, 2017.

Kaminker, P.G., et al. A novel form of the telomere-associated protein TIN2 localizes to the nuclear matrix. Cell Cycle. 2009;8(6):931-9. PubMed PMID: 19229133; PubMed Central PMCID: PMC2751576.

Kawamata, N., et al. Genetic differences between Asian and Caucasian chronic lymphocytic leukemia. Int J Oncol. 2013;43(2):561-5. doi: 10.3892/ijo.2013.1966. PubMed PMID: 23708256; PubMed Central PMCID: PMC3775563.

Kim, E., et al. SRSF2 Mutations Contribute to Myelodysplasia by Mutant-Specific Effects on Exon Recognition. Cancer Cell. 2015;27(5):617-30. doi: 10.1016/j.ccell.2015.04.006. PubMed PMID: 25965569; PubMed Central PMCID: PMC4429920.

Kim, J. et al. The splicing factor U2AF65 stabilizes TRF1 protein by inhibiting its ubiquitin-dependent proteolysis. Biochem Biophys Res Commun. 2014;443(3):1124-30. doi: 10.1016/j.bbrc.2013.12. 118. PubMed PMID: 24389012.

Kim P., et al. ChimerDB 2.0—a knowledgebase for fusion genes updated. Nucleic Acids Res. 2009;38(Database issue):D81-5. Epub Nov. 13, 2009.doi: gkp982 [pii] 10.1093/nar/gkp982. PubMed PMID: 19906715.

Kralovicova, J. et al. Branch sites haplotypes that control alternative splicing. Hum Mol Genet. 2004;13:3189-202.

Kralovicova, J. et al. The role of short RNA loops in recognition of a single-hairpin exon derived from a mammalian-wide interspersed repeat. RNA Biol. 2015;12(1):54-69. doi: 10.1080/15476286.2015. 1017207. PubMed PMID: 25826413.

Lee, J., et al. Metastasis of neuroendocrine tumors are characterized by increased cell proliferation and reduced expression of the ATM gene. PLoS ONE. 2012;7:e34456.

LeHIR, H. et al. 5'-End RET Splicing: Absence of Variants in Normal Tissues and Intron Retention in Pheochromocytomas, Oncology 63:84-91 (2002).

(56) References Cited

OTHER PUBLICATIONS

Lemaire, M., et al. CDC25B phosphorylation by p38 and MK-2. Cell Cycle. 2006;5(15)1649-53. PubMed PMID: 16861915.

Liang, Xue-Hai et al., Translation efficiency of mRNAs is increased by antisense oligonucleotides targeting upstream open reading frames,Nature Biotechnology, 34(8):875-882 (Aug. 2016).

Lianoglou, S., et al. Ubiquitously transcribed genes use alternative polyadenylation to achieve tissue-specific expression. Genes Dev. 2013;27(21):2380-96. Epub Oct. 23, 2013.doi: gad.229328.113 [pii] 10.1101/gad.229328.113. PubMed PMID: 24145798.

Litchfield, D.W., et al. Pin1: Intimate involvement with the regulatory protein kinase networks in the global phosphorylation landscape. Biochem Biophys Acta. 2015. doi: 10.1016/j.bbagen.2015.02.018. PubMed PMID: 25766872.

Lo, YL et al. ATM Polymorphisms and risk of lung cancer among never smokers, Lung Cancer 69(2):148-154 (2010).

Magi-Galuzzi, C. et al. TMPRSS2-ERG gene fusion prevalence and class are significantly difference in prostate cancer of Caucasian, African-American and Japanese patients. The Prostate. 2011;71:489-97.

Matsuoka, S., et al. Ataxia telangiectasia-mutated phosphorylates Chk2 in vivo and in vitro. Proc Natl Acad Sci USA. 2000;97:10389-94.

Matsuoka, S., et al. ATM and ATR substrate analysis reveals extensive protein networks responsive to DNA damage. Science. 2007;316(5828):1160-6. Epub May 26, 2007.doi: 316/5828/1160 [pii] 10.1126/science.1140321. PubMed PMID: 17525332.

Melhuish, et al. The Tgif2 gene contains a retained intron within the coding sequence, BMC Molecular Biology 7(2);1-10 (2006).

Mendell, J.T., ap Rhys CM, Dietz HC. Separable roles for rent1/hUpf1 in altered splicing and decay of nonsense transcripts. Science. 2002;298(5592):419-22. Epub Sep. 14, 2002.doi: 10.1126/science.1074428 1074428 [pii]. PubMed PMID: 12228722.

Merendino, L., et al. Inhibition of msl-2 splicing by Sex-lethal reveals interaction between U2AF35 and the 3' splice site AG. Nature. 1999;402(6763):838-41. PubMed PMID: 10617208.

Mirey, G., et al. CDC25B phosphorylated by pEg3 localizes to the centrosome and the spindle poles at mitosis. Cell Cycle. 2005;4(6):806-11. PubMed PMID: 15908796.

Mitelman, F., et al. The impact of translocations and gene fusions on cancer causation. Nat Rev Cancer. 2007;7(4):233-45. Epub Mar. 16, 2007.doi: nrc2091 [pii] 10.1038/nrc2091. PubMed PMID: 17361217.

Montecucco, A., et al. Pre-mRNA processing factors meet the DNA damage response. Front Genet. 2013;4:102. doi: 10.3389/fgene.2013.00102. PubMed PMID: 23761808; PubMed Central PMCID: PMC3674313.

Morrison, A.J., et al. Mec1/Tel1 phosphorylation of the INO80 chromatin remodeling complex influences DNA damage checkpoint responses. Cell. 2007;130(3):499-511. doi: 10.1016/j.cell.2007.06.010. PubMed PMID: 17693258.

Murray, S.F. et al. Allele-Specific Inhibition of Rhodopsin with an Antisense Oligonucleotide Slows Photoreceptor Cell Degeneration, Invest Ophthalmol. Vis. Sci. 56:6362-6375 (Oct. 2015).

Nguyen, L.A., et al. Physical and functional link of the leukemia-associated factors AML1 and PML. Blood. 2005;105(1):292-300. doi: 10.1182/blood-2004-03-1185. PubMed PMID: 15331439.

Nishida, A. et al. Tissue- and Case-specific retention of intron 40 in mature dystrophin mRNA, Journal of Human Genetic 60;327-333 (2015).

Nisole, S., et al. Differential Roles of PML Isoforms. Front Oncol. 2013;3:125. doi: 10.3389/fonc.2013.00125. PubMed PMID: 23734343; PubMed Central PMCID: PMC3660695.

Oustric, V. et al. Antisense oligonucleotide-based therapy in human erythropoietic protoporphyria. Am J Hum Genet. 2014;94(4):611-7. doi: 10.1016/j.ajhg.2014.02.010. PubMed PMID: 24680888; PubMed Central PMCID: PMC3980518.

Page-McCaw, P.S., et al. PUF60: a novel U2AF65-related splicing activity. RNA. 1999;5(12):1548-60. PubMed PMID: 10606266.

Passamonti, C. et al. A novel inherited SCN1A mutation associated with different neuropsychological phenotypes: Is there a common core deficit? Epilepsy & Behavior 43:89-92 (2015).

Pastor, F., et al. Induction of tumour immunity by targeted inhibition of nonsense-mediated mRNA decay. Nature. 2010;465(7295):227-30. doi: 10.1038/nature08999. PubMed PMID: 20463739; PubMed Central PMCID: PMC3107067.

Paz, A., et al. SPIKE: a database of highly curated human signaling pathways. Nucleic Acids Res. 2011;39(Database issue):D793-9. doi: 10.1093/nar/gkq1167. PubMed PMID: 21097778; PubMed Central PMCID: PMC3014840.

Pear, Warren S. New roles for Notch in tuberous sclerosis, Journal of Clinical Investigation, 120(1):84-87 (Jan. 4, 2010).

Pellagatti, A., et al. Deregulated gene expression pathways in myelodysplastic syndrome hematopoietic stem cells. Leukemia. 2010;24(4):756-64. doi: 10.1038/leu.2010.31. PubMed PMID: 20220779.

Perdiguero, E., et al. Regulation of Cdc25C activity during the meiotic G2/M transition. Cell Cycle. 2004;3(6):733-7. PubMed PMID: 15136768.

Piaceri, I., et al. Ataxia-telangiectasia mutated (ATM) genetic variant in Italian centenarians. Neurophysiology. 2013;34:573-5.

Przychodzen, B., et al. Patterns of misspicing due to somatic U2AF1 mutations in myeloid neoplasms. Blood. 2013;122:999-1006. Epub Jun. 19, 2016.doi: blood-2013-01-480970 [pii] 10.1182/blood-2013-01-480970. PubMed PMID: 23775717.

Reineke, E.L., et al. Degradation of the tumor suppressor PML by Pin1 contributes to the cancer phenotype of breast cancer MDA-MB-231 cells. Mol Cell Biol. 2008;28(3):997-1006. doi: 10.1128/MCB.01848-07. PubMed PMID: 18039859; PubMed Central PMCID: PMC2223389.

Romero, P.R., et al. Alternative splicing in concert with protein intrinsic disorder enables increased functional diversity in multicellular organisms. Proc Natl Acad Sci USA. 2006;103(22):8390-5. Epub May 24, 2006.doi: 0507916103 [pii] 10.1073/pnas.0507916103. PubMed PMID: 16717195.

Ruchlemer, R., et al. Geography, ethnicity and roots in chronic lymphocytic leukemia. Leuk Lymphoma. 2013;54(6):1142-50. doi: 10.3109/10428194.2012.740670. PubMed PMID: 23121522.

Rudd, M.F., et al. Variants in the ATM-BRCA2-CHEK2 axis predispose to chronic lymphocytic leukemia. Blood. 2006;108(2):638-44. Epub Apr. 1, 2006.doi: 2005-12-5022 [pii] 10.1182/blood-2005-12-5022. PubMed PMID: 16574953.

Shao, C., et al. Mechanisms for U2AF to define 3' splice sites and regulate alternative splicing in the human genome. Nat Struct Mol Biol. 2014;doi: 10.1038/nsmb.2906.

Shcherbakova, I., et al. Alternative spliceosome assembly pathways revealed by single-molecule fluorescence microscopy. Cell Rep. 2013;5(1):151-65. Epub Oct. 1, 2013.doi: S2211-1247(13)00467-1 [pii] 10.1016/j.celrep.2013.08.026. PubMed PMID: 24075986.

Shen, M., et al. Characterization and cell cycle regulation of the related human telomeric proteins Pin2 and TRF1 suggest a role in mitosis. Proc Natl Acad Sci USA. 1997;94(25):13618-23. PubMed PMID: 9391075; PubMed Central PMCID: PMC28355.

Shiloh, Y., et al The ATM protein kinase: regulating the cellular response to genotoxic stress, and more. Nat Rev Mol Cell Biol. 2013;14(4):197-210. doi: 10.1038/nrm3546. PubMed PMID: 23486281.

Shiria, C.L. et al. Mutant U2AF1 Expression Alters Hematopoiesis and Pre-mRNA Splicing In Vivo. Cancer Cell. 2015;27(5):631-43. doi: 10.1016/j.ccell.2015.04.008. PubMed PMID: 25965570; PubMed Central PMCID: PMC4430854.

Shirley, M.H., et al Incidence of haematological malignancies by ethnic group in England, Jul. 2001. Br J Haematol. 2013;163(4):465-77. doi: 10.1111/bjh.12562. PubMed PMID: 24033296.

Smith, C.W., et al. Scanning and competition between AGs are involved in 3' splice site selection in mammalian introns. Mol Cell Biol. 1993;13(8):4939-52. PubMed PMID: 8336728.

Smith, P.J., et al. An increased specificity score matrix for the prediction of SF2/ASF-specific exonic splicing enhancers. Hum Mol Genet. 2006;15(16):2490-508. PubMed PMID: 16825284

(56) References Cited

OTHER PUBLICATIONS

Soo, R.A., et al. Ethnic differences in survival outcome in patients with advanced stage non-small cell lung cancer. J Thorac Oncol. 2011;6:1030-8.

Stamm, S. Regulation of alternative splicing by reversible protein phosphorylation. J Biol Chem. 2008;283(3):1223-7. PubMed PMID: 18024427.

Stankovic, T., et al. Inactivation of ataxia telangiectasia mutated gene in B-cell chronic lymphocytic leukaemia. Lancet. 1999;353(9146):26-9. doi: 10.1016/S0140-6736(98)10117-4. PubMed PMID: 10023947.

Strausfeld, U., et al. Activation of p34cdc2 protein kinase by microinjection of human cdc25C into mammalian cells. Requirement for prior phosphorylation of cdc25C by p34cdc2 on sites phosphorylated at mitosis. J Biol Chem. 1994;269(8):5989-6000. PubMed PMID: 8119945.

Sun, H., et al. Multiple splicing defects in an intronic false exon. Mol Cell Biol. 2000;20(17):6414-25. PubMed PMID: 10938119.

Tavanez, J.P., et al. hnRNP A1 proofreads 3' splice site recognition by U2AF. Mol Cell. 2012;45(3):314-29. Epub Feb. 14, 2012. doi: S1097-2765(12)00032-9 [pii] 10.1016/j.molcel.2011.11.033. PubMed PMID: 22325350.

Taylor, A.M., et al. Ataxia telangiectasia: more variation at clinical and cellular levels. Clin Genet. 2015;87(3):199-208. doi: 10.1111/cge.12453. PubMed PMID: 25040471.

Taylor, A.M., et al. Leukemia and lymphoma in ataxia telangiectasia. Blood. 1996;87(2):423-38. PubMed PMID: 8555463.

Story, M.D. et al. ATM has a major role in the double-stand break repair pathway dysregulation in sporadic breast carcinomas and is an independent prognostic marker at both mRNA and protein levels, Breast Diseases: A Yearbook Quarterly, 26(4);297-299 (Mar. 17, 2015).

Trapnell, C. et al. Differential gene and transcript expression analysis of RNA-seq experiments with Top Hat and Cufflinks. Nat Protoc. 2012;7(3):562-78. Epub Mar. 3, 2012.doi: nprot.2012.016 [pii] 10.1038/nprot.2012.016. PubMed PMID: 22383036.

Suarez, F. et al. Incidence, presentation, and prognosis of malignancies in ataxia-telangiectasia: a report from the French national registry of primary immune deficiencies. J Clin Oncol. 2015;33(2):202-8. doi: 10.1200/JCO.2014.56.5101. PubMed PMID: 25488969.

U.S. Appl. No. 14/741,071 Non-Final Office Action mailed Dec. 1, 2016.

U.S. Appl. No. 14/874,420 Non-Final Office Action Mailed Mar. 21, 2017.

Wang, Z. et al. Systematic identification and analysis of exonic splicing silencers. Cell. 2004;119(6):831-45. PubMed PMID: 15607979.

Warf, M.B., et al. Role of RNA structure in regulating pre-mRNA splicing. Trends Biochem Sci. 2010;35(3):169-78. Epub Dec. 5, 2009.doi: S0968-0004(09)00196-0 [pii].

Wu, J.Y., et al. Specific interactions between proteins implicated in splice site selection and regulated alternative splicing. Cell. 1993;75(6)1061-70. Epub Dec. 17, 1993.doi: 0092-8674(93)90316-I [pii]. PubMed PMID: 8261509.

Wu, S. et al. Functional recognition of the 3' splice site AG by the splicing factor U2AF35.Nature. 1999;402(6763):832-5. PubMed PMID: 10617206.

Wu, Y. et al. MRE11-RAD5O-NBS1 and ATM function as co-mediators of TRF1 in telomere length control. Nat Struct Mol Biol. 2007;14(9):832-40. doi: 10.1038/nsmb1286. PubMed PMID: 17694070.

Xia, Y. et al. Frequencies of SF3B1, NOTCH1, MYD88, BIRC3 and IGHV mutations and TP53 disruptions in Chinese with chronic lymphocytic leukemia: disparities with Europeans. Oncotarget. 2015;6(7):5426-34. PubMed PMID: 25605254.

Yamamoto, Y., et al. BCOR as a novel fusion partner of retinoic acid receptor alpha in a t(X;17)(p11;q12) variant of acute promyelocytic leukemia. Blood. 2010;116(20):4274-83. doi: 10.1182/blood-2010-01-264432. PubMed PMID: 20807888.

Yang, S. et al. PML-dependent apoptosis after DNA damage is regulated by the checkpoint kinase hCds1/Chk2. Nat Cell Biol. 2002;4(11):865-70. doi: 10.1038/ncb869. PubMed PMID: 12402044.

Yang, S., et al. Promyelocytic leukemia activates Chk2 by mediating Chk2 autophosphorylation. J Biol Chem. 2006;281(36):26645-54. doi: 10.1074/jbc.M604391200. PubMed PMID: 16835227.

Yoshida, K., et al. Splicing factor mutations and cancer. Wiley Interdiscip Rev RNA. 2014;5(4):445-59. doi: 10.1002/wrna.1222. PubMed PMID: 24523246.

Yu, E.Y., et al. Regulation of telomere structure and functions by subunits of the INO80 chromatin remodeling complex. Mol Cell Biol. 2007;27(16):5639-49. doi: 10.1128/MCB.00418-07. PubMed PMID: 17562861; PubMed Central PMCID: PMC1952117.

Yuan X., et al. Nuclear protein profiling of Jurkat cells during heat stress-induced apoptosis by 2-DE and MS/MS. Electrophoresis. 2007;28(12):2018-26. doi: 10.1002/elps.200600821. PubMed PMID: 17523140.

Zamore, P.D., et al. Identification, purification, and biochemical characterization of U2 small nuclear ribonucleoprotein auxiliary factor. Proc Natl Acad Sci USA. 1989;86(23):9243-7. PubMed PMID: 2531895.

Zarnack K., et al. Direct competition between hnRNP C and U2AF65 protects the transcriptome from the exonization of Alu elements. Cell. 2013;152(3):453-66. Epub Feb. 5, 2013.doi: S0092-8674(12)01545-0 [pii] 10.1016/j.cell.2012.12.023. PubMed PMID: 23374342.

Zhang C., et al. RNA landscape of evolution for optimal exon and intron discrimination. Proc Natl Acad Sci USA. 2008;105(15):5797-802. Epub Apr. 9, 2008.doi: 0801692105 [pii] 10.1073/pnas.0801692105. PubMed PMID: 18391195.

Zhang, X.H., et al. Computational definition of sequence motifs governing constitutive exon splicing. Genes Dev. 2004;18:1241-50. PubMed PMID: 15145827.

Zorio, D.A., et al. Both subunits of U2AF recognize the 3' splice site in Caenorhabditis elegans. Nature. 1999;402(6763):835-8. PubMed PMID: 10617207.

Zuker, M. Mfold web server for nucleic acid folding and hybridization prediction. Nucleic Acids Res. 2003;31(13):3406-15. Epub Jun. 26, 2003. PubMed PMID: 12824337.

Goncharova et al. Tuberin regulates p70 S6 kinase activation and ribosomal protein S6 phosphorylation. A role for the TSC2 tumor suppressor gene in pulmonary lymphangioleiomyomatosis (LAM). J. Biol. Chem. (Aug. 23, 2002) 277(34);30958-67. EPub Jun. 3, 2002.

International Application No. PCT/US2015/053896 International Preliminary Report on Patentability Mailed Apr. 4, 2017.

International Application No. PCT/US2016/066414 International Search Report and Written Opinion Mailed Apr. 19, 2017.

International Application No. PCT/US2016/066417 International Search Report and Written Opinion Mailed Apr. 19, 2017.

International Application No. PCT/US2016/066705 International Search Report and Written Opinion Mailed Apr. 24, 2017.

Nomakuchi et al. Antisense-oligonucleotide-directed inhibition of nonsense-mediated mRNA decay. Nat. Biotechnol. 34(2):164-166 (Feb. 2016).

Sahashi et al. Pathological impact of SMN2 mis-splicing in adult SMA mice. EMBO Mol. Med. 5(10):1586-601 (Oct. 2013).

Sahashi et al. Tsunami: an antisense method to phenocopy splicing-associated diseases in animals. Genes Dev. 26(16):1874-1884 (Aug. 15, 2012).

Staropoli et al. Rescue of gene-expression changes in an induced mouse model of spinal muscular atrophy by an antisense oligonucleotide that promotes inclusion of SMN2 exon 7. Genomics 105:220-228 (2015).

Wu et al. AT-AC Pre-mRNA Splicing Mechanisms and Conservation of Minor Introns in Voltage-Gated Ion Channel Genes. Molecular and Cellular Biology 19(5): 3225-3236 (May 1999).

Zimrin et al. An Antisense Oligonucleotide to the Notch Ligand Jagged Enhances Fibroblast Growth Factor-induced Angiogenesis in Vitro. J. Biol. Chem. 271(51):32499-502 (Dec. 20, 1996).

(56) References Cited

OTHER PUBLICATIONS

Bassi et al. A novel mutation in the ATP1A2 gene causes alternating hemiplegia of childhood. J. Med. Genet. 41:621-628 (2004).
Corallini et al. Transcriptional and Posttranscriptional Regulation of the CTNS Gene. Pediatric Research 70(2):130-135 (Aug. 2011).
International Application No. PCT/US16/66576 International Search Report and Written Opinion Mailed May 4, 2017.
International Application No. PCT/US16/66721 International Search Report and Written Opinion mailed May 1, 2017.
Luo et al. Palmitic Acid Suppresses Apolipoprotein M Gene Expression via the Pathway of PPARb/d in HepG2 Cells. Biochemical and Biophysical Research Communications, 445(1):203-207 (Feb. 2014).
Hua et al. Antisense masking of an hnRNP A1/A2 intronic splicing silencer corrects SMN2 splicing in transgenic mice. Am. J. Hum. Genet. 82:834-848 (Mar. 27, 2008).
International Application No. PCT/US2016/066564 International Search Report and Written Opinion Mailed May 4, 2017.
Soutar et al. Mechanisms of disease: genetic causes of familial hpercholesterolemia. Nat. Clin. Pract. Cardiovasc. Med. 4:214-255 (Apr. 1, 2007).

* cited by examiner

SEQ ID NO: 467

REDUCING INTRON RETENTION

CROSS-REFERENCE

This application claims the benefit of UK Patent Application NO: 1410693.4, filed on 16 Jun. 2014, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 24, 2015, is named 47991-704-201-seqlist_ST25.txt and is 17.8 kilobytes in size.

BACKGROUND

Alternative splicing can be a frequent phenomenon in the human transcriptome. Intron retention is one example of alternative splicing in which a partially processed mRNA retains retention of at least one intron after undergoing partial splicing. In some instances, the presence of a retained intron in a partially processed mRNA can prevent or reduce translation of a functional protein.

SUMMARY

This invention relates to a method of reducing or preventing intron retention in a transcript (e.g., a partially processed mRNA transcript) and treatment or prevention of diseases related to inadvertent intron retention.

In some aspects, the invention discloses a method of prevention or treatment of a disease in a subject comprising reducing the incidence of intron retention in gene transcripts, wherein the disease is induced by defective protein expression caused by the intron retention in the gene transcripts.

In some aspects, the invention discloses a method of modulating intron splicing in a cell, comprising hybridizing a polynucleic acid polymer to a region of pre-mRNA, wherein the region comprises or consists of SEQ ID NO: 46, or a region having at least 95% identity to SEQ ID NO: 46.

In some aspects, the invention discloses a method of modulating intron splicing in a cell, comprising hybridizing a polynucleic acid polymer to a region of pre-mRNA, wherein the region comprises or consists of SEQ ID NO: 46, or a region having at least 95% identity to SEQ ID NO: 46.

In some aspects, the invention discloses a method of modulating intron splicing in a cell, comprising hybridizing a polynucleic acid polymer to a region of pre-mRNA, wherein the region comprises or consists of SEQ ID NO: 3, or a region having at least 95% identity to SEQ ID NO: 3.

In some aspects, the invention discloses a method of modulating intron splicing in a cell, comprising hybridizing a polynucleic acid polymer to a region of pre-mRNA, wherein the region comprises or consists of a sequence complementary to a sequence having at least 95% identity to any of the group of sequences comprising SEQ ID NOs: 47 to 434; or combinations thereof.

In some aspects, the invention discloses a polynucleic acid polymer which is antisense to at least part of a region of polynucleic acid polymer comprising or consisting of SEQ ID NO: 46, or a region of polynucleic acid polymer comprising or consisting of a sequence having at least 95% sequence identity to SEQ ID NO: 46.

In some aspects, the invention discloses a polynucleic acid polymer which is antisense to at least part of a region of polynucleic acid polymer comprising or consisting of SEQ ID NO: 3, or a region of polynucleic acid polymer comprising or consisting of a sequence having at least 95% sequence identity to SEQ ID NO: 3.

In some aspects, the invention discloses a polynucleic acid polymer which is antisense to at least part of a region of polynucleic acid polymer, wherein the region comprises or consists of a sequence complementary to any of the group of sequences comprising SEQ ID NOs: 47 to 434; or combinations thereof; or optionally a region of polynucleic acid polymer comprising or consisting of a sequence having at least 95% sequence identity to SEQ ID NOs: 47 to 434.

In some aspects, the invention discloses a polynucleic acid polymer comprising or consisting of a nucleic acid sequence having at least 95% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof; and optionally wherein the uracil nucleotides are substituted with thymine nucleotides In some aspects, the invention discloses a polynucleic acid polymer comprising or consisting of a nucleic acid sequence having at least 95% identity to a sequence selected from any of the group comprising SEQ ID NOs: 47 to 434; or combinations thereof; and optionally wherein the uracil nucleotides are substituted with thymine nucleotides.

In some aspects, the invention discloses a pharmaceutical composition which comprises a polynucleic acid polymer that hybridizes to a target sequence of a partially processed mRNA transcript which encodes a protein and which comprises a retained intron, wherein the target sequence is in between two G quadruplexes, wherein the polynucleic acid polymer is capable of inducing splicing out of the retained intron from the partially processed mRNA transcript; and a pharmaceutically acceptable excipient and/or a delivery vehicle. In some instances, the polynucleic acid polymer hybridizes to the retained intron of the partially processed mRNA transcript.

In some aspects, the invention discloses a pharmaceutical composition which comprises a polynucleic acid polymer that hybridizes to a target sequence of a partially processed mRNA transcript which encodes a protein and which comprises a retained intron, wherein the polynucleic acid polymer hybridizes to an intronic splicing regulatory element of the partially processed mRNA transcript, wherein the intronic splicing regulatory element comprises a first CCC motif, and wherein the polynucleic acid polymer is capable of inducing splicing out of the retained intron from the partially processed mRNA transcript; and a pharmaceutically acceptable excipient and/or a delivery vehicle.

In some instances, the intronic splicing regulatory element further comprises a second CCC motif. In some instances, the first CCC motif is about 3 or more nucleotide bases from the second CCC motif. In some instances, the polynucleic acid polymer hybridizes to an intronic splicing regulatory element comprising a CCCAG or an AGGCC motif.

In some aspects, the invention discloses a pharmaceutical composition which comprises a polynucleic acid polymer that hybridizes to a target sequence of a partially processed mRNA transcript which encodes a protein and which comprises a retained intron, wherein the polynucleic acid polymer hybridizes to a binding motif of the partially processed mRNA transcript, wherein the binding motif does not form a G quadruplex, and wherein the polynucleic acid polymer is capable of inducing splicing out of the retained intron from the partially processed mRNA transcript; and a pharmaceutically acceptable excipient and/or a delivery vehicle.

In some instances, the polynucleic acid polymer comprises a pyridine nucleotide at the 3' terminal position and/or at the 5' terminal position. In some instances, the polynucleic acid polymer comprises two consecutive pyridine nucleotides at the 3' terminal position and/or at the 5' terminal position.

In some aspects, the invention discloses a pharmaceutical composition which comprises a polynucleic acid polymer that hybridizes to a target sequence of a partially processed mRNA transcript which encodes a protein and which comprises a retained intron, wherein the polynucleic acid polymer hybridizes to a binding motif of the partially processed mRNA transcript, and wherein the binding motif forms a hairpin structure, wherein the polynucleic acid polymer is capable of inducing splicing out of the retained intron from the partially processed mRNA transcript; and a pharmaceutically acceptable excipient and/or a delivery vehicle.

In some instances, the polynucleic acid polymer is further capable of destabilizing the hairpin structure. In some instances, the delivery vehicle comprises a cell penetrating peptide or a peptide-based nanoparticle. In some instances, the delivery vehicle is complexed with the polynucleic acid polymer by ionic bonding.

In some instances, the polynucleic acid polymer is between about 10 and about 50, about 10 and about 45, about 10 and about 40, about 10 and about 30, about 10 and about 25, or about 10 and about 20 nucleotides in length. In some instances, the sequence of the polynucleic acid polymer is at least 60%, 70%, 80%, 90%, or 95% or 100% complementary to a target sequence of the partially processed mRNA transcript. In some instances, the sequence of the polynucleic acid polymer has 4 or less, 3 or less, 2 or less, or 1 or less mismatches to a target sequence of the partially processed mRNA transcript.

In some instances, the polynucleic acid polymer is modified at the nucleoside moiety or at the phosphate moiety. In some instances, the polynucleic acid polymer comprises one or more artificial nucleotide bases. In some instances, the one or more artificial nucleotide bases comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O—NMA) modified, locked nucleic acid (LNA), ethylene nucleic acid (ENA), peptide nucleic acid (PNA), 1',5'-anhydrohexitol nucleic acids (HNA), morpholino, methylphosphonate nucleotides, thiolphosphonate nucleotides, or 2'-fluoro N3-P5'-phosphoramidites. In some instances, the polynucleic acid polymer is modified at the 2' hydroxyl group of the ribose moiety of the nucleoside moiety of the polynucleic acid polymer. In some instances, the modification at the 2' hydroxyl group is by a 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O—NMA) moiety. In some instances, a methyl group is added to the 2' hydroxyl group of the ribose moiety to generate a 2'-O-methyl ribose moiety. In some instances, a methoxyethyl group is added to the 2' hydroxyl group of the ribose moiety to generate a 2'-O-methoxyethyl ribose moiety. In some instances, the modification at the 2' hydroxyl group is linked to the 4' carbon by a methylene group. In some instances, the ribose ring is substituted with a six member morpholino ring to generate a morpholino artificial nucleotide analogue. In some instances, the phosphate backbone is substituted with an oligoglycine-like moiety to generate peptide nucleic acid (PNA). In some instances, the phosphate backbone is modified by a thiol group or a methyl group. In some instances, the 5' terminus, 3' terminus, or a combination thereof is modified. In some instances, the modification protects the polynucleic acid polymer from endogenous nucleases in the subject. In some instances, the modified polynucleic acid polymer does not induce or has a reduced ability to induce RNase H cleavage of RNA. In some instances, the polynucleic acid polymer is modified to increase its stability. In some instances, the hybridization is specific hybridization.

In some instances, the polynucleic acid polymer hybridizes to an mRNA transcript comprising at least 80%, 85%, 90%, or 95% or 100% sequence identity to at least 13 contiguous bases of SEQ ID NO: 46. In some instances, the polynucleic acid polymer hybridizes to a mRNA transcript comprising at least 10 contiguous bases of SEQ ID NO: 46. In some instances, the polynucleic acid polymer hybridizes to a mRNA transcript comprising at least 63%, 70%, 80%, 90%, or 95% sequence identity to a sequence selected from the group consisting of SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, or combinations thereof. In some instances, the polynucleic acid polymer hybridizes to a mRNA transcript comprising at least 55%, 60%, 70%, 80%, 90%, or 95% sequence identity to SEQ ID NO: 3. In some instances, the polynucleic acid polymer comprises at least 63%, 70%, 80%, 90%, or 95% or 100% sequence identity to a sequence selected from the group consisting of SEQ ID NO: 4, SEQ ID NO: 5, SEQ ID NO: 7, SEQ ID NO: 8, SEQ ID NO: 10, SEQ ID NO: 11, SEQ ID NO: 13, SEQ ID NO: 14, SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 29, SEQ ID NO: 31, SEQ ID NO: 32, SEQ ID NO: 34, SEQ ID NO: 35, SEQ ID NO: 37, SEQ ID NO: 38, SEQ ID NO: 40, SEQ ID NO: 41, SEQ ID NO: 43, and SEQ ID NO: 44, or combinations thereof, and optionally wherein uracil nucleotides are substituted with thymine nucleotides. In some instances, the polynucleic acid polymer comprises at least 55%, 60%, 70%, 80%, 90%, or 95%, or comprises 100% sequence identity to a sequence selected from the group consisting of SEQ ID NO: 1, SEQ ID NO: 2, or combinations thereof, and optionally wherein uracil nucleotides are substituted with thymine nucleotides. In some instances, the polynucleic acid polymer hybridizes to an mRNA transcript comprising at least 80%, 85%, 90%, or 95% sequence identity to at least 13 contiguous bases of a sequence selected from the group consisting of SEQ ID NOs: 47-434, or combinations thereof.

In some instances, the polynucleic acid polymer is a synthesized polynucieic acid polymer.

In some instances, the pharmaceutical composition comprising the polynucleic acid polymer is administered for intravenous or subcutaneous administration.

In some aspects, the invention discloses a composition for use in the treatment of a disease or condition in a patient in need thereof, comprising administering to the patient a pharmaceutical composition disclosed herein. In some instances, the disease or condition is associated with an impaired production of a protein or is characterized by a defective splicing. In some instances, the disease or condition is a hereditary disease. In some instances, a subject with the hereditary disease has a genome that comprises a copy of a gene that comprises an exon that when properly transcribed into fully processed mRNA encodes the full-length functional form of the protein. In some instances, a subject with the hereditary disease has a genome that comprises a copy of a gene that comprises a set of exons that when properly transcribed into fully processed mRNA encodes the full-length functional form of the protein. In some instances, a subject with the hereditary disease has a genome that comprises a defective copy of the gene, which is incapable of producing a full-length functional form of the protein. In some instances, the disease or condition is diabetes. In some instances, the disease or condition is cancer. In some instances, the composition for use further comprises selecting a subject for treatment of a disease or condition associated with an impaired production of a protein which comprises (a) determining if the subject has the disease or condition associated with an impaired production of the protein; and (b) administering to the subject a pharmaceutical composition described above if the subject has the disease or condition associated with an impaired production of the protein. In some instances, the composition for use further comprises selecting a subject for treatment of a disease or condition characterized by a defective splicing, which comprises (a) determining if the subject has the disease or condition characterized by the defective splicing; and (b) administering to the subject a pharmaceutical composition described above if the subject has the disease or condition characterized by the defective splicing.

In some aspects, the invention discloses a method of treating a disease or condition characterized by impaired production of a full-length functional form of a protein in a subject in need thereof, comprising: (a) administering to the subject a pharmaceutical composition comprising: a therapeutic agent that induces an increase in splicing out of an intron in a partially processed mRNA transcript; and a pharmaceutically acceptable excipient and/or a delivery vehicle; wherein the subject has a pool of partially processed mRNA transcripts, which are capable of encoding copies of the full-length functional form of the protein and each of which comprise at least one retained intron that inhibits translation of the partially processed mRNA transcripts; and (b) contacting a target cell of the subject with the therapeutic agent to induce a portion of the pool of the partially processed mRNA transcripts to undergo splicing to remove the at least one retained intron from each of the partially processed mRNA transcripts in the portion, to produce fully processed mRNA transcripts, wherein the fully processed mRNA transcripts are translated to express copies of the full-length functional form of the protein, which treat the disease or condition.

In some instances, the therapeutic agent causes activation of one or more splicing protein complexes in the cell to remove the at least one retained intron from each of the partially processed mRNA transcripts in the portion of the pool of the partially processed mRNA transcripts. In some instances, the therapeutic agent inhibits a protein that regulates intron splicing activity. In some instances, the therapeutic agent activates a protein that regulates intron splicing activity. In some instances, the therapeutic agent binds to a protein that regulates intron splicing activity. In some instances, the therapeutic agent binds to target polynucleotide sequence of the partially processed mRNA transcripts. In some instances, the therapeutic agent is a polynucleic acid polymer. In some instances, the therapeutic agent is a small molecule.

In some instances, the pharmaceutical composition is the pharmaceutical composition described herein.

In some instances, the impaired production of a full-length functional form of the protein comprises sub-normal production of the full-length functional form of the protein. In some instances, the impaired production of a full-length functional form of the protein is due to an absence of expression of the full-length functional form of the protein or a level of expression of the full-length functional form of the protein that is sufficiently low so as to cause the disease or condition. In some instances, the impaired production of a full-length functional form of the protein comprises absence of production of the protein or production of a defective form of the protein. In some instances, the defective form of the protein is a truncated form of the protein, a mis-folded form of the protein or a form of the protein with aberrant target binding. In some instances, treating the subject results in increased expression of the full-length functional form of the protein.

In some aspects, the invention discloses a method of inducing processing of a partially processed mRNA transcript to remove a retained intron to produce a fully processed mRNA transcript that encodes a full-length functional form of a protein, comprising: (a) hybridizing an isolated polynucleic acid polymer to the partially processed mRNA transcript, which is capable of encoding the full-length functional form of the protein and which comprises at least one retained intron; (b) removing the at least one retained intron from the partially processed mRNA transcript to produce a fully processed mRNA transcript that encodes a full-length functional form of the protein; and (c) translating the full-length functional form of the protein from the fully processed mRNA transcript. In some instances, the method further comprises administering a pharmaceutical composition comprising the isolated polynucleic acid polymer to a subject in need thereof.

In some instances, the impaired production of the full-length functional form of the protein is correlated to a disease or condition. In some instances, the disease or condition is a hereditary disease. In some instances, the subject with the hereditary disease has a genome that comprises a copy of a gene that comprises an exon that when properly transcribed into fully processed mRNA encodes the full-length functional form of the protein. In some instances, the subject with the hereditary disease has a genome that comprises a copy of a gene that comprises a set of exons that when properly transcribed into fully processed mRNA encodes the full-length functional form of the protein. In some instances, the subject with the hereditary disease has a genome that comprises a defective copy of the gene, which is incapable of producing a full-length functional form of the protein. In some instances, the disease or condition is diabetes. In some instances, the disease or condition is cancer.

In some instances, the polynucleic acid polymer is an anti-sense sequence. In some instances, the anti-sense sequence hybridizes to a retained intron of the partially processed mRNA transcript. In some instances, the anti-sense sequence hybridizes to an intronic splicing regulatory element of the partially processed mRNA transcript. In some instances, the intronic splicing regulatory element comprises a CCC motif. In some instances, the anti-sense sequence hybridizes to a binding motif of the partially processed mRNA transcript wherein the binding motif does not form a G quadruplex. In some instances, the anti-sense sequence hybridizes to a binding motif of the partially processed mRNA transcript wherein the binding motif is between two G quadruplexes. In some instances, the anti-sense sequence hybridizes to a binding motif of the partially processed mRNA transcript wherein the binding motif has a first CCC motif and a second CCC motif. In some instances, the first CCC motif is about 3 or more nucleotide bases from the second CCC motif. In some instances, the sequence of the polynucleic acid polymer is at least 60%, 70%, 80%, 90%, or 95% or 100% complementary to a target sequence of the partially processed mRNA transcript. In some instances, the sequence of the polynucleic acid polymer has 4 or less, 3 or less, 2 or less, or 1 or less mismatches to a target sequence of the partially processed mRNA transcript. In some instances, the polynucleic acid polymer is between about 10 and about 50, about 10 and about 45, about 10 and about 40, about 10 and about 30, about 10 and about 25, or about 10 and about 20 nucleotides in length.

In some instances, the subject is a eukaryote. In some instances, the subject is a eukaryote selected from a human, mouse, rat, non-human primate, or non-primate mammal.

In some aspects, described is a pharmaceutical composition which comprises a polynucleic acid polymer that hybridizes to a target sequence of a partially processed mRNA transcript which encodes a protein and which comprises a retained intron, wherein the polynucleic acid polymer induces splicing out of the retained intron from the partially processed mRNA transcript; and a pharmaceutically acceptable excipient and/or a delivery vehicle.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A) by SSO6 and promotion of exon 2 skipping by SSO8. Concentration of each SSO was 2, 10, 50 and 250 nM. SSOs are shown at the top, spliced products to the right, reporter at the bottom. (B) A predicted stable hairpin between the authentic and cryptic 3'ss of INS intron 2. Bases targeted by SSO6 are denoted by asterisks and predicted splicing enhancer hexamers (listed to the right) are denoted by a dotted line. (C) SSO4 does not prevent activation of cryptic 3'ss 81 base pairs downstream of its authentic counterpart (cr3'ss+81) in cells depleted of U2AF35 but induces exon skipping. The final concentration of each SSO in COST cells was 5, 20 and 80 nM. The final concentration of the siRNA duplex U2AF35ab (77) was 70 nM. The reporter was the same as in panel A.

DETAILED DESCRIPTION

Figure 1:
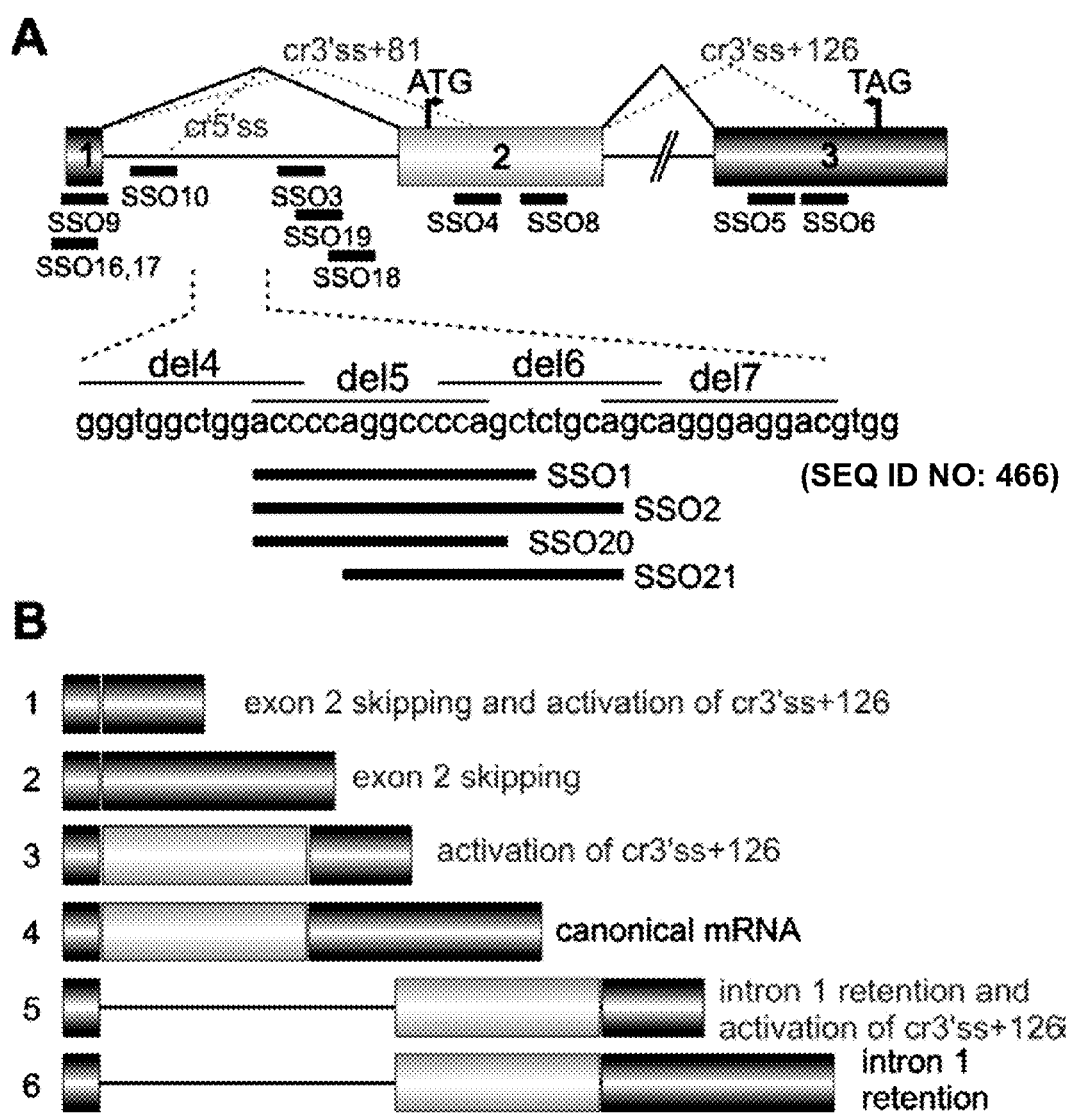
FIG. 1. Location of SSOs in the human proinsulin gene. (A) Schematics of the INS reporter and its mRNA products. SSOs are shown as black horizontal bars below exons (numbered boxes) and below intron 1 (line); their sequences are in Table 2. Start and stop codons are denoted by arrowheads. Canonical (solid lines) and cryptic (dotted lines) splicing is shown above the primary transcript; designation of cryptic splice sites is in grey. SSOs targeting intron 1 segments del4-del7 are shown in the lower panel. (B) mRNA isoforms (numbered 1-6) generated by the INS reporter construct. Description of isoforms that do not produce proinsulin is labelled with *.

Genes such as eukaryotic genes contain intervening sequences or introns that must be accurately removed from primary transcripts to create functional mRNAs capable of encoding proteins (1). This process modifies mRNA composition in a highly dynamic manner, employing interdependent interactions of five small nuclear RNAs (snRNAs) (e.g., U1, U2, U4, U5, and U6) and a large number of proteins with conserved but degenerate sequences in the pre-mRNA (2). In particular, introns can be defined by the core splice site elements that comprises the 5' splice site (5'ss) which can comprise a conserved GU motif, the 3' splice site (3'ss) which can terminates with an invariant AG motif, the branchpoint sequence which can comprise a conserved adenine base, and the polypyrimidine (Py) tract. Splicing reaction can be initiated upon binding of the U1 snRNP to the conserved GU motif on the 5'ss, followed by binding of U2 snRNP at the conserved adenine base of the branchpoint, and finally U4, U5, and U6 snRNPs interactions near the 5' and 3' splice site. The complex formed by snRNPs and the respective intron can be referred to as a spliceosome. Additional splicing factors such as U2 small nuclear RNA auxiliary factor 1 (U2AF35), U2AF2 (U2AF65) and splicing factor 1 (SF1) can contribute to the spliceosome assembly and facilitate the splicing event.

Intron splicing generally promotes mRNA accumulation and protein expression across species (3-5). This process can be altered by intronic mutations or variants that may also impair coupled gene expression pathways, including transcription, mRNA export and translation. This is exemplified by introns in the 5'UTR where natural variants or mutations modifying intron retention alter the relative abundance of transcripts with upstream open reading frames (uORFs) or other regulatory motifs and dramatically influence translation (6,7). Further, impaired protein translation due to a defective splicing such as intron retention has led to development of diseases and/or progression of diseases such as genetic disorders or conditions (e.g., hereditary diseases or cancer). However, successful sequence-specific strategies to normalize gene expression in such situations have not been developed.

Splice-switching oligonucleotides (SSOs) are antisense reagents that modulate intron splicing by binding splice-site recognition or regulatory sequences and competing with cis- and trans-acting factors for their targets (8). They have been shown to restore aberrant splicing, modify the relative expression of existing mRNAs or produce novel splice variants that are not normally expressed (8). Improved stability of targeted SSO-RNA duplexes by a number of SSO modifications, such as 2'-O-methyl and 2'-O-methoxyethyl ribose, facilitated studies exploring their therapeutic potential for a growing number of human disease genes, including DMD in muscular dystrophy (9,10), SMN2 in spinal muscular atrophy (11), ATM in ataxia-telangiectasia (12) and BTK in X-linked agammaglobulinaemia (13). Although such approaches are close to achieving their clinical potential for a restricted number of diseases (8), >300 Mendelian disorders resulting from mutation-induced aberrant splicing (14) and a growing number of complex traits may be amenable to SSO-mediated correction of gene expression.

Etiology of type 1 diabetes has a strong genetic component conferred by human leukocyte antigens (HLA) and a number of modifying non-HLA loci (15). The strongest modifier was identified in the proinsulin gene (INS) region on chromosome 11 (termed IDDM2) (15). Further mapping of this area suggested that INS is the most likely IDDM2 target (16), consistent with a critical role of this autoantigen in pathogenesis (17). Genetic risk to this disease at IDDM2 has been attributed to differential steady-state RNA levels from predisposing and protective INS haplotypes, potentially involving a minisatellite DNA sequence upstream of this gene (18,19). However, systematic examination of naturally occurring INS polymorphisms revealed haplotype-specific proinsulin expression levels in reporter constructs devoid of the minisatellite sequence, resulting from two variants in intron 1 (7), termed IVS1+5ins4 (also known as rs3842740 or INS-69) and IVS1-6A/T (rs689, INS-27 or HphI+/−) (16,20). The former variant activates a cryptic 5' splice site of intron 1 whereas adenine (A) at the latter variant, which resides 6 nucleotides upstream of the 3' splice site (3'ss), promotes intron retention, expanding the relative abundance of transcripts with extended 5'UTR (21). As compared to thymine (T), the A allele at IVS1-6A/T decreases affinity to pyrimidine-binding proteins in vitro and renders the 3'ss more dependent on the auxiliary factor of U2 small nuclear ribonucleoprotein (U2AF) (7), a heterodimer required for U2 binding, spliceosome assembly and 3'ss selection (22). Intron 1-containing transcripts are overrepresented in IVS1-6A-derived cDNA libraries prepared from insulin producing tissues (21), are exported from the nucleus (23), and contain a short, Homininae-specific uORF that co-evolved with relaxation of the 3'ss of intron 1 in higher primates (7). The lower proinsulin expression conferred by the A allele may lead to suboptimal presentation of proinsulin peptides in the fetal thymus and inadequate negative selection of autoreactive T cells, culminating in autoimmune destruction of insulin-producing β cells in the pancreas (7).

An aim of the invention is to induce processing of a partially processed mRNA transcript to remove a retained intron to produce a fully processed mRNA transcript that encodes a full-length functional form of a protein. An additional aim is to treat a disease or condition characterized by impaired production of a protein and/or a disease or condition characterized by a defective splicing in a subject in need thereof.

Another aim of the invention is to correct the low efficiency of INS intron 1 removal from the IVS1-6A-containing pre-mRNAs and reduce intron retention to the levels observed for the disease-protective T allele. A further aim of the invention is to provide new therapy approaches to genetic diseases including cancer that are characterized by (or associated with) irregular or aberrant intron retention.

According to a first aspect of the invention, there is provided a method of prevention or treatment of a disease in a subject comprising correction of intron retention in mature gene transcripts, wherein the disease is induced by defective protein expression caused by the intron retention in the gene transcripts.

Retained Intron

Retained intron is one of five types of alternative splicing that can also include exon skipping, alternative 5' splice site, alternative 3' splice site, and mutually exclusive exons. Exon skipping can occur when an exon is skipped over or is spliced out of the processed mRNA and can be the most common type of alternative splicing. Alternative 5' ss and alternative 3' ss can signify alternate splice sites such as cryptic splice sites or pseudo splice sites. Mutually exclusive exons can occur when only one of two exons is retained in the processed mRNA after splicing. Although intron retention can be less common than exon skipping, intron retention has been shown to occur more frequently than previously realized. Indeed, a study of 21,106 human genes by the De Souza group has shown that about 15% of the genes tested showed intron retention (see, Galante et al, "Detection and evaluation of intron retention events in the human transcriptome," *Bioinformatics* 10:757-765 (2004)). Further, a study by the Moore group has shown that about 35% of human 5'-UTRs and about 16% of 3'-UTRs harbor introns (Bicknell et al., "Introns in UTRs: Why we should stop ignoring them," *Bioessays* 34:1025-1034 (2012)). As such, intron retention can occur in a coding region, a non-coding region, at the 5' UTR, or at the 3' UTR. In the coding region, the retained intron can encode amino acids in frame, or can be in misalignment which can generate truncated proteins or non-functional proteins due to stop codon or frame shifts. Further, intron can be in between two exons, located at the 5' UTR, or located at the 3' UTR.

Compared to a non-retained intron, a retained intron can be characterized to have a shorter sequence length. The sequence length of the retained intron can be less than 5 kb, less than 4.5 kb, less than 4 kb, less than 3.5 kb, less than 3 kb, less than 2.5 kb, less than 2 kb, less than 1.5 kb, less than 1 kb, less than 0.5 kb, less than 0.4 kb, less than 0.3 kb, less than 0.2 kb, or less than 0.1 kb.

Further, compared to a non-retained intron, a retained intron can be characterized to have a G/C content of between about 40% to about 60%. The G/C content of the retained intron can be about 40%, 45%, 50%, 55%, or about 60%.

The retained intron can also be flanked by a weak 5' splice site, a weak 3' splice site, or both. A weak splice site can refer to a splice site that may require a regulatory protein such as an intronic splicing enhancer for function.

Furthermore, a retained intron may comprise a lower presence of a GGG motif relative to a non-retained intron. In some instances, the GGG motif is an intronic splicing enhancer.

A partially processed mRNA transcript is a mRNA transcript that has undergone partial splicing and comprises at least one retained intron. The at least one intron can be within the 5' UTR, 3' UTR, or at an internal position in between two exons. The partially processed mRNA transcript can be unable to be translated to produce a functional or full-length protein.

A partially processed mRNA transcript can comprise an intron that is characterized by a short sequence length. A partially processed mRNA transcript can comprise an intron that is characterized by a sequence of less than 3 kb, less than 2.5 kb, less than 2 kb, less than 1.5 kb, less than 1 kb, less than 0.5 kb, less than 0.4 kb, less than 0.3 kb, less than 0.2 kb, or less than 0.1 kb.

A partially processed mRNA transcript can comprise an intron that is characterized to have a G/C content of between about 40% to about 60%. A partially processed mRNA transcript can comprise an intron that is characterized to have a G/C content of about 40%, 45%, 50%, 55%, or about 60%.

A partially processed mRNA transcript can comprise an intron that is flanked by a weak 5' splice site, a weak 3' splice site, or both.

A partially processed mRNA transcript can comprise an intron that may comprise a lower presence of a GGG motif relative to a non-retained intron.

In some cases, one or more introns are retained in a partially processed mRNA transcript. The partially processed mRNA can comprise 1, 2, 3, 4, 5, 6, 7, 8, 9, 10, or more retained introns.

A fully processed mRNA transcript is one that has undergone splicing to remove introns, such as retained introns and is capable of being translated to produce a protein such as a full length functional protein. A partially processed mRNA transcript with one or more retained introns can be spliced so as to become a fully processed mRNA.

A full-length functional protein has the same length and function as the wild-type form of the protein. The full-length functional protein can be the wild-type form of the protein. The full-length functional protein can be an isoform of the wild type protein with the same length as the wild type protein. The full-length functional protein can comprise a mutation such as a substitution of an amino acid for an alternative amino acid residue with similar properties so that the phenotype (e.g., the function) of the protein is not altered by the mutation.

Exemplary amino acids with similar properties can include amino acids with electrically charged side chains: arginine, histidine, and lysine which are positively charged; or aspartic acid and glutamic acid which are negatively charged; polar amino acid residues: serine, threonine, asparagine, glutamine, cysteine, and methionine; nonpolar amino acids: glycine, alanine, valine, leucine, isoleucine, and proline; and aromatic amino acids: phenylalanine, tyrosine, and tryptophan.

In some instances, the partially processed mRNA transcript leads to impaired production of a protein. The impaired production of the protein can be the impaired production of a full-length functional form of the protein which can comprise sub-normal production of the full-length functional form of the protein. The impaired production of a full-length functional form of the protein can comprise production of a defective form of the protein. The defective form of the protein can be a truncated form of the protein, a mis-folded form of the protein, or a form of the protein that comprises an aberrant target binding site.

Polynucleic Acid Polymer

Polynucleic acid polymers described herein can be used to hybridize to a partially processed mRNA transcript to initiate removal of a retained intron. In some instances, the polynucleic acid polymer is an antisense polynucleic acid polymer. The antisense polynucleic acid polymer may hybridize to a region of a partially processed mRNA transcript with a high G/C content, such as a region that comprises between about 40% to about 60%. The antisense polynucleic acid polymer may comprise a high G/C content, such as between about 40% to about 60%. The antisense polynucleic acid polymer may hybridize to a region of a partially processed mRNA transcript that is at, next to, or near a weak 5' splice site, or a weak 3' splice site. The antisense polynucleic acid polymer may hybridize to a region of a partially processed mRNA transcript that may comprise a lower presence of a GGG motif.

The antisense sequence of the polynucleic acid polymer may hybridize to a retained intron of the partially processed mRNA transcript. The antisense sequence may hybridize to an intronic splicing regulatory element of the partially processed mRNA transcript. The intronic splicing regulatory element may include an intronic splicing enhancer or an intronic splicing silencer. The anti-sense sequence may hybridize to an intronic splicing silencer. The intronic splicing regulatory element may modulate splicing by affecting the early and/or intermediate steps of spliceosomal assembly, such as when U1 and U2 snRNPs pair at splice sites across an exon during exon definition or during subsequent transition to intron-spanning complex. Exemplary intronic splicing regulatory elements may include polypyrimidine-tract-binding protein PTB, hnRNP L and hnRNP A1. Exemplary intronic splicing regulatory elements may include binding sites for polypyrimidine-binding protein or PTB, U2AF65 and/or U2AF35, hnRNP A1 and hnRNP L.

The polynucleic acid polymer may hybridize at the 5' splice site, 3' splice site, branchpoint, polypyrimidine tract, or an intron enhancer of the intron. The polynucleic acid polymer may also hybridize at a distance of about 30 bases away, 25 bases away, 20 bases away, 15 bases away, 10 bases away, or 5 bases away from a 5' splice site, 3' splice site, branchpoint, polypyrimidine tract or an intron enhancer to promote or enhance splicing. Hybridization of the polynucleic acid polymer at or near the splice sites may promote or enhance splicing by recruiting splicing factors toward the splice sites, thereby initiating splicing.

A polynucleic acid polymer may hybridize at an intron silencer site (e.g., de novo intron silencer site), a cryptic intron splice site, or a pseudo splice site. The intron silencer site can be recognized by a silencer which suppresses the splicing reaction. The cryptic intron splice site can be created by a mutation, such as a substitution, a deletion, or an insertion. The cryptic intron splice site can be a cryptic 5' splice site or a cryptic 3' splice site. The cryptic intron splice site can be a cryptic 5' splice site. The pseudo splice site can be a weak splice site in which its activation can be resulted from a mutation of the canonical splice site. The pseudo splice site can be a pseudo 5' splice site or a pseudo 3' splice site. Hybridization at an intron silencer site may sterically block a silencer from binding and may help from preventing disruption of the assembly and processing of the spliceosome. Hybridization at a cryptic intron splice site may redirect interaction toward a canonical splice site such as a canonical weak splice site.

A polynucleic acid polymer may hybridize to an internal region of the intron. The internal region of the intron may not encompass a splice site, such as a 5' splice site (e.g., canonical, cryptic, or pseudo 5' splice site), 3' splice site (e.g., canonical, cryptic, or pseudo 3' splice site), an enhancer site or a silencer site. Hybridization of the polynucleic acid polymer at an internal region may promote or enhance splicing by recruiting splicing factors toward the splice sites, such as an intron enhancer site.

A polynucleic acid polymer may hybridize to an intronic splicing regulatory element of the partially processed mRNA transcript. The intronic splicing regulatory element may comprise a CCC motif. The anti-sense sequence may hybridize to a binding motif of the partially processed mRNA transcript wherein the binding motif does not form a G quadruplex. The anti-sense sequence may hybridize to a binding motif of the partially processed mRNA transcript wherein the binding motif is between two G quadruplexes. The anti-sense sequence may also hybridize to a binding motif of the partially processed mRNA transcript wherein the binding motif has a first CCC motif and a second CCC motif. The first CCC motif may be about 3 or more nucleotide bases from the second CCC motif.

A polynucleic acid polymer may hybridize to a binding motif of the partially processed mRNA transcript in which the binding motif forms a hairpin structure. The polynucleic acid polymer may further be capable of destabilizing the hairpin structure.

A polynucleic acid polymer may comprise a pyridine nucleotide at the 3' terminal position and/or at the 5' terminal position. The polynucleic acid polymer may further comprise two consecutive pyridine nucleotides at the 3' terminal position and/or at the 5' terminal position.

In some instances, a polynucleic acid polymer may be a splice-switching oligonucleotide (SSO). The splice-switching oligonucleotide may hybridize to a retained intron of the partially processed mRNA transcript. The splice-switching oligonucleotide may hybridize to an intronic splicing regulatory element of the partially processed mRNA transcript.

Splice-switching oligonucleotides (SSOs) have been widely used to inhibit exon usage but antisense strategies that promote removal of entire introns to increase splicing-mediated gene expression have not been developed. Using a series of splicing reporters containing the human proinsulin gene, it has been shown that INS intron 1 retention by SSOs that bind transcripts derived from a human haplotype expressing low levels of proinsulin can be reduced. The SSO-assisted promotion of weak intron removal from the 5'UTR through competing noncanonical and canonical RNA structures facilitates development of sequence-based antisense strategies to enhance gene expression.

The term "correction of intron retention" is understood to the correction of irregular or aberrant intron retention. The correction may be complete correction or partial correction. Correction may comprise reducing the incidence of intron retention. Correction may comprise reducing aberrant intron retention.

Reference to "defective" in the context of protein expression caused by the intron retention in the gene transcripts, may comprise inadequate, defective, or aberrant protein expression.

Correction of intron retention may comprise administering a polynucleic acid polymer arranged to hybridize with the gene transcript. Correction of intron retention may comprise administering a polynucleic acid polymer arranged to hybridize with the gene transcript in order to alter higher-order structures in the gene transcript. Correction of intron retention may comprise administering a polynucleic acid polymer arranged to hybridize with the gene transcript in order to interfere with one or more of conformational transitions of canonical (stem loops); noncanonical (G quadruplex) RNA structures; interactions with trans-acting factors; and the rate of RNA-protein complex formation. Correction of intron retention may comprise administering a polynucleic acid polymer arranged to hybridize with the gene transcript in order to interfere with, such as block, conformational transitions of canonical (stem loops) and/or noncanonical (G quadruplex) RNA structures. The polynucleic acid polymer may be antisense to at least part of a target region of the transcript comprising or consisting of intronic splicing regulatory elements. The polynucleic acid polymer may be antisense to at least part of a target region of the transcript comprising or consisting of overlapped intronic splicing regulatory elements conserved in mammals. The polynucleic acid polymer may be antisense to at least part of a target region of the transcript comprising or consisting of intronic segments containing short penta- to heptamer splicing regulatory motifs. Splicing regulatory motifs may comprise CCCAG or AGGCC. Splicing regulatory motifs may comprise any of the motifs provided by Yeo G W, et al (2007). PLoS Genet 3:e85 and/or Voelker R B, & Berglund J A (2007). Genome Res 17:1023-1033, both documents incorporated herein by reference. The target region may not comprise C runs in order to avoid G-quadruplex formation. The target region may not be proximal to both 5' and 3' splice sites, polypyrimidine tracts, branch sites and/or suprabranch regions.

The polynucleic acid polymer may provide binding platforms for splicing factors which have been shown to influence INS intron 1 and exon 2 splicing, including Tra2, SRSF3 or U2AF35, or other peptides, sense or antisense nucleic acids, small molecules, or other chemicals to facilitate delivery of the polynucleic acid polymer and/or target the nucleic acid to a specific tissue, cell or a developmental stage. Such antisense strategy may help reduce pervasive intron retention in cancer cells, particularly those that contain somatic mutations of splicing factor genes, as first shown for specific substitutions in the zinc finger domain of U2AF35 in myeloproliferative diseases (76). These mutations occur in many tumours and result in splicing defects that may contribute to malignant growth. The invention may help control cell proliferation and reduce malignant growth in a significant fraction of cancer patients that carry mutations in splicing factors involved in 3' splice site recognition, currently estimated at >15% (76).

The sequence of the polynucleic acid polymer may be at least 50%, 55%, 60%, 65%, 70%, 75%, 80%, 85%, 90%, 95%, 98%, 99%, or 99.5% complementary to a target sequence of the partially processed mRNA transcript. The sequence of the polynucleic acid polymer may be 100% complementary to a target sequence of the partially processed mRNA transcript.

The sequence of the polynucleic acid polymer may have 4 or less mismatches to a target sequence of the partially processed mRNA transcript. The sequence of the polynucleic acid polymer may have 3 or less mismatches to a target sequence of the partially processed mRNA transcript. The sequence of the polynucleic acid polymer may have 2 or less mismatches to a target sequence of the partially processed mRNA transcript. The sequence of the polynucleic acid polymer may have 1 or less mismatches to a target sequence of the partially processed mRNA transcript.

The polynucleic acid polymer may specifically hybridize to a target sequence of the partially processed mRNA transcript. The specificity may be a 95%, 98%, 99%, 99.5% or 100% sequence complementarity of the polynucleic acid polymer to a target sequence of the partially processed mRNA transcript. The hybridization may be under high stringent hybridization conditions.

The polynucleic acid polymer may be antisense to at least part of a target region of the transcript comprising or consisting of SEQ ID NO: 46. The polynucleic acid polymer may be antisense to at least part of a target region of the transcript comprising or consisting of a sequence having at least 99% identity with SEQ ID NO: 46. The polynucleic acid polymer may be antisense to at least part of a target region of the transcript comprising or consisting of a sequence having at least 98% identity with SEQ ID NO: 46. The polynucleic acid polymer may be antisense to at least part of a target region of the transcript comprising or consisting of a sequence having at least 95% identity with SEQ ID NO: 46. The polynucleic acid polymer may be antisense to at least part of a target region of the transcript comprising or consisting of a sequence having at least 90% identity with SEQ ID NO: 46. The polynucleic acid polymer may be antisense to at least part of a target region of the transcript comprising or consisting of a sequence having at least 85% identity with SEQ ID NO: 46. The polynucleic acid polymer may be antisense to at least part of a target region of the transcript comprising or consisting of a sequence having at least 80% identity with SEQ ID NO: 46. The polynucleic acid polymer may be antisense to at least part of a target region of the transcript comprising or consisting of a sequence having at least 75% identity with SEQ ID NO: 46. The polynucleic acid polymer may be antisense to at least part of a target region of the transcript comprising or consisting of a sequence having at least 70% identity with SEQ ID NO: 46. The polynucleic acid polymer may be antisense to at least part of a target region of the transcript comprising or consisting of a sequence having at least 65% identity with SEQ ID NO: 46. The polynucleic acid polymer may be antisense to at least part of a target region of the transcript comprising or consisting of a sequence having at least 60% identity with SEQ ID NO: 46. The polynucleic acid polymer may be antisense to at least part of a target region of the transcript comprising or consisting of a sequence having at least 55% identity with SEQ ID NO: 46. The polynucleic acid polymer may be antisense to at least part of a target region of the transcript comprising or consisting of a sequence having at least 50% identity with SEQ ID NO: 46.

A polynucleic acid polymer may hybridize to an mRNA transcript comprising at least 80%, 85%, 90%, 95%, or 99% sequence identity to at least 13 contiguous bases of SEQ ID NO: 46. The polynucleic acid polymer may hybridize to a mRNA transcript comprising 100% sequence identity to at least 13 contiguous bases of SEQ ID NO: 46.

A polynucleic acid polymer may be antisense to at least part of a target region of the transcript comprising or consisting of SEQ ID NO: 3. The polynucleic acid polymer may be antisense to at least part of a target region of the transcript comprising or consisting of a sequence having at least 99% identity with SEQ ID NO: 3. The polynucleic acid polymer may be antisense to at least part of a target region of the transcript comprising or consisting of a sequence having at least 98% identity with SEQ ID NO: 3. The polynucleic acid polymer may be antisense to at least part of a target region of the transcript comprising or consisting of a sequence having at least 95% identity with SEQ ID NO: 3. The polynucleic acid polymer may be antisense to at least part of a target region of the transcript comprising or consisting of a sequence having at least 90% identity with SEQ ID NO: 3. The polynucleic acid polymer may be antisense to at least part of a target region of the transcript comprising or consisting of a sequence having at least 85% identity with SEQ ID NO: 3. The polynucleic acid polymer may be antisense to at least part of a target region of the transcript comprising or consisting of a sequence having at least 80% identity with SEQ ID NO: 3. The polynucleic acid polymer may be antisense to at least part of a target region of the transcript comprising or consisting of a sequence having at least 75% identity with SEQ ID NO: 3. The polynucleic acid polymer may be antisense to at least part of a target region of the transcript comprising or consisting of a sequence having at least 70% identity with SEQ ID NO: 3. The polynucleic acid polymer may be antisense to at least part of a target region of the transcript comprising or consisting of a sequence having at least 65% identity with SEQ ID NO: 3. The polynucleic acid polymer may be antisense to at least part of a target region of the transcript comprising or consisting of a sequence having at least 60% identity with SEQ ID NO: 3. The polynucleic acid polymer may be antisense to at least part of a target region of the transcript comprising or consisting of a sequence having at least 55% identity with SEQ ID NO: 3. The polynucleic acid polymer may be antisense to at least part of a target region of the transcript comprising or consisting of a sequence having at least 50% identity with SEQ ID NO: 3.

Reference to antisense to at least part of a target region of the transcript may comprise at least 5 consecutive nucleotides, or at least 10 consecutive nucleotides. The polynucleic acid polymer may be antisense to at least 5 consecutive nucleotides of a target region of the transcript comprising or consisting of SEQ ID NO: 46. The polynucleic acid polymer may be antisense to at least 10 consecutive nucleotides of a target region of the transcript comprising or consisting of SEQ ID NO: 46. The polynucleic acid polymer may be antisense to at least 15 consecutive nucleotides of a target region of the transcript comprising or consisting of SEQ ID NO: 46. The polynucleic acid polymer may be antisense to at least 20 consecutive nucleotides of a target region of the transcript comprising or consisting of SEQ ID NO: 46.

A polynucleic acid polymer may hybridize to a mRNA transcript comprising at least 10 contiguous bases of SEQ ID NO: 46. The polynucleic acid polymer may hybridize to a mRNA transcript consisting of at least 10 contiguous bases of SEQ ID NO: 46.

The polynucleic acid polymer may be antisense to a target region of the transcript comprising or consisting of a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof.

A polynucleic acid polymer may be antisense to a target region of the transcript comprising or consisting of a sequence having at least 99% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 98% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 95% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 90% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 85% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 80% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 75% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 70% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 65% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 63% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 60% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof. The polynucleic acid polymer may be antisense to a target region of the transcript comprising or consisting of a sequence having at least 50% sequence identity to a sequence selected from any of the group comprising SEQ ID NO: 3; SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; SEQ ID NO: 42; SEQ ID NO: 45; or combinations thereof.

The polynucleic acid polymer may be antisense to a target region of the transcript comprising or consisting of a sequence selected from any of the group comprising SEQ ID NO: 3; SEQ ID NO: 6; SEQ ID NO: 9; and SEQ ID NO: 36; or combinations thereof. The polynucleic acid polymer may be antisense to a target region of the transcript comprising or consisting of a sequence having at least 99% identity to a sequence selected from any of the group comprising SEQ ID NO: 3; SEQ ID NO: 6; SEQ ID NO: 9; and SEQ ID NO: 36; or combinations thereof. The polynucleic acid polymer may be antisense to a target region of the transcript comprising or consisting of a sequence having at least 98% identity to a sequence selected from any of the group comprising SEQ ID NO: 3; SEQ ID NO: 6; SEQ ID NO: 9; and SEQ ID NO: 36; or combinations thereof. The polynucleic acid polymer may be antisense to a target region of the transcript comprising or consisting of a sequence having at least 95% identity to a sequence selected from any of the group comprising SEQ ID NO: 3; SEQ ID NO: 6; SEQ ID NO: 9; and SEQ ID NO: 36; or combinations thereof.

The polynucleic acid polymer may be antisense to a target region of the transcript comprising or consisting of SEQ ID NO: 3. The polynucleic acid polymer may be antisense to a target region of the transcript comprising or consisting of SEQ ID NO: 6. The polynucleic acid polymer may be antisense to a target region of the transcript comprising or consisting of SEQ ID NO: 9. The polynucleic acid polymer may be antisense to a target region of the transcript comprising or consisting of SEQ ID NO: 36.

The polynucleic acid polymer may be antisense to a target region of the transcript comprising or consisting of a sequence having at least 99%, at least 98%, at least 95%, at least 90%, at least 85%, at least 80%, at least 75%, at least 70%, at least 65%, at least 63%, at least 60%, at least 55%, or at least 50% identity to SEQ ID NO: 3. The polynucleic acid polymer may be antisense to a target region of the transcript comprising or consisting of a sequence having at least 99%, at least 98%, at least 95%, at least 90%, at least 85%, at least 80%, at least 75%, at least 70%, at least 65%, at least 63%, at least 60%, at least 55%, or at least 50% identity to SEQ ID NO: 6. The polynucleic acid polymer may be antisense to a target region of the transcript comprising or consisting of a sequence having at least 99%, at least 98%, at least 95%, at least 90%, at least 85%, at least 80%, at least 75%, at least 70%, at least 65%, at least 63%, at least 60%, at least 55%, or at least 50% identity to SEQ ID NO: 9. The polynucleic acid polymer may be antisense to a target region of the transcript comprising or consisting of a sequence having at least 99%, at least 98%, at least 95%, at least 90%, at least 85%, at least 80%, at least 75%, at least 70%, at least 65%, at least 63%, at least 60%, at least 55%, or at least 50% identity to SEQ ID NO: 36.

The polynucleic acid polymer may be antisense to a region of the transcript comprising or consisting of a sequence complementary to any of the group of sequences comprising SEQ ID NOs: 47 to 434; or combinations thereof. The polynucleic acid polymer may be antisense to a region of the transcript comprising or consisting of a sequence complementary to a sequence having at least 99% identity with any of the group of sequences comprising SEQ ID NOs: 47 to 434; or combinations thereof. The polynucleic acid polymer may be antisense to a region of the transcript comprising or consisting of a sequence complementary to a sequence having at least 98% identity with any of the group of sequences comprising SEQ ID NOs: 47 to 434; or combinations thereof. The polynucleic acid polymer may be antisense to a region of the transcript comprising or consisting of a sequence complementary to a sequence having at least 95% identity with any of the group of sequences comprising SEQ ID NOs: 47 to 434; or combinations thereof. The polynucleic acid polymer may be antisense to a region of the transcript comprising or consisting of a sequence complementary to a sequence having at least 90% identity with any of the group of sequences comprising SEQ ID NOs: 47 to 434; or combinations thereof. The polynucleic acid polymer may be antisense to a region of the transcript comprising or consisting of a sequence complementary to a sequence having at least 85% identity with any of the group of sequences comprising SEQ ID NOs: 47 to 434; or combinations thereof. The polynucleic acid polymer may be antisense to a region of the transcript comprising or consisting of a sequence complementary to a sequence having at least 80% identity with any of the group of sequences comprising SEQ ID NOs: 47 to 434; or combinations thereof. The polynucleic acid polymer may be antisense to a region of the transcript comprising or consisting of a sequence complementary to a sequence having at least 75% identity with any of the group of sequences comprising SEQ ID NOs: 47 to 434; or combinations thereof. The polynucleic acid polymer may be antisense to a region of the transcript comprising or consisting of a sequence complementary to a sequence having at least 70% identity with any of the group of sequences comprising SEQ ID NOs: 47 to 434; or combinations thereof. The polynucleic acid polymer may be antisense to a region of the transcript comprising or consisting of a sequence complementary to a sequence having at least 65% identity with any of the group of sequences comprising SEQ ID NOs: 47 to 434; or combinations thereof. The polynucleic acid polymer may be antisense to a region of the transcript comprising or consisting of a sequence complementary to a sequence having at least 60% identity with any of the group of sequences comprising SEQ ID NOs: 47 to 434; or combinations thereof. The polynucleic acid polymer may be antisense to a region of the transcript comprising or consisting of a sequence complementary to a sequence having at least 55% identity with any of the group of sequences comprising SEQ ID NOs: 47 to 434; or combinations thereof. The polynucleic acid polymer may be antisense to a region of the transcript comprising or consisting of a sequence complementary to a sequence having at least 50% identity with any of the group of sequences comprising SEQ ID NOs: 47 to 434; or combinations thereof. The skilled person will understand that uracil nucleotides may be substituted with thymine nucleotides (e.g. the DNA form of the RNA of such sequences).

The polynucleic acid polymer may comprise or consist of a polynucleic acid polymer sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof.

The polynucleic acid polymer may comprise or consist of a polynucleic acid polymer sequence having at least 99% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 98% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 95% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 90% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 85% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 80% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 75% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 70% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 65% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 60% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 55% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. The polynucleic acid polymer may comprise or consist of a polynucleic acid polymer sequence having at least 50% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof.

The polynucleic acid polymer may comprise or consist of a polynucleic acid polymer sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 99% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 98% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 95% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 90% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 85% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 80% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 75% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 70% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 65% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 60% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 55% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof. The polynucleic acid polymer may comprise or consist of a polynucleic acid polymer sequence having at least 50% identity to a sequence selected from any of the group comprising SEQ ID NO: 1; SEQ ID NO: 2; SEQ ID NO: 4; SEQ ID NO 5; SEQ ID NO: 7; SEQ ID NO: 8; SEQ ID NO: 34; and SEQ ID NO: 35; or combinations thereof.

The polynucleic acid polymer may comprise or consist of SEQ ID NO: 1 or SEQ ID NO: 2. The polynucleic acid polymer may comprise or consist of SEQ ID NO: 3 or SEQ ID NO: 4. The polynucleic acid polymer may comprise or consist of SEQ ID NO: 7 or SEQ ID NO: 8. The polynucleic acid polymer may comprise or consist of SEQ ID NO: 34 or SEQ ID NO: 35.

The polynucleic acid polymer may comprise or consist of a sequence having at least 99% identity to SEQ ID NO: 1 or SEQ ID NO: 2. The polynucleic acid polymer may comprise or consist of a sequence having at least 98% identity to SEQ ID NO: 1 or SEQ ID NO: 2. The polynucleic acid polymer may comprise or consist of a sequence having at least 95% identity to SEQ ID NO: 1 or SEQ ID NO: 2. The polynucleic acid polymer may comprise or consist of a sequence having at least 90% identity to SEQ ID NO: 1 or SEQ ID NO: 2. The polynucleic acid polymer may comprise or consist of a sequence having at least 85% identity to SEQ ID NO: 1 or SEQ ID NO: 2. The polynucleic acid polymer may comprise or consist of a sequence having at least 80% identity to SEQ ID NO: 1 or SEQ ID NO: 2. The polynucleic acid polymer may comprise or consist of a sequence having at least 75% identity to SEQ ID NO: 1 or SEQ ID NO: 2. The polynucleic acid polymer may comprise or consist of a sequence having at least 70% identity to SEQ ID NO: 1 or SEQ ID NO: 2. The polynucleic acid polymer may comprise or consist of a sequence having at least 65% identity to SEQ ID NO: 1 or SEQ ID NO: 2. The polynucleic acid polymer may comprise or consist of a sequence having at least 60% identity to SEQ ID NO: 1 or SEQ ID NO: 2.

The polynucleic acid polymer may comprise or consist of a sequence having at least 99% identity to SEQ ID NO: 3 or SEQ ID NO: 4. The polynucleic acid polymer may comprise or consist of a sequence having at least 98% identity to SEQ ID NO: 3 or SEQ ID NO: 4. The polynucleic acid polymer may comprise or consist of a sequence having at least 95% identity to SEQ ID NO: 3 or SEQ ID NO: 4. The polynucleic acid polymer may comprise or consist of a sequence having at least 90% identity to SEQ ID NO: 3 or SEQ ID NO: 4. The polynucleic acid polymer may comprise or consist of a sequence having at least 85% identity to SEQ ID NO: 3 or SEQ ID NO: 4. The polynucleic acid polymer may comprise or consist of a sequence having at least 80% identity to SEQ ID NO: 3 or SEQ ID NO: 4. The polynucleic acid polymer may comprise or consist of a sequence having at least 75% identity to SEQ ID NO: 3 or SEQ ID NO: 4. The polynucleic acid polymer may comprise or consist of a sequence having at least 70% identity to SEQ ID NO: 3 or SEQ ID NO: 4. The polynucleic acid polymer may comprise or consist of a sequence having at least 65% identity to SEQ ID NO: 3 or SEQ ID NO: 4. The polynucleic acid polymer may comprise or consist of a sequence having at least 60% identity to SEQ ID NO: 3 or SEQ ID NO: 4.

The polynucleic acid polymer may comprise or consist of a sequence having at least 99% identity to SEQ ID NO: 7 or SEQ ID NO: 8. The polynucleic acid polymer may comprise or consist of a sequence having at least 98% identity to SEQ ID NO: 7 or SEQ ID NO: 8. The polynucleic acid polymer may comprise or consist of a sequence having at least 95% identity to SEQ ID NO: 7 or SEQ ID NO: 8. The polynucleic acid polymer may comprise or consist of a sequence having at least 90% identity to SEQ ID NO: 7 or SEQ ID NO: 8. The polynucleic acid polymer may comprise or consist of a sequence having at least 85% identity to SEQ ID NO: 7 or SEQ ID NO: 8. The polynucleic acid polymer may comprise or consist of a sequence having at least 80% identity to SEQ ID NO: 7 or SEQ ID NO: 8. The polynucleic acid polymer may comprise or consist of a sequence having at least 75% identity to SEQ ID NO: 7 or SEQ ID NO: 8. The polynucleic acid polymer may comprise or consist of a sequence having at least 70% identity to SEQ ID NO: 7 or SEQ ID NO: 8. The polynucleic acid polymer may comprise or consist of a sequence having at least 65% identity to SEQ ID NO: 7 or SEQ ID NO: 8. The polynucleic acid polymer may comprise or consist of a sequence having at least 60% identity to SEQ ID NO: 7 or SEQ ID NO: 8.

The polynucleic acid polymer may comprise or consist of a sequence having at least 99% identity to SEQ ID NO: 34 or SEQ ID NO: 35. The polynucleic acid polymer may comprise or consist of a sequence having at least 98% identity to SEQ ID NO: 34 or SEQ ID NO: 35. The polynucleic acid polymer may comprise or consist of a sequence having at least 95% identity to SEQ ID NO: 34 or SEQ ID NO: 35. The polynucleic acid polymer may comprise or consist of a sequence having at least 90% identity to SEQ ID NO: 34 or SEQ ID NO: 35. The polynucleic acid polymer may comprise or consist of a sequence having at least 85% identity to SEQ ID NO: 34 or SEQ ID NO: 35. The polynucleic acid polymer may comprise or consist of a sequence having at least 80% identity to SEQ ID NO: 34 or SEQ ID NO: 35. The polynucleic acid polymer may comprise or consist of a sequence having at least 75% identity to SEQ ID NO: 34 or SEQ ID NO: 35. The polynucleic acid polymer may comprise or consist of a sequence having at least 70% identity to SEQ ID NO: 34 or SEQ ID NO: 35. The polynucleic acid polymer may comprise or consist of a sequence having at least 65% identity to SEQ ID NO: 34 or SEQ ID NO: 35. The polynucleic acid polymer may comprise or consist of a sequence having at least 60% identity to SEQ ID NO: 34 or SEQ ID NO: 35.

The polynucleic acid polymer may comprise or consist of a polynucleic acid polymer sequence selected from any of the group comprising SEQ ID NOs: 47 to 434; or combinations thereof. The polynucleic acid polymer may comprise or consist of a polynucleic acid polymer sequence selected from any of the group comprising SEQ ID NOs: 47 to 434; or combinations thereof, wherein uracil nucleotides are substituted with thymine nucleotides (e.g. the DNA form of the RNA of such sequences).

The polynucleic acid polymer may comprise or consist of a polynucleic acid polymer sequence having at least 99% identity with a sequence selected from any of the group comprising SEQ ID NOs: 47 to 434; or combinations thereof. The polynucleic acid polymer may comprise or consist of a polynucleic acid polymer sequence having at least 99% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 98% identity with a sequence selected from any of the group comprising SEQ ID NOs: 47 to 434; or combinations thereof. The polynucleic acid polymer may comprise or consist of a polynucleic acid polymer sequence having at least 98% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 95% identity with a sequence selected from any of the group comprising SEQ ID NOs: 47 to 434; or combinations thereof. The polynucleic acid polymer may comprise or consist of a polynucleic acid polymer sequence having at least 95% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 90% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 85% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 80% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 75% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 70% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 65% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 60% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 55% identity with a sequence selected from any of the group comprising SEQ ID NOs: 47 to 434; or combinations thereof, wherein uracil nucleotides are substituted with thymine nucleotides (e.g. the DNA form of the RNA of such sequences). The polynucleic acid polymer may comprise or consist of a polynucleic acid polymer sequence having at least 50% identity with a sequence selected from any of the group comprising SEQ ID NOs: 47 to 434; or combinations thereof, wherein uracil nucleotides are substituted with thymine nucleotides (e.g. the DNA form of the RNA of such sequences).

Advantageously, the invention identifies SSOs reducing the relative abundance of intron transcripts (e.g., intron 1-retaining transcripts) and delineates the optimized antisense target at a single-nucleotide resolution.

A polynucleic acid polymer may comprise a splice-switching oligonucleotide (SSO). The polynucleic acid polymer may be about 50 nucleotides in length. The polynucleic acid polymer may be about 45 nucleotides in length. The polynucleic acid polymer may be about 40 nucleotides in length. The polynucleic acid polymer may be about 35 nucleotides in length. The polynucleic acid polymer may be about 30 nucleotides in length. The polynucleic acid polymer may be about 25 nucleotides in length. The polynucleic acid polymer may be about 20 nucleotides in length. The polynucleic acid polymer may be about 19 nucleotides in length. The polynucleic acid polymer may be about 18 nucleotides in length. The polynucleic acid polymer may be about 17 nucleotides in length. The polynucleic acid polymer may be about 16 nucleotides in length. The polynucleic acid polymer may be about 15 nucleotides in length. The polynucleic acid polymer may be about 14 nucleotides in length. The polynucleic acid polymer may be about 13 nucleotides in length. The polynucleic acid polymer may be about 12 nucleotides in length. The polynucleic acid polymer may be about 11 nucleotides in length. The polynucleic acid polymer may be about 10 nucleotides in length. The polynucleic acid polymer may be between about 10 and about 50 nucleotides in length. The polynucleic acid polymer may be between about 10 and about 45 nucleotides in length. The polynucleic acid polymer may be between about 10 and about 40 nucleotides in length. The polynucleic acid polymer may be between about 10 and about 35 nucleotides in length. The polynucleic acid polymer may be between about 10 and about 30 nucleotides in length. The polynucleic acid polymer may be between about 10 and about 25 nucleotides in length. The polynucleic acid polymer may be between about 10 and about 20 nucleotides in length. The polynucleic acid polymer may be between about 15 and about 25 nucleotides in length. The polynucleic acid polymer may be between about 15 and about 30 nucleotides in length. The polynucleic acid polymer may be between about 12 and about 30 nucleotides in length.

A polynucleic acid polymer, such as the SSOs, may comprise RNA or DNA. The polynucleic acid polymer, such as the SSOs, may comprise RNA. The polynucleic acid polymer, such as the SSOs, may comprise natural or synthetic or artificial nucleotide analogues or bases, having equivalent complementation as DNA or RNA. The polynucleic acid polymer, such as the SSOs, may comprise combinations of DNA, RNA and/or nucleotide analogues. Nucleotide analogues may comprise PNA or LNA. In another embodiment, the nucleic acid, such as the SSOs, may comprise or consist of PMO.

In some instances, the synthetic or artificial nucleotide analogues or bases can comprise modifications at one or more of ribose moiety, phosphate moiety, nucleoside moiety, or a combination thereof.

Nucleotide analogues or artificial nucleotide base may comprise a nucleic acid with a modification at a 2' hydroxyl group of the ribose moiety. The modification can be a 2'-O-methyl modification or a 2'-O-methoxyethyl (2'-O-MOE) modification. The 2'-O-methyl modification can add a methyl group to the 2' hydroxyl group of the ribose moiety whereas the 2'O-methoxyethyl modification can add a methoxyethyl group to the 2' hydroxyl group of the ribose moiety. Exemplary chemical structures of a 2'-O-methyl modification of an adenosine molecule and 2'O-methoxyethyl modification of an uridine are illustrated below.

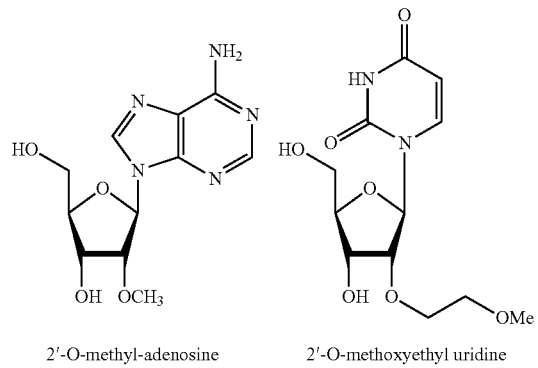

2'-O-methyl-adenosine      2'-O-methoxyethyl uridine

An additional modification at the 2' hydroxyl group can include a 2'-O-aminopropyl sugar conformation which can involve an extended amine group comprising a propyl linker that binds the amine group to the 2' oxygen. This modification can neutralize the phosphate derived overall negative charge of the oligonucleotide molecule by introducing one positive charge from the amine group per sugar and can thereby improve cellular uptake properties due to its zwitterionic properties. An exemplary chemical structure of a 2'-O-aminopropyl nucleoside phosphoramidite is illustrated below.

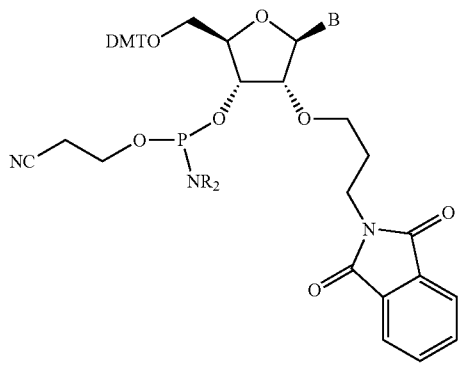

2'-O-aminopropyl nucleoside phosphoramidite

Another modification at the 2' hydroxyl group can include a locked or bridged ribose conformation (e.g., locked nucleic acid or LNA) where the 4' ribose position can also be involved. In this modification, the oxygen molecule bound at the 2' carbon can be linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^3$E) conformation of the furanose ring of an LNA monomer.

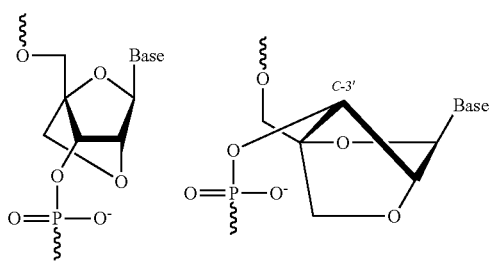

LNA (Locked Nucleic Acids)

A further modification at the 2' hydroxyl group may comprise ethylene nucleic acids (ENA) such as for example 2'-4'-ethylene-bridged nucleic acid, which locks the sugar conformation into a $C_3$'-endo sugar puckering conformation. ENA are part of the bridged nucleic acids class of modified nucleic acids that also comprises LNA. Exemplary chemical structures of the ENA and bridged nucleic acids are illustrated below.

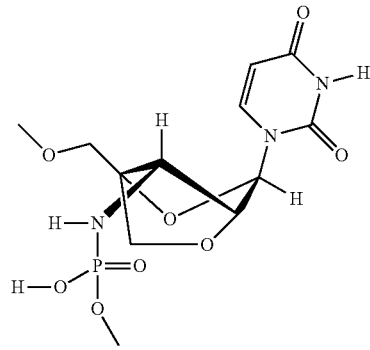

3'-amino-2',4'-BNA

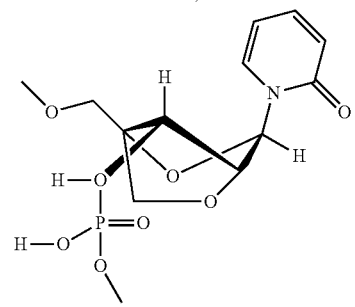

2',4'-BNA-2-pyridone

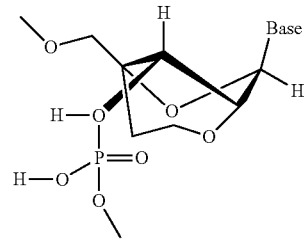

2',4'-ENA

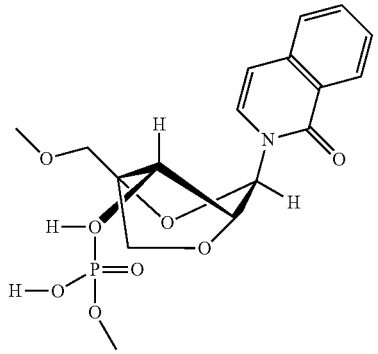

2',4'-BNA-1-isoquinolone

Still other modifications at the 2' hydroxyl group can include 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O—NMA).

Nucleotide analogues may further comprise Morpholinos, peptide nucleic acids (PNAs), methylphosphonate nucleotides, thiolphosphonate nucleotides, 2'-fluoro N3-P5'-phosphoramidites, 1',5'-anhydrohexitol nucleic acids (RNAs), or a combination thereof. Morpholino or phosphorodiamidate morpholino oligo (PMO) comprises synthetic molecules whose structure mimics natural nucleic acid structure by deviates from the normal sugar and phosphate structures. Instead, the five member ribose ring can be substituted with a six member morpholino ring containing four carbons, one nitrogen and one oxygen. The ribose monomers can be linked by a phosphordiamidate group instead of a phosphate group. These backbone alterations can remove all positive and negative charges making morpholinos neutral molecules that can cross cellular membranes without the aid of cellular delivery agents such as those used by charged oligonucleotides.

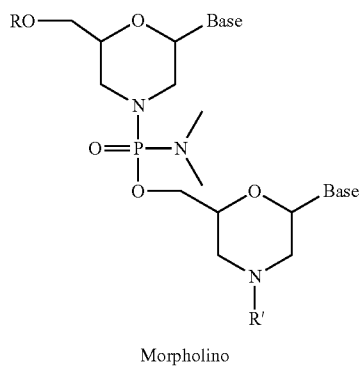

Morpholino

Peptide nucleic acid (PNA) does not contain sugar ring or phosphate linkage. Instead, the bases can be attached and appropriately spaced by oligoglycine-like molecules, therefore, eliminating a backbone charge.

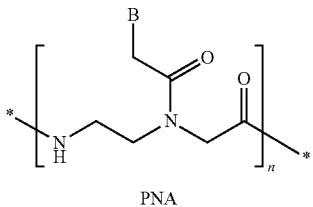

PNA

Modification of the phosphate backbone may also comprise methyl or thiol modifications such as methylphosphonate nucleotide and. Exemplary thiolphosphonate nucleotide (left) and methylphosphonate nucleotide (right) are illustrated below.

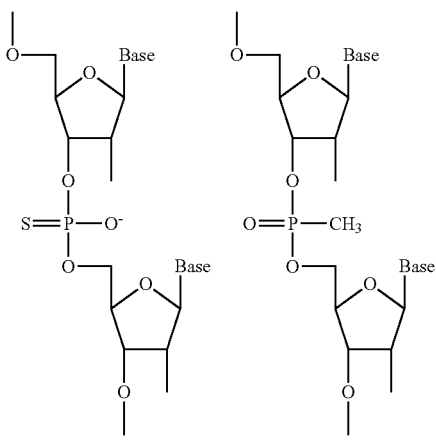

Furthermore, exemplary 2'-fluoro N3-P5'-phosphoramidites is illustrated as:

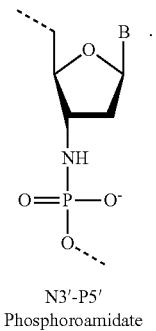

N3'-P5'
Phosphoroamidate

And exemplary hexitol nucleic acid (or 1',5'-anhydrohexitol nucleic acids (HNA)) is illustrated as:

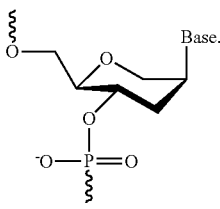

Hexitol Nucleic Acid

In addition to modification of the ribose moiety, phosphate backbone and the nucleoside, the nucleotide analogues can also be modified by for example at the 3' or the 5' terminus. For example, the 3' terminus can include a 3' cationic group, or by inverting the nucleoside at the 3'T-terminus with a 3'-3' linkage. In another alternative, the 3'-terminus can be blocked with an aminoalkyl group, e.g., a 3' C5-aminoalkyl dT. The 5'-terminus can be blocked with an aminoalkyl group, e.g., a 5'-O-alkylamino substituent. Other 5' conjugates can inhibit 5'-3' exonucleolytic cleavage. Other 3' conjugates can inhibit 3'-5' exonucleolytic cleavage.

In some cases, one or more of the artificial nucleotide analogues described herein are resistant toward nucleases such as for example ribonuclease such as RNase H, deoxyribunuclease such as DNase, or exonuclease such as 5'-3' exonuclease and 3'-5' exonuclease when compared to natural polynucleic acid polymers. In some instances, artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O—NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribunuclease such as DNase, or exonuclease such as 5'-3' exonuclease and 3'-5' exonuclease. 2'-O-methyl modified polynucleic acid polymer may be nuclease resistance (e.g., RNase H, DNase, 5'-3' exonuclease or 3'-5' exonuclease resistance). 2'O-methoxyethyl (2'-O-MOE) modified polynucleic acid polymer may be nuclease resistance (e.g., RNase H, DNase, 5'-3' exonuclease or 3'-5' exonuclease resistance). 2'-O-aminopropyl modified polynucleic acid polymer may be nuclease resistance (e.g., RNase H, DNase, 5'-3' exonuclease or 3'-5' exonuclease resistance). 2'-deoxy modified polynucleic acid polymer may be nuclease resistance (e.g., RNase H, DNase, 5'-3' exonuclease or 3'-5' exonuclease resistance). T-deoxy-2'-fluoro modified polynucleic acid polymer may be nuclease resistance (e.g., RNase H, DNase, 5'-3' exonuclease or 3'-5' exonuclease resistance). 2'-O-aminopropyl (2'-O-AP) modified polynucleic acid polymer may be nuclease resistance (e.g., RNase H, DNase, 5'-3' exonuclease or 3'-5' exonuclease resistance). 2'-O-dimethylaminoethyl (2'-O-DMAOE) modified polynucleic acid polymer may be nuclease resistance (e.g., RNase H, DNase, 5'-3' exonuclease or 3'-5' exonuclease resistance). 2'-O-dimethylaminopropyl (2'-O-DMAP) modified polynucleic acid polymer may be nuclease resistance (e.g., RNase H, DNase, 5'-3' exonuclease or 3'-5' exonuclease resistance). T-O-dimethylaminoethyloxyethyl (2'-O-DMAEOE) modified polynucleic acid polymer may be nuclease resistance (e.g., RNase H, DNase, 5'-3' exonuclease or 3'-5' exonuclease resistance). 2'-O—N-methylacetamido (2'-O—NMA) modified polynucleic acid polymer may be nuclease resistance (e.g., RNase H, DNase, 5'-3' exonuclease or 3'-5' exonuclease resistance). LNA modified polynucleic acid polymer may be nuclease resistance (e.g., RNase H, DNase, 5'-3' exonuclease or 3'-5' exonuclease resistance). ENA modified polynucleic acid polymer may be nuclease resistance (e.g., RNase H, DNase, 5'-3' exonuclease or 3'-5' exonuclease resistance). HNA modified polynucleic acid polymer may be nuclease resistance (e.g., RNase H, DNase, 5'-3' exonuclease or 3'-5' exonuclease resistance). Morpholinos may be nuclease resistance (e.g., RNase H, DNase, 5'-3' exonuclease or 3'-5' exonuclease resistance). PNA can be resistant to nucleases (e.g., RNase H, DNase, 5'-3' exonuclease or 3'-5' exonuclease resistance). Methylphosphonate nucleotides modified polynucleic acid polymer may be nuclease resistance (e.g., RNase H, DNase, 5'-3' exonuclease or 3'-5' exonuclease resistance). Thiolphosphonate nucleotides modified polynucleic acid polymer may be nuclease resistance (e.g., RNase H, DNase, 5'-3' exonuclease or 3'-5' exonuclease resistance). Polynucleic acid polymer comprising 2'-fluoro N3-P5'-phosphoramidites may be nuclease resistance (e.g., RNase H, DNase, 5'-3' exonuclease or 3'-5' exonuclease resistance).

In some instances, one or more of the artificial nucleotide analogues described herein have increased binding affinity toward their mRNA target relative to an equivalent natural polynucleic acid polymer. The one or more of the artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O—NMA) modified, LNA, ENA, PNA, HNA, morpholino, methylphosphonate nucleotides, thiolphosphonate nucleotides, or 2'-fluoro N3-P5'-phosphoramidites can have increased binding affinity toward their mRNA target relative to an equivalent natural polynucleic acid polymer. 2'-O-methyl modified polynucleic acid polymer can have increased binding affinity toward their mRNA target relative to an equivalent natural polynucleic acid polymer. 2'-O-methoxyethyl (2'-O-MOE) modified polynucleic acid polymer can have increased binding affinity toward their mRNA target relative to an equivalent natural polynucleic acid polymer. 2'-O-aminopropyl modified polynucleic acid polymer can have increased binding affinity toward their mRNA target relative to an equivalent natural polynucleic acid polymer. 2'-deoxy modified polynucleic acid polymer can have increased binding affinity toward their mRNA target relative to an equivalent natural polynucleic acid polymer. T-deoxy-2'-fluoro modified polynucleic acid polymer can have increased binding affinity toward their mRNA target relative to an equivalent natural polynucleic acid polymer. 2'-O-aminopropyl (2'-O-AP) modified polynucleic acid polymer can have increased binding affinity toward their mRNA target relative to an equivalent natural polynucleic acid polymer. 2'-O-dimethylaminoethyl (2'-O-DMAOE) modified polynucleic acid polymer can have increased binding affinity toward their mRNA target relative to an equivalent natural polynucleic acid polymer. 2'-O-dimethylaminopropyl (2'-O-DMAP) modified polynucleic acid polymer can have increased binding affinity toward their mRNA target relative to an equivalent natural polynucleic acid polymer. T-O-dimethylaminoethyloxyethyl (2'-O-DMAEOE) modified polynucleic acid polymer can have increased binding affinity toward their mRNA target relative to an equivalent natural polynucleic acid polymer. 2'-O—N-methylacetamido (2'-O—NMA) modified polynucleic acid polymer can have increased binding affinity toward their mRNA target relative to an equivalent natural polynucleic acid polymer. LNA modified polynucleic acid polymer can have increased binding affinity toward their mRNA target relative to an equivalent natural polynucleic acid polymer. ENA modified polynucleic acid polymer can have increased binding affinity toward their mRNA target relative to an equivalent natural polynucleic acid polymer. PNA modified polynucleic acid polymer can have increased binding affinity toward their mRNA target relative to an equivalent natural polynucleic acid polymer. HNA modified polynucleic acid polymer can have increased binding affinity toward their mRNA target relative to an equivalent natural polynucleic acid polymer. Morpholino modified polynucleic acid polymer can have increased binding affinity toward their mRNA target relative to an equivalent natural polynucleic acid polymer. Methylphosphonate nucleotides modified polynucleic acid polymer can have increased binding affinity toward their mRNA target relative to an equivalent natural polynucleic acid polymer. Thiolphosphonate nucleotides modified polynucleic acid polymer can have increased binding affinity toward their mRNA target relative to an equivalent natural polynucleic acid polymer. Polynucleic acid polymer comprising 2'-fluoro N3-P5'-phosphoramidites can have increased binding affinity toward their mRNA target relative to an equivalent natural polynucleic acid polymer. The increased affinity can be illustrated with a lower Kd, a higher melt temperature (Tm), or a combination thereof.

In additional instances, a polynucleic acid polymer described herein may be modified to increase its stability. In an embodiment where the polynucleic acid polymer is RNA, the polynucleic acid polymer may be modified to increase its stability. The polynucleic acid polymer may be modified by one or more of the modifications described above to increase its stability. The polynucleic acid polymer may be modified at the 2' hydroxyl position, such as by 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O—NMA) modification or by a locked or bridged ribose conformation (e.g., LNA or ENA). The polynucleic acid polymer may be modified by 2'-O-methyl and/or 2'-O-methoxyethyl ribose.

The polynucleic acid polymer may also include morpholinos, PNAs, HNA, methylphosphonate nucleotides, thiolphosphonate nucleotides, or 2'-fluoro N3-P5'-phosphoramidites to increase its stability. Suitable modifications to the RNA to increase stability for delivery will be apparent to the skilled person.

A polynucleic acid polymer described herein can be constructed using chemical synthesis and/or enzymatic ligation reactions using procedures known in the art. For example, a polynucleic acid polymer can be chemically synthesized using naturally occurring nucleotides or variously modified nucleotides designed to increase the biological stability of the molecules or to increase the physical stability of the duplex formed between the polynucleic acid polymer and target nucleic acids. Exemplary methods can include those described in: U.S. Pat. No. 5,142,047; U.S. Pat. No. 5,185,444; WO2009099942; or EP157901.5. Additional exemplary methods can include those described in: Griffey et al., "2'-O-aminopropyl ribonucleotides: a zwitterionic modification that enhances the exonuclease resistance and biological activity of antisense oligonucleotides," *J. Med. Chem.* 39(26):5100-5109 (1997)); Obika, et al. "Synthesis of 2'-0,4'-C-methyleneuridine and -cytidine. Novel bicyclic nucleosides having a fixed C3, -endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities," Indian Journal of Chemistry 48B:1721-1726 (2009). Alternatively, the polynucleic acid polymer can be produced biologically using an expression vector into which a polynucleic acid polymer has been subcloned in an antisense orientation (i.e.; RNA transcribed from the inserted polynucleic acid polymer will be of an antisense orientation to a target polynucleic acid polymer of interest).

A polynucleic acid polymer may be bound to any nucleic acid molecule, such as another antisense molecule, a peptide, or other chemicals to facilitate delivery of the polynucleic acid polymer and/or target the nucleic acid to a specific tissue, cell type, or cell developmental stage. The polynucleic acid polymer may be bound to a protein or RNA. The protein tethered to the polynucleic acid polymer may comprise a splicing factor to enhance, inhibit or modulate splicing and intron removal. RNA tethered to the polynucleic acid polymer may comprise an aptamer or any structure that enhance, inhibit or modulate splicing and intron removal. The polynucleic acid polymer may be isolated nucleic acid.

A polynucleic acid polymer may be conjugated to, or bound by, a delivery vehicle suitable for delivering the polynucleic acid polymer to cells. The cells may be a specific cell type, or specific developmental stage. The delivery vehicle may be capable of site specific, tissue specific, cell specific or developmental stage-specific delivery. For example, the delivery vehicle may be a cell specific viral particle, or component thereof, alternatively, the delivery vehicle may be a cell specific antibody particle, or component thereof. The polynucleic acid polymer may be targeted for delivery to beta cells in the pancreas. The polynucleic acid polymer may be targeted for delivery to thymic cells. The polynucleic acid polymer may be targeted for delivery to malignant cells. The polynucleic acid polymer may be targeted for delivery to pre-malignant cells (that are known to develop into overt malignant phenotypes within a foreseeable future, such as pre-leukaemias and myelodysplastic syndromes or histopathologically defined precancerous lesions or conditions.

In one embodiment the polynucleic acid polymer may be bound to a chemical molecule (e.g. non-peptide or nucleic acid based molecule), such as a drug. The drug may be a small molecule (e.g. having a MW of less than 900 Da).

In one embodiment of the invention, the delivery vehicle may comprise a cell penetrating peptide (CPP). For example, the polynucleic acid polymer may be bound or complexed with a CPP. The skilled person will understand that any suitable CPP may be conjugated with the polynucleic acid polymer to aid delivery of the polynucleic acid polymer to and/or into cells. Such CPPs may be any suitable CPP technology described by Boisguérin et al. (2015, Advanced Drug Delivery Reviews doi: 10.1016/j.addr.2015.02.008), which is herein incorporated by reference. Suitable delivery vehicles for conjugation to the polynucleic acid polymer are also described in Lochmann et at ((*European Journal of Pharmaceutics and Biopharmaceutics* 58 (2004) 237-251), which is herein incorporated by reference).

The CPP may be an arginine and/or lysine rich peptide, for example, wherein the majority of residues in the peptide is either lysine or arginine. The CPP may comprise a poly-L-lysine (PLL). Alternatively, the CPP may comprise a poly-arginine. Suitable CPPs may be selected from the group comprising Penetratin; R6-Penetratin; Transportan; oligo-arginines; F-3; B-peptide; B-MSP; Pip peptides, such as Pip1, Pip2a, Pip2b, Pip5e, Pip5f, Pip5h, Pip5j; Pip5k, Pip5l, Pip5m, Pip5n, Pip5o, Pip6a, Pip6b, Pip6c, Pip6d, Pip6e, Pip6f, Pip6g, or Pip6h; peptide of sequence PKK-KRKV; Penatratin; Lys$_4$; SPACE; Tat; Tat-DRBD (dsRNA-binding domain); (RXR)$_4$; (RFF)$_3$RXB; (KFF)$_3$K; R$_g$F$_2$; T-cell derived CPP; Pep-3; PEGpep-3; MPG-8; MPG-8-Chol; PepFect6; P5RHH; R$_{15}$; and Chol-R$_9$; or functional variants thereof (e.g. see Boisguérin et al. (2015, Advanced Drug Delivery Reviews doi: 10.1016/j.addr.2015.02.008).

In one embodiment, the CPP comprises or consists of a Pip peptide. The Pip peptide may be selected from the group comprising Pip1, Pip2a, Pip2b, Pip5e, Pip5f, Pip5h, Pip5j; Pip5k, Pip5l, Pip5m, Pip5n, Pip5o, Pip6a, Pip6b, Pip6c, Pip6d, Pip6e, Pip6f, Pip6g, and Pip6h.

In one embodiment of the invention, the delivery vehicle may comprise a peptide-based nanoparticle (PBN), wherein a plurality of CPPs (for example one or more suitable CPPs discussed herein) form a complex with the polynucleic acid polymer through charge interactions. Such nanoparticles may be between about 50 nm and 250 nm in size. In one embodiment the nanoparticles may be about 70-200 nm in size. In another embodiment the nanoparticles may be about 70-100 nm in size or 125-200 nm in size.

In one embodiment, the polynucleic acid polymer may be complexed with a delivery vehicle, for example by ionic bonding. Alternatively, the polynucleic acid polymer may be covalently bound to the delivery vehicle. Conjugation/binding methods are described in Lochmann et at ((*European Journal of Pharmaceutics and Biopharmaceutics* 58 (2004) 237-251), which is herein incorporated by reference). For example, a conjugation method may comprise introducing a suitable tether containing a reactive group (e.g. —NH2 or —SH2) to the polynucleic acid polymer and to add the delivery vehicle, such as a peptide, post-synthetically as an active intermediate, followed by carrying out the coupling reaction in aqueous medium. An alternative method may comprise carrying out the conjugation in a linear mode on a single solid-phase support.

The delivery vehicle and polynucleic acid polymer may be thiol and/or maleimide linked, such as thiol-maleimide linked. The conjugation of the polynucleic acid polymer and the delivery vehicle may be by click-chemistry, such as reaction of azido or 2'-O-propyargyl functional groups and alkyne groups on the respective molecules to be conjugated. In one embodiment, the delivery vehicle and polynucleic acid polymer may be linked by a thioether bridge. In another embodiment, the delivery vehicle and polynucleic acid polymer may be linked by a disulphide bridge. The skilled person will readily identify suitable linking groups or reactions for conjugation of polynucleic acid polymer and the delivery vehicle, such as a peptide.

The gene transcript may encode pro-insulin. The gene transcript may be transcribed from INS gene. The gene transcripts may be derived from a human haplotype expressing low levels of proinsulin. The intron may comprise INS intron 1.

The gene transcript may be transcribed from a gene or ORF selected from any of the genes or ORFs comprising ABCD4; ABCF3; ACADVL; ALKBH6; AP1G2; APEX1; ARFRP1; ATHL1; ATP1A3; ATP5D; ATP13A1; BAX; BDH2; BRD2; C1orf63; C1orf630; C1orf631; C1orf124; C2orf49; C8orf82; C16orf59; CAPRIN2; CDCA7; CEP164; CEP170; CLCN7; CPNE1; CPSF3L; DCXR; DENND4B; DFFA; DIS3L2; DNAJB12; DPF1; DRG2; DSN1; EML3; EWSR1; EWSR10; FGFR4; FTSJ1; GBAP1; GMPPA; GMPR2; GNPTG; GORASP1; GPATCH4; HGS; HMG20B; IFFO1; ISYNA1; KRI1; LOC148413; LZTR1; MAN2C1; MAP4K2; MCOLN1; MDP1; MIB2; MITD1; MOK; MOV10; MRPL35; MTMR11; MUS81; NAPEPLD; NBEAL2; NDRG4; NDUFB10; NFATC4; NFKBIB; NIT1; NKTR; NPRL2; NSUN5P1; NUDT22; PAN2; PDDC1; PDLIM4; PHF1; PIK3CD; PITPNM1; PPIL2; PPP1R35; PPP4C; PQLC2; PRPF39; PSME2; PTPMT1; QARS; RAD52; RHOT2; RMND5B; RNF123; RPL10A; RPP21; RPS6KB2; RUSC1; SCRN2; SCYL1; SFR1; SGSM3; SIRT7; SLC25A3; SLC25A3; SLC30A7; SLC37A4; STK19; STX10; TCF25; TOMM40; TP53I3; TRIM41; TRPT1; TSTA3; TTC14; TTC140; TUBGCP6; U2AF1L4; UCK1; UNC45A; VAMP1; VAMP10; VARS; VPS28; WDR24; WDR90; WRAP53; YDJC; YIPF3; YIPF3; ZCCHC8; ZCCHC18; ZFAND1; ZNF131; ZNF300; ZNF317; ZNF692; ZNF711; ZNRD1; ZWINT; or combinations thereof.

The terms "polynucleic acid polymer" and "nucleic acid" can be used interchangeable and can refer to a polynucleic acid polymer that is between about 10 to about 50 nucleotides in length.

Diseases

The methods and compositions described herein can be used to treat a disease or condition characterized by an impaired production of a protein. The methods and compositions described herein can also be used to treat a disease or condition characterized by a defective splicing. The disease or condition can be a genetic disorder or condition. The genetic disorder or condition can be characterized by an impaired production of a protein. The genetic disorder or condition can also be characterized by a defective splicing. The genetic disorder or condition can be a hereditary disorder, or a nonhereditary defect within one or more locations within the genome. The genetic disorder can be a hereditary disease. The hereditary disease can be characterized by an impaired production of a protein. The hereditary disease can be characterized by a defective splicing. A subject with a hereditary disease can have a genome that comprises a copy of a gene that comprises an exon that when properly transcribed into fully processed mRNA can encode the full-length functional for of the protein. A subject with a hereditary disease can have a genome that comprises a copy of a gene that can comprise a copy of a gene that comprises a set of exons that when properly transcribed into fully processed mRNA can encode the full-length functional form of the protein. A subject with a hereditary disease can have a genome that can comprise a defective copy of the gene, which can be incapable of producing a full-length functional form of the protein.

The genetic disorder or condition can be a nonhereditary defect within one or more locations within the genome. The nonhereditary defect can be a point mutation, a deletion, an insertion, or a frame shift. The genetic disorder or condition associated with the nonhereditary defect can be characterized by an impaired production of a protein. The genetic disorder or condition associated with the nonhereditary defect can be characterized by a defective splicing. A subject with a nonhereditary defect can have a genome that can comprise a copy of a gene that comprises an exon that when properly transcribed into fully processed mRNA can encode the full-length functional for of the protein. A subject with a nonhereditary defect can have a genome that comprises a copy of a gene that can comprise a copy of a gene that comprises a set of exons that when properly transcribed into fully processed mRNA can encode the full-length functional form of the protein. A subject with a nonhereditary defect can have a genome that can comprise a defective copy of the gene, which can be incapable of producing a full-length functional form of the protein.

The genetic disorder or condition can be an autosomal dominant disorder, an autosomal recessive disorder, X-linked dominant disorder, X-linked recessive disorder, Y-linked disorder, mitochondrial disease, or multifactorial or polygenic disorder. Sometimes, a hereditary disease can also be characterized as an autosomal dominant, autosomal recessive, X-linked dominant, X-linked recessive, Y-linked, mitochondrial, or multifactorial or polygenic hereditary disease. Autosomal dominant disorder, an autosomal recessive disorder, X-linked dominant disorder, X-linked recessive disorder, Y-linked disorder, mitochondrial disease, or multifactorial or polygenic disorder can be characterized by an impaired production of a protein. Autosomal dominant disorder, an autosomal recessive disorder, X-linked dominant disorder, X-linked recessive disorder, Y-linked disorder, mitochondrial disease, or multifactorial or polygenic disorder can be characterized by a defective splicing. A subject with an autosomal dominant disorder, an autosomal recessive disorder, X-linked dominant disorder, X-linked recessive disorder, Y-linked disorder, mitochondrial disease, or multifactorial or polygenic disorder can have a genome that can comprise a copy of a gene that comprises an exon that when properly transcribed into fully processed mRNA can encode the full-length functional for of the protein. A subject with an autosomal dominant disorder, an autosomal recessive disorder, X-linked dominant disorder, X-linked recessive disorder, Y-linked disorder, mitochondrial disease, or multifactorial or polygenic disorder can have a genome that comprises a copy of a gene that can comprise a copy of a gene that comprises a set of exons that when properly transcribed into fully processed mRNA can encode the full-length functional form of the protein. A subject with an autosomal dominant disorder, an autosomal recessive disorder, X-linked dominant disorder, X-linked recessive disorder, Y-linked disorder, mitochondrial disease, or multifactorial or polygenic disorder can have a genome that can comprise a defective copy of the gene, which can be incapable of producing a full-length functional form of the protein.

Exemplary hereditary disease can include achondroplasia, hereditary hemochromatosis, Down Syndrome, hereditary spherocytosis, Tay-Sachs Disease, Usher syndrome, hereditary fructose intolerance, hemophilia, muscular dystrophy (e.g., Duchenne muscular dystrophy or DMD), polygenic disorders, breast cancer, ovarian cancer, Parkinson's disease, Bardet-Biedl syndrome, Prader-Willi syndrome, diabetes, heart disease, arthritis, motor neuron disease, albinism, Cri-du-Chat syndrome, cystic fibrosis, fragile X syndrome, galactosemia, Huntington's disease, Jackson-Weiss syndrome, Klinefelter syndrome, Krabbe disease, Langer-Giedion syndrome, Lesch Nyhan syndrome, Marfan syndrome, myotonic dystrophy, Nail-Patella syndrome, neurofibromatosis, Noonan syndrome, triple X syndrome, osteogenesis imperfecta, Patau syndrome, phenylketonuria, porphyria, retinoblastoma, Rett syndrome, sickle cell disease, Turner syndrome, Usher syndrome, Von Hippel-Lindau syndrome, Waardenburg syndrome, Wilson's disease, xeroderma pigmentosum, XXXX syndrome, or YY syndrome.

A hereditary disease such as for example: achondroplasia, hereditary hemochromatosis, Down Syndrome, hereditary spherocytosis, Tay-Sachs Disease, Usher syndrome, hereditary fructose intolerance, hemophilia, muscular dystrophy (e.g., Duchenne muscular dystrophy or DMD), polygenic disorders, breast cancer, ovarian cancer, Parkinson's disease, Bardet-Biedl syndrome, Prader-Willi syndrome, diabetes, heart disease, arthritis, motor neuron disease, albinism, Cri-du-Chat syndrome, cystic fibrosis, fragile X syndrome, galactosemia, Huntington's disease, Jackson-Weiss syndrome, Klinefelter syndrome, Krabbe disease, Langer-Giedion syndrome, Lesch-Nyhan syndrome, Marfan syndrome, myotonic dystrophy, Nail-Patella syndrome, neurofibromatosis, Noonan syndrome, triple X syndrome, osteogenesis imperfecta, Patau syndrome, phenylketonuria, *porphyria*, retinoblastoma, Rett syndrome, sickle cell disease, Turner syndrome, Usher syndrome, Von Hippel-Lindau syndrome, Waardenburg syndrome, Wilson's disease, xeroderma pigmentosum, XXXX syndrome, or YY syndrome can be characterized by an impaired production of a protein, or by a defective splicing. A hereditary disease such as for example: achondroplasia, hereditary hemochromatosis, Down Syndrome, hereditary spherocytosis, Tay-Sachs Disease, Usher syndrome, hereditary fructose intolerance, hemophilia, muscular dystrophy (e.g., Duchenne muscular dystrohy or DMD), polygenic disorders, breast cancer, ovarian cancer, Parkinson's disease, Bardet-Biedl syndrome, Prader-Willi syndrome, diabetes, heart disease, arthritis, motor neuron disease, albinism, Cri-du-Chat syndrome, cystic fibrosis, fragile X syndrome, galactosemia, Huntington's disease, Jackson-Weiss syndrome, Klinefelter syndrome, Krabbe disease, Langer-Giedion syndrome, Lesch-Nyhan syndrome, Madan syndrome, myotonic dystrophy, Nail-Patella syndrome, neurofibromatosis, Noonan syndrome, triple X syndrome, osteogenesis imperfecta, Patau syndrome, phenylketonuria, *porphyria*, retinoblastoma, Rett syndrome, sickle cell disease, Turner syndrome, Usher syndrome, Von Hippel-Lindau syndrome, Waardenburg syndrome, Wilson's disease, xeroderma pigmentosum, XXXX syndrome, or YY syndrome can comprise a copy of a gene that comprises an exon that when properly transcribed into fully processed mRNA can encode the full-length functional for of the protein, can comprises a copy of a gene that can comprise a copy of a gene that comprises a set of exons that when properly transcribed into fully processed mRNA can encode the full-length functional form of the protein, or can comprise a defective copy of the gene, which can be incapable of producing a full-length functional form of the protein.

As described above, the genetic disorder or condition can be an autosomal dominant disorder, an autosomal recessive disorder, X-linked dominant disorder, X-linked recessive disorder, Y-linked disorder, mitochondrial disease, or multifactorial or polygenic disorder. The genetic disorder or condition can be an autosomal dominant disorder, an autosomal recessive disorder, X-linked dominant disorder, X-linked recessive disorder, Y-linked disorder, mitochondrial disease, or multifactorial or polygenic disorder can be a disorder characterized by an impaired production of a protein or by a defective splicing.

Exemplary autosomal dominant disorder can include Huntington's disease, neurofibromatosis type 1, neurofibromatosis type 2, Marfan syndrome, hereditary nonpolyposis colorectal cancer, hereditary multiple exostoses, Tuberous sclerosis, Von Willebrand disease, or acute intermittent porphyria.

An autosomal dominant disorder such as Huntington's disease, neurofibromatosis type 1, neurofibromatosis type 2, Marfan syndrome, hereditary nonpolyposis colorectal cancer, hereditary multiple exostoses, Tuberous sclerosis, Von Willebrand disease, or acute intermittent *porphyria* can be characterized by an impaired production of a protein or by a defective splicing. An autosomal dominant disorder such as Huntington's disease, neurofibromatosis type 1, neurofibromatosis type 2, Marfan syndrome, hereditary nonpolyposis colorectal cancer, hereditary multiple exostoses, Tuberous sclerosis, Von Willebrand disease, or acute intermittent *porphyria* can comprise a copy of a gene that comprises an exon that when properly transcribed into fully processed mRNA can encode the full-length functional for of the protein, can comprises a copy of a gene that can comprise a copy of a gene that comprises a set of exons that when properly transcribed into fully processed mRNA can encode the full-length functional form of the protein, or can comprise a defective copy of the gene, which can be incapable of producing a full-length functional form of the protein.

Exemplary autosomal recessive disorder can include albinism, Medium-chain acyl-CoA dehydrogenase deficiency, cystic fibrosis, sickle-cell disease, Tay-Sachs disease, Niemann-Pick disease, spinal muscular atrophy, or Roberts syndrome.

An autosomal recessive disorder such as: albinism, Medium-chain acyl-CoA dehydrogenase deficiency, cystic fibrosis, sickle-cell disease, Tay-Sachs disease, Niemann-Pick disease, spinal muscular atrophy, or Roberts syndrome can be characterized by an impaired production of a protein or by a defective splicing. An autosomal recessive disorder such as: albinism, Medium-chain acyl-CoA dehydrogenase deficiency, cystic fibrosis, sickle-cell disease, Tay-Sachs disease, Niemann-Pick disease, spinal muscular atrophy, or Roberts syndrome can comprise a copy of a gene that comprises an exon that when properly transcribed into fully processed mRNA can encode the full-length functional for of the protein, can comprises a copy of a gene that can comprise a copy of a gene that comprises a set of exons that when properly transcribed into fully processed mRNA can encode the full-length functional form of the protein, or can comprise a defective copy of the gene, which can be incapable of producing a full-length functional form of the protein.

Exemplary X-linked dominant disorder can include X-linked hypophosphatemic rickets, Rett syndrome, incontinentia pigmenti type 2, Aicardi syndrome, or Klinefelter syndrome.

An X-linked dominant disorder such as: X-linked hypophosphatemic rickets, Rett syndrome, incontinentia pigmenti type 2, Aicardi syndrome, or Klinefelter syndrome can be characterized by an impaired production of a protein or by a defective splicing. An X-linked dominant disorder such as: X-linked hypophosphatemic rickets, Rett syndrome, incontinentia pigmenti type 2, Aicardi syndrome, or Klinefelter syndrome can comprise a copy of a gene that comprises an exon that when properly transcribed into fully processed mRNA can encode the full-length functional for of the protein, can comprises a copy of a gene that can comprise a copy of a gene that comprises a set of exons that when properly transcribed into fully processed mRNA can encode the full-length functional form of the protein, or can comprise a defective copy of the gene, which can be incapable of producing a full-length functional form of the protein.

Exemplary X-linked recessive disorder can include hemophilia A, Duchenne muscular dystrophy, Lesch-Nyhan syndrome, or Turner syndrome.

An X-linked recessive disorder such as: hemophilia A, Duchenne muscular dystrophy, Lesch-Nyhan syndrome, or Turner syndrome can be characterized by an impaired production of a protein or by a defective splicing. An X-linked recessive disorder such as: hemophilia A, Duchenne muscular dystrophy, Lesch-Nyhan syndrome, or Turner syndrome can comprise a copy of a gene that comprises an exon that when properly transcribed into fully processed mRNA can encode the full-length functional for of the protein, can comprises a copy of a gene that can comprise a copy of a gene that comprises a set of exons that when properly transcribed into fully processed mRNA can encode the full-length functional form of the protein, or can comprise a defective copy of the gene, which can be incapable of producing a full-length functional form of the protein.

Exemplary Y-linked disorder can include Swyer syndrome or a form of retinitis pigmentosa.

A Y-linked disorder such as Swyer syndrome or a form of retinitis pigmentosa can be characterized by an impaired production of a protein or by a defective splicing. A Y-linked disorder such as Swyer syndrome or a form of retinitis pigmentosa can comprise a copy of a gene that comprises an exon that when properly transcribed into fully processed mRNA can encode the full-length functional for of the protein, can comprises a copy of a gene that can comprise a copy of a gene that comprises a set of exons that when properly transcribed into fully processed mRNA can encode the full-length functional form of the protein, or can comprise a defective copy of the gene, which can be incapable of producing a full-length functional form of the protein.

Exemplary mitochondrial disease can include Leber's hereditary optic neuropathy.

Mitochondrial disease such as Leber's hereditary optic neuropathy can be characterized by an impaired production of a protein or by a defective splicing. Mitochondrial disease such as Leber's hereditary optic neuropathy can comprise a copy of a gene that comprises an exon that when properly transcribed into fully processed mRNA can encode the full-length functional for of the protein, can comprises a copy of a gene that can comprise a copy of a gene that comprises a set of exons that when properly transcribed into fully processed mRNA can encode the full-length functional form of the protein, or can comprise a defective copy of the gene, which can be incapable of producing a full-length functional form of the protein.

Exemplary multifactorial or polygenic disorder can include heart disease, diabetes, autoimmune diseases such as multiple sclerosis, inflammatory bowel disease, or cancer.

Multifactorial or polygenic disorder such as heart disease, diabetes, autoimmune diseases such as multiple sclerosis, inflammatory bowel disease, or cancer can be characterized by an impaired production of a protein or by a defective splicing. Multifactorial or polygenic disorder such as heart disease, diabetes, autoimmune diseases such as multiple sclerosis, inflammatory bowel disease, or cancer can comprise a copy of a gene that comprises an exon that when properly transcribed into fully processed mRNA can encode the full-length functional for of the protein, can comprises a copy of a gene that can comprise a copy of a gene that comprises a set of exons that when properly transcribed into fully processed mRNA can encode the full-length functional form of the protein, or can comprise a defective copy of the gene, which can be incapable of producing a full-length functional form of the protein.

In some instances, compositions and methods described herein is used to treat a genetic disorder or condition such as a hereditary disease. Compositions and methods described herein can be used to treat a genetic disorder or condition such as a hereditary disease that is characterized by an impaired production of a protein. Compositions and methods described herein can be used to treat a genetic disorder or condition such as a hereditary disease that is characterized by a defective splicing.

Compositions and methods described herein can also be used to treat a genetic disorder or condition such as an autosomal dominant disorder, an autosomal recessive disorder, X-linked dominant disorder, X-linked recessive disorder, Y-linked disorder, mitochondrial disease, or multifactorial or polygenic disorder. Compositions and methods described herein can be used to treat an autosomal dominant disorder, an autosomal recessive disorder, X-linked dominant disorder, X-linked recessive disorder, Y-linked disorder, mitochondrial disease, or multifactorial or polygenic disorder, in which the disorder or condition is characterized by an impaired production of a protein. Compositions and methods described herein can also be used to treat an autosomal dominant disorder, an autosomal recessive disorder, X-linked dominant disorder, X-linked recessive disorder, Y-linked disorder, mitochondrial disease, or multifactorial or polygenic disorder, in which the disorder or condition is characterized by a defective splicing.

In some instances, a disease or condition includes muscular dystrophy, spinal muscular atrophy (SMA), ataxia-telangiectasia, X-linked agammaglobulinaemia, diabetes, or cancer.

Muscular dystrophy is a group of muscle diseases that can weaken the musculoskeletal system and can hamper locomotion. It can be characterized by the progressive skeletal muscle weakness, defects in muscle proteins, and the death of muscle cells and tissues. One common form of muscular dystrophy can be Duchenne muscular dystrophy (DMD). Additional forms of muscular dystrophy can include Becker, limb-girdle, congenital, facioscapulohumeral, myotonic, oculopharyngeal, distal, and Emery-Dreifuss muscular dystrophy.

Spinal muscular atrophy (SMA) is an autosomal recessive disorder that is one of the most common genetic causes of childhood mortality. The main characteristic of the disease can be a progressive loss of spinal cord motor neurons, resulting in skeletal muscle denervation with subsequent weakness, atrophy, and paralysis of voluntary muscles. The SMA locus can be mapped to a complex inverted repeat of ~500 kb on Chromosome 5q13 that contains several genes. The main cause of SMA can be homozygous loss of the telomeric copy of the survivor of motor neuron gene (SMN1) located within the inverted repeat. A duplicated gene within the centromeric copy of the inverted repeat (SMN2) can also be transcribed, but the SMN2 gene does not completely compensate for loss of SMN1 function.

Ataxia-telangiectasia (A-T) or Louis-Bar syndrome is a rare neurodegenerative inherited disease. The term "ataxia" refers to poor coordination and the term "telangiectasia" refers to small dilated blood vessels. Both terms characterize the hallmarks of this disease. AT can impair the cerebellum and additional areas of the brain which can cause impaired movement and coordination. AT can also weaken the immune system thereby increasing infection and can impair DNA repair, thereby increase the risk of cancer. A-T can be associated with a defect in the gene ATM, which is responsible for managing cellular response to multiple form of stress.

X-linked agammaglobulinaemia, also known as X-linked hypogammaglobulinemia, XLA, Bruton type agammaglobulinemia, Bruton syndrome, or Sex-linked agammaglobulinemia, is an X-linked genetic disorder that can affect the body's ability to fight infection. XLA patients lack mature B cells and as a result, lack the necessary antibodies to combat infection. Bruton's tyrosine kinase (BTK) can be associated with mediating B cell development and maturation and the BTK: gene can be associated with XLA.

Diabetes mellitus (DM) (commonly known as diabetes) is a group of metabolic diseases characterized by a high blood sugar level over a prolonged period. Symptoms of diabetes can include weight loss, polyuria or increased urination, polydipsia or increased thirst, and polyphagia or increased hunger. Diabetes can be classified into four categories: type 1, type 2, gestational diabetes, and other specific types of diabetes. Type 1 diabetes can be characterized by a loss of insulin-producing beta cells of the islets of Langerhans in the pancreas, leading to insulin deficiency. Type 2 diabetes can be characterized by insulin resistance, which can also be combined with a reduced insulin secretion. Gestational diabetes can resemble type 2 diabetes, and can involve combination of inadequate insulin secretion and responsiveness. Other specific types of diabetes can include prediabetes, latent autoimmune diabetes of adults (LADA) and congenital diabetes.

Cancer can be a solid tumor or a hematologic malignancy. A solid tumor can be a sarcoma or a carcinoma. Sarcoma can be a cancer of bone, cartilage, fat muscle, vascular or hematopoietic tissues. Exemplary sarcoma can include alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, telangiectatic osteosarcoma.

Carcinoma can be a cancer developed from epithelial cells. Exemplary carcinoma can include adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

Hematologic malignancy is a malignancy of the blood system and can include T-cell based and B-cell based malignancies. Exemplary hematologic malignancy can include myeloid leukaemia, myeloproliferative neoplasias, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, treatment-related T-cell lymphomas, chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, compositions and methods described herein is used to treat muscular dystrophy, spinal muscular atrophy (SMA), ataxia-telangiectasia, X-linked agammaglobulinaemia, diabetes, or cancer. Compositions and methods described herein can be used to treat muscular dystrophy, spinal muscular atrophy (SMA), ataxia-telangiectasia, X-linked agammaglobulinaemia, diabetes, or cancer in which the disease or disorder is associated with an impaired production of a protein. Compositions and methods described herein can be used to treat muscular dystrophy, spinal muscular atrophy (SMA), ataxia-telangiectasia, X-linked agammaglobulinaemia, diabetes, or cancer in which the disease or disorder is characterized by a defective splicing.

The disease may be any genetic condition caused by mutations leading to retention of entire introns in mature transcripts. The disease may be diabetes. The disease may be diabetes type I. The disease may be diabetes type II. In another embodiment, the disease may be cancer. The cancer may be myeloid leukaemia or myeloproliferative neoplasias. The cancer may sustain mutations in any of the spliceosomal components that facilitate recognition of 3' splice sites. The polynucleic acid polymer may be used to increase endogenous expression in a subject with residual β-cell activity. The polynucleic acid polymer may be used to increase expression of proinsulin in other diabetes patients, including those who received transplanted β-cells. The polynucleic acid polymer may be used as antisense therapy of malignant tumours containing mutations in genes encoding U2 components (e.g., >20% of myeloid leukaemias).

In an embodiment where the disease is diabetes, reducing the incidence of intron retention may be during fetal development of the subject. For example a pregnant mother may be administered with the polynucleic acid polymer in order to reduce the intron retention in the fetus.

The subject may be eukaryote. The subject may be mammalian. The subject may be human. The subject may be a non-human primate. The subject may be a non-primate mammal such as a rat, mouse, ferret, dog, cat, or pig. The subject may be a fetus, such as a human fetus.

The method may comprise a step of determining if a disease pathology is caused by an intron retention in a gene transcript prior to treatment. The determination may use any suitable assay or genetic analysis available to the skilled person.

In some instances, detection is done at a nucleic acid level with nucleic acid-based techniques such as in situ hybridization and RT-PCR. Sequencing technologies can include next-generation sequencing technologies such as Helicos True Single Molecule Sequencing (tSMS) (Harris T. D. et al. (2008) Science 320:106-109); 454 sequencing (Roche) (Margulies, M. et al. 2005, Nature, 437, 376-380); SOLiD technology (Applied Biosystems); SOLEXA sequencing (Illumina); single molecule, real-time (SMRT™) technology of Pacific Biosciences; nanopore sequencing (Soni G V and Meller A. (2007) Clin Chem 53: 1996-2001); semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g. Oxford Nanopore, Genia Technologies, and Nabsys). Sequencing technologies can also include Sanger sequencing, Maxam-Gilbert sequencing, Shotgun sequencing, bridge PCR, mass spectrometry based sequencing, microfluidic based Sanger sequencing, microscopy-based sequencing, RNAP sequencing, or hybridization based sequencing.

Sequencing of a gene transcript of interest may also include an amplification step. Exemplary amplification methodologies include, but are not limited to, polymerase chain reaction (PCR), nucleic acid sequence based amplification (NASBA), self-sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR, ligation mediated PCR, or methylation specific PCR.

Additional methods that can be used to obtain a nucleic acid sequence include, e.g., whole-genome RNA expression array, enzyme-linked immunosorbent assay (ELISA), genome sequencing, de novo sequencing, Pacific Biosciences SMRT sequencing, immunohistochemistry (IHC), immunoctyochemistry (ICC), mass spectrometry, tandem mass spectrometry, matrix-assisted laser desorption ionization time of flight mass spectrometry (MALDI-TOF MS), in-situ hybridization, fluorescent in-situ hybridization (FISH), chromogenic in-situ hybridization (CISH), silver in situ hybridization (SISH), digital PCR (dPCR), reverse transcription PCR, quantitative PCR (Q-PCR), single marker qPCR, real-time PCR, nCounter Analysis (Nanostring technology), Western blotting, Southern blotting, SDS-PAGE, gel electrophoresis, and Northern blotting.

In some cases, detection can be done at a protein level, using, for example, immunoprecipitation based assays such as Western blot, or ELISA. Additionally, methods such as electrophoresis and mass spectrometry analysis can also be utilized for detection of a protein of interest.

According to another aspect of the invention, there is provided a method of modulating intron splicing in a cell, comprising hybridizing a polynucleic acid polymer to a region of pre-mRNA, wherein the region comprises or consists of SEQ ID NO: 46, or optionally, a region having at least 95% identity to SEQ ID NO: 46. The region may have at least 98% or 99% identity to SEQ ID NO: 46.

According to another aspect of the invention, there is provided a method of modulating intron splicing in a cell, comprising hybridizing a polynucleic acid polymer to a region of pre-mRNA, wherein the region comprises or consists of SEQ ID NO: 3, or optionally, a region having at least 95% identity to SEQ ID NO: 3. The region may have at least 98% or 99% identity to SEQ ID NO: 3.

According to another aspect of the invention, there is provided a method of modulating intron splicing in a cell, comprising hybridizing a polynucleic acid polymer to a region of pre-mRNA, wherein the region comprises or consists of a sequence complementary to any of the group of sequences comprising SEQ ID NOs: 47 to 434; or combinations thereof.

According to another aspect of the invention, there is provided a method of modulating intron splicing in a cell, comprising hybridizing a polynucleic acid polymer to a region of pre-mRNA, wherein the region comprises or consists of a sequence complementary to a sequence having at least 95% identity to any of the group of sequences comprising SEQ ID NOs: 47 to 434; or combinations thereof. The region may comprise or consist of a sequence complementary to a sequence having at least 98% identity to any of the group of sequences comprising SEQ ID NOs: 47 to 434; or combinations thereof. The region may comprise or consist of a sequence complementary to a sequence having at least 99% identity to any of the group of sequences comprising SEQ ID NOs: 47 to 434; or combinations thereof.

The cell may be in vitro. The cell may be ex vivo. The cell may be a eukaryotic cell or a prokaryotic cell. The cell may be a eukaryotic cell. The cell may be a mammalian cell from human; non-human primate; or non-primate mammals such as cat, rat, mouse, dog, ferret, or pigs. The cell may be a human cell such as from an epithelial cell, connective tissue cell, hormone secreting cell, a nerve cell, a skeletal muscle cell, a blood cell, or an immune system cell. The cell may be a tumor cell such as a solid tumor cell or a hematologic malignant cell.

According to another aspect of the invention, there is provided polynucleic acid polymer which is antisense to at least part of a region of polynucleic acid polymer comprising or consisting of SEQ ID NO: 46, or optionally a region of polynucleic acid polymer comprising or consisting of a sequence having at least 95% sequence identity to SEQ ID NO: 46. The region may have at least 98% or 99% identity to SEQ ID NO: 46.

According to another aspect of the invention, there is provided polynucleic acid polymer which is antisense to at least part of a region of polynucleic acid polymer comprising or consisting of SEQ ID NO: 3, or optionally a region of polynucleic acid polymer comprising or consisting of a sequence having at least 95% sequence identity to SEQ ID NO: 3. The region may have at least 98% or 99% identity to SEQ ID NO: 3.

According to another aspect of the invention, there is provided polynucleic acid polymer which is antisense to at least part of a region of polynucleic acid polymer, wherein the region comprises or consists of a sequence complementary to any of the group of sequences comprising SEQ ID NOs: 47 to 434; or combinations thereof.

According to another aspect of the invention, there is provided polynucleic acid polymer which is antisense to at least part of a region of polynucleic acid polymer, wherein the region comprises or consists of a sequence complementary to any of the group of sequences comprising SEQ ID NOs: 47 to 434; or combinations thereof; or optionally a region of polynucleic acid polymer comprising or consisting of a sequence having at least 95% sequence identity to SEQ ID NOs: 47 to 434. The region may have at least 98% or 99% identity to SEQ ID SEQ ID NOs: 47 to 434.

Reference to being antisense to at least part of a region of polynucleic acid polymer may be understood by the skilled person to mean a region of at least 5 consecutive nucleotides. Reference to being antisense to at least part of a region of polynucleic acid polymer may be understood by the skilled person to mean a region of at least 10 consecutive nucleotides.

According to another aspect of the invention, there is provided polynucleic acid polymer comprising or consisting of a nucleic acid sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof.

According to another aspect of the invention, there is provided polynucleic acid polymer comprising or consisting of a nucleic acid sequence having at least 99% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof. According to another aspect of the invention, there is provided polynucleic acid polymer comprising or consisting of a nucleic acid sequence having at least 98% identity to a sequence selected from any of the group comprising SEQ ID NO: 1; SEQ ID NO: 2; SEQ ID NO: 4; SEQ ID NO: 5; SEQ ID NO: 7; SEQ ID NO: 8; SEQ ID NO: 10; SEQ ID NO: 11; SEQ ID NO: 13; SEQ ID NO: 14; SEQ ID NO: 16; SEQ ID NO: 17; SEQ ID NO: 19; SEQ ID NO: 20; SEQ ID NO: 22; SEQ ID NO: 23; SEQ ID NO: 25; SEQ ID NO: 26; SEQ ID NO: 28; SEQ ID NO: 29; SEQ ID NO: 31; SEQ ID NO: 32; SEQ ID NO: 34; SEQ ID NO: 35; SEQ ID NO: 37; SEQ ID NO: 38; SEQ ID NO: 40; SEQ ID NO: 41; SEQ ID NO: 43; and SEQ ID NO: 44; or combinations thereof.

According to another aspect of the invention, there is provided polynucleic acid polymer comprising or consisting of a nucleic acid sequence selected from any of the group comprising SEQ ID NOs: 47 to 434; or combinations thereof. It is understood that uracil nucleotides may be substituted with thymine nucleotides (e.g. the DNA form of the RNA of such sequences).

According to another aspect of the invention, there is provided polynucleic acid polymer comprising or consisting of a nucleic acid sequence having at least 99% identity to a sequence selected from any of the group comprising SEQ ID NOs: 47 to 434; or combinations thereof. According to another aspect of the invention, there is provided polynucleic acid polymer comprising or consisting of a nucleic acid sequence having at least 98% identity to a sequence selected from any of the group comprising SEQ ID NOs: 47 to 434; or combinations thereof. According to another aspect of the invention, there is provided polynucleic acid polymer comprising or consisting of a nucleic acid sequence having at least 95% identity to a sequence selected from any of the group comprising SEQ ID NOs: 47 to 434; or combinations thereof. It is understood that uracil nucleotides may be substituted with thymine nucleotides (e.g. the DNA form of the RNA of such sequences).

The polynucleic acid polymer may be isolated polynucleic acid polymer. The polynucleic acid polymer may be conjugated to, or bound by, a delivery vehicle suitable for delivering the polynucleic acid polymer to cells. The delivery vehicle may be capable of site specific, tissue specific or cell specific delivery. For example, the delivery vehicle may be a cell specific viral particle, or component thereof, alternatively, the delivery vehicle may be a cell specific antibody particle, or component thereof. The polynucleic acid polymer may be targeted for delivery to beta cells in the pancreas. The polynucleic acid polymer may be targeted for delivery to thymic cells. The polynucleic acid polymer may be targeted for delivery to malignant cells. The polynucleic acid polymer may be modified to increase its stability. In an embodiment where the polynucleic acid polymer is RNA the polynucleic acid polymer may be modified to increase its stability. The polynucleic acid polymer may be modified by 2'-O-methyl and 2'-O-methoxyethyl ribose. Suitable modifications to the RNA to increase stability for delivery will be apparent to the skilled person.

The polynucleic acid polymer may be part of a plasmid vector. The polynucleic acid polymer may be part of a viral vector. The polynucleic acid polymer may be encoded on a viral vector.

According to another aspect of the invention, there is provided a vector comprising the polynucleic acid polymer of the invention. The vector may comprise a viral vector. The viral vector may comprise adeno-associated viral vector. The vector may comprise any virus that targets the polynucleic acid polymer to malignant cells or specific cell type.

According to another aspect of the invention, there is provided a delivery vehicle comprising, or bound to, the polynucleic acid polymer of the invention. The delivery vehicle may comprise a lipid-based nanoparticle; a cationic cell penetrating peptide (CPP); or a linear or branched cationic polymer; or a bioconjugate, such as cholesterol, bile acid, lipid, peptide, polymer, protein, or an aptamer, which is conjugated to the polynucleic acid polymer for intracellular delivery and/or improved stability. The delivery vehicle may be cell or tissue specific or developmental stage specific. The delivery vehicle may comprise an antibody, or part thereof. The antibody may be specific for a cell surface marker on the cell of interest for delivery of the polynucleic acid polymer to the specific cell. For example, the antibody may comprise an anti-GAD antibody for targeted non-viral polynucleic acid polymer delivery to islet beta cells according to Ji Hoon Jeong et al (Journal of Controlled Release 107 (2005) 562-570), incorporated herein by reference. For example, the anti-GAD antibody conjugating anti-GAD Fab' fragment to PEI via a PEG linker (PEI-PEG-Fab'). Other specific antibodies may be used in such a conjugation for targeted tissue delivery of the polynucleic acid polymer.

Pharmaceutical Composition/Formulations, Dosing, and Treatment Regimens

According to one aspect of the invention, there is provided a therapeutic agent for the treatment of a disease or condition characterized by impaired production of a functional form of a protein which comprises administering to the subject a pharmaceutical composition comprising a therapeutic agent that induces an increase in splicing out of an intron in a partially processed mRNA transcript, wherein the subject has a pool of partially processed mRNA transcripts, which are capable of encoding copies of the full-length functional form of the protein and each of which comprise at least one retained intron that inhibits translation of the partially processed mRNA transcripts; and contacting a target cell of the subject with the therapeutic agent to induce a portion of the pool of the partially processed mRNA transcripts to undergo splicing to remove the at least one retained intron from each of the partially processed mRNA transcripts in the portion, to produce fully processed mRNA transcripts, wherein the fully processed mRNA transcripts are translated to express copies of the full-length functional form of the protein, which treat the disease or condition.

The therapeutic agent can causes activation of one or more splicing protein complexes in the cell to remove the at least one retained intron from each of the partially processed mRNA transcripts in the portion of the pool of the partially processed mRNA transcripts. The therapeutic agent can inhibit a protein that regulates intron splicing activity. The therapeutic agent can activate a protein that regulates intron splicing activity. The therapeutic agent may interact or bind to a protein that regulates intron splicing activity. The therapeutic agent may interact or bind to target polynucleotide sequence of the partially processed mRNA transcripts. In some embodiments the therapeutic agent can be a polynucleic acid polymer, such as the polynucleic acid polymers described herein. In some embodiments, the therapeutic agent can be a small molecule.

The small molecule can be a molecule of less than 900 Daltons, and can initiate one or more splicing protein complexes in the cell to remove the at least one retained intron from each of the partially processed mRNA transcripts in the portion of the pool of the partially processed mRNA transcripts. The small molecule can inhibit a protein that regulates intron splicing activity. The small molecule can activate a protein that regulates intron splicing activity. The small molecule may interact or bind to a protein that regulates intron splicing activity, or may interact or bind to target polynucleotide sequence of the partially processed mRNA transcripts.

According to another aspect of the invention, there is provided a composition comprising the polynucleic acid polymer of the invention. The composition may be a pharmaceutically acceptable composition. The composition may comprise a pharmaceutically acceptable carrier. The composition may comprise an additional active agent, such as a drug or pro-drug. The composition may comprise combinations of different polynucleic acid polymers, such as SSOs, for therapy.

The composition may comprise at least one other biologically active molecule in addition to the polynucleic acid polymer. The biologically active molecule may be drug or a pro-drug. The biologically active molecule may comprise nucleic acid or amino acid. The biologically active molecule may comprise a small molecule (e.g. a molecule of <900 Daltons).

A pharmaceutical composition described herein may comprise a polynucleic acid polymer that hybridizes to a target sequence of a partially processed mRNA transcript which encodes a protein and which comprises a retained intron, wherein the target sequence is in between two G quadruplexes, wherein the polynucleic acid polymer is capable of inducing splicing out of the retained intron from the partially processed mRNA transcript; and a pharmaceutically acceptable excipient and/or a delivery vehicle. The pharmaceutical composition described herein may also comprise a polynucleic acid polymer that hybridizes to a target sequence of a partially processed mRNA transcript which encodes a protein and which comprises a retained intron, wherein the polynucleic acid polymer hybridizes to an intronic splicing regulatory element of the partially processed mRNA transcript, wherein the intronic splicing regulatory element comprises a first CCC motif, and wherein the polynucleic acid polymer is capable of inducing splicing out of the retained intron from the partially processed mRNA transcript; and a pharmaceutically acceptable excipient and/or a delivery vehicle. In addition, the pharmaceutical composition described herein may comprise a polynucleic acid polymer that hybridizes to a target sequence of a partially processed mRNA transcript which encodes a protein and which comprises a retained intron, wherein the polynucleic acid polymer hybridizes to a binding motif of the partially processed mRNA transcript, wherein the binding motif does not form a G quadruplex, and wherein the polynucleic acid polymer is capable of inducing splicing out of the retained intron from the partially processed mRNA transcript; and a pharmaceutically acceptable excipient and/or a delivery vehicle.

A pharmaceutical composition described herein may further comprise a polynucleic acid polymer that hybridizes to a target sequence of a partially processed mRNA transcript which encodes a protein and which comprises a retained intron, wherein the polynucleic acid polymer hybridizes to a binding motif of the partially processed mRNA transcript, and wherein the binding motif forms a hairpin structure, wherein the polynucleic acid polymer is capable of inducing splicing out of the retained intron from the partially processed mRNA transcript; and a pharmaceutically acceptable excipient and/or a delivery vehicle.

A pharmaceutical formulations described herein can be administered to a subject by multiple administration routes, including but not limited to, parenteral (e.g., intravenous, subcutaneous, intramuscular), oral, intranasal, buccal, topical, rectal, or transdermal administration routes. In some instances, the pharmaceutical composition describe herein is formulated for parenteral (e.g., intravenous, subcutaneous, intramuscular) administration. In other instances, the pharmaceutical composition describe herein is formulated for oral administration. In still other instances, the pharmaceutical composition describe herein is formulated for intranasal administration.

A pharmaceutical formulations described herein may include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

A pharmaceutical formulations may include a carrier or carrier materials which may include any commonly used excipients in pharmaceutics and should be selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials may include, but are not limited to, *acacia*, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

A pharmaceutical formulations may include dispersing agents, and/or viscosity modulating agents which may include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum *acacia*, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

A pharmaceutical formulations may include pH adjusting agents or buffering agents which may include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

A pharmaceutical formulation may also include one or more salts in an amount required to bring osmolality of the composition into an acceptable range. Such salts may include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

A pharmaceutical formulations may further include diluent which may also be used to stabilize compounds because they can provide a more stable environment. Salts dissolved in buffered solutions (which also can provide pH control or maintenance) can be utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar;

monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

A pharmaceutical formulations may include disintegration agents or disintegrants to facilitate the breakup or disintegration of a substance. The term "disintegrate" can include both the dissolution and dispersion of the dosage form when contacted with gastrointestinal fluid. Examples of disintegration agents can include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

A pharmaceutical formulations may include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

A pharmaceutical formulations may include flavoring agents and/or sweeteners" such as for example, *acacia* syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof.

Lubricants and glidants may also be included in the pharmaceutical formulations described herein which can prevent, reduce or inhibit adhesion or friction of materials. Exemplary lubricants can include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers can be compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers can include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers can include compounds such as any antioxidation agents, buffers, acids, preservatives and the like.

Suspending agents can include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum *acacia*, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants can include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants can include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants may be included to enhance physical stability or for other purposes.

Viscosity enhancing agents can include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, *acacia*, chitosans and combinations thereof.

Wetting agents can include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Injectable Formulations

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Oral Formulations

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients can include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores can be provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Solid dosage forms may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other instances, the pharmaceutical formulation is in the form of a powder. In still other instances, the pharmaceutical formulation is in the form of a tablet, including but not limited to, a fast-melt tablet. Additionally, pharmaceutical formulations described herein may be administered as a single capsule or in multiple capsule dosage form. In some cases, the pharmaceutical formulation is administered in two, or three, or four, capsules or tablets.

The pharmaceutical solid dosage forms can include a composition described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences,* 20th Edition (2000).

Suitable carriers for use in the solid dosage forms can include, but are not limited to, *acacia*, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms can include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as *acacia*, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

Suitable lubricants or glidants for use in the solid dosage forms can include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms can include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms can include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms can include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms can include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum *acacia*, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms include, for example, e.g., butylated hydroxytoluene (BHT), sodium ascorbate, and tocopherol.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another aspect, an aqueous suspension can be re-suspended into a homogenous suspension by physical agitation lasting less than 45 seconds. In yet another aspect, an aqueous suspension can be re-suspended into a homogenous suspension by physical agitation lasting less than 30 seconds. In still another embodiment, no agitation is necessary to maintain a homogeneous aqueous dispersion.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

Plasticizers may include polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compositions may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

Intranasal Formulations

Intranasal formulations are known in the art and are described in, for example, U.S. Pat. Nos. 4,476,116 and 6,391,452. Formulations that include the compositions described herein, which are prepared according to the above described and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in Remington: The Science and Practice of Pharmacy, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation described herein may be in a form as an aerosol, a mist or a powder. Pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Therapeutic Regimens

The compositions may be administered for therapeutic applications or as a maintenance therapy, for example for a patient in remission. The composition may be administered once per day, twice per day, three times per day or more. The composition may be administered daily, every day, every alternate day, five days a week, once a week, every other week, two weeks per month, three weeks per month, once a month, twice a month, three times per month, or more. The composition may be administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, the severity of the disease, the identity (e.g., weight) of the subject or host in need of treatment, but can nevertheless be routinely determined in a manner known in the art according to the particular circumstances surrounding the case, including, e.g., the specific agent being administered, the route of administration, and the subject or host being treated. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it can be expressed as the ratio between LD50 and ED50. Compounds exhibiting high therapeutic indices are preferred. The data obtained from cell culture assays and animal studies can be used in formulating a range of dosage for use in human. The dosage of such compounds lies preferably within a range of circulating concentrations that include the ED50 with minimal toxicity. The dosage may vary within this range depending upon the dosage form employed and the route of administration utilized.

According to another aspect of the invention, there is provided a method of selecting a subject for treatment, comprising determining if the subject has a disease induced by defective protein expression caused by the intron retention in gene transcripts, wherein the subject is selected for treatment upon positive confirmation; and optionally treating the subject.

The treatment may comprise correction of intron retention in the gene transcripts. The treatment may comprise hybridizing a polynucleic acid polymer according to the invention to the gene transcript in order to induce intron removal from the gene transcript.

According to another aspect of the invention, there is provided the use of antisense polynucleic acid polymer to normalize gene expression by correction of retention of introns in cancer cells.

According to another aspect of the invention, there is provided the polynucleic acid polymer according to the invention, the composition according to the invention, the vector according to the invention, or the delivery vehicle according to the invention, for use in the treatment or prevention of a disease.

According to another aspect of the invention, there is provided the polynucleic acid polymer according to the invention, the composition according to the invention, the vector according to the invention, or the delivery vehicle according to the invention, for use in the manufacture of a medicament for the treatment or prevention of a disease.

The disease may be diabetes or cancer.

Where reference is made to a polynucleic acid polymer sequence, the skilled person will understand that one or more substitutions may be tolerated, optionally two substitutions may be tolerated in the sequence, such that it maintains the ability to hybridize to the target sequence, or where the substitution is in a target sequence, the ability to be recognized as the target sequence. References to sequence identity may be determined by BLAST sequence alignment kwww.ncbi.nlm.nih.gov/BLAST/) using standard/default parameters. For example, the sequence may have 99% identity and still function according to the invention. In other embodiments, the sequence may have 98% identity and still function according to the invention. In another embodiment, the sequence may have 95% identity and still function according to the invention.

Where reference is made to reducing or correcting intron retention, the reduction may be complete, e.g. 100%, or may be partial. The reduction may be clinically significant. The reduction/correction may be relative to the level of intron retention in the subject without treatment, or relative to the amount of intron retention in a population of similar subjects. The reduction/correction may be at least 10% less intron retentions relative to the average subject, or the subject prior to treatment. The reduction may be at least 20% less intron retentions relative to an average subject, or the subject prior to treatment. The reduction may be at least 40% less intron retentions relative to an average subject, or the subject prior to treatment. The reduction may be at least 50% less intron retentions relative to an average subject, or the subject prior to treatment. The reduction may be at least 60% less intron retentions relative to an average subject, or the subject prior to treatment. The reduction may be at least 80% less intron retentions relative to an average subject, or the subject prior to treatment. The reduction may be at least 90% less intron retentions relative to an average subject, or the subject prior to treatment.

Kits/Articles of Manufacture

Kits and articles of manufacture are provided herein for use with one or more methods described herein. The kits can contain one or more of the polynucleic acid polymers described herein, such as the polynucleic acid polymers identified as SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 13, SEQ ID NO: 14, SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 29, SEQ ID NO: 31, SEQ ID NO: 32, SEQ ID NO: 34, SEQ ID NO: 35, SEQ ID NO: 37, SEQ ID NO: 38, SEQ ID NO: 40, SEQ ID NO: 41, SEQ ID NO: 43, or SEQ ID NO: 44. The kits can also contain one or more of the polynucleic acid polymers that are antisense to polynucleic acid polymers described herein, such as for example SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 46, or SEQ ID NOs: 47-434. The kits can further contain reagents, and buffers necessary for the makeup and delivery of the polynucleic acid polymers.

The kits can also include a carrier, package, or container that is compartmentalized to receive one or more containers such as vials, tubes, and the like, each of the container(s) comprising one of the separate elements, such as the polynucleic acid polymers and reagents, to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

EXAMPLES

These examples are provided for illustrative purposes only and not to limit the scope of the claims provided herein.

Example 1

Most eukaryotic genes contain intervening sequences or introns that must be accurately removed from primary transcripts to create functional mRNAs capable of encoding proteins (1). This process modifies mRNP composition in a highly dynamic manner, employing interdependent interactions of five small nuclear RNAs and a large number of proteins with conserved but degenerate sequences in the pre-mRNA (2). Intron splicing generally promotes mRNA accumulation and protein expression across species (3-5). This process can be altered by intronic mutations or variants that may also impair coupled gene expression pathways, including transcription, mRNA export and translation. This is best exemplified by introns in the 5'untranslated region (5'UTR) where natural variants or mutations modifying intron retention alter the relative abundance of transcripts with upstream open reading frames (uORFs) or other regulatory motifs and dramatically influence translation (6,7). However, successful sequence-specific strategies to normalize gene expression in such situations have not been developed.

Splice-switching oligonucleotides (SSOs) are antisense reagents that modulate intron splicing by binding splice-site recognition or regulatory sequences and competing with cis- and trans-acting factors for their targets (8). They have been shown to restore aberrant splicing, modify the relative expression of existing mRNAs or produce novel splice variants that are not normally expressed (8). Improved stability of targeted SSO-RNA duplexes by a number of SSO modifications, such as 2'-O-methyl and 2'-O-methoxyethyl ribose, facilitated studies exploring their therapeutic potential for a growing number of human disease genes, including DMD in muscular dystrophy (9,10), SMN2 in spinal muscular atrophy (11), ATM in ataxia-telangiectasia (12) and BTK in X-linked agammaglobulinemia (13). Although such approaches are close to achieving their clinical potential for a restricted number of diseases (8), >300 Mendelian disorders resulting from mutation-induced aberrant splicing (14) and a growing number of complex traits may be amenable to SSO-mediated correction of gene expression.

Etiology of type 1 diabetes has a strong genetic component conferred by human leukocyte antigens (HLA) and a number of modifying non-HLA loci (15). The strongest modifier was identified in the proinsulin gene (INS) region on chromosome 11 (termed IDDM2) (15). Further mapping of this area suggested that INS is the most likely IDDM2 target (16), consistent with a critical role of this autoantigen in pathogenesis (17). Genetic risk to this disease at IDDM2 has been attributed to differential steady-state RNA levels from predisposing and protective INS haplotypes, potentially involving a minisatellite DNA sequence upstream of this gene (18,19). However, systematic examination of naturally occurring INS polymorphisms revealed haplotype-specific proinsulin expression levels in reporter constructs devoid of the minisatellite sequence, resulting from two variants in intron 1 (7), termed IVS1+5ins4 (also known as rs3842740 or INS-69) and IVS1-6A/T (rs689, INS-27 or HphI+/−) (16,20). The former variant activates a cryptic 5' splice site of intron 1 whereas adenine (A) at the latter variant, which resides 6 nucleotides upstream of the 3' splice site (3'ss), promotes intron retention, expanding the relative abundance of transcripts with extended 5'UTR (21). As compared to thymine (T), the A allele at IVS1-6A/T decreases affinity to pyrimidine-binding proteins in vitro and renders the 3'ss more dependent on the auxiliary factor of U2 small nuclear ribonucleoprotein (U2AF) (7), a heterodimer required for U2 binding, spliceosome assembly and 3'ss selection (22). Intron 1-containing transcripts are overrepresented in IVS1-6A-derived cDNA libraries prepared from insulin producing tissues (21), are exported from the nucleus (23) and contain a short, Homininae-specific uORF that co-evolved with relaxation of the 3'ss of intron 1 in higher primates (7). The lower proinsulin expression conferred by the A allele may lead to suboptimal presentation of proinsulin peptides in the fetal thymus and inadequate negative selection of autoreactive T cells, culminating in autoimmune destruction of insulin-producing β cells in the pancreas (7). However, no attempts have been made to correct the low efficiency of INS intron 1 removal from the IVS1-6A-containing pre-mRNAs and reduce intron retention to the levels observed for the disease-protective T allele.

This study set out to search for SSOs that increase the efficiency of INS intron 1 splicing and repress splicing silencers or decoy splice sites in the pre-mRNA to enhance proinsulin expression. SSOs reducing the relative abundance of intron 1-retaining transcripts were identified, delineation of the optimized antisense target at a single-nucleotide resolution is shown, and evidence is shown for formation of a parallel G-quadruplex adjacent to the antisense target sequence and identification of proteins that bind to this region.

Materials and Methods

Antisense Oligonucleotides

SSOs were purchased from the MWG Biotech (Germany). All SSOs and scrambled controls had a full-length phos-phorothioate backbone with 2'-O-methyl ribonucleotides at the second ribose position. Apart from INS SSOs and their scrambled versions, we employed SSOs that target other human genes as additional controls, as described (13). Location of each SSO is shown in FIG. 1A and their sequences in Table 2.

Splicing Reporter Constructs

The wild-type splicing reporter carrying the type 1 diabetes associated haplotype termed IC was reported previously (7, 21). Each construct contains all INS exons and unabridged introns but differ in the length of the last exon. The IC reporters were cloned using primers D-C, D-F and D-B; IC D-B lacks the cryptic 3'ss of intron 2. The relative abundance of isoforms spliced to this site is lower for IC DF than for IC D-C (7, 21). To test SSOs targeting the cryptic 5' splice site of intron 1, the IC construct was modified by a 4-nt insertion at rs3842740 to create a reporter termed ICIVS1+5ins4. TSC2 and F9 constructs were reported previously (24). Plasmids were propagated in the E. coli strain DH5a and plasmid DNA was extracted using the Wizard Plus SV Miniprep kit (Promega, USA). Their inserts were completely sequenced to confirm the identity of each of the 14 intragenic natural variants and to exclude undesired mutations.

Cell Cultures and Transfections

Human embryonic kidney 293 (HEK293), human hepatocellular liver carcinoma HepG2 and African green monkey COS7 cells were cultured in Dulbecco's modified Eagle medium, 10% fetal calf serum and penicillin/streptomycin (Life technologies, USA). Transient transfections were carried out as described (13), using jetPRIME (Polyplus, USA) according to manufacturer's recommendations. Downregulation of U2AF35 by RNA interference (RNAi) to induce cryptic 3'ss of intron 1 was performed with two hits of small interfering RNA (siRNA) U2AF35ab, as reported earlier (7,25); siRNA duplex targeting DHX36 was as described (26). The second hit was applied 24 h before the addition of SSOs and/or reporter. Cell cultures were harvested 24 h after addition of reporter constructs.

Analysis of Spliced Products

Total RNA was extracted with TRI Reagent and treated with DNase (Life technologies, USA). The first-strand cDNA was reverse transcribed using oligo-(dT)15 primers and Moloney murine virus reverse transcriptase (Promega, USA). Polymerase chain reaction (PCR) was carried out with a combination of a vector-specific primer PL3 and primer E targeting the 3'UTR, as reported previously (7). PCR products were separated on polyacrylamide gels and their signal intensity was measured as described (27). The identity of each mRNA isoform was confirmed by Sanger nucleotide sequencing.

Circular Dichroism and Nuclear Magnetic Resonance Spectroscopy

Oligoribonucleotides for circular dichroism (CD) and nuclear magnetic resonance (NMR) were purchased from Thermo Scientific, deprotected according to manufacturer's instructions, lyophilized and stored at −20° C. Stock solutions were prepared from the desalted, lyophilized samples by resuspending in milliQ water or KCl buffer (100 mM KCl, 10 m MK$_2$HPO4/KH2PO$_4$, pH 7.0, milliQ water) to a final concentration of 2-4 µM. CDspectra were acquired using a PiStar-180 spectrophotometer (Applied Photophysics Ltd, Surrey, UK), equipped with a LTD6G circulating water bath (Grant Instruments, UK) and thermoelectric temperature controller (Melcor, USA). Samples were heated in the cell to 95° C. for a total period of 15 min, samples were then annealed by allowing to cool to room temperature for a minimum period of 4 h. CD spectra were recorded over a wavelength range of 215-340 nm using a 1 cm path length strain-free quartz cuvette and at the temperatures indicated. Data points recorded at 1 nm intervals. A bandwidth of 3 nm was used and 5000 counts acquired at each point with adaptive sampling enabled. Each trace is shown as the mean of three scans (±SD). CD temperature ramps were acquired at 265 nm corresponding to the band maxima of the folded quadruplex species. Ranges between 5 and 99° C. were used, with points acquired at 0.5° C. intervals with a 120-180 s time step between 0.5° C. increments. Points were acquired with 10,000 counts and adaptive sampling enabled. Heating and cooling studies were compared to check for hysteresis and overall reversibility. NMR spectra (1H) were collected at 800 MHz using a Bruker Avance III spectrometer with a triple resonance cryoprobe. Standard Bruker acquisition parameters were used. Data were collected using Topspin (v. 3.0) and processed in CCPN Analysis (v. 2.1).

Pull-Down Assays and Western Blotting

In vitro transcription was carried out using MEGAshortscript™ T7 (LifeTechnologies, USA) and T7-tagged PCR products amplified with primers 5'-ATTAATACGACTCAC-TATAGGGCTCAGGGTTCCAGG (SEQ ID NO: 463) and 5'-TGCAGCAGGGAGGACG (SEQ ID NO: 464), and DNA of the indicated plasmids as a template. Indicated synthetic RNAs were purchased from Eurofins UK. Five hundred pmols of each RNA was treated with 5 mM sodium m-periodate and bound to adipic acid dehydrazide agarose beads (Sigma, USA). Beads with bound RNAs were washed three times in 2 ml of 2 M NaCl and three times in buffer D (20 mM HEPES-KOH, pH 7, 6.5% v/v glycerol, 100 mM KCl, 0.2 mM EDTA, 0.5 mM dithiothreitol), incubated with HeLa nuclear extracts and buffer D with heparin at a final concentration of 0.5 mg/ml. Unbound proteins were washed five times with buffer D. Bound proteins were separated on 10% sodium dodecyl sulphate polyacrylamide gel electrophoresis, stained by Coomassie blue and/or blotted nitrocellulose membranes.

Western blotting was carried out as described (7). Antibodies were purchased from Sigma (hnRNP E1/E2, product number R4155, U2AF65, product number U4758 and SFRS2, product number S2320), Abcam (DHX36, product number ab70269) and Millipore (SC35, clone 1SC-4F11). Antiserum against hnRNP F and hnRNP H provided by Prof Douglas Black, UCLA.

Mass Spectrometry Analysis

Following trypsin digestion, samples were freeze dried and resuspended with 25 µl of 5% ACN/0.1% formic acid for mass spectrometry (MS). Peptides were analysed by LC/MS/MS using a Surveyor LC system and LCQ Deca XP Plus (ThermoScientific). The raw data files were converted into mascot generic files using the MassMatrix File Conversion Tool (Version 2.0; http://www.massmatrix.net) for input into the Mascot searching algorithm (Matrix Science).

Enzymatic Structural Probing

RNA secondary structure determination with the use of limited V1 RNAse (Ambion), T1 RNAse (Ambion) and S1 nuclease (Fermentas) digestion has been described in detail elsewhere (28). Briefly, 1 µg aliquots of RNAs from the insertion (ins) and deletion (del) pre-mRNAs were digested with 0.002 U of RNAse V1, 0.05 U of RNAse T1 and 19 U of S1 nuclease in a 100 µl at 30.0 for 10 min. An enzyme free aliquot was used as a control (C). The cleaved RNAs were retro-transcribed according to standard protocols using antisense primers labeled with [$^{32}$P]-ATP at the 5' end.

Results

Figure 2:
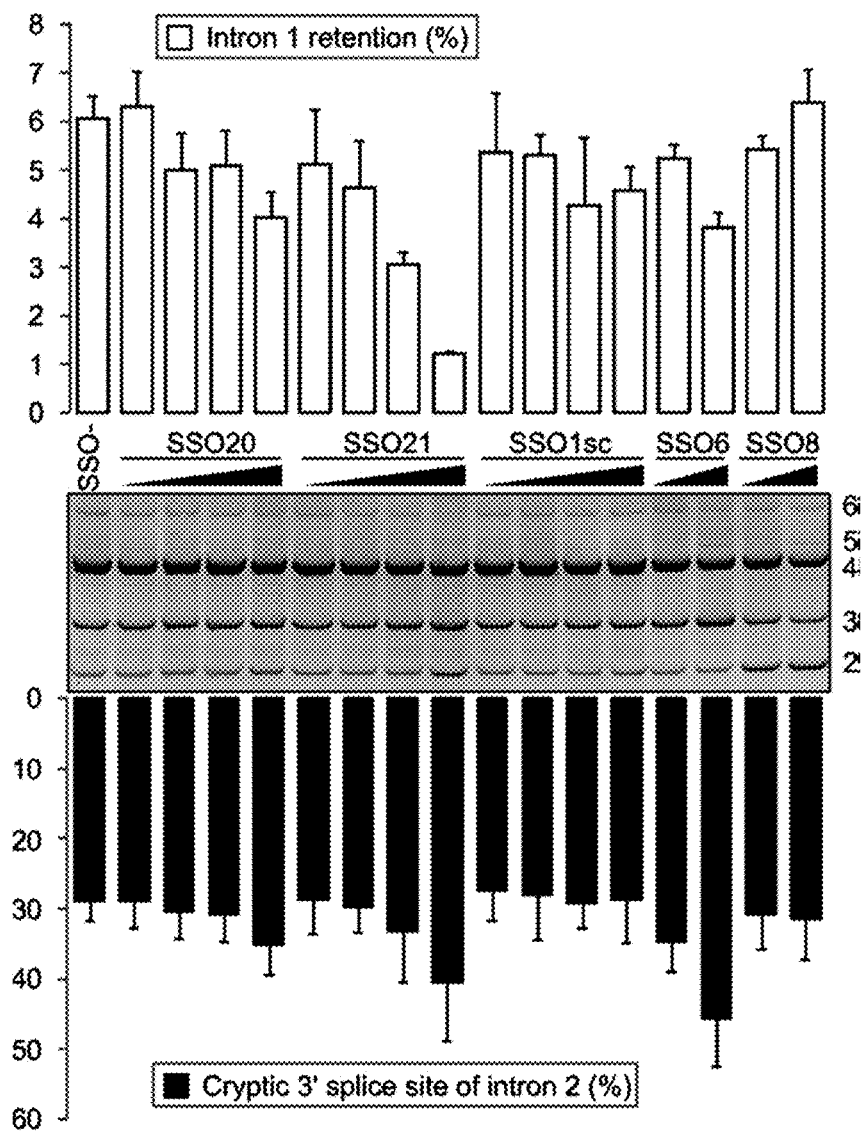
FIG. 2. SSO-induced inhibition of INS intron 1 retention. (A) Cotransfection of the INS reporter construct (IC D-F) with the indicated SSOs into HEK293 cells. Spliced products described in FIG. 1B are shown to the right. Bars represent percentage of intron 1-containing isoforms relative to natural transcripts (upper panel) or percentage of splicing to the cryptic 3' splice site of intron 2 relative to the total (lower panel). Error bars denote SD; sc, scrambled control; SSO-, 'no SSO' control. Final concentration of SSOs was 1, 3, 10 and 30 nM, except for SSO6 and SSO8 (10 and 30 nM). (B) SSO21-mediated promotion of intron 1 splicing in clones lacking the cryptic 3ss of intron 2. RNA products are to the right. (C) A fold change in SSO21-induced intron 1 retention in transcripts containing and lacking the cryptic 3'ss of intron 2. The final concentration of SSO21 was 30 nM in duplicate transfection. Designation of the reporter constructs is at the bottom.
Figure 2:
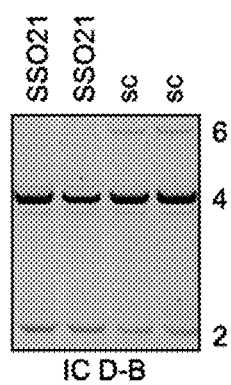
Figure 2:
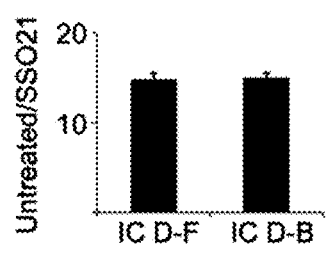
Figure 3:
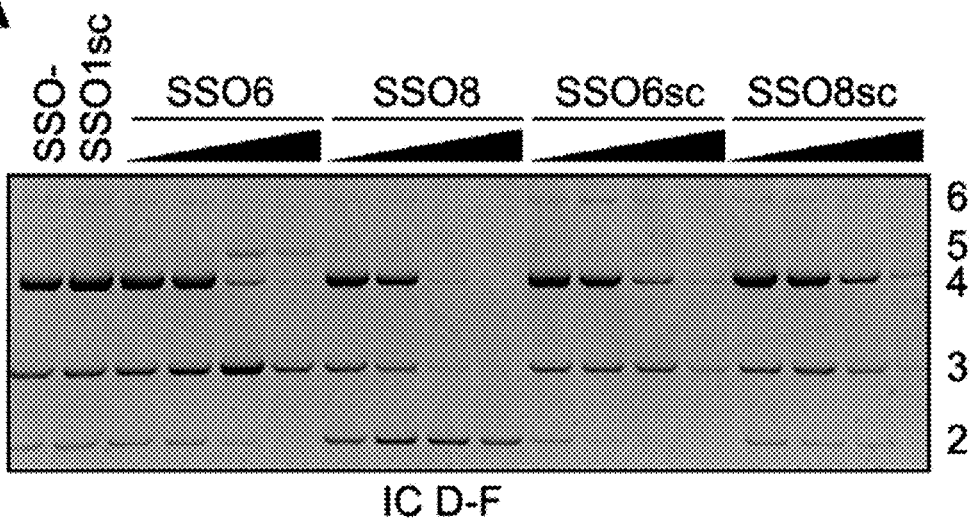
FIG. 3. INS SSOs targeting cryptic 3' splice sites. (A) Activation of cryptic 3'ss of intron 2 (cr3'ss+126.
Figure 3:
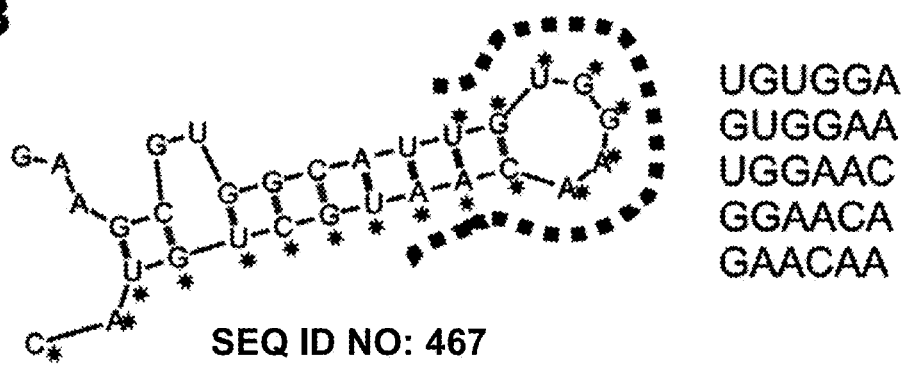
Figure 3:
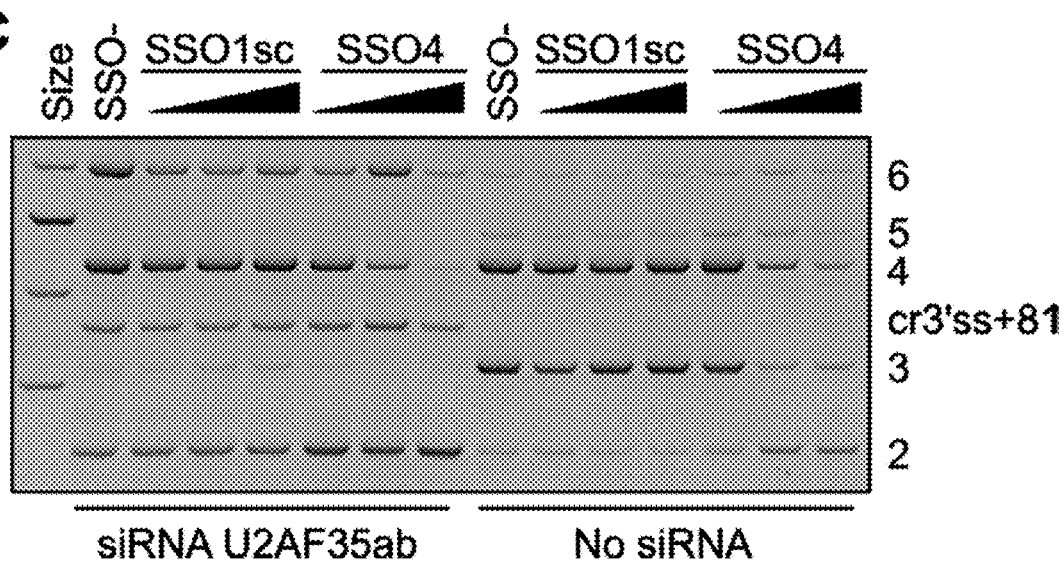

Antisense Oligonucleotides that Promote Pre-mRNA Splicing of a Weak Intron in 5'UTR To identify SSOs capable of reducing retention of INS intron 1 and increase splicing-mediated translational enhancement, we designed a series of 2'-O-methyl-modified phosphorothioate SSOs, individually co-expressed each SSO with a splicing reporter construct carrying haplotype IC in HEK293 cells and examined the relative abundance of exogenous mRNA products (FIGS. 1A and B). The IC haplotype in the reporter was devoid of the minisatellite sequence and contained a total of 14 polymorphic sites (7,20), including the A allele at rs689. This allele inhibits intron 1 splicing and yields lower proinsulin levels as compared to the more common T allele (21). SSOs targeting intron 1 and exon 2 were chosen in regions that showed the most prominent alterations of exon inclusion or intron retention in previous systematic deletion analyses of these sequences (7). SSOs in exon 3 were located between authentic 3'ss of intron 2 and a strong competing cryptic 3'ss 126 nt downstream to identify pre-mRNA motifs that modify their usage (FIG. 1A). Of the initial set of 15 INS SSOs tested in HEK293 cells, 11 showed reproducible alterations in the relative abundance of mRNA isoforms (Table 2). Intron 1 retention was significantly reduced by a single oligoribonucleotide SSO21 (P<0.01, Mann-Whitney rank sum test; FIG. 2A). SSO21 targeted intron 1 positions 59-74, encompassing a motif (termed del5) previously found to confer the largest reduction of intron retention upon deletion (7). The decrease in intron retention levels induced by SSO21 was dose-dependent (FIG. 2A) and was also observed in HepG2 cells and Chlorocebus aethiops COST cells, consistent with ubiquitous expression and a high degree of evolutionary conservation of spliceosome components that employ auxiliary splicing sequences (1,2). In addition to reducing intron 1 retention, SSO21 promoted cryptic 3'ss of intron 2 (FIG. 2A). However, this effect was also seen for other INS SSOs and for scrambled controls (FIG. 3 and Table 2), suggesting non-specific interactions. To confirm that the SSO21-induced enhancement of intron 1 splicing is not facilitated by the cryptic 3'ss of intron 2, we co-transfected this SSO with a shorter reporter lacking this site and retaining only the first 89 nucleotides of exon 3. FIG. 2B shows that SSO21 was capable of promoting intron 1 splicing to the same extent as the reporter with longer exon 3. In contrast, the SSO21-induced decrease of intron retention was not observed for the reporter lacking the del5 segment. Apart from intron retention, an increase of exon 2 skipping was observed for five SSOs, including SSO8 that bound downstream of the cryptic 3'ss of intron 1 (cr3'ss+81; FIGS. 1 and 3C, Table 2). This cryptic 3'ss was induced by RNAi-mediated depletion of the small subunit of U2AF (U2AF35) and was not reversed by a bridging oligoribonucleotide (SSO4) in cells lacking U2AF35; instead exon 2 skipping was observed (FIG. 3C). Depletion of U2AF35 also repressed the cryptic 3'ss of intron 2. Taken together, a single SSO was identified that reduced INS intron 1 retention in several primate cell lines.

Optimization of the Intron Retention Target at the Single Nucleotide Level

Figure 4:
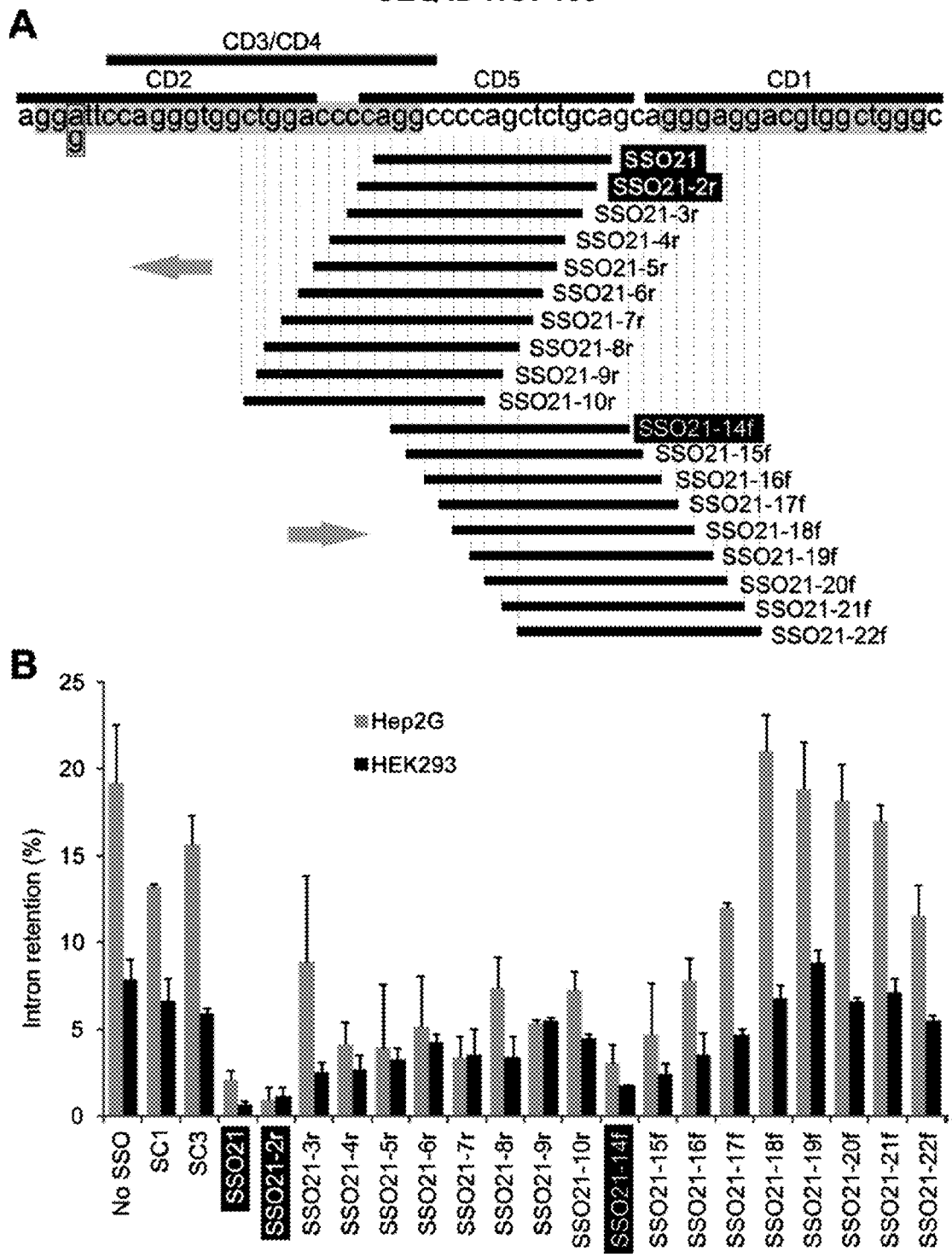
FIG. 4. Optimization of the intron retention target by antisense microwalk at a single-nucleotide resolution. (A) Location of oligoribonucleotides. Microwalk SSOs and oligos used for CD/NMR are represented by horizontal black bars below and above the primary transcript, respectively. Intron 1 sequences predicted to form RNA G-quadruplexes are highlighted in grey. Microwalk direction is shown by grey arrows; winner oligos are highlighted in black. A box denotes a single nucleotide polymorphism reported previously (20). (B) Intron retention levels of each microwalk SSO in two cell lines. Error bars denote SDs obtained from two independent cotransfections with reporter IC D-F.

Interestingly, other SSOs designed to target the del5 segment did not reduce intron 1 retention, except for a small effect of SSO20 (FIGS. 1A and 2A). To test the importance of nucleotides flanking SSO21 and to map the optimal target at a single-base resolution, a detailed antisense microwalk was carried out in this region. The INS reporter was individually co-transfected with additional eighteen 16-mers bound 1-9 nucleotides 5' and 3' of SSO21 into HEK293 cells and their RNA products examined. Intron 1 retention was most repressed by SSO21 and by SSOs that were shifted by 1-2 nucleotides in each direction (FIG. 4). In agreement with the initial screen, SSOs targeting more than one cytosine in the upstream run of four Cs (C4, see SSO1 and SSO2, FIG. 1A) were not effective (SSO21-3r through SSO21-10r, FIG. 4). In the opposite direction, SSOs targeting consecutive Gs, which are often found in intronic splicing enhancers (29-31), increased intron retention. Thus, the optimal antisense target for reducing retention of INS intron 1 was mapped at a single nucleotide resolution to a region previously identified as the most repressive by a systematic deletion analysis of the entire intron (7).

Antisense Target for Intron Retention is Adjacent to a Parallel RNA Quadruplex

It was noticed that the target was sandwiched between two intronic segments predicted to form stable RNA guanine (G) quadruplexes (intron 1 nucleotides 36-61 and 78-93; highlighted in FIG. 4A). These structures are produced by stacking G-quartets that consist of four Gs organized in a cyclic Hoogsteen hydrogen bonding arrangement (32) and have been implicated in important cellular processes, including replication, recombination, transcription, translation (33, 34) and RNA processing (35-39). To test if they are formed in vitro, synthetic ribonucleotides derived from this region were employed in CD spectroscopy that has been used widely to characterize DNA and RNA quadruplex structures in vitro (40-43). The CD spectrum of a downstream 19-mer (termed CD1) recorded between 215 and 330 nm at 25° C. revealed strong positive ellipticity at 265 nm with negative intensity at around 240 nm, indicative of a parallel quadruplex (FIG. 5A). To confirm the presence of a quadruplex, rather than other stable secondary structure motifs, UV absorbance spectra was recorded at 5° C. and 95° C. The UV absorbance difference spectrum at the two temperatures (below and above the melting transition point) showed the characteristic hyperchromic shift at ~295 nm and a double maximum at 240 nm and 280 nm, providing evidence for formation of a stable parallel-stranded RNA quadruplex in vitro. This was confirmed by 1H NMR studies of CD1 (FIG. 5B) which showed a characteristic envelope of signals between 10 and 12 ppm corresponding to Hoogsteen H-bonded Gs within G-tetrad structures. Thermal stability measurements by CD produced a highly reversible sigmoidal co-operative unfolding transition with a $T_m=56.8\pm0.2°$ C. (FIG. 5C). FIG. 5D (upper panel) shows a possible arrangement of the 19-mer into two stacked G-tetrads connected by relatively short loop sequences of 1-4 nucleotides.

Conformational Transition Model for Splicing Inhibitory Sequences in INS Intron 1

CD of a synthetic 20-mer derived from a region upstream of the antisense target (termed CD2) also showed evidence of stable structure formation, giving a broader absorption envelope centered around 270 nm and a sigmoidal thermal unfolding transition ($T_m=69.0\pm0.45°$ C.; FIG. 5A). Unlike the downstream oligo CD1, no hyperchromic shift in the UV was found in the thermal difference spectrum. However, a well-defined set of sharp signals in the 1H NMR spectrum between 12 and 14 ppm that differed from those for CD1 showed the formation of Watson-Crick H-bonded base pairs characteristic of double-stranded RNA (FIG. 5B). Secondary structure predictions of overlapping intronic segments using Mfold suggested that the pre-mRNA forms stable local stem-loops; one of them was further stabilized by a G→C mutation (termed G2; FIG. 5D, lower panel) that increased intron 1 retention (7). Another G→C substitution (termed G3) located further downstream and destabilizing the quadruplex structure (FIG. 5D, upper panel) also repressed intron splicing (7). Finally, CD2 oligonucleotides containing either A or G at a single-nucleotide polymorphism (FIG. 4A and (20) exhibited very similar CD spectra with well-defined melting transitions and $T_m$ values, suggesting that the G and A alleles form the same structure.

Figure 6:
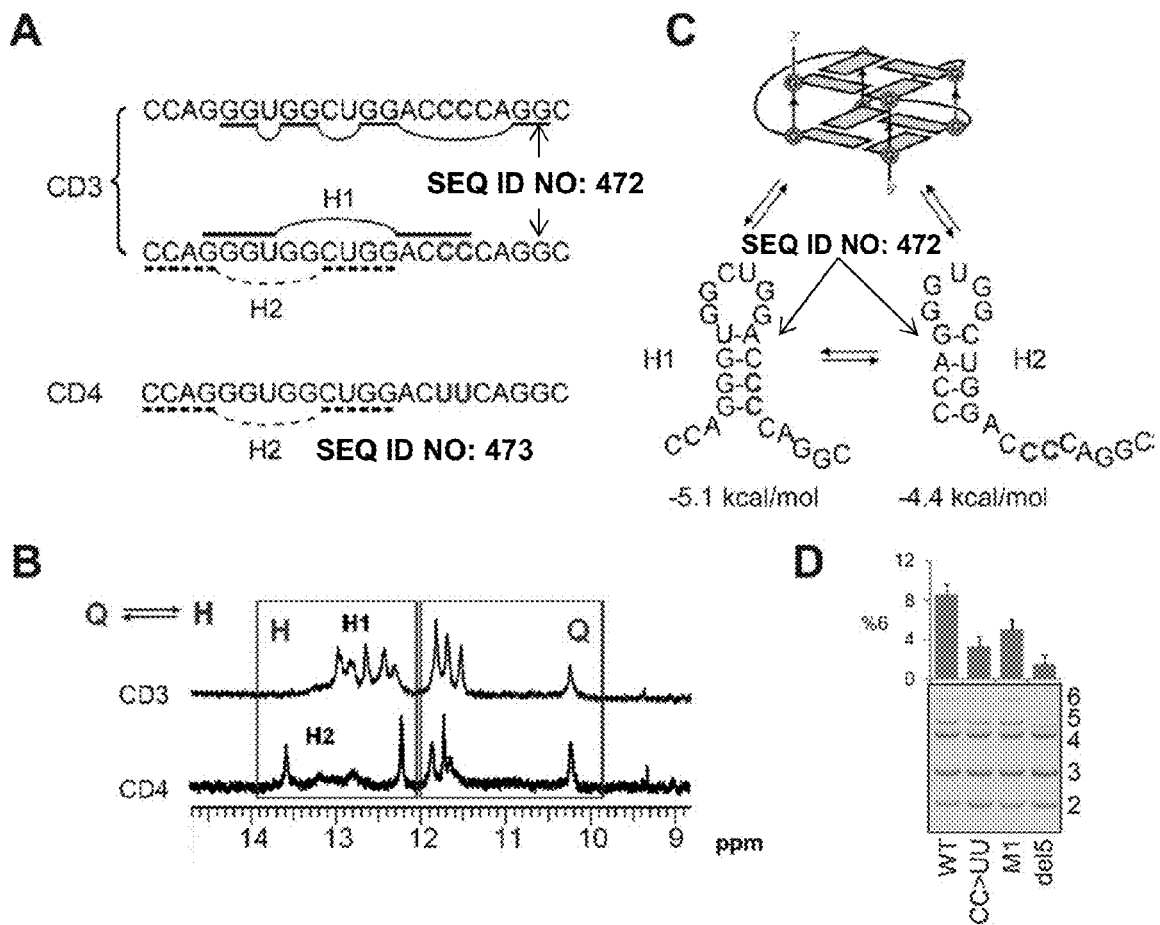
FIG. 6. Conformational quadruplex/hairpin transitions involving the antisense target. (A) Schematic equilibrium between hairpin (black) and quadruplex (dark blue) structures proposed to form within the G-rich motif encompassing oligoribonucleotide CD3. CD4 contains a CC→UU mutation (highlighted by *). (B) The NMR spectrum in the 9-15 ppm region reveals imino proton signals corresponding to hydrogen bonded bases. The signals between 10 and 12 ppm are characteristic of Hoogsteen hydrogen bonded Gs within a G-tetrad (Q box), while signals >12 ppm are indicative of Watson-Crick A-U and G-C base pairs within hairpin structures (H box). In CD3, hairpin H1 is significantly populated, but mutations in CD4 destabilize H1 making H2 the major species, with both in equilibrium with the quadruplex structure. (C) Mfold predictions of two possible hairpins, consistent with the NMR data. (D) Reduction of intron retention upon destabilization of the hairpin structure by the CC→UU mutation. Error bars denote SD of a duplicate experiment with reporter IC D-C. Del5, the IC D-C reporter lacking segment del5 (FIG. 1A); M1, a reporter containing two substitutions (Table 1A) to destabilize both the G-quadruplex and the stem-loop.

To test further the importance of a tentative equilibrium between canonical and noncanonical structures in intron splicing, a combination of CD, NMR and mutagenesis experiments was used (FIG. 6). An oligoribonucleotide CD3 encompassing the 5' end of the intron retention target was synthesized and stem-loops/quadruplex were predicted (FIGS. 4A and 6A). A mutated version CD4 was also synthesized, which carried two C→*U transitions destabilizing the hairpin but maintaining stability of the quadruplex. The same mutation was also introduced in the IC reporter construct transfected into HEK293 cells. The NMR spectrum of CD3 revealed the co-existence of signals for both G-tetrad and canonical base-paired hairpin structures (termed H1 and H2) in equilibrium (FIGS. 6B and C). The effects of Mg2+ on the conformational equilibrium between quadruplex and hairpin were investigated by adding 2 mM and then 6 mM $MgCl_2$ to the buffered solution containing 100 mM KCl. As reported by Bugaut et al. (57), the conformational equilibrium was not significantly perturbed by the addition of Mg2+ in the presence of KCl. Thus, we observed formation of the RNA hairpin and quadruplex structures in an environment that mimics the cellular context where both $K^+$ and $Mg^{2+}$ ions were present at high concentrations. The CD melting curve showed a broad transition ($T_m$=79.9° C.), consistent with multiple conformational states with different stabilities. The CC→UU mutation in CD4 resulted in the loss of NMR signals for H1 (FIG. 6B) and a reduction in the Tm by 13° C., consistent with the selective destabilization of the more stable hairpin H1, leading to an increase in the population of H2 in equilibrium with the quadruplex. Transient transfections showed that the CC→UU mutation improved intron 1 splicing while a mutation termed M1 predicted to destabilize both the quadruplex and the hairpin had only a small effect (FIG. 6D, Table 1A).

Figure 7:
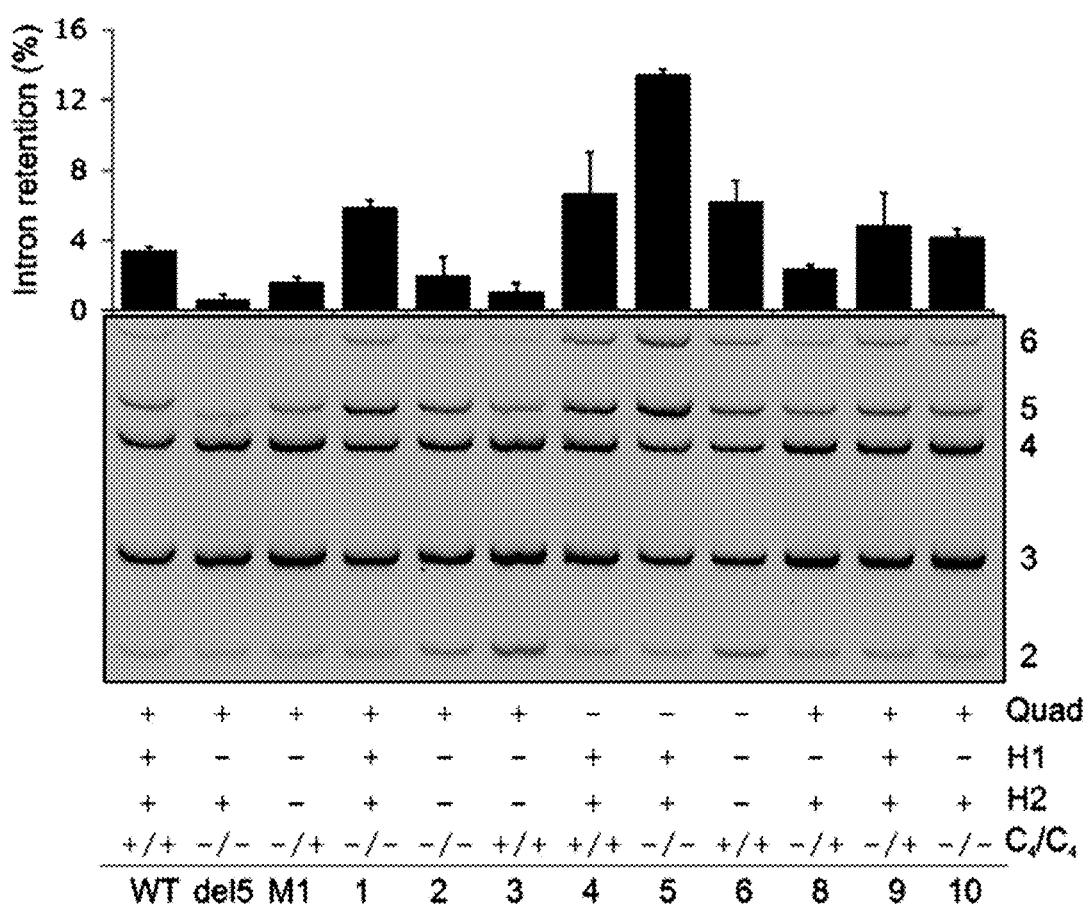
FIG. 7. Identification of proteins that interact with pre-mRNAs encompassing the antisense target for intron retention. (A) Intron retention levels for wild type and mutated reporter constructs (IC D-C) following transient transfections into HEK293T cells. Mutations are shown in Table 1A. RNA products are to the right. The presence of predicted RNA quadruplexes, hairpins H1/H2 and the upstream and downstream C4 run are indicated below the gel figure. Error bars denote SDs obtained from two replicate experiments. (B) Intron retention levels of tested RNAs correlate with their predicted stabilities across the antisense target. (C) Western blot analysis of a pull-down assay with antibodies indicated to the right. NE, nuclear extracts; B, beads-only control; AV3, control RNA oligo containing a cytosine run and a 3'ss AG (7). The sequence of CD5 RNA is shown in FIG. 4A.
Figure 7:
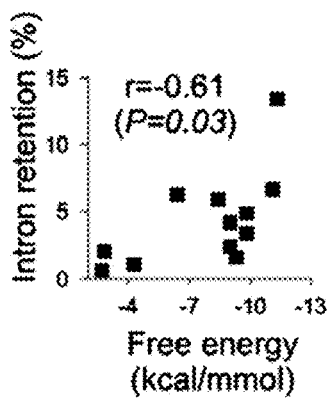
Figure 7:
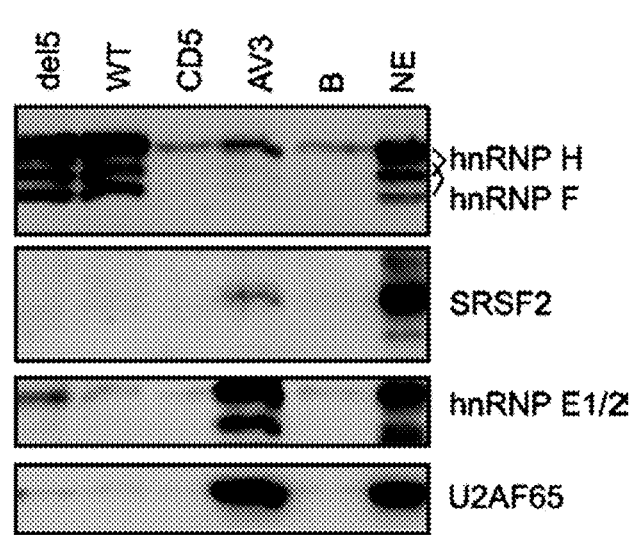

To explore how the equilibrium of these structures affects intron splicing more systematically, a series of mutated constructs were prepared in order to destabilize/maintain predicted quadruplex, H1/H2 structures and two cytosine runs (Table 1A). Their transcripts showed significant differences in intron retention levels (FIG. 7; P=0.0001, Kruskal-Wallis one-way ANOVA on ranks) First, elimination of the G-quadruplex increased intron 1 retention, which was further enhanced by removing each cytosine run (cf. mutations 4-6 with the wild-type, P=0.0004). These mutations appeared to have additive effects on intron retention (cf. wild-type versus mutations 1 or 9; 3 versus 2 and 4 versus 5). Second, the increased intron retention in the absence of the G-quadruplex was not altered by removing H1 and H2, but their elimination enhanced exon skipping (cf. isoform 2 for mutations 4 versus 6). Third, when only one of the two C4 runs was present, removal of H1 somewhat improved intron 1 splicing (cf. 8 versus 9), consistent with a statistically significant correlation between intron retention and predicted stability of tested RNAs (FIG. 7B). The efficiency of intron splicing was thus controlled by conformational transitions between canonical and noncanonical structures in equilibrium.

TABLE 1A

INS intron 1 mutations altering predicted RNA G quadruplexes, stem loops and two cytosines runs in plasmid constructs

| Mutation | Input sequence for computation predictions1 | Predicted RNA quadruplex | H2 | H1 | C runs | The most stable RNA structure | Free energy (kcal/mmol) |
|---|---|---|---|---|---|---|---|
| Wildtype sequence | GGAUUCCAGGG UGGCUGGACCC CAGGCCCC | + | + | + | + | 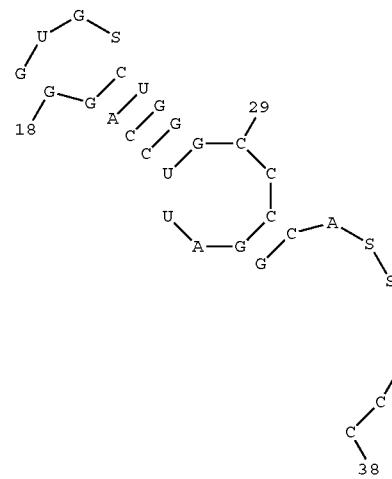 | −9.8 |
| Del5 | GGAUUCCAGGG UGGCUGG---- -------- | + | + | − | − | 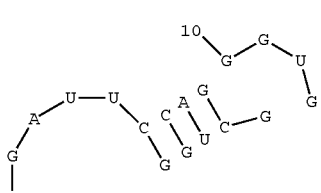 | −2.7 |

TABLE 1A-continued

INS intron 1 mutations altering predicted RNA G quadruplexes, stem loops and two cytosines runs in plasmid constructs

| Mutation | Input sequence for computation predictions1 | Predicted RNA quadruplex | H2 | H1 | C runs | The most stable RNA structure | Free energy (kcal/mmol) |
|---|---|---|---|---|---|---|---|
| M1 | GGAUUCCAGGG UGGCUGCACGC CAGGCCCC | + | − | − | − | 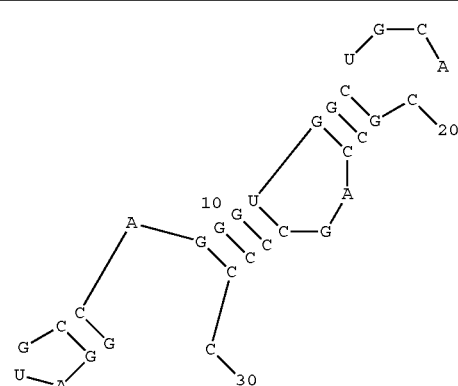 | −9.3 |
| 1 | GGAUUCCAGGG UGGCUGGACCC GAGGCGCC | + | + | + | − | 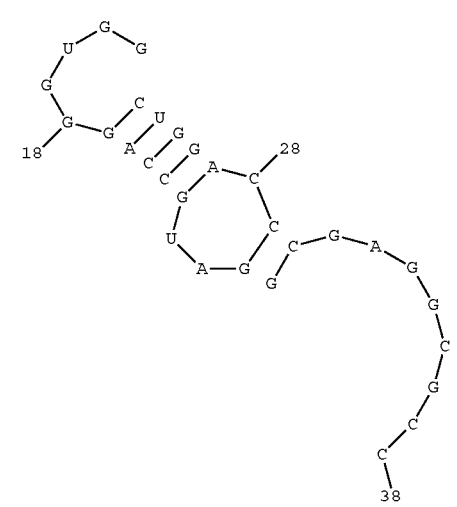 | −8.4 |
| 2 | GGAUUCCAGGA UGGUAGGACCC GAGGCGCC | + | − | − | − | 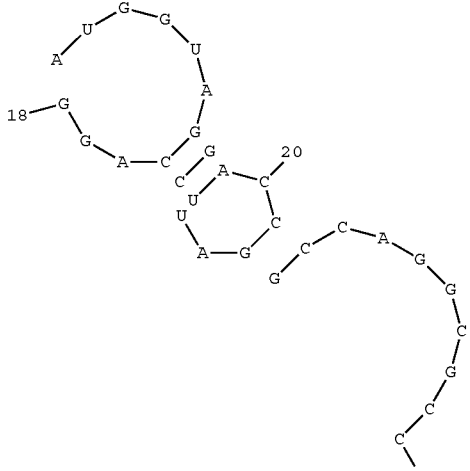 | −2.8 |

TABLE 1A-continued

INS intron 1 mutations altering predicted RNA G quadruplexes, stem loops and two cytosines runs in plasmid constructs

| Mutation | Input sequence for computation predictions1 | Predicted RNA quadruplex | H2 | H1 | C runs | The most stable RNA structure | Free energy (kcal/mmol) |
|---|---|---|---|---|---|---|---|
| 3 | GGAUUCCAGGA UGGUAGGACCC CAGGCCCC | + | − | − | + | 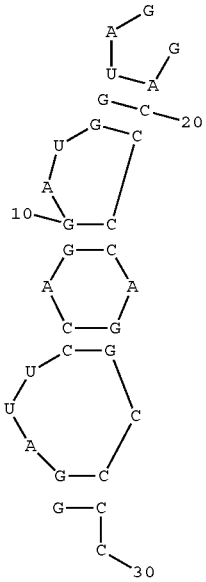 | −4.3 |
| 4 | GGAUUCCAGGG UUGCUGGACCC CAGUCCCC | − | + | + | + | 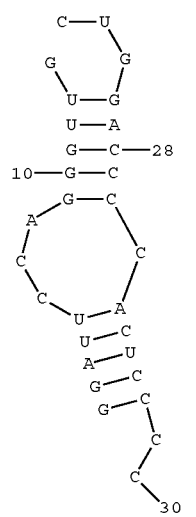 | −11.1 |

TABLE 1A-continued

INS intron 1 mutations altering predicted RNA G quadruplexes, stem loops and two cytosines runs in plasmid constructs

| Mutation | Input sequence for computation predictions1 | Predicted RNA quadruplex | H2 | H1 | C runs | The most stable RNA structure | Free energy (kcal/mmol) |
|---|---|---|---|---|---|---|---|
| 5 | GGAUUCCAGGG UUGCUGGACCC GAGUCGCC | − | + | + | − | 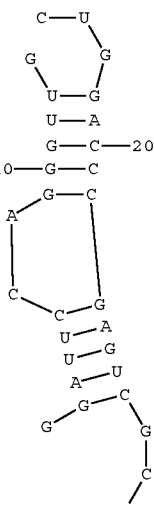 | −11.3 |

Protein-RNA Interactions in the Region Targeted by Winner SSOs

To identify proteins that interact with RNAs encompassing the antisense target and/or associated canonical and noncanonical structures, pull-down assays were carried out using wild type and del5 RNAs transcribed from T7-tagged PCR products, a synthetic RNA(CD5) representing the target sequence, and a control oligo containing a 3'ss CAG, termed AV3. Western blotting showed that both wild type and del5 transcripts bound hnRNPs F/H but this binding was absent for CD5 (FIG. 7C). These proteins were also detected by MS/MS analysis of differentially stained fragments from pull down gels with wild type and del5 RNAs as compared to beads-only controls. Two antibodies against SRSF2, which showed the highest score for putative binding activity among several SR proteins, failed to detect any specific interaction (FIG. 7C). Although the signal from hnRNP E1/E2, which constitute a major poly(C) binding activity in mammalian cells (44), was above background for del5 (FIG. 7C), no change in intron retention was observed in cells lacking hnRNP E1/E2.

Splicing Pattern of G-Rich and G-Poor Reporters Upon DHX36 Depletion

Figure 8:
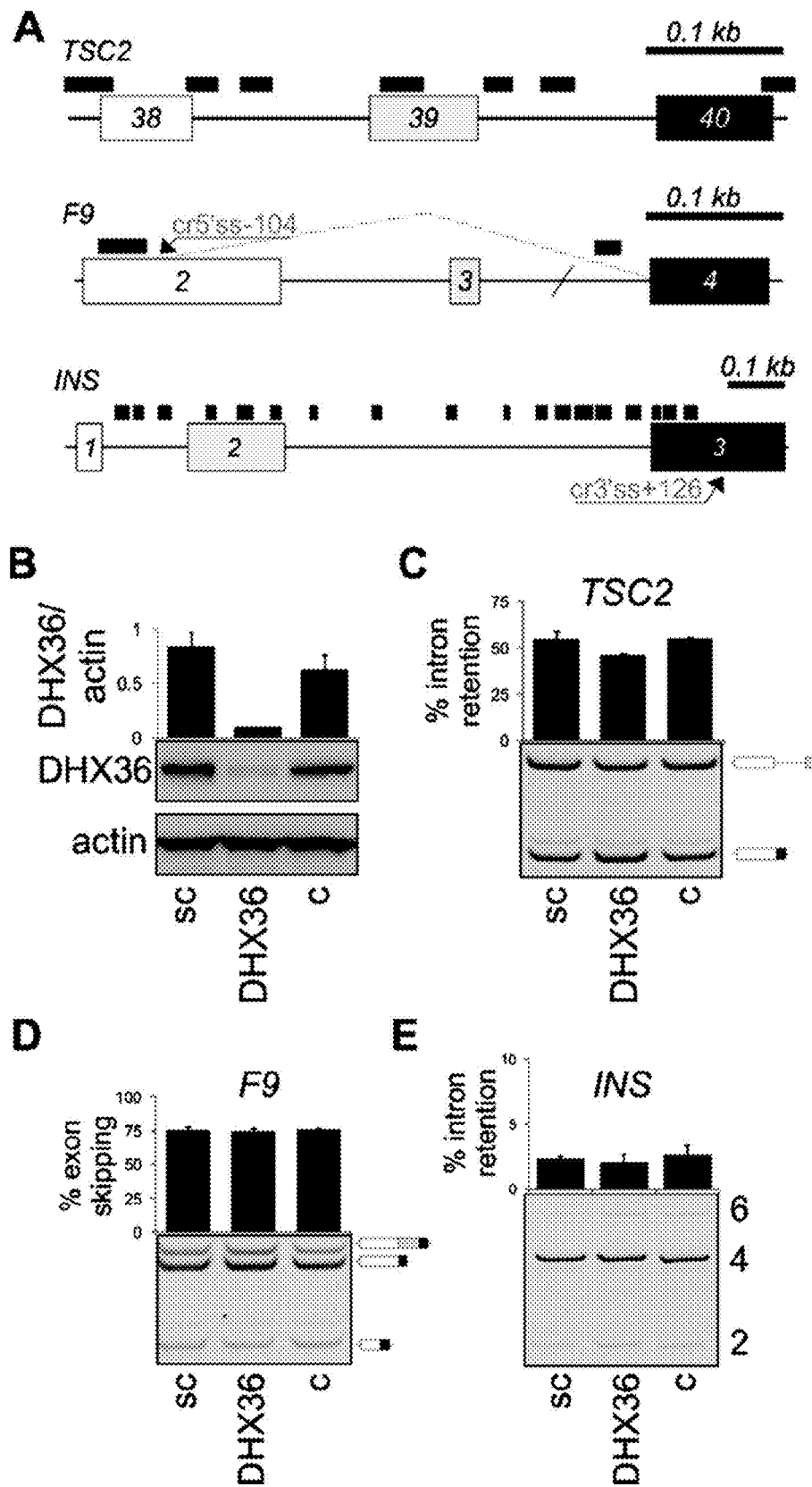
FIG. 8. Splicing pattern of quadruplex-rich and -poor minigenes upon DHX36 depletion. (A) Schematics of reporter constructs. Predicted quadruplexes are denoted by black rectangles; their densities are shown in Table 1. Exons (boxes) are numbered; forward slash denotes shortening of F9 intron 3 (24). The F9 and TSC2 minigenes contain branch point substitutions c.253-25C and c.5069-18C, respectively, that impair splicing (24). Cr5'ss-104; cryptic 5'ss 104 upstream of authentic 5'ss of intron 2. (B) Immunoblot with antibodies against DHX36. sc, scrambled siRNA; c, untreated cells. Error bars are SDs of two transfection experiments. (C-E) Intron retention and exon skipping of the indicated reporters. The final concentration of DHX36 siRNA was 50 nM. RNA products are shown schematically to the right. Error bars are SDs of two transfection experiments.

RNA G-quadruplexes bind helicase DHX36, which is capable of converting quadruplex RNA to a stable duplex and is a major source of quadruplex-resolving activity in HeLa cells (26,45). DHX36 was crosslinked to an intronic splicing enhancer in the ATM pre-mRNA (46) and could unwind the quadruplex structure within the 5' region of TERC (26). To test if DHX36 depletion can influence INS splicing, G-quadruplex-poor and -rich reporters were transiently transfected (FIG. 8A, Table 1) into depleted cells. Control constructs were chosen to give approximately equal representation of spliced products, which was achieved by weakening the branch site (24), thus providing a sensitive ex vivo splicing assay. However, despite efficient DHX36 depletion (FIG. 8B), statistically significant alterations of INS intron 1 retention were not seen in either short or long constructs, nor did we observe major changes in G-poor and G-rich controls (FIG. 8C-E). These results are in agreement with a previous lack of significant enrichment of quadruplex sequences among transcripts down regulated in DHX36-depleted cells (47) and with the absence of ATM response to the knockdown (46).

SSO-Induced Repression of a Population-Specific Cryptic 5' Splice Site of INS Intron 1

In addition to rs689, INS intron 1 splicing is influenced by a polymorphic TTGC insertion at rs3842740 located in the vicinity of the natural 5'ss (21). This insertion is present in a quarter of all African chromosomes but is absent on Caucasian IC haplotypes (20). The insertion activates a downstream cryptic 5'ss (FIG. 1A), extending the 5'UTR of the resulting mRNAs by further 26 nucleotides and repressing proinsulin expression (7, 21). To test if the new 5'ss can be efficiently inhibited by SSOs, the same insertion was introduced in the IC construct and the wild type and mutated reporters co-expressed with a bridging oligoribonucleotide termed SSO10. Although the cryptic splicing was inhibited, canonical splicing of intron 1 was not completely restored even at high SSO10 concentrations, most likely as a result of suboptimal recognition of the authentic 5'ss weakened by the insertion.

To gain initial insights into folding of 5'UTR sequences in the presence and absence of the insertion, enzymatic structural probing was carried out using partial RNA digestion with single- and double-strand specific RNAses. The overall cleavage positions and intensities detected for the wild-type RNA were broadly consistent with mfold predictions, in which two major stem loop regions (SL1 and SL2) were interrupted by several internal bulges. Both the structural probing and mfold predictions suggested that the insertion at rs3842740 extended the central bulge in SL1 as the number of T1 and S1 cleavages in this region increased in contrast to the remaining portions of SL1 and in SL2. Finally, transcripts were not digested by RNase V1 in regions showing quadruplex formation in vitro.

Discussion

Antisense Intron Retention Target in a Splicing Silencer of INS Intron 1

Here it is demonstrated the first use of antisense technology to reduce retention of the entire intron in mature transcripts and to modify the haplotype-dependent INS expression using SSOs. Identification of winner SSOs that compensate the adverse impact of the A allele at rs689 on efficient RNA processing was facilitated by systematic mutagenesis of intron 1 (7), and by macro- (FIG. 1) and micro-walk (FIG. 4) strategies. Interestingly, the target sequence contains a tandem CAG(G/C) motif, which resembles a 3'ss consensus (FIG. 4). Such 'pseudo-acceptors' were previously implicated in splice-site repression experimentally (27) and are overrepresented in splicing silencers. For example, the two tetramers are more common among high-confidence 102 intronic splicing silencers (49) and are depleted in 109 enhancers (50) identified by fluorescence activated screen of random 10-mers. The YAG motifs were also more frequent than expected among QUE-PASA splicing silencers (51), suggesting that they are important functional components of the retention target. The intervening cytosine tract may also play an important role as the frequency of C4 runs among QUEPASA silencers is ~2 times higher than expected. These motifs were also found in 4% of intronic splicing regulatory elements identified by a systematic screening of sequences inserted at positions −62/−51 relative to a tested 3'ss (52). This study identified an element termed ISS22 (AAATAGAGGCCCCAG; SEQ ID NO: 465) that shared a 3' nonamer (underlined) with the optimal intron retention target. However, unlike an optimal 3'ss recognition sequence of AV3, our pull-down assay coupled with western blotting revealed only a very weak binding if any to U2AF65 (FIG. 7C).

Figure 5:
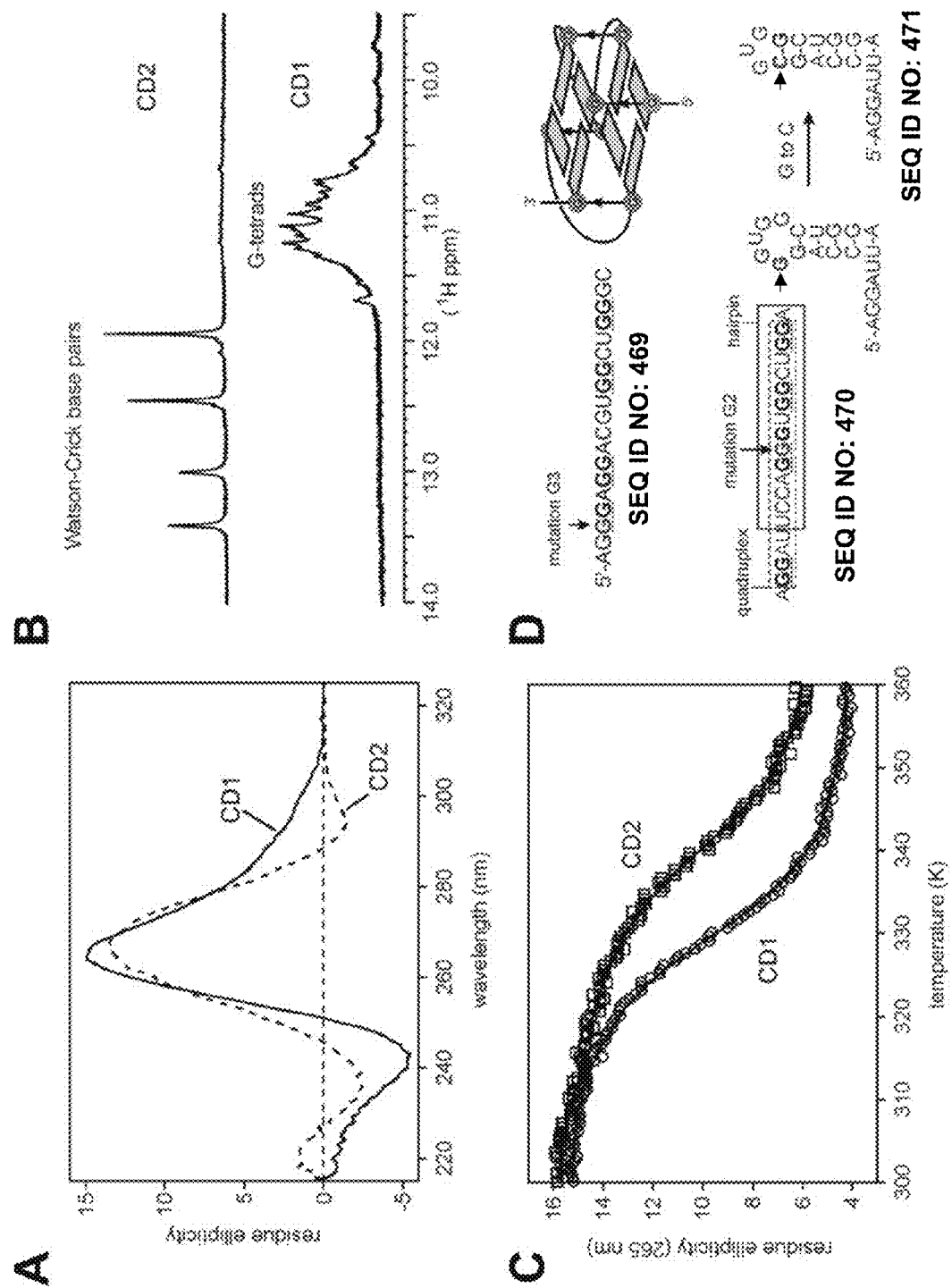
FIG. 5. Biophysical characterization of RNA secondary structure formation. (A) Far-UV CD spectrum at 25° C. for CD1 (19-mer) and CD2 (20-mer) RNAs, revealing ellipticity maximum at 265 and 270 nm, respectively. (B) 1H NMR spectra of CD1 and CD2 recorded at 800 MHz and 298 K showing characteristic groups of resonances from H-bonded G bases. (C) Sigmoidal CD melting curves for the two RNAs showing a transition mid-point at 56.8±0.2° C. and 69.0±0.45° C., respectively. The two curves have been displaced slightly from each other for clarity. (D) The proposed parallel quadruplex structure with two stacked G-tetrads connected by short loop sequences for CD1 (top panel). Predicted hairpin structures for CD2 are shown at the bottom panel. G→C mutations are indicated by arrow.

Conformational Transition Between Quadruplex and Hairpins in RNA Processing Control The antisense target was identified just upstream of a potential G-quadruplex forming RNA whose structure was subsequently confirmed by CD and NMR analysis (FIGS. 1A and 5). RNA quadruplexes are more stable than their DNA counterparts, have been increasingly implicated in regulation of RNA metabolism (33, 34, 41, 42) and offer unique avenues for drug development (53). The 2-quartet quadruplexes are thermodynamically less stable than their 3- or 4-quartet counterparts and are probably kinetically more labile, yet they still display pronounced stability and may serve as more compliant and dynamic switches between quadruplex and non-quadruplex structures in response to cellular environment (54-56). The winner SSOs may block interactions with trans-acting factors, alter higher-order structures, the rate of RNA-protein complex formation or impair conformational transition between the 2-quartet quadruplex and H1/H2 (FIG. 5). A similar transition has been recently described for a quadruplex not predicted ab initio (57), raising a possibility that additional sequences in the G-rich intron 1 may participate in the equilibria near the antisense target, possibly involving multiple quadruplex motifs and competing stem-loops.

The binding (FIG. 7C) and functional experiments showing the increased intron 1 retention upon hnRNP F/H depletion and the opposite effect upon hnRNP F/H overexpression (7) indicate that these proteins interact with key splicing auxiliary sequences in this intron. In contrast to a previous report concluding that hnRNP F binds directly to the RNA quadruplex (58), hnRNP F has been shown to prevent formation of RNA quadruplexes by binding exclusively single-stranded G-tracts (59). Predictions based on primate genomes suggest that the majority of putative quadruplexes are likely to fold into canonical structures (60). Decreased pre-mRNA occupancy by these proteins, presumably promoting quadruplex formation (59), and potentially reducing splicing efficiency.

RNA Quadruplexes in Coupled Splicing and Translational Gene Expression Control

RNA quadruplexes were predicted in ~8.0% of 5'UTR and were proposed to act as general inhibitors of translation (60, 61). INS intron 1 is weakly spliced and U2AF35-dependent (7) and a significant fraction of intron 1-containing transcripts is exported from the nucleus (23). This suggests that the RNA G-quadruplex formed by CD1 could influence translation of these mRNAs, which contain a three-amino acid uORF specific for Homininae (7). This uORF markedly inhibits proinsulin expression and is located just a few base-pairs downstream, prompting a concept that the G-quadruplexes can promote translation by sequestering uORFs. Functional 2-quartet quadruplexes are required for activity of internal ribosomal entry sites (54).

TABLE 1

Density of predicted RNA G-quadruplexes in reporter constructs

| Reporter | TSC2 | F9 | INS |
| --- | --- | --- | --- |
| G-quadruplexes per nucleotide[a] | 0.25 | 0.05 | 0.27 |
| G score per nucleotide[a] | 0.20 | 0.04 | 0.22 |

[a]The length of non-overlapping quadruplex sequences and their G scores were computed as described (78).

Antisense Strategies for Dependencies in Splice-Site Selection

Apart from canonical mRNA isoform 4, isoforms 2, 3 and 6 (FIG. 1B) have been found in expressed sequence tag databases derived from cDNA libraries from insulin producing tissues (21). This suggests that cryptic splice sites produced by the reporter construct are recognized in vivo and that our haplotype-dependent reporter system recapitulates these events accurately in cultured cells no matter whether the cells express or not endogenous insulin. Apart from repressing intron 1-retaining transcripts, optimal SSOs increased utilization of cryptic 3'ss of exon 3 (FIG. 2). This undesired effect could be explained by coordination of splicing of adjacent exons and introns, which was observed previously for individual genes and globally (63-67). Also, G-richness downstream transcription start sites have been associated with RNA polymerase II pausing sites (68). Although the two robustly competing 3'ss of intron 2 are likely to respond to non-specific signals that influence RNA folding (FIG. 3, Table 2), it might be possible to alleviate the observed dependencies and reduce cryptic 3'ss activation using SSO combinations at linked splice sites and examine their synergisms or antagonisms, benefiting from the use of full-gene constructs as opposed to minigenes.

Multifunctional Antisense Oligonucleotides to Reduce INS Intron 1 Retention

Since the first use of 2'-O-methyl-phosphorothioate SSOs (69), this type of chemical modification has been successfully exploited for many in vitro and in vivo applications (9, 10, 70). To further fine-tune expression of mRNA isoforms, optimized SSOs can be designed to tether suitable trans-acting splicing factors to their target sequences (11,71). An obvious candidate for this system is U2AF35 because intron 1 is weak as a result of relaxation of the 3'ss in higher primates and is further undermined by the A allele at rs689, which renders this intron highly U2AF35-dependent (FIG. 3) (7). Apart from U2AF35, future bi- or multifunctional antisense strategies can employ binding platforms for splicing factors previously shown to influence INS intron 1 and exon 2 splicing, such as Tra2β or SRSF3 (7). Tra2β is likely to bind the SSO6 target which forms a predicted stable hairpin structure with a potent GAA splicing enhancer in a terminal loop (FIG. 3B). SRSF3 is required for repression of the cryptic 3'ss of intron 2 (7) and binds pyrimidine-rich sequence with a consensus (A/U)C(A/U)(A/U)C (72). The CAUC motif, which interacts with the RNA-recognition motif of SRSF3 (73), is present just upstream of the cryptic 3'ss.

Normalizing Intron Retention Levels in Human Genetic Disease

These results provide an opportunity to use non-genetic means to compensate less efficient splicing and lower INS expression from haplotypes predisposing to type 1 diabetes.

Common variants such as rs689 contribute to a great extent to the heritability of complex traits, including autoimmune diseases (74), but their functional and structural consequences are largely unknown. If optimized INS SSOs can be safely and efficiently introduced into the developing *thymus*, this approach may offer a novel preventive approach to promote tolerance to the principal self-antigen in type 1 diabetes. The most obvious candidates for such intervention are mothers who had an affected child homozygous for disease-predisposing alleles at both HLA and INS loci. Such genotypes were associated with an extremely high disease risk for siblings (75). Apart from primary prevention of type 1 diabetes, future SSO-based therapeutics might be applicable to patients with significant residual β-cell activity at diagnosis and to those who are eligible to receive β-cell transplants and may benefit from increased intron-mediated enhancement of proinsulin expression from transplanted cells. It is also possible to envisage use of this therapeutic modality for other patients with diabetes through a more dramatic enhancement of intron splicing and proinsulin expression by targeting multiple splicing regulatory motifs with multifunctional SSOs. The SSOs may have utility in thymic epithelial cells and 13-cells that may provide a more natural system for testing their impact on both exo- and endogenous proinsulin expression. Finally, similar antisense strategies may help reduce pervasive intron retention in cancer cells resulting from somatic mutations of splicing factor genes, as illustrated by specific substitutions in the zinc finger domain of U2AF35 in myeloproliferative diseases (76).

Reducing Intron Retention in Malignant Cells

A set of 146 intronic sequences that are preferentially retained in U2AF-deficient HEK293 cells was selected using RNAseq data from replicated, polyA-selected samples, followed by inspection of each intron retention event in genome browsers. These sequences were repeat-masked using a sensitive version of RepeatMasker, available at http://www.repeatmasker.org/cgi-bin/WEBRepeatMasker. Because the optimal antisense target for reducing INS intron 1 retention [Kralovicova J et al (2014). *Nucleic Acids Res doi:* 10.1093/nar/gku507, published on 17 Jun. 2014] overlapped intronic splicing regulatory elements conserved in mammals [Yeo G W, et al (2007). *PLoS Genet* 3:e85], including CCCAG, AGGCC (FIG. 4 in Kralovicova et al. 2014), antisense targets in intronic segments containing these short penta- to heptamer motifs and an independently derived set of intronic splicing regulatory motifs [Voelker R B, & Berglund J A (2007). *Genome Res* 17:1023-1033], were selected, thus increasing the chance of oligonucleotides interacting with these targets to influence RNA processing. The target sequences were subjected to routine antisense oligonucleotides design, including removal of sequences containing C runs to avoid G-quadruplex formation. The proximity of both 5' and 3' splice sites, polypyrimidine tracts, branch sites and suprabranch regions were also avoided. This selection yielded a set of 388 compounds (Table 3), covering ~15% of the total lengths of U2AF-sensitive introns and representing ~0.001% of all human intronic sequences. Thus, this set of oligonucleotides target regions enriched for splicing inhibitory sequences of U2-dependent introns, which do not have sufficient help from auxiliary factors in malignant cells that sustain mutations or deletions in the U2 pathway.

Insulin Related Sequences

```
            Candidate SSO sequences

CD5
RNA form-
                                        (SEQ ID NO: 1)
CUGCAGAGCUGGGGCCUG DNA form-
                                        (SEQ ID NO: 2)
CTGCAGAGCTGGGGCCTG (SEQ ID NO: 3)
Binds to caggccccagcucugcag SSO21*
RNA form-
                                        (SEQ ID NO: 4)
UGCAGAGCUGGGGCCU DNA form-
                                        (SEQ ID NO: 5)
TGCAGAGCTGGGGCCT (SEQ ID NO: 6)
Binds to aggccccagcucugca SSO21-2r*
RNA form-
                                        (SEQ ID NO: 7)
GCAGAGCUGGGGCCUG DNA form-
                                        (SEQ ID NO: 8)
GCAGAGCTGGGGCCTG (SEQ ID NO: 9)
Binds to caggccccagcucugc SSO21-3r
RNA form-
                                        (SEQ ID NO: 10)
CAGAGCUGGGGCCUGG DNA form-
                                        (SEQ ID NO: 11)
CAGAGCTGGGGCCTGG (SEQ ID NO: 12)
Binds to ccaggccccagcucug
```

| Candidate SSO sequences | | Candidate SSO sequences | |
|---|---|---|---|
| SSO21-4r<br>RNA form-<br>AGAGCUGGGGCCUGGG | (SEQ ID NO: 13) | DNA form-<br>GGGGCCTGGGGTCCAG | (SEQ ID NO: 32) |
| DNA form-<br>AGAGCTGGGGCCTGGG | (SEQ ID NO: 14) | Binds to cuggaccccaggcccc | (SEQ ID NO: 33) |
| Binds to cccaggccccagcucu | (SEQ ID NO: 15) | SSO21-14f*<br>RNA form-<br>CUGCAGAGCUGGGGCC | (SEQ ID NO: 34) |
| SSO21-5r<br>RNA form-<br>GAGCUGGGGCCUGGGG | (SEQ ID NO: 16) | DNA form-<br>CTGCAGAGCTGGGGCC | (SEQ ID NO: 35) |
| DNA form-<br>GAGCTGGGGCCTGGGG | (SEQ ID NO: 17) | Binds to ggccccagcucugcag | (SEQ ID NO: 36) |
| Binds to ccccaggccccagcuc | (SEQ ID NO: 18) | SSO21-15f<br>RNA form-<br>GCUGCAGAGCUGGGC | (SEQ ID NO: 37) |
| SSO21-6r<br>RNA form-<br>AGCUGGGGCCUGGGGU | (SEQ ID NO: 19) | DNA form-<br>GCTGCAGAGCTGGGGC | (SEQ ID NO: 38) |
| DNA form-<br>AGCTGGGGCCTGGGGT | (SEQ ID NO: 20) | Binds to gccccagcucugcagc | (SEQ ID NO: 39) |
| Binds to accccaggccccagcu | (SEQ ID NO: 21) | SSO21-16f<br>RNA form-<br>UGCUGCAGAGCUGGGG | (SEQ ID NO: 40) |
| SSO21-7r<br>RNA form-<br>GCUGGGGCCUGGGGUC | (SEQ ID NO: 22) | DNA form-<br>TGCTGCAGAGCTGGGG | (SEQ ID NO: 41) |
| DNA form-<br>GCTGGGGCCTGGGGTC | (SEQ ID NO: 23) | Binds to ccccagcucugcagca | (SEQ ID NO: 42) |
| Binds to gaccccaggccccagc | (SEQ ID NO: 24) | SSO21-17f<br>RNA form-<br>CUGCUGCAGAGCUGGG | (SEQ ID NO: 43) |
| SSO21-8r<br>RNA form-<br>CUGGGGCCUGGGGUCC | (SEQ ID NO: 25) | DNA form-<br>CTGCTGCAGAGCTGGG | (SEQ ID NO: 44) |
| DNA form-<br>CTGGGGCCTGGGGTCC | (SEQ ID NO: 26) | Binds to cccagcucugcagcag | (SEQ ID NO: 45) |
| Binds to ggaccccaggccccag | (SEQ ID NO: 27) | Sequence of target region of pre-mRNA transcript (e.g. for binding SSOs)<br>cuggaccccaggccccagcucugcagcag | (SEQ ID NO: 46) |
| SSO21-9r<br>RNA form-<br>UGGGGCCUGGGGUCCA | (SEQ ID NO: 28) | | |
| DNA form-<br>TGGGGCCTGGGGTCCA | (SEQ ID NO: 29) | | |
| Binds to uggaccccaggcccca | (SEQ ID NO: 30) | | |
| SSO21-10r<br>RNA form-<br>GGGGCCUGGGGUCCAG | (SEQ ID NO: 31) | | |

Note: candidates marked with "*" are the winner oligos discussed in FIG. 4.

TABLE 2

| SSO | Location1 | Sequence (5'-3') | Effects on the relative abundance of INS mRNA isoforms |
|---|---|---|---|
| 1 | Intron 1 (del5, del6) | AGCUGGGGCCUGGGGU | Activation of the cryptic 3'ss of intron 2 |
| 2 | Intron 1 (del5, del6) | UGCAGAGCUGGGGCCUGGGGU | Activation of the cryptic 3'ss of intron 2 |
| 3 | Intron 1 (del8, del9) | CAUGCUUCACGAGCCCAGCC | Increased exon 2 skipping |
| 4 | Exon 2 (cryptic 3'ss + 81, del8, del9) | AAGGCUGCGGCUGGGUC | Increased exon 2 skipping |
| 5 | Exon 3 | UGGUAGAGGGAGCAGAUGCUG | Decreased efficiency of intron 2 splicing; Activation of the cryptic 3'ss of intron 2 |
| 6 | Exon 3 | UGGUACAGCAUUGUUCCACA | Activation of the cryptic 3'ss of intron 2 at high concentration |
| 8 | Exon 2 (del13-15) | CGCACACUAGGUAGAGAGC | Increased exon 2 skipping |
| 9 | Exon 1 | GAUGCAGCCUGUCCUGGAG | None |
| 10 | Intron 1, (del1, del2 cryptic 5' splice site + 30) | GAGCCCACCUGACGCAAAGGC | Partial restoration of authentic 5' splice site |
| 16 | Exon 1 | UGGAGGGCUGAGGGCUGCU | None |
| 17 | Exon 1 | AUGGCCUCUUCUGAUGCA | None |
| 18 | Intron 1 (del9, del10) | UCACCCCCACAUGCUUC | Increased exon 2 skipping |
| 19 | Intron 1 (del9) | ACAUGCUUCACGAG | Increased exon 2 skipping |
| 20 | Intron 1 (del5) | CUGGGGCCUGGGGU | Minor reduction of intron 1 retention; activation of the cryptic 3'ss of intron 2 |
| 21 | Intron 1 (del5, del6) | UGCAGAGCUGGGGCCU | Reduction of intron 1 retention; activation of the cryptic 3' ss of intron 2 |
| 1sc | Scrambled control | AGGUGCUCGCGGGUGG | None |
| 2sc | Scrambled control | GGGUGGAAGCGUCCGGUCGUG | Stimulation of the cryptic 3'ss of intron 2 |
| 3sc | Scrambled control | ACACACUGUGCCUCGCCAGC | None |
| 6sc | Scrambled control | GACUCACUUGCCGUAGUUAA | Stimulation of the cryptic 3'ss of intron 2 |

TABLE 2-continued

| SSO | Location1 | Sequence (5'-3') | Effects on the relative abundance of INS mRNA isoforms |
|---|---|---|---|
| 8sc | Scrambled control | CACGCUCAGUAGAGAAGGC | None |

1, sequence of deleted segments (del) is shown in Fig. 2

Cancer Related Sequences

The sequences of the following table (Table 3) may also be provided with thymine residues substituting the uracil residues (e.g. in DNA form). Each sequence of the following table may be an embodiment of the polynucleic acid polymer of the invention. Each gene or ORF referred to in the table below (Table 3) under "name of compound", may comprise the gene target for correction of intron retention.

TABLE 3

| Name of compound | Corresponding nucleotide sequence of antisense oligoribonucleotide | |
|---|---|---|
| ABCD4-1 | SEQ ID NO: 47. | UAGAGAGGUGUGGGAAGGGAAGCAGA |
| ABCD4-2 | SEQ ID NO: 48. | AAUUCCUUCAUCAUGGCACAUUUAUCCUUGCAGACAGG |
| ABCD4-3 | SEQ ID NO: 49. | CCUGAGGAUACUCACAGAAAGGCAACAG |
| ABCF3-1 | SEQ ID NO: 50. | UUUCCCCAACACACUCCAGCA |
| ACADVL-1 | SEQ ID NO: 51. | GGGCCGCUGCCCACCGUC |
| ALKBH6-1 | SEQ ID NO: 52. | CAGCACAGCUCAGAAGUCUGAG |
| ALKBH6-2 | SEQ ID NO: 53. | CCAAGCCAGGGACAGGGAGGUGAAUGCC |
| AP1G2-1 | SEQ ID NO: 54. | CUUCUGCCCAGCUCUCUGACUG |
| APEX1-1 | SEQ ID NO: 55. | UCUUCACAAACCCCUGCAAAAAUGAG |
| ARFRP1-1 | SEQ ID NO: 56. | CCCAAAGCCCCCGCAGGUGCAGCC |
| ATHL1-1 | SEQ ID NO: 57. | CCCCUCCCCACGCUCUGGAAA |
| ATHL1-2 | SEQ ID NO: 58. | GCAGCACCGGGAGGCUCAGACAAC |
| ATHL1-3 | SEQ ID NO: 59. | GAGCCUCAUCAAAGAAACGG |
| ATP13A1-1 | SEQ ID NO: 60. | GCUCCCACUGGGACUGAGCG |
| ATP1A3-1 | SEQ ID NO: 61. | AGAUGGGAAGAGAGAGAAGAG |
| ATP1A3-2 | SEQ ID NO: 62. | AGAGACAAGGAAACCACACAGACAGAGACC |
| ATP1A3-3 | SEQ ID NO: 63. | GCCGCCCAGCAGAGAGAGG |
| ATP5D-1 | SEQ ID NO: 64. | AGCUGGCUGGGCCCACCUGGCAU |
| ATP5D-2 | SEQ ID NO: 65. | GGGCCCAGGCAGAAGCCU |
| ATP5D-3 | SEQ ID NO: 66. | UCCCCAGAGCUUUCAACACAG |
| ATP5D-4 | SEQ ID NO: 67. | GCAGCCACAGCUCAAAGCUGAGGA |
| BAX-1 | SEQ ID NO: 68. | GAUCAGACACGUAAGGAAAACGCAUUAUA |
| BAX-2 | SEQ ID NO: 69. | GCAGAAGGCACUAAUCAAGUCAAGGUCACA |
| BAX-3 | SEQ ID NO: 70. | CGGGCAUUAAAGAGCUGGACUCAG |
| BDH2-1 | SEQ ID NO: 71. | ACCAAUUUUGAAAAAGCAG |
| BDH2-2 | SEQ ID NO: 72. | CCACAUUUUAAUUUAAUUUUAC |
| BDH2-3 | SEQ ID NO: 73. | CCAUUAGAAAGAAUAAAAG |
| BDH2-4 | SEQ ID NO: 74. | UAUUUUAAAUUAAUUAAAUGUUAAAUGG |
| BDH2-5 | SEQ ID NO: 75. | AUUUCAUUUUAAACUCACAGAU |

TABLE 3-continued

| Name of compound | Corresponding nucleotide sequence of antisense oligoribonucleotide | |
|---|---|---|
| BDH2-6 | SEQ ID NO: 76. | AUCCUUGCAAAGAGAAGAAAUG |
| BDH2-7 | SEQ ID NO: 77. | UCCUUCAACUUGACUUCUUGCUGAUGGCUCAGAUCAACU |
| BRD2-1 | SEQ ID NO: 78. | UAUUUUAUAAAAGUAAAAUGCCAAGAACCAAAGACU |
| BRD2-2 | SEQ ID NO: 79. | UUCAAACUCCAAGAAAUACAAAUUCUCAAAACAC |
| BRD2-3 | SEQ ID NO: 80. | UUUUCUCAAGACAAAGAAACCC |
| C16orf59-1 | SEQ ID NO: 81. | GGGUGGAGCAGUCAAGCC |
| C16orf59-2 | SEQ ID NO: 82. | ACUUCCCAACCCACACACACAGAC |
| C1orf124-1 | SEQ ID NO: 83. | GUCACAUAAAAAUCAGAAGAAU |
| C1orf124-2 | SEQ ID NO: 84. | CAAAUAUUAUCAGAGAUUGAA |
| C1orf124-3 | SEQ ID NO: 85. | CUUGAAUUAUUGUUUUUAUUUUGACAAUC |
| C1orf124-4 | SEQ ID NO: 86. | ACUCAAUAAUUAAAGAUUUGGGAAAUAU |
| C1orf124-5 | SEQ ID NO: 87. | AGGCAACAUUUACCUUGAAAAU |
| C1orf124-6 | SEQ ID NO: 88. | GAGGGCAAUCUUCAGAAUUCAG |
| C1orf63-1 | SEQ ID NO: 89. | UAAUCAGAUUUGACAGUUGGCUUUCUGAAAGUUUU |
| C1orf63-10 | SEQ ID NO: 90. | ACAUUUCUGGAGAAUUAUAAUAAACUUAU |
| C1orf63-11 | SEQ ID NO: 91. | CAAUUACACAGAUUCAUUUAGAUA |
| C1orf63-2 | SEQ ID NO: 92. | UCAGAUUUGCUACUUUGAAUUUAGCACAUUAU |
| C1orf63-3 | SEQ ID NO: 93. | AAAUAAAGCUCAUUAAUCUCCCAUUUUCAUG |
| C1orf63-4 | SEQ ID NO: 94. | UGAAAAUGAAAAAAAUAAAUGU |
| C1orf63-5 | SEQ ID NO: 95. | GCUACAAACACUCUGUAAAUAGCUUAGAAAAACU |
| C1orf63-6 | SEQ ID NO: 96. | CAUGAUUUCUAUAAGACAGAAAUAGAGCAGAUAA |
| C1orf63-7 | SEQ ID NO: 97. | CAAUUACCAACAGAUUUUCUUCAUCAAUG |
| C1orf63-8 | SEQ ID NO: 98. | ACAUAAACUUCAAAUUAAACCU |
| C1orf63-9 | SEQ ID NO: 99. | GUACCUUUGCUUAGUUUAAAAAUUG |
| C2orf49-1 | SEQ ID NO: 100. | GGAAUUUGAUAAUUUUCUAAAGG |
| C8orf82-1 | SEQ ID NO: 101. | CGGAAGGGAGAAAGAAGGG |
| C8orf82-2 | SEQ ID NO: 102. | CCUGGCCUCACUCAGCG |
| CAPRIN2-1 | SEQ ID NO: 103. | UAAAGAAAUAAUGCUUACUGGU |
| CAPRIN2-3 | SEQ ID NO: 104. | UGUGGUAAUCAAAGCAAAUAGA |
| CAPRIN2-4 | SEQ ID NO: 105. | AUGAUUUAGAACAGCAUGAAAAAUCAAAAUA |
| CAPRIN2-5 | SEQ ID NO: 106. | CUUAAAUUUAAAUUAAGAAAUGAG |
| CAPRIN2-6 | SEQ ID NO: 107. | UAAAAGAAAAUGGAUUCUAAUUAAUAU |
| CASKIN2-1 | SEQ ID NO: 108. | GCAAAGCCACAGCUGAGGGUGACAGCACG |
| CASKIN2-2 | SEQ ID NO: 109. | CCAGCCAGAGGAGAAAAGGCA |
| CDCA7-1 | SEQ ID NO: 110. | CACACAAAUAAAGAAAUUAGAUUU |
| CDCA7-3 | SEQ ID NO: 111. | UUUUCUUCUUUUAUUUUCAUUCUCCAAUUUUAAA |
| CDCA7-4 | SEQ ID NO: 112. | AAGCCAGGAAAAAGAAAUCUUUUCUAUCA |
| CDCA7-5 | SEQ ID NO: 113. | AGAAACACAUUCAGUUUCUAC |

TABLE 3-continued

| Name of compound | Corresponding nucleotide sequence of antisense oligoribonucleotide |
|---|---|
| CDCA7-6 | SEQ ID NO: 114. UCUAAAAAAAAAAAUUUCUC |
| CDCA7-7 | SEQ ID NO: 115. UGCAUAAUGCAUGGCAAAAUGAGC |
| CEP164-1 | SEQ ID NO: 116. GCUAGAGAAGCUAUGACUCUGAGGUCAAGGAC |
| CEP170-1 | SEQ ID NO: 117. CUUCAUCAAAGAAUGCAAUCA |
| CEP170-2 | SEQ ID NO: 118. ACUUUGAGUAAAAGAAU |
| CEP170-3 | SEQ ID NO: 119. CUUUGCUUUCUCAAGUUUUGUAUGU |
| CLCN7-1 | SEQ ID NO: 120. CCAGCAGAGGCAGGCAGAGAAGGAAG |
| CLCN7-2 | SEQ ID NO: 121. CUGAAAUGAGAAACAGAAGACACAUAAGAGAACCC |
| CLCN7-3 | SEQ ID NO: 122. GCCGCGUACAUACACAGAACAACC |
| CPNE1-1 | SEQ ID NO: 123. UGAGCAUCCCUUGGGCCUCAACCCUACUCACAUCAGGGAAAGGUGAAAGGGUAAACU |
| CPNE1-2 | SEQ ID NO: 124. AGGCUUAGAGGAAAAGGUGAGCAU |
| CPNE1-3 | SEQ ID NO: 125. UAUUUCAUGCUCAAGAACCCAACCA |
| CPNE1-IVSB-1 | SEQ ID NO: 126. CACAUCAGGGAAAGGUGAAAGGGUAAA |
| CPSF3L-1 | SEQ ID NO: 127. CCCACGCCGCCCGCCCG |
| CPSF3L-1 | SEQ ID NO: 128. UCUGAGGCCCAGGGUCCAGCUGUGGAUG |
| CPSF3L-2 | SEQ ID NO: 129. CAGCCAUCCAAGCACAACCACUGCU |
| CPSF3L-4 | SEQ ID NO: 130. CUCACUGACAGAUGUGAGCUGGAAGCUGA |
| CPSF3L-5 | SEQ ID NO: 131. GGGUUCUAUGUGCAGACUCAG |
| DCXR-1 | SEQ ID NO: 132. CAUCACUCACGAGAAUUCC |
| DENND4B-1 | SEQ ID NO: 133. ACAGACCAGGGAUCACCCAGA |
| DFFA-1 | SEQ ID NO: 134. UUUAGAUUAAUGAGAUUUUUGC |
| DFFA-2 | SEQ ID NO: 135. UGCAUUUUCUUUAAAGCUAUUUUG |
| DFFA-3 | SEQ ID NO: 136. AAGACCCAGAAGCCAUCUCAGAAGAUUG |
| DFFA-4 | SEQ ID NO: 137. AUGACAGGGACAAGGACAAUGAAUCAGAAGUAG |
| DFFA-5 | SEQ ID NO: 138. UUUUCUUACAACACCAACAGGAAGAAGU |
| DFFA-6 | SEQ ID NO: 139. GUUUAUGUUACCUCUUUACACUGAAAUG |
| DIS3L2-1 | SEQ ID NO: 140. GGGACACAGAUGAAGGAAUGAG |
| DIS3L2-2 | SEQ ID NO: 141. CAAGGAAGGGAAGGUGGUGCCAGAAAGCAGG |
| DIS3L2-3 | SEQ ID NO: 142. AGGCUUAUGAAACACAACC |
| DNAJB12-1 | SEQ ID NO: 143. AGGGCCAAAGCUGCCAGGAGU |
| DNAJB12-2 | SEQ ID NO: 144. CUCCCUUUCUCCCCCUCCCUCCUCUGCUCA |
| DNAJB12-3 | SEQ ID NO: 145. CUGGAGCCAGGGAGCAGAGCG |
| DNAJB12-4 | SEQ ID NO: 146. CUCAGCAACAGUUUCAAGUUCCCAC |
| DNAJB12-5 | SEQ ID NO: 147. CCGCCACCAAGACUGCCAGCUCCCACCCACCUC |
| DNAJB12-6 | SEQ ID NO: 148. AGUGCCUCAGAUCCCACCAGAGG |
| DNAJB12-7 | SEQ ID NO: 149. GCCUGCUACCAGCAACUCUCAUUUCC |
| DNAJB12-8 | SEQ ID NO: 150. CACAGAGAAGAACCUUCACUGCUUCUGC |
| DNAJB12-9 | SEQ ID NO: 151. GAGGACACAGGCAAAGGAGGG |

TABLE 3-continued

| Name of compound | Corresponding nucleotide sequence of antisense oligoribonucleotide |
|---|---|
| DNAJB12-IVSB-1 | SEQ ID NO: 152. CCAAAGCUGCCAGGAGUUGCA |
| DNAJB12-IVSB-2 | SEQ ID NO: 153. GCUGGAGGUCAGGCUGGG |
| DNAJB12-IVSB-3 | SEQ ID NO: 154. CCCUCAGCAACAGUUUCAAGUUC |
| DNAJB12-IVSB-4 | SEQ ID NO: 155. AAUAGUCUGCUGUGCUGGAGAAAGGG |
| DNAJB12-IVSB-5 | SEQ ID NO: 156. UUCCUCCUAGCUGGAGGGAUGGAGAAAG |
| DNAJB12-IVSB-6 | SEQ ID NO: 157. AGAGAGUGCCUCAGAUCCCACCAGA |
| DNAJB12-IVSB-7 | SEQ ID NO: 158. AGAAGGAGGGAGCCUGCUACCAGCAACUCUCAUUUC |
| DNAJB12-IVSB-8 | SEQ ID NO: 159. CACACAGAGAAGAACCUUCAC |
| DNAJB12-IVSB-9 | SEQ ID NO: 160. CAGCACAGAGGCAGGCACAAAUG |
| DPF1-1 | SEQ ID NO: 161. UCUGGAACGGGAGGGAGAGGG |
| DPF1-2 | SEQ ID NO: 162. CUCAGCCAGAGACCUGAGCAGC |
| DRG2-1 | SEQ ID NO: 163. CAAUUUCAACGAUCAGUAACAGAGC |
| DRG2-2 | SEQ ID NO: 164. UUCUGGAAAGCGGGAUAAUGGAC |
| DRG2-3 | SEQ ID NO: 165. CAUCAUAAAAGGAGUAACAGGAUAAUA |
| DRG2-4 | SEQ ID NO: 166. CUUAUUUCAGAAGAAAAUCCGA |
| DRG2-5 | SEQ ID NO: 167. CAAGCUUGGCAUUUUUCUUUAAUCCA |
| DSN1-1 | SEQ ID NO: 168. GUGGAAACAUAAAGAAAGCAUC |
| DSN1-2 | SEQ ID NO: 169. UGCAAAAAGUGGAAAAAGUAAAUGUA |
| EML3-1 | SEQ ID NO: 170. AUCUUCAGGUUUCUGGACUCUCACCCA |
| EWSR1-1 | SEQ ID NO: 171. AAACAAAAUUAGGUAAAAGGAG |
| EWSR1-10 | SEQ ID NO: 172. CUUUAAACACAAAAGUUUACA |
| EWSR1-2 | SEQ ID NO: 173. GGAAAUGCAGAAAUUAAUUUCUUAUG |
| EWSR1-3 | SEQ ID NO: 174. AUUUCAAGACAACCAUUCAAAGGCAGUUAGUUAACAA |
| EWSR1-4 | SEQ ID NO: 175. CUAAACAAAGUUUUCUAAACCAGAUU |
| EWSR1-5 | SEQ ID NO: 176. GGACAGAACACACACAGAAC |
| EWSR1-6 | SEQ ID NO: 177. AGUUAAAAAUCAACUUUAAUUUUGAAG |
| EWSR1-7 | SEQ ID NO: 178. UUUUCCAAAUCAGAAGAUUG |
| EWSR1-8 | SEQ ID NO: 179. UAUUUUAAAACAUCCAAAAAGAAGU |
| EWSR1-9 | SEQ ID NO: 180. GACAAAGCAUGUUAAAAAGUUUCCA |
| FGFR4-1 | SEQ ID NO: 181. AUCAGAUGAGCAGCAGCGG |
| FTSJ1-1 | SEQ ID NO: 182. GGGUCAAGGCAGGCUGAGAG |
| FTSJ1-2 | SEQ ID NO: 183. CCAGAAACCAUGAGAUUUGGGUCAGAAAAAGGCA |
| FTSJ1-IVSB-1 | SEQ ID NO: 184. CAGUCGGCGUCCCAGAGAUCC |

TABLE 3-continued

| Name of compound | Corresponding nucleotide sequence of antisense oligoribonucleotide | |
|---|---|---|
| GBAP1-1 | SEQ ID NO: 185. | CAUUUAAGUAGCAAAUUCUGGGC |
| GBAP1-2 | SEQ ID NO: 186. | CUCAUCUUCUUCAGAGAAGU |
| GBAP1-3 | SEQ ID NO: 187. | CCAAAGAAUUGGCAAAGAAAAG |
| GBAP1-4 | SEQ ID NO: 188. | AUUUCACUGGCAUUAAGACAG |
| GBAP1-5 | SEQ ID NO: 189. | GUCCGUAGCAGUUAGCAGAUGA |
| GBAP1-6 | SEQ ID NO: 190. | GUCUGAGUCAGGGCCAAAGGAA |
| GMPPA-1 | SEQ ID NO: 191. | GGGAAACAGCAUGAAGAUAAGCAGG |
| GMPPA-2 | SEQ ID NO: 192. | AUGAGAAACUAGAUUAGGG |
| GMPPA-3 | SEQ ID NO: 193. | GAAAAGCAAUAAAGAAAUGAGCAACA |
| GMPPA-4 | SEQ ID NO: 194. | AAGUCCAGAAACCAGUUUCAGUC |
| GMPR2-1 | SEQ ID NO: 195. | GAGCUGGGAAAGGGUUGUGAGAGAC |
| GMPR2-2 | SEQ ID NO: 196. | GGUCCCUGAAGCCUGUCACC |
| GMPR2-3 | SEQ ID NO: 197. | CGCUUAAGUUGUGGAAGGUCG |
| GNPTG-1 | SEQ ID NO: 198. | AGCACUACAGGGCCUCCAGCAGGGC |
| GORASP1-2 | SEQ ID NO: 199. | ACAAAACCAGACACUUCUCAUGGACAGCA |
| GPATCH4-1 | SEQ ID NO: 200. | AUCUGAAGACAUCUCUUCCCACAUU |
| GPATCH4-2 | SEQ ID NO: 201. | CCAGUCAAGCAUUAGAUUUAGC |
| GPATCH4-3 | SEQ ID NO: 202. | UCCUCCUUCUAAAACAUU |
| HGS-1 | SEQ ID NO: 203. | AGGAUGCACCCCAUGCU |
| HMG20B-1 | SEQ ID NO: 204. | CGGAGCCACAAGCAAUUCAAAUCCAGC |
| HMG20B-2 | SEQ ID NO: 205. | GUCAGCAGUCGGGACACGGUGGGUUAGA |
| IFFO1-1 | SEQ ID NO: 206. | UGGUUAAAGAAACUGGAGAAAGAAAAGCAAAAGGAUAAAGGAA |
| IFFO1-2 | SEQ ID NO: 207. | CAAGUCAGGGAGAGAGAGAGAGG |
| ISYNA1-1 | SEQ ID NO: 208. | AGCCGCCCCGCUCUCCCCAGC |
| KRI1-2 | SEQ ID NO: 209. | GAGGAUGAAAGAGGAAAGG |
| KRI1-3 | SEQ ID NO: 210. | CUGAGGGCACAAGAGAGACAG |
| KRI1-4 | SEQ ID NO: 211. | GGGAAGACAAAGACUUGACAAGG |
| KRI1-5 | SEQ ID NO: 212. | AGGUCAAACAGGUGGUCAAACAGCAGGA |
| LOC148413-1 | SEQ ID NO: 213. | UAAGGACUGAAGACACGACG |
| LOC148413-2 | SEQ ID NO: 214. | GAGUGUUGAAGGCAAGACUUUGCAG |
| LZTR1-1 | SEQ ID NO: 215. | CCCACUCAGUGGGAGCUGCAGCCAU |
| MAN2C1-1 | SEQ ID NO: 216. | GGAAGACCCAUUUCUCCAUGCC |
| MAP4K2-1 | SEQ ID NO: 217. | CCCAGAGCUCUGAGGGUGCCCUGGGC |
| MCOLN1-2 | SEQ ID NO: 218. | GUGCUCACCCAGCAGGCA |
| MCOLN1-3 | SEQ ID NO: 219. | GCCACGUGCUGACUCUGCAGCUGGCAGG |
| MDP1-1 | SEQ ID NO: 220. | UCGCCCCCAGUCUUCCCU |
| MIB2-1 | SEQ ID NO: 221. | GGCAGCACAGCAAGAGG |
| MITD1-1 | SEQ ID NO: 222. | CAAAAACAGUGCUACACAUUUACUCA |

TABLE 3-continued

| Name of compound | Corresponding nucleotide sequence of antisense oligoribonucleotide |
|---|---|
| MOK-1 | SEQ ID NO: 223. UCAGAAAGCCUGUGACAAAUCUU |
| MOK-2 | SEQ ID NO: 224. AAGAAGAGUCCAAAAUGGUU |
| MOK-3 | SEQ ID NO: 225. UGAGAAGAAUGAAAUAAAAUUUAACAAAA |
| MOK-4 | SEQ ID NO: 226. UGUUAUGCUAAAAAUGUAAGAAAAC |
| MOV10-4 | SEQ ID NO: 227. AUCAGAAUUUCCAAGAGAGAGGCC |
| MOV10-5 | SEQ ID NO: 228. UAAGGAAAGAAAACAGCAUUGCAAAGAACACG |
| MRPL35-1 | SEQ ID NO: 229. AGUUUUAAAACUUUUCUAAGUUUAAUGU |
| MRPL35-5 | SEQ ID NO: 230. AAUGAAAACAUGAAAUCUGA |
| MRPL35-6 | SEQ ID NO: 231. GAAAAUUUGUGGGAAAAGUUUAUCCUUAC |
| MRPL35-7 | SEQ ID NO: 232. UCUGAAACAGUAAUUCAUGCAUAAUUCU |
| MRPL35-8 | SEQ ID NO: 233. UGCAGAACUUCAAUUUCAUAAUUUU |
| MTMR11-1 | SEQ ID NO: 234. AAACAAAUCAAGACCAAACUUCAGAGAGU |
| MTMR11-2 | SEQ ID NO: 235. CCUGAAAAUGAGAAUAAAUCUCC |
| MTMR11-3 | SEQ ID NO: 236. GACAAAUCAUGAGAUUCUCACC |
| MUS81-1 | SEQ ID NO: 237. UCCCUGCCACUCCCUCCA |
| MUS81-2 | SEQ ID NO: 238. CUGCAGGAAGAGAGGCAGCGA |
| NAPEPLD-1 | SEQ ID NO: 239. GCCUUUUCAUUAAAAG |
| NAPEPLD-2 | SEQ ID NO: 240. UUUCAUUUGUUUUUAAACUUAGAU |
| NAPEPLD-3 | SEQ ID NO: 241. UAUUCAUGAAUUUCUAA |
| NAPEPLD-4 | SEQ ID NO: 242. UUUCCAAAUGUAAAAUAAUCACA |
| NAPEPLD-5 | SEQ ID NO: 243. CACAAAACAUAAAACAUAAAC |
| NAPEPLD-6 | SEQ ID NO: 244. UACUAGGAAGCAAGUUAUUA |
| NAPEPLD-7 | SEQ ID NO: 245. AAUUCAUUAUUUAAAUGAC |
| NAPEPLD-8 | SEQ ID NO: 246. AUGAAAUUUAAAAUCCACAUUAGC |
| NBEAL2-1 | SEQ ID NO: 247. ACAUUCUGAUUAGGGAGG |
| NDRG4-1 | SEQ ID NO: 248. GAAGGCAACAGAGGUGAGUGUGA |
| NDRG4-2 | SEQ ID NO: 249. CCAGAGGGCAGGCAAGGCAGAAGUG |
| NDUFB10-1 | SEQ ID NO: 250. GGAAGAUUUGCAAUGGUUCUG |
| NFATC4-1 | SEQ ID NO: 251. ACACACAGACAAAAGAGUUGCAAGAGACAGAGAC |
| NFATC4-2 | SEQ ID NO: 252. GGCAAACUAGAAUAGAAAGA |
| NFATC4-3 | SEQ ID NO: 253. CCAGAGCAGAGAGAGGGUUAAACAGG |
| NFATC4-4 | SEQ ID NO: 254. UCAGCAGUAGACACACAAAUAAACCAG |
| NFKBIB-1 | SEQ ID NO: 255. GUCGGUGCCUAAUUAUCUUCUUGGG |
| NFKBIB-2 | SEQ ID NO: 256. AGUUUUCAGCCACUUCU |
| NFKBIB-3 | SEQ ID NO: 257. UCUUGCUGCCUAAAAUCAC |
| NFKBIB-4 | SEQ ID NO: 258. UGCCUUUACCCAAAUUCCUC |
| NFKBIB-5 | SEQ ID NO: 259. UUCAAGGUCAUUUCUACAGACCAAUUUCU |
| NIT1-1 | SEQ ID NO: 260. GGACACUGUCCAACAAAGAUUCUAC |
| NIT1-2 | SEQ ID NO: 261. CUGGCAACCCAGGGACAC |

TABLE 3-continued

| Name of compound | Corresponding nucleotide sequence of antisense oligoribonucleotide | |
|---|---|---|
| NKTR-1 | SEQ ID NO: 262. | AAUAAAAUUGAGUUUAUAGAAUUA |
| NKTR-2 | SEQ ID NO: 263. | AUUUGCCAGAUUUCAAUUUAAAGUUUAAAAG |
| NKTR-3 | SEQ ID NO: 264. | AAACUGAAAACACACAAAUCUUUGAAAUGAAAUGC |
| NKTR-6 | SEQ ID NO: 265. | CUUUUUUAUUUUAAGAGUUCCA |
| NKTR-7 | SEQ ID NO: 266. | AUGAUUUUCACAAAGAGAACAAUA |
| NKTR-8 | SEQ ID NO: 267. | AUUUCAUAAUAAAAGCACAUAAAAUUAGU |
| NPRL2-1 | SEQ ID NO: 268. | CCUGCCACCCACCGCUCACCC |
| NPRL2-2 | SEQ ID NO: 269. | CCUUCCUCCUCCUGGGACAA |
| NSUN5P1-1 | SEQ ID NO: 270. | AUUAAAGUGUCAGAACUAAGACCAAAACAGAUG |
| NSUN5P1-2 | SEQ ID NO: 271. | CCUGAAAUCCUUGCCUCACAGAGGAGAACU |
| NSUN5P1-3 | SEQ ID NO: 272. | GCCUCAGUCCUGAAAUCCU |
| NUDT22-1 | SEQ ID NO: 273. | GGCAGUAAAACGUGCCAUCUUC |
| NUDT22-2 | SEQ ID NO: 274. | UGUCGCAGACCUCCUGAGGG |
| PAN2-1 | SEQ ID NO: 275. | UCUUCCUUUUCCCUCUGCUAAGUUU |
| PAN2-2 | SEQ ID NO: 276. | GUGACUAUGGAAAAUCCCCUAACAG |
| PDDC1-1 | SEQ ID NO: 277. | GUGCAGCUCUGAUGUGGCAGG |
| PDLIM4-1 | SEQ ID NO: 278. | UGCAGGGAGUGGGAAGGCAGAU |
| PDLIM4-2 | SEQ ID NO: 279. | GGGCCGCAGAGACCGAAGAGGGCAGGUG |
| PDLIM4-3 | SEQ ID NO: 280. | GAAGCCAGGGCGUAGCAAGGUUGUAGCAA |
| PDLIM4-4 | SEQ ID NO: 281. | GGGCAACCUGGGCACUGCA |
| PHF1-1 | SEQ ID NO: 282. | UUUUUCCUUCAUUUCCUGGGAU |
| PHF1-2 | SEQ ID NO: 283. | GUCCCAAACCCUAAACUUACCUC |
| PIK3CD-1 | SEQ ID NO: 284. | CUGGGAUUCCCACAGAACGG |
| PIK3CD-2 | SEQ ID NO: 285. | GCUGGAAACGUCCCCAGUGGCCUUCC |
| PITPNM1-1 | SEQ ID NO: 286. | GGCGGAGCCCUCCCGCAGAGGC |
| PPIL2-1 | SEQ ID NO: 287. | GCAGCAGGCAAGCAAUUUAUUG |
| PPIL2-2 | SEQ ID NO: 288. | GCCCUUGGCAACAGGUUAAGGGA |
| PPIL2-3 | SEQ ID NO: 289. | CAGGUCCUGGAAACAGGGCCAA |
| PPIL2-5 | SEQ ID NO: 290. | GGGUAAGAAAACCAGACAUA |
| PPIL2-7 | SEQ ID NO: 291. | GCACAUUUAACAGAAAAAUG |
| PPIL2-8 | SEQ ID NO: 292. | UGAAGACGAAGAAAAAGCCAGCCAGG |
| PPP1R35-1 | SEQ ID NO: 293. | CGCACGCGGCCGGCCGCCCGC |
| PPP4C-1 | SEQ ID NO: 294. | CCACCCCCAAAAGCAGAAU |
| PPP4C-2 | SEQ ID NO: 295. | CUGCCCCUCCCAGAAUGCUG |
| PPP4C-3 | SEQ ID NO: 296. | UCUUUCACCUACCAGACACAGAC |
| PPP4C-4 | SEQ ID NO: 297. | CCUCCAGAGAAUGUAAAGCUGA |
| PQLC2-1 | SEQ ID NO: 298. | GGAGAGGGCUGGAAGGAUGUGGCA |
| PQLC2-2 | SEQ ID NO: 299. | AAAAACGAAGCCAUCAGAUGCCAAG |

TABLE 3-continued

| Name of compound | Corresponding nucleotide sequence of antisense oligoribonucleotide | |
|---|---|---|
| PRPF39-1 | SEQ ID NO: 300. | GUGACAAAUGCAAAUAAAUAC |
| PRPF39-2 | SEQ ID NO: 301. | CUGCCAACAAAGAGAGAAAAUAUUAGCU |
| PRPF39-3 | SEQ ID NO: 302. | UGUUUGGAAAAUGAGAAAUAAAUGU |
| PRPF39-4 | SEQ ID NO: 303. | UAGCAAAUGUGACUAGCAAACCAAC |
| PRPF39-5 | SEQ ID NO: 304. | CUAAUUACUGGAAUUUUGUUUAAAUAAUC |
| PSME2-1 | SEQ ID NO: 305. | UUGUUAGCUAGAGAGGGUGGGCAAAGGG |
| PSME2-2 | SEQ ID NO: 306. | CCUAAUCCACUAUUUGAAAC |
| PSME2-3 | SEQ ID NO: 307. | CAUGCCUCACGCCAUCCUAAUG |
| PTPMT1-1 | SEQ ID NO: 308. | GACAGGGACGGAGCGGCGG |
| QARS-1 | SEQ ID NO: 309. | ACCUCCCUCACCCCAAACC |
| RAD52-1 | SEQ ID NO: 310. | GGCCGCAGAGGAAAGGAGG |
| RAD52-2 | SEQ ID NO: 311. | GCAGCCCCGUGACACAGGAG |
| RHOT2-1 | SEQ ID NO: 312. | CACAGGCCGCGCCGCCCC |
| RHOT2-2 | SEQ ID NO: 313. | CCAUGCUGGGCCAGAUCUGCCAGG |
| RMND5B-1 | SEQ ID NO: 314. | CUGAGAGGUCGAAGCAGAAUGC |
| RMND5B-2 | SEQ ID NO: 315. | GUGAAAUGAAGACCACAGUCAAGCCC |
| RMND5B-3 | SEQ ID NO: 316. | GAGACAGGGCUGCAGGCAAGUCAAGUA |
| RNF123-1 | SEQ ID NO: 317. | ACACACACAACCAAACACGCACAACAC |
| RNF123-2 | SEQ ID NO: 318. | GGCAGCAGGAGCAGAAACCAG |
| RNF123-3 | SEQ ID NO: 319. | CACAACAGUCAGCAGGUCAGACUG |
| RPL10A-1 | SEQ ID NO: 320. | GAAGGGUCUGGGACCGCAGCA |
| RPP21-1 | SEQ ID NO: 321. | UACAGUGAGAAAGGCGCU |
| RPP21-2 | SEQ ID NO: 322. | AGGAACUUAAUCCAAACCCGAAGAAGGAAGAC |
| RPP21-3 | SEQ ID NO: 323. | CCUCUUAAAAGUUAUUAUUUAUU |
| RPP21-5 | SEQ ID NO: 324. | AAUUUCAAUGAGAAUAAUGAAU |
| RPP21-7 | SEQ ID NO: 325. | UCUUUAAGAUAAAGUUCAAAC |
| RPP21-8 | SEQ ID NO: 326. | CAAUUUGAAUGCACAUUUGAU |
| RPS6KB2-1 | SEQ ID NO: 327. | CGACAGACGUGGCCAAGGCA |
| RPS6KB2-2 | SEQ ID NO: 328. | AGACACAGCAACCGAAGCCAACACU |
| RPS6KB2-3 | SEQ ID NO: 329. | ACACAGGCCGCGGGCUCCACAAAC |
| RUSC1-1 | SEQ ID NO: 330. | GAGCUCCAUUACUCUCCUCAU |
| RUSC1-2 | SEQ ID NO: 331. | CACCUCCCGCCAACCAUUCC |
| SCRN2-1 | SEQ ID NO: 332. | UUCCUUCAUAUUUCCAGAGUC |
| SCRN2-2 | SEQ ID NO: 333. | UCCCCAGCUCUGAAAUCUCU |
| SCRN2-3 | SEQ ID NO: 334. | CUCACACAAGCAGGAGAAAGGAGAU |
| SCYL1-1 | SEQ ID NO: 335. | CUAGUCUUCAGCCCACCCAG |
| SFR1-1 | SEQ ID NO: 336. | ACAAUACUUAGAAACACAUAAUGG |
| SFR1-2 | SEQ ID NO: 337. | CGUAGAAUUUAAACCACC |
| SFR1-3 | SEQ ID NO: 338. | CACAUUAUGUUAAUUAACAAC |

TABLE 3-continued

| Name of compound | Corresponding nucleotide sequence of antisense oligoribonucleotide |
|---|---|
| SFR1-4 | SEQ ID NO: 339. AGAAGAAAAACAAAAUUAUUUAAUAAAAU |
| SFR1-5 | SEQ ID NO: 340. UAACUGAAAUGAAUUCAUUCAAGAGGAAAAUAUGGAA |
| SFR1-6 | SEQ ID NO: 341. UCAGAAUUACAGAGUAAGGAAAAGACCU |
| SFR1-7 | SEQ ID NO: 342. GGCAUCACAAAAUGACUUUAAUUUCUGGA |
| SGSM3-1 | SEQ ID NO: 343. CUAACCCCAGAGAGGUCUCUA |
| SIRT7-1 | SEQ ID NO: 344. UGGAGACCCUGGGUCCCUGCAG |
| SLC25A3-1 | SEQ ID NO: 345. CCACAGGAGCUCUGGGCU |
| SLC25A3-2 | SEQ ID NO: 346. UGGGCCCACCGCCAAAGCAGCG |
| SLC25A3-3 | SEQ ID NO: 347. UCCACGCCCUUGAAGAGGUCACGGCGG |
| SLC30A7-1 | SEQ ID NO: 348. AUUUCUCUCUUUUAAAAAGCUG |
| SLC30A7-2 | SEQ ID NO: 349. GCACAAAAGAAAAGACCAAAAGU |
| SLC30A7-3 | SEQ ID NO: 350. CAGAAGUCAAAAAGAUUUGGAGGAAAG |
| SLC30A7-4 | SEQ ID NO: 351. AAACCUCAGAAGUCAAAAAGAU |
| SLC37A4-1 | SEQ ID NO: 352. UAUGACAAUCCAAACAGGC |
| SLC37A4-2 | SEQ ID NO: 353. UAAGAAAGGGCGCUCCCACAUGCUCUUUAGG |
| SLC37A4-3 | SEQ ID NO: 354. UCCUAAAAUAUCUUGACAAGCAAU |
| SLC37A4-4 | SEQ ID NO: 355. AAGCUCACAUUACAGGGAAGAGGGA |
| STK19-1 | SEQ ID NO: 356. UCAUUUUAUUAACAAGAAGAGUC |
| STK19-2 | SEQ ID NO: 357. ACCAAGAACUGAAUUCUAUUUCAGG |
| STK19-3 | SEQ ID NO: 358. GAAACACGGGCAACCAUGCAAGAGAGACU |
| STX10-1 | SEQ ID NO: 359. CCCACCAGGACUGACCCCUCCC |
| TCF25-1 | SEQ ID NO: 360. CCCUCCUGCUGCUGGAAGCAGGUCC |
| TCF25-2 | SEQ ID NO: 361. GUCACAGAAAUGUGAAAAUGCACC |
| TCF25-3 | SEQ ID NO: 362. UUCUUUAGGAAGCAGGACUGA |
| TOMM40-1 | SEQ ID NO: 363. GACUCAGCCCCAGCAAAUCCGC |
| TOMM40-2 | SEQ ID NO: 364. GCACCCGGCUCCGGCCCC |
| TP53I3-1 | SEQ ID NO: 365. GCAAAUCACACUCCCUCUGAGUUGGAAGC |
| TP53I3-2 | SEQ ID NO: 366. CCGCCUCCAGACCGAUCCCACCCGGAACACAGAUGGG |
| TRIM41-1 | SEQ ID NO: 367. AUACCGAAGAGAAGCAGGGAC |
| TRIM41-3 | SEQ ID NO: 368. CCCAGAGGGAAAAGCAAAAGCUGAGG |
| TRPT1-1 | SEQ ID NO: 369. GCAGACAGGCUCACGUUUCUCU |
| TRPT1-2 | SEQ ID NO: 370. CCCAGACAAGAACUCUCCUCAG |
| TSTA3-1 | SEQ ID NO: 371. GCUGGGCCUCAGCAGGA |
| TSTA3-3 | SEQ ID NO: 372. CUUACUGAGGCUGGCACGAAGACC |
| TTC14-1 | SEQ ID NO: 373. CCUUAAGUUUAAAAAUACUGA |
| TTC14-10 | SEQ ID NO: 374. AAAUGUUUCUAAAUUAUUCAUAAAGAUG |
| TTC14-2 | SEQ ID NO: 375. AAUACUUUCAUAUUUUUAUUUACUUUACCUCC |
| TTC14-3 | SEQ ID NO: 376. UCUUUAAUAAGAAAAUACAUGGAACACA |

TABLE 3-continued

| Name of compound | Corresponding nucleotide sequence of antisense oligoribonucleotide |
|---|---|
| TTC14-4 | SEQ ID NO: 377. UAUUCUAUAUUUUAAUUCUAAGAUACUCU |
| TTC14-7 | SEQ ID NO: 378. UGAAAGACAGACUUUUUUCAACACUACCUUAAAAACUUAAGAC |
| TTC14-8 | SEQ ID NO: 379. AAGAUCUAAUUUUACUAUUAAGCAC |
| TTC14-9 | SEQ ID NO: 380. UAUUUGUUUCCUUUAAAGAUUUUAUAAAAGCU |
| TUBGCP6-1 | SEQ ID NO: 381. CCUGCCAACAGCAACUGC |
| TUBGCP6-2 | SEQ ID NO: 382. ACGUGCUGGGAACCAGCCAGC |
| TUBGCP6-3 | SEQ ID NO: 383. UCCGCCCCCAUCCACAGGAGAUG |
| U2AF1L4-1 | SEQ ID NO: 384. GGCUUAGGGUUAGGCUCAUCUGAGGAU |
| U2AF1L4-2 | SEQ ID NO: 385. CUGAAAUAACUAGAGUUCUAAGACACGA |
| UCK1-1 | SEQ ID NO: 386. CAGGACCUGCCGCCAGCCUCGGCCAGGCAGGCACGG |
| UNC45A-1 | SEQ ID NO: 387. CCACAGAAGCCCUACAGCUCC |
| UNC45A-2 | SEQ ID NO: 388. CGGUGCAGCGGUCCCAGAGUCC |
| VAMP1-1 | SEQ ID NO: 389. AGGCUUGUCCAUCAAAGAAAUC |
| VAMP1-10 | SEQ ID NO: 390. AGGGCGAAAGGAAAGGAAGGAUG |
| VAMP1-2 | SEQ ID NO: 391. AGCCCCACUUCCUCAGAACAGG |
| VAMP1-3 | SEQ ID NO: 392. GGAAAAGAGAAAGAGACAGGAGAAAACAAGAGGGU |
| VAMP1-4 | SEQ ID NO: 393. AACUUGAGAGUACAGAAAAAGCAGG |
| VAMP1-5 | SEQ ID NO: 394. CCAGUGGCCAGGUUUUCUAGA |
| VAMP1-6 | SEQ ID NO: 395. ACGAACAGAUUAGAAAUAACU |
| VAMP1-7 | SEQ ID NO: 396. CUGUAGAAAAUGUAAAGAAGAGAAAGC |
| VAMP1-8 | SEQ ID NO: 397. UAGAAUUCAGACAGGAAAGGG |
| VAMP1-9 | SEQ ID NO: 398. CAAACCAUGCAAAGAGGAGGAAGAGAAA |
| VARS-1 | SEQ ID NO: 399. CCUCCAGACCCUCAAAGC |
| VPS28-1 | SEQ ID NO: 400. CCGCCUGGCUGGGAGGG |
| WDR24-1 | SEQ ID NO: 401. AGCAGCCCCAGCCCCUGG |
| WDR90-1 | SEQ ID NO: 402. CCCCACCCACAGUGCCAG |
| WRAP53-1 | SEQ ID NO: 403. CUCAGGGAUCCGACGCAGAG |
| YDJC-1 | SEQ ID NO: 404. UGUUUGAAUGCGGAAGUCAUCC |
| YIPF3-1 | SEQ ID NO: 405. AUCCUCAGGCAGCUUUCAACC |
| YIPF3-2 | SEQ ID NO: 406. UGAUCUCAGCCUCACCUAG |
| ZCCHC18-1 | SEQ ID NO: 407. CACAGAUUUAUGAUAAUAAGAAACCAUUA |
| ZCCHC18-2 | SEQ ID NO: 408. CUUCUAAUUCUAGAUGACAUAG |
| ZCCHC18-3 | SEQ ID NO: 409. GCCGCUUCCGUUUAAUAAAAGCAUC |
| ZCCHC18-4 | SEQ ID NO: 410. CUGGUAGAAAGAGACUGAGC |
| ZCCHC8-1 | SEQ ID NO: 411. CUUAGUGGCAAGAUGCAUAAAAG |
| ZCCHC8-2 | SEQ ID NO: 412. UGCAAAAUUUGGAAAUUGUUUUAA |
| ZFAND1-1 | SEQ ID NO: 413. CACUUAAACAGAUAUACAAAGUGUGAA |
| ZNF131-1 | SEQ ID NO: 414. UGACAGCUGAAGUUCCACAA |

TABLE 3-continued

| Name of compound | Corresponding nucleotide sequence of antisense oligoribonucleotide |
|---|---|
| ZNF131-2 | SEQ ID NO: 415. AUGGAACAAGUCCUUCACAU |
| ZNF300-1 | SEQ ID NO: 416. UUCAGGAAAGACAACAAAUAUAAACA |
| ZNF300-2 | SEQ ID NO: 417. UAUUUGACAUUUAAUUUAAUACA |
| ZNF300-3 | SEQ ID NO: 418. UAAUUUUCUCUGAACUUCUAAAACAGU |
| ZNF300-5 | SEQ ID NO: 419. CAACUAACAAAUAAUAGAAAAAUCCAA |
| ZNF300-6 | SEQ ID NO: 420. UUAAUUUCAUUUAUAUUAUAAAUCAUGU |
| ZNF300-7 | SEQ ID NO: 421. GACAGACAAGAAUGUUAAACAGAAAUA |
| ZNF317-1 | SEQ ID NO: 422. GAAGCUCUGCAAGAAUUCCAGCAUGCAC |
| ZNF317-2 | SEQ ID NO: 423. GGAAACAGAUGCUACAUAAAUC |
| ZNF317-3 | SEQ ID NO: 424. GAGCAAGGGCCUGAGAUUUUGCAAGCAUG |
| ZNF317-4 | SEQ ID NO: 425. CUUCAGAUGCAACCCUGACAAGGGACUAAU |
| ZNF692-1 | SEQ ID NO: 426. GCCCCUGCCCUUUCUGUCUCA |
| ZNF711-1 | SEQ ID NO: 427. GUUAAAACAUAGGUUAUAAAAGAAGAAC |
| ZNF711-2 | SEQ ID NO: 428. UAGAAGAAAGCAAAACAACAAAACU |
| ZNF711-3 | SEQ ID NO: 429. AGUAAACCAAAAAUAAUGG |
| ZNF711-4 | SEQ ID NO: 430. UUUGAGAAAAAAAUGCAAUUGACAA |
| ZNRD1-1 | SEQ ID NO: 431. AUUCUGUCCCAGGACCUAGGAGU |
| ZWINT-1 | SEQ ID NO: 432. UGCAGAGCAGCUUGUCUUUCUUCUGAGAG |
| ZWINT-2 | SEQ ID NO: 433. UACUCACGGCUCGUGUCUUCAGAAGCCAAGG |
| ZWINT-3 | SEQ ID NO: 434. CCUUCCCCACUCAGGUCAGCUGCUA |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The particular methods, compositions, and kits described can vary. It is also to be understood that the terminology used herein is for the purpose of describing particular embodiments only, and is not intended to be limiting, since the scope of the present invention will be limited only by the appended claims.

When values are provided, it can be understood that each value can be expressed as "about" a particular value or range. "About" can also include an exact amount. For example, "about 5 µL" can mean "about 5 µL" or "5 µL." Generally, the term "about" can include an amount that would be expected to be within 10% of a recited value.

The section headings used herein are for organizational purposes only and are not to be construed as limiting the subject matter described.

Unless defined otherwise, all technical and scientific terms used herein can have the same meaning as is commonly understood by one of skill in the art to which the claimed subject matter belongs. The descriptions herein are exemplary and explanatory only and are not restrictive of any subject matter claimed. In this application, the use of the singular can include the plural unless specifically stated otherwise. As used in the specification and the appended claims, the singular forms "a," "an" and "the" can include plural referents unless the context clearly dictates otherwise. In this application, the use of "or" can mean "and/or" unless stated otherwise. Furthermore, use of the term "including" as well as other forms, such as "include", "includes," and "included," is not limiting.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference.

1. Smith, C. W. and Valcarcel, J. (2000) Alternative pre-mRNA splicing: the logic of combinatorial control. *Trends Biochem. Sci.*, 25, 381-388.
2. Wahl, M. C., Will, C. L. and Luhrmann, R. (2009) The spliceosome: design principles of a dynamic RNP machine. *Cell*, 136, 701-718.
3. Callis, J., Fromm, M. and Walbot, V. (1987) Introns increase gene expression in cultured maize cells. *Genes Dev.*, 1, 1183-1200.

4. Buchman, A. R. and Berg, P. (1988) Comparison of intron-dependent and intron-independent gene expression. *Mol. Cell. Biol.*, 8, 4395-4405.
5. Le Hir, H., Nott, A. and Moore, M. J. (2003) How introns influence and enhance eukaryotic gene expression. *Trends Biochem. Sci.*, 28, 215-220.
6. Cazzola, M. and Skoda, R. C. (2000) Translational pathophysiology: a novel molecular mechanism of human disease. *Blood*, 95, 3280-3288.
7. Kralovicova, J. and Vorechovsky, I. (2010) Allele-dependent recognition of the 3' splice site of INS intron 1. *Hum. Genet.*, 128, 383-400.
8. Kole, R., Krainer, A. R. and Altman, S. (2012) RNA therapeutics: beyond RNA interference and antisense oligonucleotides. *Nat. Rev. Drug Discov.*, 11, 125-140.
9. Aartsma-Rus, A. and van Ommen, G. J. (2007) Antisense-mediated exon skipping: a versatile tool with therapeutic and research applications. *RNA*, 13, 1609-1624.
10. Goyenvalle, A., Seto, J. T., Davies, K. E. and Chamberlain, J. (2012) Therapeutic approaches to muscular dystrophy. *Hum. Mol. Genet.*, 20, R69-78.
11. Hua, Y., Sahashi, K., Hung, G., Rigo, F., Passini, M. A., Bennett, C. F. and Krainer, A. R. (2010) Antisense correction of SMN2 splicing in the CNS rescues necrosis in a type III SMA mouse model. *Genes Dev.*, 24, 1634-1644.
12. Du, L., Pollard, J. M. and Gatti, R. A. (2007) Correction of prototypic ATM splicing mutations and aberrant ATM function with antisense morpholino oligonucleotides. *Proc. Natl Acad. Sci. U.S.A.*, 104, 6007-6012.
13. Kralovicova, J., Hwang, G., Asplund, A. C., Churbanov, A., Smith, C. I. and Vorechovsky, I. (2011) Compensatory signals associated with the activation of human GC 5' splice sites. *Nucleic Acids Res.*, 39, 7077-7091.
14. Buratti, E., Chivers, M. C., Hwang, G. and Vorechovsky, I. (2011) DBASS3 and DBASS5: databases of aberrant 3' and 5' splice sites in human disease genes. *Nucleic Acids Res.*, 39, D86-D91.
15. Davies, J. L., Kawaguchi, Y., Bennett, S. T., Copeman, J. B., Cordell, H. J., Pritchard, L. E., Reed, P. W., Gough, S. C., Jenkins, S. C., Palmer, S. M. et al. (1994) A genome-wide search for human type 1 diabetes susceptibility genes. *Nature*, 371, 130-136.
16. Barratt, B. J., Payne, F., Lowe, C. E., Hermann, R., Healy, B. C., Harold, D., Concannon, P., Gharani, N., McCarthy, M. I., Olavesen, M. G. et al. (2004) Remapping the insulin gene/IDDM2 locus in type 1 diabetes. *Diabetes*, 53, 1884-1889.
17. Zhang, L., Nakayama, M. and Eisenbarth, G. S. (2008) Insulin as an autoantigen in NOD/human diabetes. *Curr. Opin. Immunol.*, 20, 111-118.
18. Vafiadis, P., Bennett, S. T., Todd, J. A., Nadeau, J., Grabs, R., Goodyer, C. G., Wickramasinghe, S., Colle, E. and Polychronakos, C. (1997) Insulin expression in human *thymus* is modulated by INS VNTR alleles at the IDDM2 locus. *Nat. Genet.*, 15, 289-292.
19. Pugliese, A., Zeller, M., Fernandez, A. Jr, Zalcberg, L. J., Bartlett, R. J., Ricordi, C., Pietropaolo, M., Eisenbarth, G. S., Bennett, S. T. and Patel, D. D. (1997) The insulin gene is transcribed in the human *thymus* and transcription levels correlated with allelic variation at the INS VNTR-IDDM2 susceptibility locus for type 1 diabetes. *Nat. Genet.*, 15, 293-297.
20. Stead, J. D., Hurles, M. E. and Jeffreys, A. J. (2003) Global haplotype diversity in the human insulin gene region. *Genome Res.*, 13, 2101-2111.
21. Kralovicova, J., Gaunt, T. R., Rodriguez, S., Wood, P. J., Day, I. N. M. and Vorechovsky, I. (2006) Variants in the human insulin gene that affect pre-mRNA splicing: is −23HphI a functional single nucleotide polymorphism at IDDM2? *Diabetes*, 55, 260-264.
22. Ruskin, B., Zamore, P. D. and Green, M. R. (1988) A factor, U2AF, is required for U2 snRNP binding and splicing complex assembly. *Cell*, 52, 207-219.
23. Wang, J., Shen, L., Najafi, H., Kolberg, J., Matschinsky, F. M., Urdea, M. and German, M. (1997) Regulation of insulin preRNA splicing by glucose. *Proc. Natl Acad. Sci. U.S.A.*, 94, 4360-4365.
24. Kralovicova, J., Haixin, L. and Vorechovsky, I. (2006) Phenotypic consequences of branchpoint substitutions. *Hum. Mutat.*, 27, 803-813.
25. Pacheco, T. R., Gomes, A. Q., Barbosa-Morais, N. L., Benes, V., Ansorge, W., Wollerton, M., Smith, C. W., Valcarcel, J. and Carmo-Fonseca, M. (2004) Diversity of vertebrate splicing factor U2AF35: identification of alternatively spliced U2AF1 mRNAS. *J. Biol. Chem.*, 279, 27 039-27 049.
26. Booy, E. P., Meier, M., Okun, N., Novakowski, S. K., Xiong, S., Stetefeld, J. and McKenna, S. A. (2012) The RNA helicase RHAU (DHX36) unwinds a G4-quadruplex in human telomerase RNA and promotes the formation of the P1 helix template boundary. *Nucleic Acids Res.*, 40, 4110-4124.
27. Lei, H. and Vorechovsky, I. (2005) Identification of splicing silencers and enhancers in sense Alus: a role for pseudo-acceptors in splice site repression. *Mol. Cell. Biol.*, 25, 6912-6920.
28. Buratti, E., Muro, A. F., Giombi, M., Gherbassi, D., Iaconcig, A. and Baralle, F. E. (2004) RNA folding affects the recruitment of SR proteins by mouse and human polypurinic enhancer elements in the fibronectin EDA exon. *Mol. Cell. Biol.*, 24, 1387-1400.
29. Nussinov, R. (1988) Conserved quartets near 5' intron junctions in primate nuclear pre-mRNA. *J. Theon. Biol.*, 133, 73-84.
30. Sirand-Pugnet, P., Durosay, P., Brody, E. and Marie, J. (1995) An intronic (A/U)GGG repeat enhances the splicing of an alternative intron of the chicken beta-tropomyosin pre-mRNA. *Nucleic Acids Res.*, 23, 3501-3507.
31. Kralovicova, J. and Vorechovsky, I. (2006) Position-dependent repression and promotion of DQB1 intron 3 splicing by GGGG motifs. *J. Immunol.*, 176, 2381-2388.
32. Neidle, S. and Balasubramanian, S. (2006) *Quadruplex Nucleic Acids*. RSC Biomolecular Sciences, Cambridge, UK.
33. Bugaut, A. and Balasubramanian, S. (2012) 5'-UTR RNA G-quadruplexes: translation regulation and targeting. *Nucleic Acids Res.*, 40, 4727-4741.
34. Millevoi, S., Moine, H. and Vagner, S. (2012) G-quadruplexes in RNA biology. *Wiley Interdiscip. Rev. RNA*, 3, 495-507.
35. Gomez, D., Lemarteleur, T., Lacroix, L., Mailliet, P., Mergny, J. L. and Riou, J. F. (2004) Telomerase downregulation induced by the G-quadruplex ligand 12459 in A549 cells is mediated by hTERT RNA alternative splicing. *Nucleic Acids Res.*, 32, 371-379.
36. Didiot, M. C., Tian, Z., Schaeffer, C., Subramanian, M., Mandel, J. L. and Moine, H. (2008) The G-quartet containing FMRP binding site in FMR1 mRNA is a potent exonic splicing enhancer. *Nucleic Acids Res.*, 36, 4902-4912.
37. Hai, Y., Cao, W., Liu, G., Hong, S. P., Elela, S. A., Klinck, R., Chu, J. and Xie, J. (2008) A G-tract element in apoptotic agents-induced alternative splicing. *Nucleic Acids Res.*, 36, 3320-3331.

38. Marcel, V., Tran, P. L., Sagne, C., Martel-Planche, G., Vaslin, L., Teulade-Fichou, M. P., Hall, J., Mergny, J. L., Hainaut, P. and Van Dyck, E. (2011) G-quadruplex structures in TP53 intron 3: role in alternative splicing and in production of p53 mRNA isoforms. *Carcinogenesis*, 32, 271-278.

39. Melko, M., Douguet, D., Bensaid, M., Zongaro, S., Verheggen, C., Gecz, J. and Bardoni, B. (2011) Functional characterization of the AFF (AF4/FMR2) family of RNA-binding proteins: insights into the molecular pathology of FRAXE intellectual disability. *Hum. Mol. Genet.*, 20, 1873-1885.

40. Balagurumoorthy, P., Brahmachari, S. K., Mohanty, D., Bansal, M. and Sasisekharan, V. (1992) Hairpin and parallel quartet structures for telomeric sequences. *Nucleic Acids Res.*, 20, 4061-4067.

41. Derecka, K., Balkwill, G. D., Garner, T. P., Hodgman, C., Flint, A. P. and Searle, M. S. (2010) Occurrence of a quadruplex motif in a unique insert within exon C of the bovine estrogen receptor alpha gene (ESR1). *Biochemistry (Mosc.).* 49, 7625-7633.

42. Balkwill, G. D., Derecka, K., Garner, T. P., Hodgman, C., Flint, A. P. and Searle, M. S. (2009) Repression of translation of human estrogen receptor alpha by G-quadruplex formation. *Biochemistry (Mosc.).* 48, 11487-11495.

43. Garner, T. P., Williams, H. E., Gluszyk, K. I., Roe, S., Oldham, N. J., Stevens, M. F., Moses, J. E. and Searle, M. S. (2009) Selectivity of small molecule ligands for parallel and anti-parallel DNA G-quadruplex structures. *Org. Biomol. Chem.*, 7, 4194-4200.

44. Thisted, T., Lyakhov, D. L. and Liebhaber, S. A. (2001) Optimized RNA targets of two closely related triple KH domain proteins, heterogeneous nuclear ribonucleoprotein K and alphaCP-2KL, suggest Distinct modes of RNA recognition. *J. Biol. Chem.*, 276, 17484-17496.

45. Creacy, S. D., Routh, E. D., Iwamoto, F., Nagamine, Y., Akman, S. A. and Vaughn, J. P. (2008) G4 resolvase 1 binds both DNA and RNA tetramolecular quadruplex with high affinity and is the major source of tetramolecular quadruplex G4-DNA and G4-RNA resolving activity in HeLa cell lysates. *J. Biol. Chem.*, 283, 34626-34634.

46. Pastor, T. and Pagani F. (2011) Interaction of hnRNPA1/A2 and DAZAP1 with an Alu-derived intronic splicing enhancer regulates ATM aberrant splicing. *PLoS One*, 6, e23349.

47. Iwamoto, F., Stadler, M., Chalupnikova, K., Oakeley, E. and Nagamine, Y. (2008) Transcription-dependent nucleolar cap localization and possible nuclear function of DExH RNA helicase RHAU. *Exp. Cell Res.*, 314, 1378-1391.

48. Singh, N. N., Hollinger, K., Bhattacharya, D. and Singh, R. N. (2010) An antisense microwalk reveals critical role of an intronic position linked to a unique long-distance interaction in pre-mRNA splicing. *RNA*, 16, 1167-1181.

49. Wang, Y., Xiao, X., Zhang, J., Choudhury, R., Robertson, A., Li, K., Ma, M., Burge, C. B. and Wang, Z. (2012) A complex network of factors with overlapping affinities represses splicing through intronic elements. *Nat. Struct. Mol. Biol.*, 20, 36-45.

50. Wang, Y., Ma, M., Xiao, X. and Wang, Z. (2012) Intronic splicing enhancers, cognate splicing factors and context-dependent regulation rules. *Nat. Struct. Mol. Biol.*, 19, 1044-1052.

51. Ke, S., Shang, S., Kalachikov, S. M., Morozova, I., Yu, L., Russo, J. J., Ju, J. and Chasin, L. A. (2011) Quantitative evaluation of all hexamers as exonic splicing elements. *Genome Res.*, 21, doi10.1101/gr.119628.119110.

52. Culler, S. J., Hoff, K. G., Voelker, R. B., Berglund, J. A. and Smolke, C. D. (2010) Functional selection and systematic analysis of intronic splicing elements identify active sequence motifs and associated splicing factors. *Nucleic Acids Res.*, 38, 5152-5165.

53. Collie, G. W. and Parkinson, G. N. (2011) The application of DNA and RNA G-quadruplexes to therapeutic medicines. *Chem. Soc. Rev.*, doi 10.1039/c1cs15067g.

54. Morris, M. J., Negishi, Y., Pazsint, C., Schonhoft, J. D. and Basu, S. (2010) An RNA G-quadruplex is essential for cap-independent translation initiation in human VEGF IRES. *J. Am. Chem. Soc.*, 132, 17831-17839.

55. Wieland, M. and Hartig, J. S. (2007) RNA quadruplex-based modulation of gene expression. *Chem. Biol.*, 14, 757-763.

56. Zhang, A. Y. and Balasubramanian, S. (2012) The kinetics and folding pathways of intramolecular g-quadruplex nucleic acids. *J. Am. Chem. Soc.*, 134, 19297-19308.

57. Bugaut, A., Murat, P. and Balasubramanian, S. (2012) An RNA hairpin to g-quadruplex conformational transition. *J. Am. Chem. Soc.*, 134, 19953-19956.

58. Decorsiere, A., Cayrel, A., Vagner, S. and Millevoi, S. (2011) Essential role for the interaction between hnRNP H/F and a G quadruplex in maintaining p53 pre-mRNA 3'-end processing and function during DNA damage. *Genes Dev.*, 25, 220-225.

59. Samatanga, B., Dominguez, C., Jelesarov, I. and Allain, F. H. (2013) The high kinetic stability of a G-quadruplex limits hnRNP F qRRM3 binding to G-tract RNA. *Nucleic Acids Res.*, 41, 2505-2516.

60. Lorenz, R., Bernhart, S. H., Qin, J., Honer, Zu, Siederdissen, C., Tanzer, A., Amman, F., Hofacker, I. L. and Stadler, P. F. (2013) 2D meets 4G: G-quadruplexes in RNA secondary structure prediction. *IEEE/ACM Trans. Comput. Biol. Bioinform.*

61. Beaudoin, J. D. and Perreault, J. P. (2010) 5'-UTR G-quadruplex structures acting as translational repressors. *Nucleic Acids Res.*, 38, 7022-7036.

62. Fred, R. G., Sandberg, M., Pelletier, J. and Welsh, N. (2011) The human insulin mRNA is partly translated via a cap- and eIF4A-independent mechanism. *Biochem. Biophys. Res. Commun.*, 412, 693-698.

63. Schwarze, U., Starman, B. J. and Byers, P. H. (1999) Redefinition of exon 7 in the COL1A1 gene of type I collagen by an intron 8 splice-donor-site mutation in a form of osteogenesis imperfecta: influence of intron splice order on outcome of splice-site mutation. *Am. J. Hum. Genet.*, 65, 336-344.

64. Xing, Y., Resch, A. and Lee, C. (2004) The multiassembly problem: reconstructing multiple transcript isoforms from EST fragment mixtures. *Genome Res.*, 14, 426-441.

65. Fededa, J. P., Petrillo, E., Gelfand, M. S., Neverov, A. D., Kadener, S., Nogues, G., Pelisch, F., Baralle, F. E., Muro, A. F. and Kornblihtt, A. R. (2005) A polar mechanism coordinates different regions of alternative splicing within a single gene. *Mol. Cell*, 19, 393-404.

66. Emerick, M. C., Parmigiani, G. and Agnew, W. S. (2007) Multivariate analysis and visualization of splicing correlations in single-gene transcriptomes. *BMC Bioinformatics*, 8, 16.

67. Peng, T., Xue, C., Bi, J., Li, T., Wang, X., Zhang, X. and Li, Y. (2008) Functional importance of different patterns of correlation between adjacent cassette exons in human and mouse. *BMC Genomics*, 9, 191.

68. Eddy, J., Vallur, A. C., Varma, S., Liu, H., Reinhold, W. C., Pommier, Y. and Maizels, N. (2011) G4 motifs correlate with promoter-proximal transcriptional pausing in human genes. *Nucleic Acids Res.*, 39, 4975-4983.
69. Mayeda, A., Hayase, Y., Inoue, H., Ohtsuka, E. and Ohshima, Y. (1990) Surveying cis-acting sequences of pre-mRNA by adding antisense 2-O-methyl oligoribonucleotides to a splicing reaction. *J. Biochem.*, 108, 399-405.
70. Dominski, Z. and Kole, R. (1993) Restoration of correct splicing in thalassemic pre-mRNA by antisense oligonucleotides. *Proc. Natl Acad. Sci. U.S.A.*, 90, 8673-8677.
71. Baughan, T. D., Dickson, A., Osman, E. Y. and Lorson, C. L. (2009) Delivery of bifunctional RNAs that target an intronic repressor and increase SMN levels in an animal model of spinal muscular atrophy. *Hum. Mol. Genet.*, 18, 1600-1611.
72. Cavaloc, Y., Bourgeois, C. F., Kister, L. and Stevenin, J. (1999) The splicing factors 9G8 and SRp20 transactivate splicing through different and specific enhancers. *RNA*, 5, 468-483.
73. Hargous, Y., Hautbergue, G. M., Tintaru, A. M., Skrisovska, L., Golovanov, A. P., Stevenin, J., Lian, L. Y., Wilson, S. A. and Allain, F. H. (2006) Molecular basis of RNA recognition and TAP binding by the SR proteins SRp20 and 9G8. *EMBO J.*, 25, 5126-5137.
74. Hunt, K. A., Mistry, V., Bockett, N. A., Ahmad, T., Ban, M., Barker, J. N., Barrett, J. C., Blackburn, H., Brand, O., Burren, O. et al. (2013) Negligible impact of rare autoimmune-locus coding-region variants on missing heritability. *Nature*, 498, 232-235.
75. Aly, T. A., Ide, A., Jahromi, M. M., Barker, J. M., Fernando, M. S., Babu, S. R., Yu, L., Miao, D., Erlich, H. A., Fain, P. R. et al. (2006) Extreme genetic risk for type 1A diabetes. *Proc. Natl Acad. Sci. U.S.A.*, 103, 14074-14079.
76. Yoshida, K., Sanada, M., Shiraishi, Y., Nowak, D., Nagata, Y., Yamamoto, R., Sato, Y., Sato-Otsubo, A., Kon, A., Nagasaki, M. et al. (2011) Frequent pathway mutations of splicing machinery in myelodysplasia. *Nature*, 478, 64-69.
77. Pacheco, T. R., Moita, L. F., Gomes, A. Q., Hacohen, N. and Carmo-Fonseca, M. (2006) RNA interference knockdown of hU2AF35 impairs cell cycle progression and modulates alternative splicing of Cdc25 transcripts. *Mol. Biol. Cell*, 17, 4187-4199.
78. Kikin, O., D_Antonio, L. and Bagga, P. S. (2006) QGRS Mapper: a web-based server for predicting G-quadruplexes in nucleotide sequences. *Nucleic Acids Res.*, 34, W676-W682.

What is claimed is:

1. A pharmaceutical composition comprising:
a polynucleic acid polymer that is from about 10 to about 50 nucleotides in length and hybridizes to a wild-type target sequence of a partially processed mRNA transcript, wherein the polynucleic acid polymer comprises a sequence that is complementary to at least 10 contiguous bases of the wild-type target sequence, wherein the partially processed mRNA transcript encodes a protein and comprises an entire retained intron, wherein the polynucleic acid polymer induces splicing out of the entire retained intron from the partially processed mRNA transcript; and
a pharmaceutically acceptable excipient and/or a pharmaceutically acceptable delivery vehicle.

2. The pharmaceutical composition of claim 1, wherein the wild-type target sequence is a binding motif that forms a hairpin structure.

3. The pharmaceutical composition of claim 1, wherein the wild-type target sequence is between two G quadruplexes of a partially processed mRNA transcript.

4. The pharmaceutical composition of claim 1, wherein the wild-type target sequence is within the entire retained intron of the partially processed mRNA transcript.

5. The pharmaceutical composition of claim 1, wherein the wild-type target sequence does not form a G quadruplex.

6. The pharmaceutical composition of claim 1, wherein the wild-type target sequence is an intronic sequence.

7. The pharmaceutical composition of claim 6, wherein the intronic sequence comprises an intronic splicing regulatory element comprising a first CCC motif or a second CCC motif.

8. The pharmaceutical composition of claim 1, wherein the delivery vehicle comprises a cell penetrating peptide or a peptide-based nanoparticle.

9. The pharmaceutical composition of claim 1, wherein the polynucleic acid polymer is from about 10 to about 30 nucleotides in length.

10. The pharmaceutical composition of claim 1, wherein the polynucleic acid polymer comprises a sequence that is at least 60% complementary to the wild-type target sequence of the partially processed mRNA transcript.

11. The pharmaceutical composition of claim 1, wherein the polynucleic acid polymer is modified at a nucleoside moiety, at a phosphate moiety, at a 5' terminus, at a 3' terminus, or a combination thereof.

12. The pharmaceutical composition of claim 11, wherein the polynucleic acid polymer comprises an artificial nucleotide.

13. The pharmaceutical composition of claim 12, wherein the artificial nucleotide is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

14. The pharmaceutical composition of claim 1, wherein the polynucleic acid polymer comprises a sequence that is complementary to a sequence with:
  (i) at least 80% sequence identity to at least 13 contiguous bases of SEQ ID NO: 46;
  (ii) at least 10 contiguous bases of SEQ ID NO: 46;
  (iii) at least 80% sequence identity to a sequence selected from the group consisting of SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, and SEQ ID NO: 45; or
  (iv) at least 60% sequence identity to SEQ ID NO: 3.

15. The pharmaceutical composition of claim 1, wherein the polynucleic acid polymer comprises a sequence having at least 80% sequence identity to at least 13 contiguous bases of a sequence selected from the group consisting of SEQ ID NOs: 47-434.

16. The pharmaceutical composition of claim 1, wherein the splicing occurs within a human cell.

17. The pharmaceutical composition of any one of claims 1-8, 9-14, or 15-16, wherein the wild-type target sequence does not comprise a mutation-induced aberrant splice site.

* * * * *

```
                           SEQUENCE LISTING

<160> NUMBER OF SEQ ID NOS: 473

<210> SEQ ID NO 1
<211> LENGTH: 18
<212> TYPE: RNA
<213> ORGANISM: Artificial Sequence
<220> FEATURE:
<223> OTHER INFORMATION: SSO

<400> SEQUENCE: 1
cugcagagcu ggggccug                                              18

<210> SEQ ID NO 2
<211> LENGTH: 18
<212> TYPE: DNA
<213> ORGANISM: Artificial Sequence
<220> FEATURE:
<223> OTHER INFORMATION: SSO

<400> SEQUENCE: 2
ctgcagagct ggggcctg                                              18

<210> SEQ ID NO 3
<211> LENGTH: 18
<212> TYPE: RNA
<213> ORGANISM: Homo sapiens

<400> SEQUENCE: 3
caggccccag cucugcag                                              18

<210> SEQ ID NO 4
<211> LENGTH: 16
<212> TYPE: RNA
<213> ORGANISM: Artificial Sequence
<220> FEATURE:
<223> OTHER INFORMATION: SSO

<400> SEQUENCE: 4
ugcagagcug gggccu                                                16
```

```
<210> SEQ ID NO 5
<211> LENGTH: 16
<212> TYPE: DNA
<213> ORGANISM: Artificial Sequence
<220> FEATURE:
<223> OTHER INFORMATION: SSO

<400> SEQUENCE: 5
tgcagagctg gggcct                                                      16

<210> SEQ ID NO 6
<211> LENGTH: 16
<212> TYPE: RNA
<213> ORGANISM: Homo sapiens

<400> SEQUENCE: 6
aggccccagc ucugca                                                      16

<210> SEQ ID NO 7
<211> LENGTH: 16
<212> TYPE: RNA
<213> ORGANISM: Artificial Sequence
<220> FEATURE:
<223> OTHER INFORMATION: SSO

<400> SEQUENCE: 7
gcagagcugg ggccug                                                      16

<210> SEQ ID NO 8
<211> LENGTH: 16
<212> TYPE: DNA
<213> ORGANISM: Artificial Sequence
<220> FEATURE:
<223> OTHER INFORMATION: SSO

<400> SEQUENCE: 8
gcagagctgg ggcctg                                                      16

<210> SEQ ID NO 9
<211> LENGTH: 16
<212> TYPE: RNA
<213> ORGANISM: Homo sapiens

<400> SEQUENCE: 9
caggccccag cucugc                                                      16

<210> SEQ ID NO 10
<211> LENGTH: 16
<212> TYPE: RNA
<213> ORGANISM: Artificial Sequence
<220> FEATURE:
<223> OTHER INFORMATION: SSO

<400> SEQUENCE: 10
cagagcuggg gccugg                                                      16

<210> SEQ ID NO 11
<211> LENGTH: 16
<212> TYPE: DNA
<213> ORGANISM: Artificial Sequence
<220> FEATURE:
<223> OTHER INFORMATION: SSO

<400> SEQUENCE: 11
``` cagagcugggg gccugg                                                          16

<210> SEQ ID NO 12
<211> LENGTH: 16
<212> TYPE: RNA
<213> ORGANISM: Homo sapiens

<400> SEQUENCE: 12
ccaggcccca gcucug                                                           16

<210> SEQ ID NO 13
<211> LENGTH: 16
<212> TYPE: RNA
<213> ORGANISM: Artificial Sequence
<220> FEATURE:
<223> OTHER INFORMATION: SSO

<400> SEQUENCE: 13
agagcugggg ccuggg                                                           16

<210> SEQ ID NO 14
<211> LENGTH: 16
<212> TYPE: DNA
<213> ORGANISM: Artificial Sequence
<220> FEATURE:
<223> OTHER INFORMATION: SSO

<400> SEQUENCE: 14
agagctgggg cctggg                                                           16

<210> SEQ ID NO 15
<211> LENGTH: 16
<212> TYPE: RNA
<213> ORGANISM: Homo sapiens

<400> SEQUENCE: 15
cccaggcccc agcucu                                                           16

<210> SEQ ID NO 16
<211> LENGTH: 16
<212> TYPE: RNA
<213> ORGANISM: Artificial Sequence
<220> FEATURE:
<223> OTHER INFORMATION: SSO

<400> SEQUENCE: 16
gagcuggggc cuggg                                                            16

<210> SEQ ID NO 17
<211> LENGTH: 16
<212> TYPE: DNA
<213> ORGANISM: Artificial Sequence
<220> FEATURE:
<223> OTHER INFORMATION: SSO

<400> SEQUENCE: 17
gagctggggc ctgggg                                                           16

<210> SEQ ID NO 18
<211> LENGTH: 16
<212> TYPE: RNA
<213> ORGANISM: Homo sapiens

<400> SEQUENCE: 18
ccccaggccc cagcuc                                                           16

<210> SEQ ID NO 19
<211> LENGTH: 16
<212> TYPE: RNA
<213> ORGANISM: Artificial Sequence
<220> FEATURE:
<223> OTHER INFORMATION: SSO

<400> SEQUENCE: 19
agcuggggcc uggggu                                                          16

<210> SEQ ID NO 20
<211> LENGTH: 16
<212> TYPE: DNA
<213> ORGANISM: Artificial Sequence
<220> FEATURE:
<223> OTHER INFORMATION: SSO

<400> SEQUENCE: 20
agctggggcc tggggt                                                          16

<210> SEQ ID NO 21
<211> LENGTH: 16
<212> TYPE: RNA
<213> ORGANISM: Homo sapiens

<400> SEQUENCE: 21
accccaggcc ccagcu                                                          16

<210> SEQ ID NO 22
<211> LENGTH: 16
<212> TYPE: RNA
<213> ORGANISM: Artificial Sequence
<220> FEATURE:
<223> OTHER INFORMATION: SSO

<400> SEQUENCE: 22
gcuggggccu gggguc                                                          16

<210> SEQ ID NO 23
<211> LENGTH: 16
<212> TYPE: DNA
<213> ORGANISM: Artificial Sequence
<220> FEATURE:
<223> OTHER INFORMATION: SSO

<400> SEQUENCE: 23
gctggggcct ggggtc                                                          16

<210> SEQ ID NO 24
<211> LENGTH: 16
<212> TYPE: RNA
<213> ORGANISM: Homo sapiens

<400> SEQUENCE: 24
gaccccaggc cccagc                                                          16

<210> SEQ ID NO 25
<211> LENGTH: 16
<212> TYPE: RNA
<213> ORGANISM: Artificial Sequence
<220> FEATURE:
<223> OTHER INFORMATION: SSO

<400> SEQUENCE: 25

```
cuggggccug gggucc                                                        16

<210> SEQ ID NO 26
<211> LENGTH: 16
<212> TYPE: DNA
<213> ORGANISM: Artificial Sequence
<220> FEATURE:
<223> OTHER INFORMATION: SSO

<400> SEQUENCE: 26
ctggggcctg gggtcc                                                        16

<210> SEQ ID NO 27
<211> LENGTH: 16
<212> TYPE: RNA
<213> ORGANISM: Homo sapiens

<400> SEQUENCE: 27
ggaccccagg ccccag                                                        16

<210> SEQ ID NO 28
<211> LENGTH: 16
<212> TYPE: RNA
<213> ORGANISM: Artificial Sequence
<220> FEATURE:
<223> OTHER INFORMATION: SSO

<400> SEQUENCE: 28 ugggccugg ggucca                                                         16

<210> SEQ ID NO 29
<211> LENGTH: 16
<212> TYPE: DNA
<213> ORGANISM: Artificial Sequence
<220> FEATURE:
<223> OTHER INFORMATION: SSO

<400> SEQUENCE: 29
tggggcctgg ggtcca                                                        16

<210> SEQ ID NO 30
<211> LENGTH: 16
<212> TYPE: RNA
<213> ORGANISM: Homo sapiens

<400> SEQUENCE: 30
uggaccccag gcccca                                                        16

<210> SEQ ID NO 31
<211> LENGTH: 16
<212> TYPE: RNA
<213> ORGANISM: Artificial Sequence
<220> FEATURE:
<223> OTHER INFORMATION: SSO

<400> SEQUENCE: 31
ggggccuggg guccag                                                        16

<210> SEQ ID NO 32
<211> LENGTH: 16
<212> TYPE: DNA
<213> ORGANISM: Artificial Sequence
<220> FEATURE:
<223> OTHER INFORMATION: SSO

<400> SEQUENCE: 32
``` gggggcctggg gtccag                                              16

<210> SEQ ID NO 33
<211> LENGTH: 16
<212> TYPE: RNA
<213> ORGANISM: Homo sapiens

<400> SEQUENCE: 33
cuggacccca ggcccc                                               16

<210> SEQ ID NO 34
<211> LENGTH: 16
<212> TYPE: RNA
<213> ORGANISM: Artificial Sequence
<220> FEATURE:
<223> OTHER INFORMATION: SSO

<400> SEQUENCE: 34
cugcagagcu ggggcc                                               16

<210> SEQ ID NO 35
<211> LENGTH: 16
<212> TYPE: DNA
<213> ORGANISM: Artificial Sequence
<220> FEATURE:
<223> OTHER INFORMATION: SSO

<400> SEQUENCE: 35
ctgcagagct ggggcc                                               16

<210> SEQ ID NO 36
<211> LENGTH: 16
<212> TYPE: RNA
<213> ORGANISM: Homo sapiens

<400> SEQUENCE: 36
ggccccagcu cugcag                                               16

<210> SEQ ID NO 37
<211> LENGTH: 16
<212> TYPE: RNA
<213> ORGANISM: Artificial Sequence
<220> FEATURE:
<223> OTHER INFORMATION: SSO

<400> SEQUENCE: 37
gcugcagagc uggggc                                               16

<210> SEQ ID NO 38
<211> LENGTH: 16
<212> TYPE: DNA
<213> ORGANISM: Artificial Sequence
<220> FEATURE:
<223> OTHER INFORMATION: SSO

<400> SEQUENCE: 38
gctgcagagc tggggc                                               16

<210> SEQ ID NO 39
<211> LENGTH: 16
<212> TYPE: RNA
<213> ORGANISM: Homo sapiens

<400> SEQUENCE: 39
gccccagcuc ugcagc                                                          16

<210> SEQ ID NO 40
<211> LENGTH: 16
<212> TYPE: RNA
<213> ORGANISM: Artificial Sequence
<220> FEATURE:
<223> OTHER INFORMATION: SSO

<400> SEQUENCE: 40
ugcugcagag cugggg                                                          16

<210> SEQ ID NO 41
<211> LENGTH: 16
<212> TYPE: DNA
<213> ORGANISM: Artificial Sequence
<220> FEATURE:
<223> OTHER INFORMATION: SSO

<400> SEQUENCE: 41
tgctgcagag ctgggg                                                          16

<210> SEQ ID NO 42
<211> LENGTH: 16
<212> TYPE: RNA
<213> ORGANISM: Homo sapiens

<400> SEQUENCE: 42
ccccagcucu gcagca                                                          16

<210> SEQ ID NO 43
<211> LENGTH: 16
<212> TYPE: RNA
<213> ORGANISM: Artificial Sequence
<220> FEATURE:
<223> OTHER INFORMATION: SSO

<400> SEQUENCE: 43
cugcugcaga gcuggg                                                          16

<210> SEQ ID NO 44
<211> LENGTH: 16
<212> TYPE: DNA
<213> ORGANISM: Artificial Sequence
<220> FEATURE:
<223> OTHER INFORMATION: SSO

<400> SEQUENCE: 44
ctgctgcaga gctggg                                                          16

<210> SEQ ID NO 45
<211> LENGTH: 16
<212> TYPE: RNA
<213> ORGANISM: Homo sapiens

<400> SEQUENCE: 45
cccagcucug cagcag                                                          16

<210> SEQ ID NO 46
<211> LENGTH: 29
<212> TYPE: RNA
<213> ORGANISM: Homo sapiens

<400> SEQUENCE: 46
cuggacccca ggccccagcu cugcagcag                                            29

```
<210> SEQ ID NO 47
<211> LENGTH: 26
<212> TYPE: RNA
<213> ORGANISM: Homo sapiens

<400> SEQUENCE: 47
uagagaggug ugggaaggga agcaga                                          26

<210> SEQ ID NO 48
<211> LENGTH: 38
<212> TYPE: RNA
<213> ORGANISM: Homo sapiens

<400> SEQUENCE: 48
aauuccuuca ucauggcaca uuuauccuug cagacagg                             38

<210> SEQ ID NO 49
<211> LENGTH: 28
<212> TYPE: RNA
<213> ORGANISM: Homo sapiens

<400> SEQUENCE: 49
ccugaggaua cucacagaaa ggcaacag                                        28

<210> SEQ ID NO 50
<211> LENGTH: 21
<212> TYPE: RNA
<213> ORGANISM: Homo sapiens

<400> SEQUENCE: 50 uuucccaac acacuccagc a                                                21

<210> SEQ ID NO 51
<211> LENGTH: 18
<212> TYPE: RNA
<213> ORGANISM: Homo sapiens

<400> SEQUENCE: 51
gggccgcugc ccaccguc                                                   18

<210> SEQ ID NO 52
<211> LENGTH: 22
<212> TYPE: RNA
<213> ORGANISM: Homo sapiens

<400> SEQUENCE: 52
cagcacagcu cagaagucug ag                                              22

<210> SEQ ID NO 53
<211> LENGTH: 28
<212> TYPE: RNA
<213> ORGANISM: Homo sapiens

<400> SEQUENCE: 53
ccaagccagg gacagggagg ugaaugcc                                        28

<210> SEQ ID NO 54
<211> LENGTH: 22
<212> TYPE: RNA
<213> ORGANISM: Homo sapiens

<400> SEQUENCE: 54
```

-continued cuucugccca gcucucugac ug    22

<210> SEQ ID NO 55
<211> LENGTH: 26
<212> TYPE: RNA
<213> ORGANISM: Homo sapiens

<400> SEQUENCE: 55
ucuucacaaa ccccugcaaa aaugag    26

<210> SEQ ID NO 56
<211> LENGTH: 24
<212> TYPE: RNA
<213> ORGANISM: Homo sapiens

<400> SEQUENCE: 56
cccaaagccc ccgcaggugc agcc    24

<210> SEQ ID NO 57
<211> LENGTH: 21
<212> TYPE: RNA
<213> ORGANISM: Homo sapiens

<400> SEQUENCE: 57
ccccucccca cgcucuggaa a    21

<210> SEQ ID NO 58
<211> LENGTH: 24
<212> TYPE: RNA
<213> ORGANISM: Homo sapiens

<400> SEQUENCE: 58
gcagcaccgg gaggcucaga caac    24

<210> SEQ ID NO 59
<211> LENGTH: 20
<212> TYPE: RNA
<213> ORGANISM: Homo sapiens

<400> SEQUENCE: 59
gagccucauc aaagaaacgg    20

<210> SEQ ID NO 60
<211> LENGTH: 20
<212> TYPE: RNA
<213> ORGANISM: Homo sapiens

<400> SEQUENCE: 60
gcucccacug ggacugagcg    20

<210> SEQ ID NO 61
<211> LENGTH: 21
<212> TYPE: RNA
<213> ORGANISM: Homo sapiens

<400> SEQUENCE: 61
agaugggaag agagagaaga g    21

<210> SEQ ID NO 62
<211> LENGTH: 30
<212> TYPE: RNA
<213> ORGANISM: Homo sapiens

<400> SEQUENCE: 62
agagacaagg aaaccacaca gacagagacc                                30

<210> SEQ ID NO 63
<211> LENGTH: 19
<212> TYPE: RNA
<213> ORGANISM: Homo sapiens

<400> SEQUENCE: 63
gccgcccagc agagagagg                                            19

<210> SEQ ID NO 64
<211> LENGTH: 23
<212> TYPE: RNA
<213> ORGANISM: Homo sapiens

<400> SEQUENCE: 64
agcuggcugg gcccaccugg cau                                       23

<210> SEQ ID NO 65
<211> LENGTH: 18
<212> TYPE: RNA
<213> ORGANISM: Homo sapiens

<400> SEQUENCE: 65
gggcccaggc agaagccu                                             18

<210> SEQ ID NO 66
<211> LENGTH: 21
<212> TYPE: RNA
<213> ORGANISM: Homo sapiens

<400> SEQUENCE: 66
uccccagagc uuucaacaca g                                         21

<210> SEQ ID NO 67
<211> LENGTH: 24
<212> TYPE: RNA
<213> ORGANISM: Homo sapiens

<400> SEQUENCE: 67
gcagccacag cucaaagcug agga                                      24

<210> SEQ ID NO 68
<211> LENGTH: 29
<212> TYPE: RNA
<213> ORGANISM: Homo sapiens

<400> SEQUENCE: 68
gaucagacac guaaggaaaa cgcauuaua                                 29

<210> SEQ ID NO 69
<211> LENGTH: 30
<212> TYPE: RNA
<213> ORGANISM: Homo sapiens

<400> SEQUENCE: 69
gcagaaggca cuaaucaagu caaggucaca                                30

<210> SEQ ID NO 70
<211> LENGTH: 24
<212> TYPE: RNA
<213> ORGANISM: Homo sapiens

```
<400> SEQUENCE: 70
cgggcauuaa agagcuggac ucag                                          24

<210> SEQ ID NO 71
<211> LENGTH: 20
<212> TYPE: RNA
<213> ORGANISM: Homo sapiens

<400> SEQUENCE: 71
accaauuuug aaaaaagcag                                               20

<210> SEQ ID NO 72
<211> LENGTH: 22
<212> TYPE: RNA
<213> ORGANISM: Homo sapiens

<400> SEQUENCE: 72
ccacauuuua auuuaauuuu ac                                            22

<210> SEQ ID NO 73
<211> LENGTH: 19
<212> TYPE: RNA
<213> ORGANISM: Homo sapiens

<400> SEQUENCE: 73
ccauuagaaa gaauaaaag                                                19

<210> SEQ ID NO 74
<211> LENGTH: 28
<212> TYPE: RNA
<213> ORGANISM: Homo sapiens

<400> SEQUENCE: 74 uauuuaaau uaauaaaug uuaaaugg                                        28

<210> SEQ ID NO 75
<211> LENGTH: 22
<212> TYPE: RNA
<213> ORGANISM: Homo sapiens

<400> SEQUENCE: 75
auuucauuuu aaacucacag au                                            22

<210> SEQ ID NO 76
<211> LENGTH: 22
<212> TYPE: RNA
<213> ORGANISM: Homo sapiens

<400> SEQUENCE: 76
auccuugcaa agagaagaaa ug                                            22

<210> SEQ ID NO 77
<211> LENGTH: 39
<212> TYPE: RNA
<213> ORGANISM: Homo sapiens

<400> SEQUENCE: 77
uccuucaacu ugacuucuug cugauggcuc agaucaacu                          39

<210> SEQ ID NO 78
<211> LENGTH: 36
<212> TYPE: RNA
<213> ORGANISM: Homo sapiens
```

```
<400> SEQUENCE: 78
uauuuuauaa aaguaaaaug ccaagaacca aagacu                                  36

<210> SEQ ID NO 79
<211> LENGTH: 34
<212> TYPE: RNA
<213> ORGANISM: Homo sapiens

<400> SEQUENCE: 79
uucaaacucc aagaaauaca aauucucaaa acac                                    34

<210> SEQ ID NO 80
<211> LENGTH: 22
<212> TYPE: RNA
<213> ORGANISM: Homo sapiens

<400> SEQUENCE: 80
uuuucucaag acaaagaaac cc                                                 22

<210> SEQ ID NO 81
<211> LENGTH: 18
<212> TYPE: RNA
<213> ORGANISM: Homo sapiens

<400> SEQUENCE: 81
ggguggagca gucaagcc                                                      18

<210> SEQ ID NO 82
<211> LENGTH: 24
<212> TYPE: RNA
<213> ORGANISM: Homo sapiens

<400> SEQUENCE: 82
acuucccaac ccacacacac agac                                               24

<210> SEQ ID NO 83
<211> LENGTH: 22
<212> TYPE: RNA
<213> ORGANISM: Homo sapiens

<400> SEQUENCE: 83
gucacauaaa aaucagaaga au                                                 22

<210> SEQ ID NO 84
<211> LENGTH: 21
<212> TYPE: RNA
<213> ORGANISM: Homo sapiens

<400> SEQUENCE: 84
caaauauuau cagagauuga a                                                  21

<210> SEQ ID NO 85
<211> LENGTH: 29
<212> TYPE: RNA
<213> ORGANISM: Homo sapiens

<400> SEQUENCE: 85
cuugaauuau uguuuuauu uugacaauc                                           29

<210> SEQ ID NO 86
<211> LENGTH: 28
<212> TYPE: RNA
```

```
<213> ORGANISM: Homo sapiens

<400> SEQUENCE: 86
acucaauaau uaaagauuug ggaaauau                                            28

<210> SEQ ID NO 87
<211> LENGTH: 22
<212> TYPE: RNA
<213> ORGANISM: Homo sapiens

<400> SEQUENCE: 87
aggcaacauu uaccuugaaa au                                                  22

<210> SEQ ID NO 88
<211> LENGTH: 22
<212> TYPE: RNA
<213> ORGANISM: Homo sapiens

<400> SEQUENCE: 88
gagggcaauc uucagaauuc ag                                                  22

<210> SEQ ID NO 89
<211> LENGTH: 35
<212> TYPE: RNA
<213> ORGANISM: Homo sapiens

<400> SEQUENCE: 89
uaaucagauu ugacaguugg cuuucugaaa guuuu                                    35

<210> SEQ ID NO 90
<211> LENGTH: 29
<212> TYPE: RNA
<213> ORGANISM: Homo sapiens

<400> SEQUENCE: 90
acauuucugg agaauuauaa uaaacuuau                                           29

<210> SEQ ID NO 91
<211> LENGTH: 24
<212> TYPE: RNA
<213> ORGANISM: Homo sapiens

<400> SEQUENCE: 91
caauuacaca gauucauuua gaua                                                24

<210> SEQ ID NO 92
<211> LENGTH: 32
<212> TYPE: RNA
<213> ORGANISM: Homo sapiens

<400> SEQUENCE: 92
ucagauuugc uacuugaau uuagcacauu au                                        32

<210> SEQ ID NO 93
<211> LENGTH: 31
<212> TYPE: RNA
<213> ORGANISM: Homo sapiens

<400> SEQUENCE: 93
aaauaaagcu cauuaaucuc ccauuuucau g                                        31

<210> SEQ ID NO 94
<211> LENGTH: 22
```

```
<212> TYPE: RNA
<213> ORGANISM: Homo sapiens

<400> SEQUENCE: 94 ugaaaugaa aaaauaaau gu                                          22

<210> SEQ ID NO 95
<211> LENGTH: 34
<212> TYPE: RNA
<213> ORGANISM: Homo sapiens

<400> SEQUENCE: 95
gcuacaaaca cucuguaaau agcuuagaaa aacu                           34

<210> SEQ ID NO 96
<211> LENGTH: 34
<212> TYPE: RNA
<213> ORGANISM: Homo sapiens

<400> SEQUENCE: 96
caugauuucu auaagacaga aauagagcag auaa                           34

<210> SEQ ID NO 97
<211> LENGTH: 29
<212> TYPE: RNA
<213> ORGANISM: Homo sapiens

<400> SEQUENCE: 97
caauuaccaa cagauuuucu ucaucaaug                                 29

<210> SEQ ID NO 98
<211> LENGTH: 22
<212> TYPE: RNA
<213> ORGANISM: Homo sapiens

<400> SEQUENCE: 98
acauaaacuu caaauuaaac cu                                        22

<210> SEQ ID NO 99
<211> LENGTH: 25
<212> TYPE: RNA
<213> ORGANISM: Homo sapiens

<400> SEQUENCE: 99
guaccuuugc uuaguuuaaa aauug                                     25

<210> SEQ ID NO 100
<211> LENGTH: 23
<212> TYPE: RNA
<213> ORGANISM: Homo sapiens

<400> SEQUENCE: 100
ggaauuugau aauuuucuaa agg                                       23

<210> SEQ ID NO 101
<211> LENGTH: 19
<212> TYPE: RNA
<213> ORGANISM: Homo sapiens

<400> SEQUENCE: 101
cggaagggag aaagaaggg                                            19

<210> SEQ ID NO 102
```

```
<211> LENGTH: 17
<212> TYPE: RNA
<213> ORGANISM: Homo sapiens

<400> SEQUENCE: 102
ccuggccuca cucagcg                                                        17

<210> SEQ ID NO 103
<211> LENGTH: 22
<212> TYPE: RNA
<213> ORGANISM: Homo sapiens

<400> SEQUENCE: 103
uaaagaaaua augcuuacug gu                                                  22

<210> SEQ ID NO 104
<211> LENGTH: 22
<212> TYPE: RNA
<213> ORGANISM: Homo sapiens

<400> SEQUENCE: 104
ugugguaauc aaagcaaaua ga                                                  22

<210> SEQ ID NO 105
<211> LENGTH: 31
<212> TYPE: RNA
<213> ORGANISM: Homo sapiens

<400> SEQUENCE: 105
augauuuaga acagcaugaa aaaucaaaau a                                        31

<210> SEQ ID NO 106
<211> LENGTH: 24
<212> TYPE: RNA
<213> ORGANISM: Homo sapiens

<400> SEQUENCE: 106
cuuaaauuua aauuaagaaa ugag                                                24

<210> SEQ ID NO 107
<211> LENGTH: 27
<212> TYPE: RNA
<213> ORGANISM: Homo sapiens

<400> SEQUENCE: 107
uaaaagaaaa uggauucuaa uuaauau                                             27

<210> SEQ ID NO 108
<211> LENGTH: 29
<212> TYPE: RNA
<213> ORGANISM: Homo sapiens

<400> SEQUENCE: 108
gcaaagccac agcugagggu gacagcacg                                           29

<210> SEQ ID NO 109
<211> LENGTH: 21
<212> TYPE: RNA
<213> ORGANISM: Homo sapiens

<400> SEQUENCE: 109
ccagccagag gagaaaaggc a                                                   21
```

-continued

```
<210> SEQ ID NO 110
<211> LENGTH: 24
<212> TYPE: RNA
<213> ORGANISM: Homo sapiens

<400> SEQUENCE: 110
cacacaaaua aagaaauuag auuu                                              24

<210> SEQ ID NO 111
<211> LENGTH: 34
<212> TYPE: RNA
<213> ORGANISM: Homo sapiens

<400> SEQUENCE: 111
uuuucuucuu uuauuuucau ucuccaauuu uaaa                                   34

<210> SEQ ID NO 112
<211> LENGTH: 29
<212> TYPE: RNA
<213> ORGANISM: Homo sapiens

<400> SEQUENCE: 112
aagccaggaa aagaaaucu uucuauca                                           29

<210> SEQ ID NO 113
<211> LENGTH: 21
<212> TYPE: RNA
<213> ORGANISM: Homo sapiens

<400> SEQUENCE: 113
agaaacacau ucaguuucua c                                                 21

<210> SEQ ID NO 114
<211> LENGTH: 21
<212> TYPE: RNA
<213> ORGANISM: Homo sapiens

<400> SEQUENCE: 114
ucuaaaaaaa aaaauuuucu c                                                 21

<210> SEQ ID NO 115
<211> LENGTH: 24
<212> TYPE: RNA
<213> ORGANISM: Homo sapiens

<400> SEQUENCE: 115
ugcauaaugc auggcaaaau gagc                                              24

<210> SEQ ID NO 116
<211> LENGTH: 32
<212> TYPE: RNA
<213> ORGANISM: Homo sapiens

<400> SEQUENCE: 116
gcuagagaag cuaugacucu gaggucaagg ac                                     32

<210> SEQ ID NO 117
<211> LENGTH: 21
<212> TYPE: RNA
<213> ORGANISM: Homo sapiens

<400> SEQUENCE: 117
cuucaucaaa gaaugcaauc a                                                 21
```

```
<210> SEQ ID NO 118
<211> LENGTH: 17
<212> TYPE: RNA
<213> ORGANISM: Homo sapiens

<400> SEQUENCE: 118
acuuugagua aaagaau                                            17

<210> SEQ ID NO 119
<211> LENGTH: 25
<212> TYPE: RNA
<213> ORGANISM: Homo sapiens

<400> SEQUENCE: 119
cuuugcuuuc ucaaguuuug uaugu                                   25

<210> SEQ ID NO 120
<211> LENGTH: 26
<212> TYPE: RNA
<213> ORGANISM: Homo sapiens

<400> SEQUENCE: 120
ccagcagagg caggcagaga aggaag                                  26

<210> SEQ ID NO 121
<211> LENGTH: 35
<212> TYPE: RNA
<213> ORGANISM: Homo sapiens

<400> SEQUENCE: 121
cugaaaugag aaacagaaga cacauaagag aaccc                        35

<210> SEQ ID NO 122
<211> LENGTH: 26
<212> TYPE: RNA
<213> ORGANISM: Homo sapiens

<400> SEQUENCE: 122
gccgcguaca uacacacaga acaacc                                  26

<210> SEQ ID NO 123
<211> LENGTH: 57
<212> TYPE: RNA
<213> ORGANISM: Homo sapiens

<400> SEQUENCE: 123
ugagcauccc uugggccuca acccacucu caucagggaa aggugaaagg guaaacu  57

<210> SEQ ID NO 124
<211> LENGTH: 24
<212> TYPE: RNA
<213> ORGANISM: Homo sapiens

<400> SEQUENCE: 124
aggcuuagag gaaaaggugu gcau                                    24

<210> SEQ ID NO 125
<211> LENGTH: 25
<212> TYPE: RNA
<213> ORGANISM: Homo sapiens

<400> SEQUENCE: 125
uauuucaugc ucaagaaccc aacca                                   25
```

```
<210> SEQ ID NO 126
<211> LENGTH: 27
<212> TYPE: RNA
<213> ORGANISM: Homo sapiens

<400> SEQUENCE: 126
cacaucaggg aaaggugaaa ggguaaa                                          27

<210> SEQ ID NO 127
<211> LENGTH: 17
<212> TYPE: RNA
<213> ORGANISM: Homo sapiens

<400> SEQUENCE: 127
cccacgccgc ccgcccg                                                     17

<210> SEQ ID NO 128
<211> LENGTH: 28
<212> TYPE: RNA
<213> ORGANISM: Homo sapiens

<400> SEQUENCE: 128
ucugaggccc aggguccagc uguggaug                                         28

<210> SEQ ID NO 129
<211> LENGTH: 25
<212> TYPE: RNA
<213> ORGANISM: Homo sapiens

<400> SEQUENCE: 129
cagccaucca agcacaacca cugcu                                            25

<210> SEQ ID NO 130
<211> LENGTH: 29
<212> TYPE: RNA
<213> ORGANISM: Homo sapiens

<400> SEQUENCE: 130
cucacugaca gaugugagcu ggaagcuga                                        29

<210> SEQ ID NO 131
<211> LENGTH: 21
<212> TYPE: RNA
<213> ORGANISM: Homo sapiens

<400> SEQUENCE: 131
ggguucuaug ugcagacuca g                                                21

<210> SEQ ID NO 132
<211> LENGTH: 19
<212> TYPE: RNA
<213> ORGANISM: Homo sapiens

<400> SEQUENCE: 132
caucacucac gagaauucc                                                   19

<210> SEQ ID NO 133
<211> LENGTH: 21
<212> TYPE: RNA
<213> ORGANISM: Homo sapiens

<400> SEQUENCE: 133
```
acagaccagg gaucacccag a                                           21

<210> SEQ ID NO 134
<211> LENGTH: 22
<212> TYPE: RNA
<213> ORGANISM: Homo sapiens

<400> SEQUENCE: 134
uuuagauuaa ugagauuuuu gc                                          22

<210> SEQ ID NO 135
<211> LENGTH: 25
<212> TYPE: RNA
<213> ORGANISM: Homo sapiens

<400> SEQUENCE: 135
ugcauuuuuc uuuaaagcua uuuug                                       25

<210> SEQ ID NO 136
<211> LENGTH: 28
<212> TYPE: RNA
<213> ORGANISM: Homo sapiens

<400> SEQUENCE: 136
aagacccaga agccaucuca gaagauug                                    28

<210> SEQ ID NO 137
<211> LENGTH: 33
<212> TYPE: RNA
<213> ORGANISM: Homo sapiens

<400> SEQUENCE: 137
augacaggga caaggacaau gaaucagaag uag                              33

<210> SEQ ID NO 138
<211> LENGTH: 28
<212> TYPE: RNA
<213> ORGANISM: Homo sapiens

<400> SEQUENCE: 138
uuuucuuaca acaccaacag gaagaagu                                    28

<210> SEQ ID NO 139
<211> LENGTH: 28
<212> TYPE: RNA
<213> ORGANISM: Homo sapiens

<400> SEQUENCE: 139
guuuauguua ccucuuuaca cugaaaug                                    28

<210> SEQ ID NO 140
<211> LENGTH: 22
<212> TYPE: RNA
<213> ORGANISM: Homo sapiens

<400> SEQUENCE: 140
gggacacaga ugaaggaaug ag                                          22

<210> SEQ ID NO 141
<211> LENGTH: 31
<212> TYPE: RNA
<213> ORGANISM: Homo sapiens

<400> SEQUENCE: 141

```
caaggaaggg aaggugguc cagaaagcag g                                31

<210> SEQ ID NO 142
<211> LENGTH: 19
<212> TYPE: RNA
<213> ORGANISM: Homo sapiens

<400> SEQUENCE: 142
aggcuuauga aacacaacc                                             19

<210> SEQ ID NO 143
<211> LENGTH: 21
<212> TYPE: RNA
<213> ORGANISM: Homo sapiens

<400> SEQUENCE: 143
agggccaaag cugccaggag u                                          21

<210> SEQ ID NO 144
<211> LENGTH: 30
<212> TYPE: RNA
<213> ORGANISM: Homo sapiens

<400> SEQUENCE: 144
cucccuuucu cccccucccu ccucugcuca                                 30

<210> SEQ ID NO 145
<211> LENGTH: 21
<212> TYPE: RNA
<213> ORGANISM: Homo sapiens

<400> SEQUENCE: 145
cuggagccag ggagcagagc g                                          21

<210> SEQ ID NO 146
<211> LENGTH: 25
<212> TYPE: RNA
<213> ORGANISM: Homo sapiens

<400> SEQUENCE: 146
cucagcaaca guucaaguu cccac                                       25

<210> SEQ ID NO 147
<211> LENGTH: 33
<212> TYPE: RNA
<213> ORGANISM: Homo sapiens

<400> SEQUENCE: 147
ccgccaccaa gacugccagc ucccacccac cuc                             33

<210> SEQ ID NO 148
<211> LENGTH: 23
<212> TYPE: RNA
<213> ORGANISM: Homo sapiens

<400> SEQUENCE: 148
agugccucag aucccaccag agg                                        23

<210> SEQ ID NO 149
<211> LENGTH: 26
<212> TYPE: RNA
<213> ORGANISM: Homo sapiens
```

```
<400> SEQUENCE: 149
gccugcuacc agcaacucuc auuucc                                       26

<210> SEQ ID NO 150
<211> LENGTH: 28
<212> TYPE: RNA
<213> ORGANISM: Homo sapiens

<400> SEQUENCE: 150
cacagagaag aaccuucacu gcuucugc                                     28

<210> SEQ ID NO 151
<211> LENGTH: 21
<212> TYPE: RNA
<213> ORGANISM: Homo sapiens

<400> SEQUENCE: 151
gaggacacag gcaaaggagg g                                            21

<210> SEQ ID NO 152
<211> LENGTH: 21
<212> TYPE: RNA
<213> ORGANISM: Homo sapiens

<400> SEQUENCE: 152
ccaaagcugc caggaguugc a                                            21

<210> SEQ ID NO 153
<211> LENGTH: 18
<212> TYPE: RNA
<213> ORGANISM: Homo sapiens

<400> SEQUENCE: 153
gcuggagguc aggcuggg                                                18

<210> SEQ ID NO 154
<211> LENGTH: 23
<212> TYPE: RNA
<213> ORGANISM: Homo sapiens

<400> SEQUENCE: 154
cccucagcaa caguuucaag uuc                                          23

<210> SEQ ID NO 155
<211> LENGTH: 26
<212> TYPE: RNA
<213> ORGANISM: Homo sapiens

<400> SEQUENCE: 155
aauagucugc ugugcuggag aaaggg                                       26

<210> SEQ ID NO 156
<211> LENGTH: 28
<212> TYPE: RNA
<213> ORGANISM: Homo sapiens

<400> SEQUENCE: 156
uuccuccuag cuggagggau ggagaaag                                     28

<210> SEQ ID NO 157
<211> LENGTH: 25
<212> TYPE: RNA
<213> ORGANISM: Homo sapiens
```

<400> SEQUENCE: 157
agagagugcc ucagauccca ccaga                                          25

<210> SEQ ID NO 158
<211> LENGTH: 36
<212> TYPE: RNA
<213> ORGANISM: Homo sapiens

<400> SEQUENCE: 158
agaaggaggg agccugcuac cagcaacucu cauuuc                              36

<210> SEQ ID NO 159
<211> LENGTH: 21
<212> TYPE: RNA
<213> ORGANISM: Homo sapiens

<400> SEQUENCE: 159
cacacagaga agaaccuuca c                                              21

<210> SEQ ID NO 160
<211> LENGTH: 23
<212> TYPE: RNA
<213> ORGANISM: Homo sapiens

<400> SEQUENCE: 160
cagcacagag gcaggcacaa aug                                            23

<210> SEQ ID NO 161
<211> LENGTH: 21
<212> TYPE: RNA
<213> ORGANISM: Homo sapiens

<400> SEQUENCE: 161
ucuggaacgg gagggagagg g                                              21

<210> SEQ ID NO 162
<211> LENGTH: 22
<212> TYPE: RNA
<213> ORGANISM: Homo sapiens

<400> SEQUENCE: 162
cucagccaga gaccugagca gc                                             22

<210> SEQ ID NO 163
<211> LENGTH: 25
<212> TYPE: RNA
<213> ORGANISM: Homo sapiens

<400> SEQUENCE: 163
caauuucaac gaucaguaac agagc                                          25

<210> SEQ ID NO 164
<211> LENGTH: 23
<212> TYPE: RNA
<213> ORGANISM: Homo sapiens

<400> SEQUENCE: 164
uucuggaaag cgggauaaug gac                                            23

<210> SEQ ID NO 165
<211> LENGTH: 27
<212> TYPE: RNA

<213> ORGANISM: Homo sapiens

<400> SEQUENCE: 165
caucauaaaa ggaguaacag gauaaua                                          27

<210> SEQ ID NO 166
<211> LENGTH: 22
<212> TYPE: RNA
<213> ORGANISM: Homo sapiens

<400> SEQUENCE: 166
cuuauuucag aagaaaaucc ga                                               22

<210> SEQ ID NO 167
<211> LENGTH: 26
<212> TYPE: RNA
<213> ORGANISM: Homo sapiens

<400> SEQUENCE: 167
caagcuuggc auuuuucuuu aaucca                                           26

<210> SEQ ID NO 168
<211> LENGTH: 22
<212> TYPE: RNA
<213> ORGANISM: Homo sapiens

<400> SEQUENCE: 168
guggaaacau aaagaaagca uc                                               22

<210> SEQ ID NO 169
<211> LENGTH: 27
<212> TYPE: RNA
<213> ORGANISM: Homo sapiens

<400> SEQUENCE: 169
ugcaaaaaag uggaaaaagu aaaugua                                          27

<210> SEQ ID NO 170
<211> LENGTH: 27
<212> TYPE: RNA
<213> ORGANISM: Homo sapiens

<400> SEQUENCE: 170
aucuucaggu uucuggacuc ucaccca                                          27

<210> SEQ ID NO 171
<211> LENGTH: 22
<212> TYPE: RNA
<213> ORGANISM: Homo sapiens

<400> SEQUENCE: 171
aaacaaaauu agguaaaagg ag                                               22

<210> SEQ ID NO 172
<211> LENGTH: 21
<212> TYPE: RNA
<213> ORGANISM: Homo sapiens

<400> SEQUENCE: 172
cuuuaaacac aaaaguuuac a                                                21

<210> SEQ ID NO 173
<211> LENGTH: 26

```
<212> TYPE: RNA
<213> ORGANISM: Homo sapiens

<400> SEQUENCE: 173
ggaaaugcag aaauuaauuu cuuaug                                              26

<210> SEQ ID NO 174
<211> LENGTH: 37
<212> TYPE: RNA
<213> ORGANISM: Homo sapiens

<400> SEQUENCE: 174
auuucaagac aaccauucaa aggcaguuag uuaacaa                                  37

<210> SEQ ID NO 175
<211> LENGTH: 26
<212> TYPE: RNA
<213> ORGANISM: Homo sapiens

<400> SEQUENCE: 175
cuaaacaaag uuuucuaaac cagauu                                              26

<210> SEQ ID NO 176
<211> LENGTH: 20
<212> TYPE: RNA
<213> ORGANISM: Homo sapiens

<400> SEQUENCE: 176
ggacagaaca cacacagaac                                                     20

<210> SEQ ID NO 177
<211> LENGTH: 27
<212> TYPE: RNA
<213> ORGANISM: Homo sapiens

<400> SEQUENCE: 177
aguuaaaaau caacuuuaau uuugaag                                             27

<210> SEQ ID NO 178
<211> LENGTH: 20
<212> TYPE: RNA
<213> ORGANISM: Homo sapiens

<400> SEQUENCE: 178
uuuuccaaau cagaagauug                                                     20

<210> SEQ ID NO 179
<211> LENGTH: 25
<212> TYPE: RNA
<213> ORGANISM: Homo sapiens

<400> SEQUENCE: 179
uauuuuaaaa cauccaaaaa gaagu                                               25

<210> SEQ ID NO 180
<211> LENGTH: 25
<212> TYPE: RNA
<213> ORGANISM: Homo sapiens

<400> SEQUENCE: 180
gacaaagcau guuaaaaagu uucca                                               25

<210> SEQ ID NO 181
```

```
<211> LENGTH: 19
<212> TYPE: RNA
<213> ORGANISM: Homo sapiens

<400> SEQUENCE: 181
aucagaugag cagcagcgg                                                  19

<210> SEQ ID NO 182
<211> LENGTH: 20
<212> TYPE: RNA
<213> ORGANISM: Homo sapiens

<400> SEQUENCE: 182
gggucaaggc aggcugagag                                                 20

<210> SEQ ID NO 183
<211> LENGTH: 34
<212> TYPE: RNA
<213> ORGANISM: Homo sapiens

<400> SEQUENCE: 183
ccagaaacca ugagauuugg gucagaaaaa ggca                                 34

<210> SEQ ID NO 184
<211> LENGTH: 21
<212> TYPE: RNA
<213> ORGANISM: Homo sapiens

<400> SEQUENCE: 184
cagucggcgu cccagagauc c                                               21

<210> SEQ ID NO 185
<211> LENGTH: 23
<212> TYPE: RNA
<213> ORGANISM: Homo sapiens

<400> SEQUENCE: 185
cauuuaagua gcaaauucug ggc                                             23

<210> SEQ ID NO 186
<211> LENGTH: 20
<212> TYPE: RNA
<213> ORGANISM: Homo sapiens

<400> SEQUENCE: 186
cucaucuucu ucagagaagu                                                 20

<210> SEQ ID NO 187
<211> LENGTH: 22
<212> TYPE: RNA
<213> ORGANISM: Homo sapiens

<400> SEQUENCE: 187
ccaaagaauu ggcaaagaaa ag                                              22

<210> SEQ ID NO 188
<211> LENGTH: 21
<212> TYPE: RNA
<213> ORGANISM: Homo sapiens

<400> SEQUENCE: 188
auuucacugg cauuaagaca g                                               21
```

-continued

```
<210> SEQ ID NO 189
<211> LENGTH: 22
<212> TYPE: RNA
<213> ORGANISM: Homo sapiens

<400> SEQUENCE: 189
guccguagca guuagcagau ga                                             22

<210> SEQ ID NO 190
<211> LENGTH: 23
<212> TYPE: RNA
<213> ORGANISM: Homo sapiens

<400> SEQUENCE: 190
gucugaguca gggccaaaag gaa                                            23

<210> SEQ ID NO 191
<211> LENGTH: 25
<212> TYPE: RNA
<213> ORGANISM: Homo sapiens

<400> SEQUENCE: 191
gggaaacagc augaagauaa gcagg                                          25

<210> SEQ ID NO 192
<211> LENGTH: 19
<212> TYPE: RNA
<213> ORGANISM: Homo sapiens

<400> SEQUENCE: 192
augagaaacu agauuaggg                                                 19

<210> SEQ ID NO 193
<211> LENGTH: 26
<212> TYPE: RNA
<213> ORGANISM: Homo sapiens

<400> SEQUENCE: 193
gaaaagcaau aaagaaauga gcaaca                                         26

<210> SEQ ID NO 194
<211> LENGTH: 23
<212> TYPE: RNA
<213> ORGANISM: Homo sapiens

<400> SEQUENCE: 194
aaguccagaa accaguuuca guc                                            23

<210> SEQ ID NO 195
<211> LENGTH: 25
<212> TYPE: RNA
<213> ORGANISM: Homo sapiens

<400> SEQUENCE: 195
gagcugggaa aggguuguga gagac                                          25

<210> SEQ ID NO 196
<211> LENGTH: 20
<212> TYPE: RNA
<213> ORGANISM: Homo sapiens

<400> SEQUENCE: 196
ggucccugaa gccugucacc                                                20
```

```
<210> SEQ ID NO 197
<211> LENGTH: 21
<212> TYPE: RNA
<213> ORGANISM: Homo sapiens

<400> SEQUENCE: 197
cgcuuaaguu guggaagguc g                                              21

<210> SEQ ID NO 198
<211> LENGTH: 25
<212> TYPE: RNA
<213> ORGANISM: Homo sapiens

<400> SEQUENCE: 198
agcacuacag ggccuccagc agggc                                          25

<210> SEQ ID NO 199
<211> LENGTH: 29
<212> TYPE: RNA
<213> ORGANISM: Homo sapiens

<400> SEQUENCE: 199
acaaaaccag acacuucuca uggacagca                                      29

<210> SEQ ID NO 200
<211> LENGTH: 25
<212> TYPE: RNA
<213> ORGANISM: Homo sapiens

<400> SEQUENCE: 200
aucugaagac aucucuuccc acauu                                          25

<210> SEQ ID NO 201
<211> LENGTH: 22
<212> TYPE: RNA
<213> ORGANISM: Homo sapiens

<400> SEQUENCE: 201
ccagucaagc auuagauuua gc                                             22

<210> SEQ ID NO 202
<211> LENGTH: 18
<212> TYPE: RNA
<213> ORGANISM: Homo sapiens

<400> SEQUENCE: 202
uccuccuucu aaaacauu                                                  18

<210> SEQ ID NO 203
<211> LENGTH: 17
<212> TYPE: RNA
<213> ORGANISM: Homo sapiens

<400> SEQUENCE: 203
aggaugcacc ccaugcu                                                   17

<210> SEQ ID NO 204
<211> LENGTH: 27
<212> TYPE: RNA
<213> ORGANISM: Homo sapiens

<400> SEQUENCE: 204
cggagccaca agcaauucaa auccagc                                        27
```

```
<210> SEQ ID NO 205
<211> LENGTH: 28
<212> TYPE: RNA
<213> ORGANISM: Homo sapiens

<400> SEQUENCE: 205
gucagcaguc gggacacggu ggguuaga                                        28

<210> SEQ ID NO 206
<211> LENGTH: 43
<212> TYPE: RNA
<213> ORGANISM: Homo sapiens

<400> SEQUENCE: 206
ugguuaaaga aacuggagaa agaaaagcaa aaggauaaag gaa                       43

<210> SEQ ID NO 207
<211> LENGTH: 25
<212> TYPE: RNA
<213> ORGANISM: Homo sapiens

<400> SEQUENCE: 207
caagucaggg agagagagag agagg                                           25

<210> SEQ ID NO 208
<211> LENGTH: 21
<212> TYPE: RNA
<213> ORGANISM: Homo sapiens

<400> SEQUENCE: 208
agccgccccg cucuccccag c                                               21

<210> SEQ ID NO 209
<211> LENGTH: 19
<212> TYPE: RNA
<213> ORGANISM: Homo sapiens

<400> SEQUENCE: 209
gaggaugaaa gaggaaagg                                                  19

<210> SEQ ID NO 210
<211> LENGTH: 21
<212> TYPE: RNA
<213> ORGANISM: Homo sapiens

<400> SEQUENCE: 210
cugagggcac aagagagaca g                                               21

<210> SEQ ID NO 211
<211> LENGTH: 23
<212> TYPE: RNA
<213> ORGANISM: Homo sapiens

<400> SEQUENCE: 211
gggaagacaa agacuugaca agg                                             23

<210> SEQ ID NO 212
<211> LENGTH: 28
<212> TYPE: RNA
<213> ORGANISM: Homo sapiens

<400> SEQUENCE: 212
```

-continued aggucaaaca gguggucaaa cagcagga                              28

<210> SEQ ID NO 213
<211> LENGTH: 20
<212> TYPE: RNA
<213> ORGANISM: Homo sapiens

<400> SEQUENCE: 213
uaaggacuga agacacgacg                                       20

<210> SEQ ID NO 214
<211> LENGTH: 25
<212> TYPE: RNA
<213> ORGANISM: Homo sapiens

<400> SEQUENCE: 214
gaguguugaa ggcaagacuu ugcag                                 25

<210> SEQ ID NO 215
<211> LENGTH: 25
<212> TYPE: RNA
<213> ORGANISM: Homo sapiens

<400> SEQUENCE: 215
cccacucagu gggagcugca gccau                                 25

<210> SEQ ID NO 216
<211> LENGTH: 22
<212> TYPE: RNA
<213> ORGANISM: Homo sapiens

<400> SEQUENCE: 216
ggaagaccca uuucuccaug cc                                    22

<210> SEQ ID NO 217
<211> LENGTH: 26
<212> TYPE: RNA
<213> ORGANISM: Homo sapiens

<400> SEQUENCE: 217
cccagagcuc ugagggugcc cugggc                                26

<210> SEQ ID NO 218
<211> LENGTH: 18
<212> TYPE: RNA
<213> ORGANISM: Homo sapiens

<400> SEQUENCE: 218
gugcucaccc agcaggca                                         18

<210> SEQ ID NO 219
<211> LENGTH: 28
<212> TYPE: RNA
<213> ORGANISM: Homo sapiens

<400> SEQUENCE: 219
gccacgugcu gacucugcag cuggcagg                              28

<210> SEQ ID NO 220
<211> LENGTH: 18
<212> TYPE: RNA
<213> ORGANISM: Homo sapiens

<400> SEQUENCE: 220 ucgccccag ucuucccu                                                   18

<210> SEQ ID NO 221
<211> LENGTH: 17
<212> TYPE: RNA
<213> ORGANISM: Homo sapiens

<400> SEQUENCE: 221
ggcagcacag caagagg                                                   17

<210> SEQ ID NO 222
<211> LENGTH: 26
<212> TYPE: RNA
<213> ORGANISM: Homo sapiens

<400> SEQUENCE: 222
caaaaacagu gcuacacauu uacuca                                         26

<210> SEQ ID NO 223
<211> LENGTH: 23
<212> TYPE: RNA
<213> ORGANISM: Homo sapiens

<400> SEQUENCE: 223
ucagaaagcc ugugacaaau cuu                                            23

<210> SEQ ID NO 224
<211> LENGTH: 20
<212> TYPE: RNA
<213> ORGANISM: Homo sapiens

<400> SEQUENCE: 224
aagaagaguc caaaaugguu                                                20

<210> SEQ ID NO 225
<211> LENGTH: 29
<212> TYPE: RNA
<213> ORGANISM: Homo sapiens

<400> SEQUENCE: 225
ugagaagaau gaaauaaaau uuaacaaaa                                      29

<210> SEQ ID NO 226
<211> LENGTH: 25
<212> TYPE: RNA
<213> ORGANISM: Homo sapiens

<400> SEQUENCE: 226
uguuaugcua aaaauguaag aaaac                                          25

<210> SEQ ID NO 227
<211> LENGTH: 24
<212> TYPE: RNA
<213> ORGANISM: Homo sapiens

<400> SEQUENCE: 227
aucagaauuu ccaagagaga ggcc                                           24

<210> SEQ ID NO 228
<211> LENGTH: 32
<212> TYPE: RNA
<213> ORGANISM: Homo sapiens

```
<400> SEQUENCE: 228
uaaggaaaga aaacagcauu gcaaagaaca cg                           32

<210> SEQ ID NO 229
<211> LENGTH: 28
<212> TYPE: RNA
<213> ORGANISM: Homo sapiens

<400> SEQUENCE: 229
aguuuuaaaa cuuuucuaag uuuaaugu                                28

<210> SEQ ID NO 230
<211> LENGTH: 20
<212> TYPE: RNA
<213> ORGANISM: Homo sapiens

<400> SEQUENCE: 230
aaugaaaaca ugaaaucuga                                         20

<210> SEQ ID NO 231
<211> LENGTH: 29
<212> TYPE: RNA
<213> ORGANISM: Homo sapiens

<400> SEQUENCE: 231
gaaaauuugu gggaaaaguu uauccuuac                               29

<210> SEQ ID NO 232
<211> LENGTH: 28
<212> TYPE: RNA
<213> ORGANISM: Homo sapiens

<400> SEQUENCE: 232
ucugaaacag uaauucaugc auaauucu                                28

<210> SEQ ID NO 233
<211> LENGTH: 25
<212> TYPE: RNA
<213> ORGANISM: Homo sapiens

<400> SEQUENCE: 233
ugcagaacuu caauuucaua auuuu                                   25

<210> SEQ ID NO 234
<211> LENGTH: 29
<212> TYPE: RNA
<213> ORGANISM: Homo sapiens

<400> SEQUENCE: 234
aaacaaauca agaccaaacu ucagagagu                               29

<210> SEQ ID NO 235
<211> LENGTH: 23
<212> TYPE: RNA
<213> ORGANISM: Homo sapiens

<400> SEQUENCE: 235
ccugaaaaug agaauaaauc ucc                                     23

<210> SEQ ID NO 236
<211> LENGTH: 22
<212> TYPE: RNA
<213> ORGANISM: Homo sapiens
```

<400> SEQUENCE: 236
gacaaaucau gagauucuca cc                                          22

<210> SEQ ID NO 237
<211> LENGTH: 18
<212> TYPE: RNA
<213> ORGANISM: Homo sapiens

<400> SEQUENCE: 237
ucccugccac ucccucca                                               18

<210> SEQ ID NO 238
<211> LENGTH: 21
<212> TYPE: RNA
<213> ORGANISM: Homo sapiens

<400> SEQUENCE: 238
cugcaggaag agaggcagcg a                                           21

<210> SEQ ID NO 239
<211> LENGTH: 17
<212> TYPE: RNA
<213> ORGANISM: Homo sapiens

<400> SEQUENCE: 239
gccuuuuuca uuaaaag                                                17

<210> SEQ ID NO 240
<211> LENGTH: 24
<212> TYPE: RNA
<213> ORGANISM: Homo sapiens

<400> SEQUENCE: 240
uuucauuugu uuuuaaacuu agau                                        24

<210> SEQ ID NO 241
<211> LENGTH: 17
<212> TYPE: RNA
<213> ORGANISM: Homo sapiens

<400> SEQUENCE: 241
uauucaugaa uuucuaa                                                17

<210> SEQ ID NO 242
<211> LENGTH: 23
<212> TYPE: RNA
<213> ORGANISM: Homo sapiens

<400> SEQUENCE: 242
uuuccaaaug uaaaauaauc aca                                         23

<210> SEQ ID NO 243
<211> LENGTH: 21
<212> TYPE: RNA
<213> ORGANISM: Homo sapiens

<400> SEQUENCE: 243
cacaaaacau aaaacauaaa c                                           21

<210> SEQ ID NO 244
<211> LENGTH: 20
<212> TYPE: RNA

```
<213> ORGANISM: Homo sapiens

<400> SEQUENCE: 244
uacuaggaag caaguuauua                                          20

<210> SEQ ID NO 245
<211> LENGTH: 19
<212> TYPE: RNA
<213> ORGANISM: Homo sapiens

<400> SEQUENCE: 245
aauucauuau uuaaaugac                                           19

<210> SEQ ID NO 246
<211> LENGTH: 24
<212> TYPE: RNA
<213> ORGANISM: Homo sapiens

<400> SEQUENCE: 246
augaaauuua aaauccacau uagc                                     24

<210> SEQ ID NO 247
<211> LENGTH: 18
<212> TYPE: RNA
<213> ORGANISM: Homo sapiens

<400> SEQUENCE: 247
acauucugau uagggagg                                            18

<210> SEQ ID NO 248
<211> LENGTH: 23
<212> TYPE: RNA
<213> ORGANISM: Homo sapiens

<400> SEQUENCE: 248
gaaggcaaca gaggugagug uga                                      23

<210> SEQ ID NO 249
<211> LENGTH: 25
<212> TYPE: RNA
<213> ORGANISM: Homo sapiens

<400> SEQUENCE: 249
ccagagggca ggcaaggcag aagug                                    25

<210> SEQ ID NO 250
<211> LENGTH: 21
<212> TYPE: RNA
<213> ORGANISM: Homo sapiens

<400> SEQUENCE: 250
ggaagauuug caaugguucu g                                        21

<210> SEQ ID NO 251
<211> LENGTH: 34
<212> TYPE: RNA
<213> ORGANISM: Homo sapiens

<400> SEQUENCE: 251
acacacagac aaaagaguug caagagacag agac                          34

<210> SEQ ID NO 252
<211> LENGTH: 20
```

```
<212> TYPE: RNA
<213> ORGANISM: Homo sapiens

<400> SEQUENCE: 252
ggcaaacuag aauagaaaga                                          20

<210> SEQ ID NO 253
<211> LENGTH: 26
<212> TYPE: RNA
<213> ORGANISM: Homo sapiens

<400> SEQUENCE: 253
ccagagcaga gagaggguua aacagg                                   26

<210> SEQ ID NO 254
<211> LENGTH: 27
<212> TYPE: RNA
<213> ORGANISM: Homo sapiens

<400> SEQUENCE: 254
ucagcaguag acacacaaau aaaccag                                  27

<210> SEQ ID NO 255
<211> LENGTH: 25
<212> TYPE: RNA
<213> ORGANISM: Homo sapiens

<400> SEQUENCE: 255
gucggugccu aauuaucuuc uuggg                                    25

<210> SEQ ID NO 256
<211> LENGTH: 18
<212> TYPE: RNA
<213> ORGANISM: Homo sapiens

<400> SEQUENCE: 256 aguuuucag ccacuucu                                             18

<210> SEQ ID NO 257
<211> LENGTH: 19
<212> TYPE: RNA
<213> ORGANISM: Homo sapiens

<400> SEQUENCE: 257
ucuugcugcc uaaaaucac                                           19

<210> SEQ ID NO 258
<211> LENGTH: 20
<212> TYPE: RNA
<213> ORGANISM: Homo sapiens

<400> SEQUENCE: 258
ugccuuuacc caaauuccuc                                          20

<210> SEQ ID NO 259
<211> LENGTH: 29
<212> TYPE: RNA
<213> ORGANISM: Homo sapiens

<400> SEQUENCE: 259
uucaagguca uuucuacaga ccaauuucu                                29

<210> SEQ ID NO 260
```

```
<211> LENGTH: 25
<212> TYPE: RNA
<213> ORGANISM: Homo sapiens

<400> SEQUENCE: 260
ggacacuguc caacaaagau ucuac                                              25

<210> SEQ ID NO 261
<211> LENGTH: 18
<212> TYPE: RNA
<213> ORGANISM: Homo sapiens

<400> SEQUENCE: 261
cuggcaaccc agggacac                                                      18

<210> SEQ ID NO 262
<211> LENGTH: 24
<212> TYPE: RNA
<213> ORGANISM: Homo sapiens

<400> SEQUENCE: 262
aauaaaauug aguuuauaga auua                                               24

<210> SEQ ID NO 263
<211> LENGTH: 32
<212> TYPE: RNA
<213> ORGANISM: Homo sapiens

<400> SEQUENCE: 263
auuugccaga uuucaauuua aaguuuaaaa ag                                      32

<210> SEQ ID NO 264
<211> LENGTH: 35
<212> TYPE: RNA
<213> ORGANISM: Homo sapiens

<400> SEQUENCE: 264
aaacugaaaa cacacaaauc uuugaaauga aaugc                                   35

<210> SEQ ID NO 265
<211> LENGTH: 22
<212> TYPE: RNA
<213> ORGANISM: Homo sapiens

<400> SEQUENCE: 265 cuuuuuauu uuaagaguuc ca                                                  22

<210> SEQ ID NO 266
<211> LENGTH: 24
<212> TYPE: RNA
<213> ORGANISM: Homo sapiens

<400> SEQUENCE: 266
augauuuuca caaagagaac aaua                                               24

<210> SEQ ID NO 267
<211> LENGTH: 29
<212> TYPE: RNA
<213> ORGANISM: Homo sapiens

<400> SEQUENCE: 267
auuucauaau aaaagcacau aaaauuagu                                          29
```

-continued

```
<210> SEQ ID NO 268
<211> LENGTH: 21
<212> TYPE: RNA
<213> ORGANISM: Homo sapiens

<400> SEQUENCE: 268
ccugccaccc accgcucacc c                                              21

<210> SEQ ID NO 269
<211> LENGTH: 20
<212> TYPE: RNA
<213> ORGANISM: Homo sapiens

<400> SEQUENCE: 269
ccuuccuccu ccugggacaa                                                20

<210> SEQ ID NO 270
<211> LENGTH: 33
<212> TYPE: RNA
<213> ORGANISM: Homo sapiens

<400> SEQUENCE: 270
auuaaagugu cagaacuaag accaaaacag aug                                 33

<210> SEQ ID NO 271
<211> LENGTH: 30
<212> TYPE: RNA
<213> ORGANISM: Homo sapiens

<400> SEQUENCE: 271
ccugaaaucc uugccucaca gaggagaacu                                     30

<210> SEQ ID NO 272
<211> LENGTH: 19
<212> TYPE: RNA
<213> ORGANISM: Homo sapiens

<400> SEQUENCE: 272
gccucagucc ugaaauccu                                                 19

<210> SEQ ID NO 273
<211> LENGTH: 22
<212> TYPE: RNA
<213> ORGANISM: Homo sapiens

<400> SEQUENCE: 273
ggcaguaaaa cgugccaucu uc                                             22

<210> SEQ ID NO 274
<211> LENGTH: 20
<212> TYPE: RNA
<213> ORGANISM: Homo sapiens

<400> SEQUENCE: 274
ugucgcagac cuccugaggg                                                20

<210> SEQ ID NO 275
<211> LENGTH: 25
<212> TYPE: RNA
<213> ORGANISM: Homo sapiens

<400> SEQUENCE: 275
ucuuccuuuu cccucugcua aguuu                                          25
```

<210> SEQ ID NO 276
<211> LENGTH: 25
<212> TYPE: RNA
<213> ORGANISM: Homo sapiens

<400> SEQUENCE: 276
gugacuaugg aaaauccccu aacag                                        25

<210> SEQ ID NO 277
<211> LENGTH: 21
<212> TYPE: RNA
<213> ORGANISM: Homo sapiens

<400> SEQUENCE: 277
gugcagcucu gauguggcag g                                            21

<210> SEQ ID NO 278
<211> LENGTH: 22
<212> TYPE: RNA
<213> ORGANISM: Homo sapiens

<400> SEQUENCE: 278
ugcagggagu gggaaggcag au                                           22

<210> SEQ ID NO 279
<211> LENGTH: 28
<212> TYPE: RNA
<213> ORGANISM: Homo sapiens

<400> SEQUENCE: 279
gggccgcaga gaccgaagag ggcaggug                                     28

<210> SEQ ID NO 280
<211> LENGTH: 29
<212> TYPE: RNA
<213> ORGANISM: Homo sapiens

<400> SEQUENCE: 280
gaagccaggg cguagcaagg uuguagcaa                                    29

<210> SEQ ID NO 281
<211> LENGTH: 19
<212> TYPE: RNA
<213> ORGANISM: Homo sapiens

<400> SEQUENCE: 281
gggcaaccug ggcacugca                                               19

<210> SEQ ID NO 282
<211> LENGTH: 22
<212> TYPE: RNA
<213> ORGANISM: Homo sapiens

<400> SEQUENCE: 282
uuuuuccuuc auuuccuggg au                                           22

<210> SEQ ID NO 283
<211> LENGTH: 23
<212> TYPE: RNA
<213> ORGANISM: Homo sapiens

<400> SEQUENCE: 283
gucccaaacc cuaaacuuac cuc                                          23

<210> SEQ ID NO 284
<211> LENGTH: 20
<212> TYPE: RNA
<213> ORGANISM: Homo sapiens

<400> SEQUENCE: 284
cugggauucc cacagaacgg                                           20

<210> SEQ ID NO 285
<211> LENGTH: 26
<212> TYPE: RNA
<213> ORGANISM: Homo sapiens

<400> SEQUENCE: 285
gcuggaaacg uccccagugg ccuucc                                    26

<210> SEQ ID NO 286
<211> LENGTH: 22
<212> TYPE: RNA
<213> ORGANISM: Homo sapiens

<400> SEQUENCE: 286
ggcggagccc ucccgcagag gc                                        22

<210> SEQ ID NO 287
<211> LENGTH: 22
<212> TYPE: RNA
<213> ORGANISM: Homo sapiens

<400> SEQUENCE: 287
gcagcaggca agcaauuuau ug                                        22

<210> SEQ ID NO 288
<211> LENGTH: 23
<212> TYPE: RNA
<213> ORGANISM: Homo sapiens

<400> SEQUENCE: 288
gcccuuggca acagguuaag gga                                       23

<210> SEQ ID NO 289
<211> LENGTH: 22
<212> TYPE: RNA
<213> ORGANISM: Homo sapiens

<400> SEQUENCE: 289
cagguccugg aaacagggcc aa                                        22

<210> SEQ ID NO 290
<211> LENGTH: 20
<212> TYPE: RNA
<213> ORGANISM: Homo sapiens

<400> SEQUENCE: 290
ggguaagaaa accagacaua                                           20

<210> SEQ ID NO 291
<211> LENGTH: 20
<212> TYPE: RNA
<213> ORGANISM: Homo sapiens

<400> SEQUENCE: 291

```
gcacauuuaa cagaaaaaug                                               20

<210> SEQ ID NO 292
<211> LENGTH: 26
<212> TYPE: RNA
<213> ORGANISM: Homo sapiens

<400> SEQUENCE: 292
ugaagacgaa gaaaaagcca gccagg                                        26

<210> SEQ ID NO 293
<211> LENGTH: 21
<212> TYPE: RNA
<213> ORGANISM: Homo sapiens

<400> SEQUENCE: 293
cgcacgcggc cggccgcccg c                                             21

<210> SEQ ID NO 294
<211> LENGTH: 19
<212> TYPE: RNA
<213> ORGANISM: Homo sapiens

<400> SEQUENCE: 294
ccacccccaa aagcagaau                                                19

<210> SEQ ID NO 295
<211> LENGTH: 20
<212> TYPE: RNA
<213> ORGANISM: Homo sapiens

<400> SEQUENCE: 295
cugccccucc cagaaugcug                                               20

<210> SEQ ID NO 296
<211> LENGTH: 23
<212> TYPE: RNA
<213> ORGANISM: Homo sapiens

<400> SEQUENCE: 296
ucuuucaccu accagacaca gac                                           23

<210> SEQ ID NO 297
<211> LENGTH: 22
<212> TYPE: RNA
<213> ORGANISM: Homo sapiens

<400> SEQUENCE: 297
ccuccagaga auguaaagcu ga                                            22

<210> SEQ ID NO 298
<211> LENGTH: 24
<212> TYPE: RNA
<213> ORGANISM: Homo sapiens

<400> SEQUENCE: 298
ggagagggcu ggaaggaugu ggca                                          24

<210> SEQ ID NO 299
<211> LENGTH: 25
<212> TYPE: RNA
<213> ORGANISM: Homo sapiens

<400> SEQUENCE: 299
```
aaaaacgaag ccaucagaug ccaag                                                    25

<210> SEQ ID NO 300
<211> LENGTH: 21
<212> TYPE: RNA
<213> ORGANISM: Homo sapiens

<400> SEQUENCE: 300
gugacaaaug caaauaaaua c                                                        21

<210> SEQ ID NO 301
<211> LENGTH: 28
<212> TYPE: RNA
<213> ORGANISM: Homo sapiens

<400> SEQUENCE: 301
cugccaacaa agagagaaaa uauuagcu                                                 28

<210> SEQ ID NO 302
<211> LENGTH: 25
<212> TYPE: RNA
<213> ORGANISM: Homo sapiens

<400> SEQUENCE: 302
uguuuggaaa augagaaaua aaugu                                                    25

<210> SEQ ID NO 303
<211> LENGTH: 25
<212> TYPE: RNA
<213> ORGANISM: Homo sapiens

<400> SEQUENCE: 303
uagcaaaugu gacuagcaaa ccaac                                                    25

<210> SEQ ID NO 304
<211> LENGTH: 29
<212> TYPE: RNA
<213> ORGANISM: Homo sapiens

<400> SEQUENCE: 304
cuaauuacug gaauuuuguu uaaauaauc                                                29

<210> SEQ ID NO 305
<211> LENGTH: 28
<212> TYPE: RNA
<213> ORGANISM: Homo sapiens

<400> SEQUENCE: 305
uuguuagcua gagagggugg gcaaaggg                                                 28

<210> SEQ ID NO 306
<211> LENGTH: 20
<212> TYPE: RNA
<213> ORGANISM: Homo sapiens

<400> SEQUENCE: 306
ccuaauccac uauuugaaac                                                          20

<210> SEQ ID NO 307
<211> LENGTH: 22
<212> TYPE: RNA
<213> ORGANISM: Homo sapiens

<400> SEQUENCE: 307
caugccucac gccauccuaa ug							22

<210> SEQ ID NO 308
<211> LENGTH: 19
<212> TYPE: RNA
<213> ORGANISM: Homo sapiens

<400> SEQUENCE: 308
gacagggacg gagcggcgg							19

<210> SEQ ID NO 309
<211> LENGTH: 19
<212> TYPE: RNA
<213> ORGANISM: Homo sapiens

<400> SEQUENCE: 309
accucccuca ccccaaacc							19

<210> SEQ ID NO 310
<211> LENGTH: 19
<212> TYPE: RNA
<213> ORGANISM: Homo sapiens

<400> SEQUENCE: 310
ggccgcagag gaaaggagg							19

<210> SEQ ID NO 311
<211> LENGTH: 20
<212> TYPE: RNA
<213> ORGANISM: Homo sapiens

<400> SEQUENCE: 311
gcagccccgu gacacaggag							20

<210> SEQ ID NO 312
<211> LENGTH: 18
<212> TYPE: RNA
<213> ORGANISM: Homo sapiens

<400> SEQUENCE: 312
cacaggccgc gccgcccc							18

<210> SEQ ID NO 313
<211> LENGTH: 24
<212> TYPE: RNA
<213> ORGANISM: Homo sapiens

<400> SEQUENCE: 313
ccaugcuggg ccagaucugc cagg							24

<210> SEQ ID NO 314
<211> LENGTH: 22
<212> TYPE: RNA
<213> ORGANISM: Homo sapiens

<400> SEQUENCE: 314
cugagagguc gaagcagaau gc							22

<210> SEQ ID NO 315
<211> LENGTH: 26
<212> TYPE: RNA
<213> ORGANISM: Homo sapiens -continued

<400> SEQUENCE: 315
gugaaaugaa gaccacaguc aagccc                                          26

<210> SEQ ID NO 316
<211> LENGTH: 27
<212> TYPE: RNA
<213> ORGANISM: Homo sapiens

<400> SEQUENCE: 316
gagacagggc ugcaggcaag ucaagua                                         27

<210> SEQ ID NO 317
<211> LENGTH: 27
<212> TYPE: RNA
<213> ORGANISM: Homo sapiens

<400> SEQUENCE: 317
acacacacaa ccaaacacgc acaacac                                         27

<210> SEQ ID NO 318
<211> LENGTH: 21
<212> TYPE: RNA
<213> ORGANISM: Homo sapiens

<400> SEQUENCE: 318
ggcagcagga gcagaaacca g                                               21

<210> SEQ ID NO 319
<211> LENGTH: 24
<212> TYPE: RNA
<213> ORGANISM: Homo sapiens

<400> SEQUENCE: 319
cacaacaguc agcaggucag acug                                            24

<210> SEQ ID NO 320
<211> LENGTH: 21
<212> TYPE: RNA
<213> ORGANISM: Homo sapiens

<400> SEQUENCE: 320
gaagggucug ggaccgcagc a                                               21

<210> SEQ ID NO 321
<211> LENGTH: 18
<212> TYPE: RNA
<213> ORGANISM: Homo sapiens

<400> SEQUENCE: 321
uacagugaga aaggcgcu                                                   18

<210> SEQ ID NO 322
<211> LENGTH: 32
<212> TYPE: RNA
<213> ORGANISM: Homo sapiens

<400> SEQUENCE: 322
aggaacuuaa uccaaacccg aagaaggaag ac                                   32

<210> SEQ ID NO 323
<211> LENGTH: 23
<212> TYPE: RNA

```
<213> ORGANISM: Homo sapiens

<400> SEQUENCE: 323
ccucuuaaaa guuauuauuu auu                                        23

<210> SEQ ID NO 324
<211> LENGTH: 22
<212> TYPE: RNA
<213> ORGANISM: Homo sapiens

<400> SEQUENCE: 324
aauuucaaug agaauaauga au                                         22

<210> SEQ ID NO 325
<211> LENGTH: 21
<212> TYPE: RNA
<213> ORGANISM: Homo sapiens

<400> SEQUENCE: 325
ucuuuaagau aaaguucaaa c                                          21

<210> SEQ ID NO 326
<211> LENGTH: 21
<212> TYPE: RNA
<213> ORGANISM: Homo sapiens

<400> SEQUENCE: 326
caauuugaau gcacauuuga u                                          21

<210> SEQ ID NO 327
<211> LENGTH: 20
<212> TYPE: RNA
<213> ORGANISM: Homo sapiens

<400> SEQUENCE: 327
cgacagacgu ggccaaggca                                            20

<210> SEQ ID NO 328
<211> LENGTH: 25
<212> TYPE: RNA
<213> ORGANISM: Homo sapiens

<400> SEQUENCE: 328
agacacagca accgaagcca acacu                                      25

<210> SEQ ID NO 329
<211> LENGTH: 24
<212> TYPE: RNA
<213> ORGANISM: Homo sapiens

<400> SEQUENCE: 329
acacaggccg cgggcuccac aaac                                       24

<210> SEQ ID NO 330
<211> LENGTH: 21
<212> TYPE: RNA
<213> ORGANISM: Homo sapiens

<400> SEQUENCE: 330
gagcuccauu acucuccuca u                                          21

<210> SEQ ID NO 331
<211> LENGTH: 20
```

```
<212> TYPE: RNA
<213> ORGANISM: Homo sapiens

<400> SEQUENCE: 331
caccucccgc caaccauucc                                             20

<210> SEQ ID NO 332
<211> LENGTH: 21
<212> TYPE: RNA
<213> ORGANISM: Homo sapiens

<400> SEQUENCE: 332
uuccuucaua uuuccagagu c                                           21

<210> SEQ ID NO 333
<211> LENGTH: 20
<212> TYPE: RNA
<213> ORGANISM: Homo sapiens

<400> SEQUENCE: 333
uccccagcuc ugaaaucucu                                             20

<210> SEQ ID NO 334
<211> LENGTH: 25
<212> TYPE: RNA
<213> ORGANISM: Homo sapiens

<400> SEQUENCE: 334
cucacacaag caggagaaag gagau                                       25

<210> SEQ ID NO 335
<211> LENGTH: 20
<212> TYPE: RNA
<213> ORGANISM: Homo sapiens

<400> SEQUENCE: 335
cuagucuuca gcccacccag                                             20

<210> SEQ ID NO 336
<211> LENGTH: 24
<212> TYPE: RNA
<213> ORGANISM: Homo sapiens

<400> SEQUENCE: 336
acaauacuua gaaacacaua augg                                        24

<210> SEQ ID NO 337
<211> LENGTH: 18
<212> TYPE: RNA
<213> ORGANISM: Homo sapiens

<400> SEQUENCE: 337
cguagaauuu aaaccacc                                               18

<210> SEQ ID NO 338
<211> LENGTH: 21
<212> TYPE: RNA
<213> ORGANISM: Homo sapiens

<400> SEQUENCE: 338
cacauuaugu uaauuaacaa c                                           21

<210> SEQ ID NO 339
```

```
<211> LENGTH: 29
<212> TYPE: RNA
<213> ORGANISM: Homo sapiens

<400> SEQUENCE: 339
agaagaaaaa caaaauuauu uaauaaaau                              29

<210> SEQ ID NO 340
<211> LENGTH: 37
<212> TYPE: RNA
<213> ORGANISM: Homo sapiens

<400> SEQUENCE: 340
uaacugaaau gaauucauuc aagaggaaaa uauggaa                     37

<210> SEQ ID NO 341
<211> LENGTH: 28
<212> TYPE: RNA
<213> ORGANISM: Homo sapiens

<400> SEQUENCE: 341
ucagaauuac agaguaagga aaagaccu                               28

<210> SEQ ID NO 342
<211> LENGTH: 29
<212> TYPE: RNA
<213> ORGANISM: Homo sapiens

<400> SEQUENCE: 342
ggcaucacaa aaugacuuua auuucugga                              29

<210> SEQ ID NO 343
<211> LENGTH: 21
<212> TYPE: RNA
<213> ORGANISM: Homo sapiens

<400> SEQUENCE: 343
cuaaccccag agagucucu a                                       21

<210> SEQ ID NO 344
<211> LENGTH: 22
<212> TYPE: RNA
<213> ORGANISM: Homo sapiens

<400> SEQUENCE: 344
uggagacccu ggucccugc ag                                      22

<210> SEQ ID NO 345
<211> LENGTH: 18
<212> TYPE: RNA
<213> ORGANISM: Homo sapiens

<400> SEQUENCE: 345
ccacaggagc ucugggcu                                          18

<210> SEQ ID NO 346
<211> LENGTH: 22
<212> TYPE: RNA
<213> ORGANISM: Homo sapiens

<400> SEQUENCE: 346
ugggcccacc gccaaagcag cg                                     22
```

```
<210> SEQ ID NO 347
<211> LENGTH: 27
<212> TYPE: RNA
<213> ORGANISM: Homo sapiens

<400> SEQUENCE: 347
uccacgcccu ugaagagguc acggcgg                                        27

<210> SEQ ID NO 348
<211> LENGTH: 22
<212> TYPE: RNA
<213> ORGANISM: Homo sapiens

<400> SEQUENCE: 348
auuucucucu uuuaaaaagc ug                                             22

<210> SEQ ID NO 349
<211> LENGTH: 23
<212> TYPE: RNA
<213> ORGANISM: Homo sapiens

<400> SEQUENCE: 349
gcacaaaaga aaagaccaaa agu                                            23

<210> SEQ ID NO 350
<211> LENGTH: 27
<212> TYPE: RNA
<213> ORGANISM: Homo sapiens

<400> SEQUENCE: 350
cagaagucaa aaagauuugg aggaaag                                        27

<210> SEQ ID NO 351
<211> LENGTH: 22
<212> TYPE: RNA
<213> ORGANISM: Homo sapiens

<400> SEQUENCE: 351
aaaccucaga agucaaaaag au                                             22

<210> SEQ ID NO 352
<211> LENGTH: 19
<212> TYPE: RNA
<213> ORGANISM: Homo sapiens

<400> SEQUENCE: 352
uaugacaauc caaacaggc                                                 19

<210> SEQ ID NO 353
<211> LENGTH: 31
<212> TYPE: RNA
<213> ORGANISM: Homo sapiens

<400> SEQUENCE: 353
uaagaaaggg cgcucccaca ugcucuuuag g                                   31

<210> SEQ ID NO 354
<211> LENGTH: 24
<212> TYPE: RNA
<213> ORGANISM: Homo sapiens

<400> SEQUENCE: 354
uccuaaaaua ucuugacaag caau                                           24
```

```
<210> SEQ ID NO 355
<211> LENGTH: 25
<212> TYPE: RNA
<213> ORGANISM: Homo sapiens

<400> SEQUENCE: 355
aagcucacau uacagggaag aggga                                              25

<210> SEQ ID NO 356
<211> LENGTH: 23
<212> TYPE: RNA
<213> ORGANISM: Homo sapiens

<400> SEQUENCE: 356
ucauuuuauu aacaagaaga guc                                                23

<210> SEQ ID NO 357
<211> LENGTH: 25
<212> TYPE: RNA
<213> ORGANISM: Homo sapiens

<400> SEQUENCE: 357
accaagaacu gaauucuauu ucagg                                              25

<210> SEQ ID NO 358
<211> LENGTH: 29
<212> TYPE: RNA
<213> ORGANISM: Homo sapiens

<400> SEQUENCE: 358
gaaacacggg caaccaugca agagagacu                                          29

<210> SEQ ID NO 359
<211> LENGTH: 22
<212> TYPE: RNA
<213> ORGANISM: Homo sapiens

<400> SEQUENCE: 359
cccaccagga cugaccccuc cc                                                 22

<210> SEQ ID NO 360
<211> LENGTH: 25
<212> TYPE: RNA
<213> ORGANISM: Homo sapiens

<400> SEQUENCE: 360
cccuccugcu gcuggaagca ggucc                                              25

<210> SEQ ID NO 361
<211> LENGTH: 24
<212> TYPE: RNA
<213> ORGANISM: Homo sapiens

<400> SEQUENCE: 361
gucacagaaa ugugaaaaug cacc                                               24

<210> SEQ ID NO 362
<211> LENGTH: 21
<212> TYPE: RNA
<213> ORGANISM: Homo sapiens

<400> SEQUENCE: 362
uucuuuagga agcaggacug a                                                  21
```

<210> SEQ ID NO 363
<211> LENGTH: 22
<212> TYPE: RNA
<213> ORGANISM: Homo sapiens

<400> SEQUENCE: 363
gacucagccc cagcaaaucc gc                                              22

<210> SEQ ID NO 364
<211> LENGTH: 18
<212> TYPE: RNA
<213> ORGANISM: Homo sapiens

<400> SEQUENCE: 364
gcacccggcu ccggcccc                                                   18

<210> SEQ ID NO 365
<211> LENGTH: 29
<212> TYPE: RNA
<213> ORGANISM: Homo sapiens

<400> SEQUENCE: 365
gcaaaucaca cucccucuga guuggaagc                                       29

<210> SEQ ID NO 366
<211> LENGTH: 37
<212> TYPE: RNA
<213> ORGANISM: Homo sapiens

<400> SEQUENCE: 366
ccgccuccag accgauccca cccggaacac agaugggg                             37

<210> SEQ ID NO 367
<211> LENGTH: 21
<212> TYPE: RNA
<213> ORGANISM: Homo sapiens

<400> SEQUENCE: 367
auaccgaaga gaagcaggga c                                               21

<210> SEQ ID NO 368
<211> LENGTH: 26
<212> TYPE: RNA
<213> ORGANISM: Homo sapiens

<400> SEQUENCE: 368
cccagaggga aaagcaaaag cugagg                                          26

<210> SEQ ID NO 369
<211> LENGTH: 22
<212> TYPE: RNA
<213> ORGANISM: Homo sapiens

<400> SEQUENCE: 369
gcagacaggc ucacguuucu cu                                              22

<210> SEQ ID NO 370
<211> LENGTH: 22
<212> TYPE: RNA
<213> ORGANISM: Homo sapiens

<400> SEQUENCE: 370

```
cccagacaag aacucuccuc ag                                          22

<210> SEQ ID NO 371
<211> LENGTH: 17
<212> TYPE: RNA
<213> ORGANISM: Homo sapiens

<400> SEQUENCE: 371
gcugggccuc agcagga                                                17

<210> SEQ ID NO 372
<211> LENGTH: 24
<212> TYPE: RNA
<213> ORGANISM: Homo sapiens

<400> SEQUENCE: 372
cuuacugagg cuggcacgaa gacc                                        24

<210> SEQ ID NO 373
<211> LENGTH: 21
<212> TYPE: RNA
<213> ORGANISM: Homo sapiens

<400> SEQUENCE: 373
ccuuaaguuu aaaaauacug a                                           21

<210> SEQ ID NO 374
<211> LENGTH: 28
<212> TYPE: RNA
<213> ORGANISM: Homo sapiens

<400> SEQUENCE: 374
aaauguuucu aaauuauuca uaaagaug                                    28

<210> SEQ ID NO 375
<211> LENGTH: 32
<212> TYPE: RNA
<213> ORGANISM: Homo sapiens

<400> SEQUENCE: 375
aauacuuuca uauuuuauu uacuuuaccu cc                                32

<210> SEQ ID NO 376
<211> LENGTH: 28
<212> TYPE: RNA
<213> ORGANISM: Homo sapiens

<400> SEQUENCE: 376
ucuuuaauaa gaaaauacau ggaacaca                                    28

<210> SEQ ID NO 377
<211> LENGTH: 29
<212> TYPE: RNA
<213> ORGANISM: Homo sapiens

<400> SEQUENCE: 377
uauucuauau uuuaauucua agauacucu                                   29

<210> SEQ ID NO 378
<211> LENGTH: 43
<212> TYPE: RNA
<213> ORGANISM: Homo sapiens

<400> SEQUENCE: 378
```
ugaaagacag acuuuuuca acacuaccuu aaaaacuuaa gac    43

<210> SEQ ID NO 379
<211> LENGTH: 25
<212> TYPE: RNA
<213> ORGANISM: Homo sapiens

<400> SEQUENCE: 379
aagaucuaau uuuacuauua agcac    25

<210> SEQ ID NO 380
<211> LENGTH: 32
<212> TYPE: RNA
<213> ORGANISM: Homo sapiens

<400> SEQUENCE: 380
uauuuguuuc cuuaaagau uuuauaaaag cu    32

<210> SEQ ID NO 381
<211> LENGTH: 18
<212> TYPE: RNA
<213> ORGANISM: Homo sapiens

<400> SEQUENCE: 381
ccugccaaca gcaacugc    18

<210> SEQ ID NO 382
<211> LENGTH: 21
<212> TYPE: RNA
<213> ORGANISM: Homo sapiens

<400> SEQUENCE: 382
acgugcuggg aaccagccag c    21

<210> SEQ ID NO 383
<211> LENGTH: 23
<212> TYPE: RNA
<213> ORGANISM: Homo sapiens

<400> SEQUENCE: 383
uccgccccca uccacaggag aug    23

<210> SEQ ID NO 384
<211> LENGTH: 27
<212> TYPE: RNA
<213> ORGANISM: Homo sapiens

<400> SEQUENCE: 384
ggcuuagggu uaggcucauc ugaggau    27

<210> SEQ ID NO 385
<211> LENGTH: 28
<212> TYPE: RNA
<213> ORGANISM: Homo sapiens

<400> SEQUENCE: 385
cugaaauaac uagaguucua agacacga    28

<210> SEQ ID NO 386
<211> LENGTH: 36
<212> TYPE: RNA
<213> ORGANISM: Homo sapiens

<400> SEQUENCE: 386
caggaccugc cgccagccuc ggccaggcag gcacgg                                    36

<210> SEQ ID NO 387
<211> LENGTH: 21
<212> TYPE: RNA
<213> ORGANISM: Homo sapiens

<400> SEQUENCE: 387
ccacagaagc ccuacagcuc c                                                    21

<210> SEQ ID NO 388
<211> LENGTH: 22
<212> TYPE: RNA
<213> ORGANISM: Homo sapiens

<400> SEQUENCE: 388
cggugcagcg gucccagagu cc                                                   22

<210> SEQ ID NO 389
<211> LENGTH: 22
<212> TYPE: RNA
<213> ORGANISM: Homo sapiens

<400> SEQUENCE: 389
aggcuugucc aucaaagaaa uc                                                   22

<210> SEQ ID NO 390
<211> LENGTH: 23
<212> TYPE: RNA
<213> ORGANISM: Homo sapiens

<400> SEQUENCE: 390
agggcgaaag gaaaggaagg aug                                                  23

<210> SEQ ID NO 391
<211> LENGTH: 22
<212> TYPE: RNA
<213> ORGANISM: Homo sapiens

<400> SEQUENCE: 391
agccccacuu ccucagaaca gg                                                   22

<210> SEQ ID NO 392
<211> LENGTH: 35
<212> TYPE: RNA
<213> ORGANISM: Homo sapiens

<400> SEQUENCE: 392
ggaaaagaga aagagacagg agaaaacaag agggu                                     35

<210> SEQ ID NO 393
<211> LENGTH: 25
<212> TYPE: RNA
<213> ORGANISM: Homo sapiens

<400> SEQUENCE: 393
aacuugagag uacagaaaaa gcagg                                                25

<210> SEQ ID NO 394
<211> LENGTH: 21
<212> TYPE: RNA
<213> ORGANISM: Homo sapiens

```
<400> SEQUENCE: 394
ccaguggcca gguuuucuag a                                          21

<210> SEQ ID NO 395
<211> LENGTH: 21
<212> TYPE: RNA
<213> ORGANISM: Homo sapiens

<400> SEQUENCE: 395
acgaacagau uagaaauaac u                                          21

<210> SEQ ID NO 396
<211> LENGTH: 27
<212> TYPE: RNA
<213> ORGANISM: Homo sapiens

<400> SEQUENCE: 396
cuguagaaaa uguaaagaag agaaagc                                    27

<210> SEQ ID NO 397
<211> LENGTH: 21
<212> TYPE: RNA
<213> ORGANISM: Homo sapiens

<400> SEQUENCE: 397
uagaauucag acaggaaagg g                                          21

<210> SEQ ID NO 398
<211> LENGTH: 28
<212> TYPE: RNA
<213> ORGANISM: Homo sapiens

<400> SEQUENCE: 398
caaaccaugc aaagaggagg aagagaaa                                   28

<210> SEQ ID NO 399
<211> LENGTH: 18
<212> TYPE: RNA
<213> ORGANISM: Homo sapiens

<400> SEQUENCE: 399
ccuccagacc cucaaagc                                              18

<210> SEQ ID NO 400
<211> LENGTH: 17
<212> TYPE: RNA
<213> ORGANISM: Homo sapiens

<400> SEQUENCE: 400
ccgccuggcu gggaggg                                               17

<210> SEQ ID NO 401
<211> LENGTH: 18
<212> TYPE: RNA
<213> ORGANISM: Homo sapiens

<400> SEQUENCE: 401
agcagcccca gccccugg                                              18

<210> SEQ ID NO 402
<211> LENGTH: 18
<212> TYPE: RNA
```

```
<213> ORGANISM: Homo sapiens

<400> SEQUENCE: 402
ccccacccac agugccag                                           18

<210> SEQ ID NO 403
<211> LENGTH: 20
<212> TYPE: RNA
<213> ORGANISM: Homo sapiens

<400> SEQUENCE: 403
cucagggauc cgacgcagag                                         20

<210> SEQ ID NO 404
<211> LENGTH: 22
<212> TYPE: RNA
<213> ORGANISM: Homo sapiens

<400> SEQUENCE: 404
uguuugaaug cggaagucau cc                                      22

<210> SEQ ID NO 405
<211> LENGTH: 21
<212> TYPE: RNA
<213> ORGANISM: Homo sapiens

<400> SEQUENCE: 405
auccucaggc agcuuucaac c                                       21

<210> SEQ ID NO 406
<211> LENGTH: 19
<212> TYPE: RNA
<213> ORGANISM: Homo sapiens

<400> SEQUENCE: 406
ugaucucagc cucaccuag                                          19

<210> SEQ ID NO 407
<211> LENGTH: 29
<212> TYPE: RNA
<213> ORGANISM: Homo sapiens

<400> SEQUENCE: 407
cacagauuua ugauaauaag aaaccauua                               29

<210> SEQ ID NO 408
<211> LENGTH: 22
<212> TYPE: RNA
<213> ORGANISM: Homo sapiens

<400> SEQUENCE: 408
cuucuaauuc uagaugacau ag                                      22

<210> SEQ ID NO 409
<211> LENGTH: 25
<212> TYPE: RNA
<213> ORGANISM: Homo sapiens

<400> SEQUENCE: 409
gccgcuuccg uuuaauaaaa gcauc                                   25

<210> SEQ ID NO 410
<211> LENGTH: 20
```

```
<212> TYPE: RNA
<213> ORGANISM: Homo sapiens

<400> SEQUENCE: 410
cugguagaaa gagacugagc                                                   20

<210> SEQ ID NO 411
<211> LENGTH: 23
<212> TYPE: RNA
<213> ORGANISM: Homo sapiens

<400> SEQUENCE: 411
cuuaguggca agaugcauaa aag                                               23

<210> SEQ ID NO 412
<211> LENGTH: 24
<212> TYPE: RNA
<213> ORGANISM: Homo sapiens

<400> SEQUENCE: 412
ugcaaaauuu ggaaauuguu uuaa                                              24

<210> SEQ ID NO 413
<211> LENGTH: 27
<212> TYPE: RNA
<213> ORGANISM: Homo sapiens

<400> SEQUENCE: 413
cacuuaaaca gauauacaaa gugugaa                                           27

<210> SEQ ID NO 414
<211> LENGTH: 20
<212> TYPE: RNA
<213> ORGANISM: Homo sapiens

<400> SEQUENCE: 414
ugacagcuga aguccacaa                                                    20

<210> SEQ ID NO 415
<211> LENGTH: 20
<212> TYPE: RNA
<213> ORGANISM: Homo sapiens

<400> SEQUENCE: 415
auggaacaag uccuucacau                                                   20

<210> SEQ ID NO 416
<211> LENGTH: 26
<212> TYPE: RNA
<213> ORGANISM: Homo sapiens

<400> SEQUENCE: 416
uucaggaaag acaacaaaua uaaaca                                            26

<210> SEQ ID NO 417
<211> LENGTH: 23
<212> TYPE: RNA
<213> ORGANISM: Homo sapiens

<400> SEQUENCE: 417
uauuugacau uuaauuuaau aca                                               23

<210> SEQ ID NO 418
```

```
<211> LENGTH: 27
<212> TYPE: RNA
<213> ORGANISM: Homo sapiens

<400> SEQUENCE: 418 uaauuucuc ugaacuucua aaacagu                                          27

<210> SEQ ID NO 419
<211> LENGTH: 27
<212> TYPE: RNA
<213> ORGANISM: Homo sapiens

<400> SEQUENCE: 419
caacuaacaa auaauagaaa aauccaa                                         27

<210> SEQ ID NO 420
<211> LENGTH: 28
<212> TYPE: RNA
<213> ORGANISM: Homo sapiens

<400> SEQUENCE: 420
uuaauuucau uuauauuaua aaucaugu                                        28

<210> SEQ ID NO 421
<211> LENGTH: 27
<212> TYPE: RNA
<213> ORGANISM: Homo sapiens

<400> SEQUENCE: 421
gacagacaag aauguuaaac agaaaua                                         27

<210> SEQ ID NO 422
<211> LENGTH: 28
<212> TYPE: RNA
<213> ORGANISM: Homo sapiens

<400> SEQUENCE: 422
gaagcucugc aagaauucca gcaugcac                                        28

<210> SEQ ID NO 423
<211> LENGTH: 22
<212> TYPE: RNA
<213> ORGANISM: Homo sapiens

<400> SEQUENCE: 423
ggaaacagau gcuacauaaa uc                                              22

<210> SEQ ID NO 424
<211> LENGTH: 29
<212> TYPE: RNA
<213> ORGANISM: Homo sapiens

<400> SEQUENCE: 424
gagcaagggc cugagauuuu gcaagcaug                                       29

<210> SEQ ID NO 425
<211> LENGTH: 30
<212> TYPE: RNA
<213> ORGANISM: Homo sapiens

<400> SEQUENCE: 425
cuucagaugc aacccugaca agggacuaau                                      30
```

```
<210> SEQ ID NO 426
<211> LENGTH: 21
<212> TYPE: RNA
<213> ORGANISM: Homo sapiens

<400> SEQUENCE: 426
gccccugccc uuucugucuc a                                              21

<210> SEQ ID NO 427
<211> LENGTH: 28
<212> TYPE: RNA
<213> ORGANISM: Homo sapiens

<400> SEQUENCE: 427
guuaaaacau agguuauaaa agaagaac                                       28

<210> SEQ ID NO 428
<211> LENGTH: 25
<212> TYPE: RNA
<213> ORGANISM: Homo sapiens

<400> SEQUENCE: 428
uagaagaaag caaaacaaca aaacu                                          25

<210> SEQ ID NO 429
<211> LENGTH: 19
<212> TYPE: RNA
<213> ORGANISM: Homo sapiens

<400> SEQUENCE: 429
aguaaaccaa aaauaaugg                                                 19

<210> SEQ ID NO 430
<211> LENGTH: 25
<212> TYPE: RNA
<213> ORGANISM: Homo sapiens

<400> SEQUENCE: 430
uuugagaaaa aaaugcaauu gacaa                                          25

<210> SEQ ID NO 431
<211> LENGTH: 23
<212> TYPE: RNA
<213> ORGANISM: Homo sapiens

<400> SEQUENCE: 431
auucuguccc aggaccuagg agu                                            23

<210> SEQ ID NO 432
<211> LENGTH: 29
<212> TYPE: RNA
<213> ORGANISM: Homo sapiens

<400> SEQUENCE: 432
ugcagagcag cuugucuuuc uucugagag                                      29

<210> SEQ ID NO 433
<211> LENGTH: 31
<212> TYPE: RNA
<213> ORGANISM: Homo sapiens

<400> SEQUENCE: 433
uacucacggc ucgugucuuc agaagccaag g                                   31
```

<210> SEQ ID NO 434
<211> LENGTH: 25
<212> TYPE: RNA
<213> ORGANISM: Homo sapiens

<400> SEQUENCE: 434
ccuuccccac ucaggucagc ugcua                                              25

<210> SEQ ID NO 435
<211> LENGTH: 16
<212> TYPE: RNA
<213> ORGANISM: Artificial Sequence
<220> FEATURE:
<223> OTHER INFORMATION: SSO

<400> SEQUENCE: 435
agcuggggcc uggggu                                                        16

<210> SEQ ID NO 436
<211> LENGTH: 21
<212> TYPE: RNA
<213> ORGANISM: Artificial Sequence
<220> FEATURE:
<223> OTHER INFORMATION: SSO

<400> SEQUENCE: 436
ugcagagcug gggccugggg u                                                  21

<210> SEQ ID NO 437
<211> LENGTH: 20
<212> TYPE: RNA
<213> ORGANISM: Artificial Sequence
<220> FEATURE:
<223> OTHER INFORMATION: SSO

<400> SEQUENCE: 437
caugcuucac gagcccagcc                                                    20

<210> SEQ ID NO 438
<211> LENGTH: 17
<212> TYPE: RNA
<213> ORGANISM: Artificial Sequence
<220> FEATURE:
<223> OTHER INFORMATION: SSO

<400> SEQUENCE: 438
aaggcugcgg cuggguc                                                       17

<210> SEQ ID NO 439
<211> LENGTH: 21
<212> TYPE: RNA
<213> ORGANISM: Artificial Sequence
<220> FEATURE:
<223> OTHER INFORMATION: SSO

<400> SEQUENCE: 439
ugguagaggg agcagaugcu g                                                  21

<210> SEQ ID NO 440
<211> LENGTH: 20
<212> TYPE: RNA
<213> ORGANISM: Artificial Sequence
<220> FEATURE:
<223> OTHER INFORMATION: SSO

<400> SEQUENCE: 440

-continued

```
ugguacagca uuguuccaca                                                20

<210> SEQ ID NO 441
<211> LENGTH: 19
<212> TYPE: RNA
<213> ORGANISM: Artificial Sequence
<220> FEATURE:
<223> OTHER INFORMATION: SSO

<400> SEQUENCE: 441
cgcacacuag guagagagc                                                 19

<210> SEQ ID NO 442
<211> LENGTH: 19
<212> TYPE: RNA
<213> ORGANISM: Artificial Sequence
<220> FEATURE:
<223> OTHER INFORMATION: SSO

<400> SEQUENCE: 442
gaugcagccu guccuggag                                                 19

<210> SEQ ID NO 443
<211> LENGTH: 21
<212> TYPE: RNA
<213> ORGANISM: Artificial Sequence
<220> FEATURE:
<223> OTHER INFORMATION: SSO

<400> SEQUENCE: 443
gagcccaccu gacgcaaagg c                                              21

<210> SEQ ID NO 444
<211> LENGTH: 19
<212> TYPE: RNA
<213> ORGANISM: Artificial Sequence
<220> FEATURE:
<223> OTHER INFORMATION: SSO

<400> SEQUENCE: 444
uggagggcug agggcugcu                                                 19

<210> SEQ ID NO 445
<211> LENGTH: 18
<212> TYPE: RNA
<213> ORGANISM: Artificial Sequence
<220> FEATURE:
<223> OTHER INFORMATION: SSO

<400> SEQUENCE: 445
auggccucuu cugaugca                                                  18

<210> SEQ ID NO 446
<211> LENGTH: 17
<212> TYPE: RNA
<213> ORGANISM: Artificial Sequence
<220> FEATURE:
<223> OTHER INFORMATION: SSO

<400> SEQUENCE: 446 ucaccccac augcuuc                                                    17

<210> SEQ ID NO 447
<211> LENGTH: 14
<212> TYPE: RNA
```

```
<213> ORGANISM: Artificial Sequence
<220> FEATURE:
<223> OTHER INFORMATION: SSO

<400> SEQUENCE: 447
acaugcuuca cgag                                                        14

<210> SEQ ID NO 448
<211> LENGTH: 14
<212> TYPE: RNA
<213> ORGANISM: Artificial Sequence
<220> FEATURE:
<223> OTHER INFORMATION: SSO

<400> SEQUENCE: 448
cuggggccug gggu                                                        14

<210> SEQ ID NO 449
<211> LENGTH: 16
<212> TYPE: RNA
<213> ORGANISM: Artificial Sequence
<220> FEATURE:
<223> OTHER INFORMATION: SSO

<400> SEQUENCE: 449
ugcagagcug gggccu                                                      16

<210> SEQ ID NO 450
<211> LENGTH: 16
<212> TYPE: RNA
<213> ORGANISM: Artificial Sequence
<220> FEATURE:
<223> OTHER INFORMATION: SSO

<400> SEQUENCE: 450
aggugcucgc gggugg                                                      16

<210> SEQ ID NO 451
<211> LENGTH: 21
<212> TYPE: RNA
<213> ORGANISM: Artificial Sequence
<220> FEATURE:
<223> OTHER INFORMATION: SSO

<400> SEQUENCE: 451
ggguggaagc guccggucgu g                                                21

<210> SEQ ID NO 452
<211> LENGTH: 20
<212> TYPE: RNA
<213> ORGANISM: Artificial Sequence
<220> FEATURE:
<223> OTHER INFORMATION: SSO

<400> SEQUENCE: 452
acacacugug ccucgccagc                                                  20

<210> SEQ ID NO 453
<211> LENGTH: 20
<212> TYPE: RNA
<213> ORGANISM: Artificial Sequence
<220> FEATURE:
<223> OTHER INFORMATION: SSO

<400> SEQUENCE: 453
gacucacuug ccguaguuaa                                                  20
```

<210> SEQ ID NO 454
<211> LENGTH: 19
<212> TYPE: RNA
<213> ORGANISM: Artificial Sequence
<220> FEATURE:
<223> OTHER INFORMATION: SSO

<400> SEQUENCE: 454
cacgcucagu agagaaggc                                                19

<210> SEQ ID NO 455
<211> LENGTH: 30
<212> TYPE: RNA
<213> ORGANISM: Homo sapiens

<400> SEQUENCE: 455
ggauuccagg guggcuggac cccaggcccc                                    30

<210> SEQ ID NO 456
<211> LENGTH: 18
<212> TYPE: RNA
<213> ORGANISM: Homo sapiens

<400> SEQUENCE: 456
ggauuccagg guggcugg                                                 18

<210> SEQ ID NO 457
<211> LENGTH: 30
<212> TYPE: RNA
<213> ORGANISM: Homo sapiens

<400> SEQUENCE: 457
ggauuccagg guggcugcac gccaggcccc                                    30

<210> SEQ ID NO 458
<211> LENGTH: 30
<212> TYPE: RNA
<213> ORGANISM: Homo sapiens

<400> SEQUENCE: 458
ggauuccagg guggcuggac ccgaggcgcc                                    30

<210> SEQ ID NO 459
<211> LENGTH: 30
<212> TYPE: RNA
<213> ORGANISM: Homo sapiens

<400> SEQUENCE: 459
ggauuccagg augguaggac ccgaggcgcc                                    30

<210> SEQ ID NO 460
<211> LENGTH: 30
<212> TYPE: RNA
<213> ORGANISM: Homo sapiens

<400> SEQUENCE: 460
ggauuccagg augguaggac cccaggcccc                                    30

<210> SEQ ID NO 461
<211> LENGTH: 30
<212> TYPE: RNA
<213> ORGANISM: Homo sapiens

```
<400> SEQUENCE: 461
ggauuccagg guugcuggac cccagucccc                                    30

<210> SEQ ID NO 462
<211> LENGTH: 30
<212> TYPE: RNA
<213> ORGANISM: Homo sapiens

<400> SEQUENCE: 462
ggauuccagg guugcuggac ccgagucgcc                                    30

<210> SEQ ID NO 463
<211> LENGTH: 36
<212> TYPE: DNA
<213> ORGANISM: Homo sapiens

<400> SEQUENCE: 463
attaatacga ctcactatag ggctcagggt tccagg                             36

<210> SEQ ID NO 464
<211> LENGTH: 16
<212> TYPE: DNA
<213> ORGANISM: Homo sapiens

<400> SEQUENCE: 464
tgcagcaggg aggacg                                                   16

<210> SEQ ID NO 465
<211> LENGTH: 15
<212> TYPE: DNA
<213> ORGANISM: Homo sapiens

<400> SEQUENCE: 465
aaatagaggc cccag                                                    15

<210> SEQ ID NO 466
<211> LENGTH: 46
<212> TYPE: DNA
<213> ORGANISM: Homo sapiens

<400> SEQUENCE: 466
gggtggctgg accccaggcc ccagctctgc agcagggagg acgtgg                  46

<210> SEQ ID NO 467
<211> LENGTH: 30
<212> TYPE: RNA
<213> ORGANISM: Homo sapiens

<400> SEQUENCE: 467
gaagcguggc auuguggaac aaugcuguac                                    30

<210> SEQ ID NO 468
<211> LENGTH: 61
<212> TYPE: DNA
<213> ORGANISM: Homo sapiens
<220> FEATURE:
<221> NAME/KEY: misc_feature
<222> LOCATION: (4)..(4)
<223> OTHER INFORMATION: A or G

<400> SEQUENCE: 468
aggrttccag ggtggctgga ccccaggccc cagctctgca gcagggagga cgtggctggg   60
c                                                                   61
```

```
<210> SEQ ID NO 469
<211> LENGTH: 19
<212> TYPE: RNA
<213> ORGANISM: Homo sapiens

<400> SEQUENCE: 469
agggaggacg uggcugggc                                                    19

<210> SEQ ID NO 470
<211> LENGTH: 20
<212> TYPE: RNA
<213> ORGANISM: Homo sapiens

<400> SEQUENCE: 470
aggauuccag gguggcugga                                                   20

<210> SEQ ID NO 471
<211> LENGTH: 20
<212> TYPE: RNA
<213> ORGANISM: Homo sapiens

<400> SEQUENCE: 471
aggauuccag cguggcugga                                                   20

<210> SEQ ID NO 472
<211> LENGTH: 22
<212> TYPE: RNA
<213> ORGANISM: Homo sapiens

<400> SEQUENCE: 472
ccaggguggc uggacnccag gc                                                22

<210> SEQ ID NO 473
<211> LENGTH: 22
<212> TYPE: RNA
<213> ORGANISM: Homo sapiens

<400> SEQUENCE: 473
ccaggguggc uggacuucag gc                                                22
```